(12) United States Patent
Ying et al.

(10) Patent No.: US 12,258,405 B2
(45) Date of Patent: Mar. 25, 2025

(54) CD3 ANTIBODY AND PHARMACEUTICAL USE THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Hua Ying, Shanghai (CN); Ling Zhang, Shanghai (CN); Xiaoying Yang, Shanghai (CN); Hu Ge, Shanghai (CN); Weikang Tao, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 955 days.

(21) Appl. No.: 17/298,703

(22) PCT Filed: Dec. 6, 2019

(86) PCT No.: PCT/CN2019/123548
§ 371 (c)(1),
(2) Date: Jun. 1, 2021

(87) PCT Pub. No.: WO2020/114478
PCT Pub. Date: Jun. 11, 2020

(65) Prior Publication Data
US 2022/0242953 A1 Aug. 4, 2022

(30) Foreign Application Priority Data
Dec. 7, 2018 (CN) .......................... 201811491781.3

(51) Int. Cl.
C07K 16/28 (2006.01)
A61P 35/00 (2006.01)
C07K 16/46 (2006.01)
A61K 39/00 (2006.01)

(52) U.S. Cl.
CPC .......... *C07K 16/2809* (2013.01); *A61P 35/00* (2018.01); *C07K 16/2827* (2013.01); *C07K 16/468* (2013.01); *A61K 2039/505* (2013.01); *A61K 2039/545* (2013.01); *C07K 2317/24* (2013.01); *C07K 2317/31* (2013.01); *C07K 2317/33* (2013.01); *C07K 2317/565* (2013.01); *C07K 2317/622* (2013.01); *C07K 2317/92* (2013.01)

(58) Field of Classification Search
CPC ..................... C07K 16/2809; C07K 2317/565
USPC .................................................... 424/136.1
See application file for complete search history.

(56) References Cited

U.S. PATENT DOCUMENTS

| 4,816,567 A | 3/1989 | Cabilly et al. |
| 5,641,870 A | 6/1997 | Rinderknecht et al. |
| 5,807,715 A | 9/1998 | Morrison et al. |
| 5,866,692 A | 2/1999 | Shitara et al. |
| 6,331,415 B1 | 12/2001 | Cabilly et al. |
| 10,954,311 B2 | 3/2021 | Baeuerle et al. |
| 2014/0255407 A1 | 9/2014 | Koenig |

FOREIGN PATENT DOCUMENTS

| CN | 107849148 A | | 3/2018 |
| RU | 2802272 | * | 12/2019 |
| WO | 2008119567 A2 | | 10/2008 |
| WO | 2010037837 A2 | | 4/2010 |
| WO | 2014144722 A2 | | 9/2014 |
| WO | 2016187594 A1 | | 11/2016 |
| WO | 2017030926 A1 | | 2/2017 |
| WO | 2017055314 A1 | | 4/2017 |
| WO | WO 2020114479 | * | 12/2019 |

OTHER PUBLICATIONS

International Search Report; China National Intellectual Property Administration; International Application No. PCT/CN2019/123548; Mar. 6, 2020; 7 pages.
Gruber, M. et al.; Efficient tumor cell lysis mediated by a bispecific single chain antibody expressed in *Escherichia coli*.; The Journal of Immunology; 1994; 1 page; vol. 152; No. 11; American Association of Immunologists.
Roth, Timothy J. et al.; B7-H3 Ligand Expression by Prostate Cancer: A Novel Marker of Prognosis and Potential Target for Therapy; Cancer Research; Aug. 15, 2007; pp. 7893-7900; vol. 67, No. 16; American Association for Cancer Research.
Chetty, Runjan et al.; CD3: Structure, Function, and Role of Immunostaining in Clinical Practice; Journal of Pathology; 1994; pp. 303-307; vol. 173; John Wiley & Sons, Ltd.
Crispen, Paul L. et al.; Tumor Cell and Tumor Vasculature Expression of B7-H3 Predict Survival in Clear Cell Renal Cell Carcinoma; Clinical Cancer Research; Aug. 15, 2008; pp. 5150-5157; vol. 14, No. 16; American Association for Cancer Research.
Kuhns, Michael S. et al.; Deconstructing the Form and Function of the TCR/CD3 Complex; Immunity; Feb. 2006; pp. 133-139; vol. 24; Elsevier Inc.
Zhang, Guangbo et al.; Diagnosis value of serum B7-H3 expression in non-small cell lung cancer; Lung Cancer; 2009; pp. 245-249; vol. 66; Elsevier Ireland Ltd.

(Continued)

*Primary Examiner* — Lynn A Bristol
(74) *Attorney, Agent, or Firm* — Taft Stettinius & Hollister LLP

(57) ABSTRACT

The present disclosure relates to a CD3 antibody and a pharmaceutical use thereof. Specifically, the present disclosure relates to forming a multi-specificity antibody by using CD3 antibody and binding molecules of another target. The multi-specificity antibody may simultaneously bind to CD3 and another tumor-associated antigen, and bind and activate CD3-positive T cells while binding tumor-associated antigen-expressing cells, thereby promoting T cells specifically killing tumor cells that express tumor-associated antigens. In addition, the present disclosure also provides a preparation and application of a multi-specific antibody.

14 Claims, 15 Drawing Sheets
Specification includes a Sequence Listing.

(56) References Cited

OTHER PUBLICATIONS

Sun, Zhen-Yu J. et al.; Mechanisms Contributing to T Cell Receptor Signaling and Assembly Revealed by the Solution Structure of an Ectodomain Fragment of the CD3εγ Heterodimer; Cell; Jun. 29, 2001; pp. 913-923; vol. 105; Cell Press.
Thomas, Sharyn et al.; Molecular immunology lessons from therapeutic T-cell receptor gene transfer; Immunology; 2010; pp. 170-177; vol. 129; Blackwell Publishing Ltd.
Guy, Clifford S. et al.; Organization of proximal signal initiation at the TCR:CD3 complex; Immunological Reviews; 2009; pp. 7-21; vol. 232; John Wiley & Sons A/S.
Wucherpfennig, Kai W. et al.; Structural Biology of the T-cell Receptor: Insights into Receptor Assembly, Ligand Recognition, and Initiation of Signaling; Cold Spring Harbor Perspectives in Biology; 2010; 14 pages; vol. 2; Cold Spring Harbor Laboratory Press.
Zhou, Y.-H. et al.; 4IgB7-H3 is the major isoform expressed on immunocytes as well as malignant cells; Tissue Antigens; 2007; pp. 96-104; vol. 70; Blackwell Munksgaard.
Written Opinion of the International Searching Authority; China National Intellectual Property Administration; International Application No. PCT/CN2019/123548; Mar. 6, 2020; 7 pages,.
International Preliminary Report on Patentability; The International Bureau of WIPO; International Application No. PCT/CN2019/123548; Jun. 8, 2021; 9 pages.
Smith-Garvin, Jennifer E. et al.; T Cell Activation; Annu Rev Immunol.; 2009; pp. 591-619; vol. 27.

\* cited by examiner

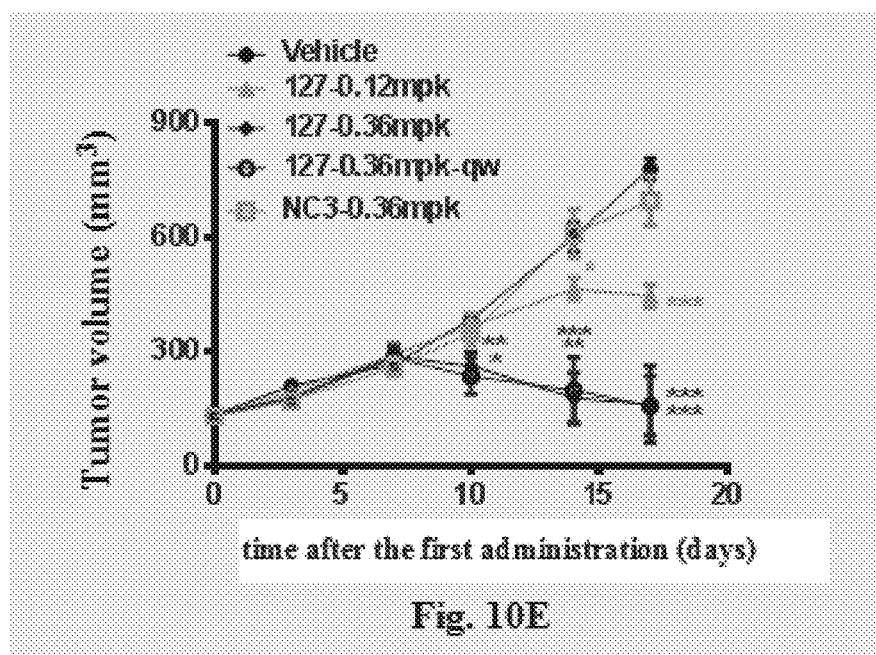
Fig. 10E
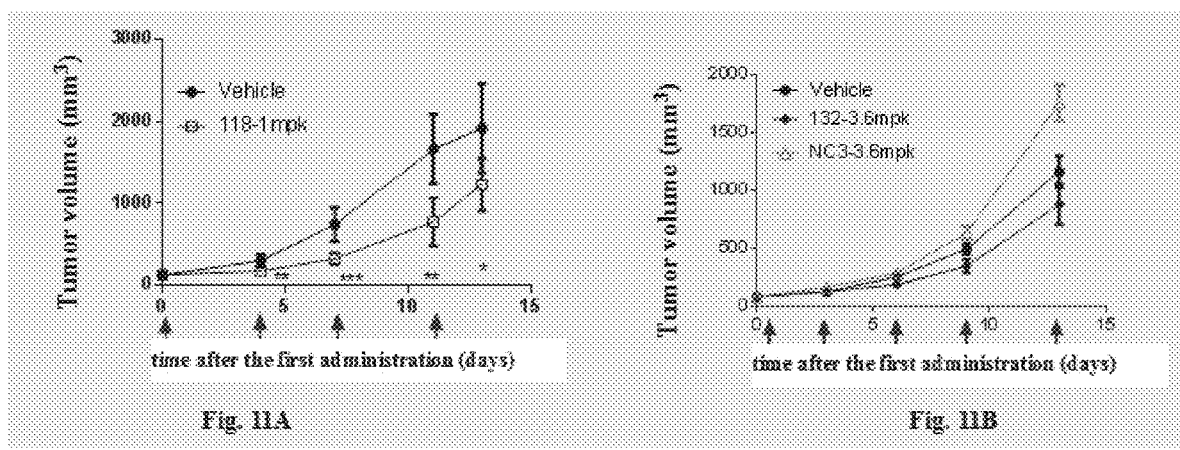
Fig. 11A
Fig. 11B

CD3 ANTIBODY AND PHARMACEUTICAL USE THEREOF

CROSS-REFERENCE TO RELATED APPLICATIONS

This application is a U.S. National Phase of International PCT Application No. PCT/CN2019/123548 filed Dec. 6, 2019, which claims priority to Chinese Patent Application Serial No. 201811491781.3 filed Dec. 7, 2018, the contents of each application are incorporated herein by reference in their entireties.

SEQUENCE LISTING

This application incorporates by reference the material in the ASCII text file titled 719084CPUS-sequence-listing-amend.txt, which was created on Aug. 20, 2024 and is 260 KB.

FIELD OF THE INVENTION

The present invention relates to CD3 antibodies such as humanized CD3 antibodies, and multispecific antibodies simultaneously binding to CD3 and tumor-associated antigen(s).

BACKGROUND OF THE INVENTION

The descriptions herein only provide background information about the present invention, and do not necessarily constitute prior art.

CD3 is a T cell co-receptor composed of four different chains (Wucherpfennig, K W et al. (2010) Structural Biology of The T cell Receptor: Insights Into Receptor Assembly, Ligand Recognition, and Initiation of Signaling, Cold Spring Harb. Perspect. Biol. 2(4):A005140; pages 1-14; Chetty, R. et al. (1994) CD3:Structure, Function, And Role Of Immunostaining In Clinical Practice, J. Pathol. 173(4): 303-307; Guy, C. S. et al. (2009) Organization of Proximal Signal Initiation at the TCR:CD3 Complex, Immunol. Rev. 232(1):7-21).

In mammals, the complex formed by CD3 multi-subunits is associated with T cell receptor (TCR) molecule to generate activation signals in T lymphocytes (Smith-Garvin, J E et al. (2009) T Cell Activation, Annu. Rev. Immunol. 27:591-619). In the absence of CD3, TCR neither can be assembled properly nor be degraded (Thomas, S. et al. (2010) Molecular Immunology Lessons From Therapeutic T cell Receptor Gene Transfer, Immunology 129(2): 170-177). Studies have found that CD3 binds to the membranes of all mature T cells and hardly binds to other cell types (Janeway, C. A. et al. (2005): Immunobiology: The Immune System in Health and Disease, 6th Edition, Garland Science Publishing, NY, pp. 214-216; Sun, Z. J. et al. (2001) Mechanisms Contributing to T Cell Receptor Signaling and Assembly Revealed by the Solution Structure of an Ectodomain Fragment of the CD3ε: γ Heterodimer, Cell 105 (7): 913-923; Kuhns, M. S. et al. (2006) Deconstructing the Form and Function of the TCR/CD3 Complex, Immunity. 2006 February, 24(2): 133-139).

The constant CD3ε signaling component of the T cell receptor (TCR) complex on T cells has been used as a target to promote the formation of immunological synapses between T cells and tumor cells. The co-engagement of CD3 and tumor antigen(s) activates T cells, resulting in the lysis of tumor cells expressing tumor antigen(s) (Baeuerle et al. (2011) Bispecific T Cell Engager for Cancer Therapy, In: Bispecific Antibodies, Kontermann, R. E. (Ed.) Springer-Verlag; 2011:273-287). This method allows bispecific antibodies to fully interact with T cell compartments with a specificity which is as high as that for tumor cells, and the method is widely applicable to a variety of cell surface tumor antigens.

B7H3 is a member of the B7 family and belongs to the type I transmembrane protein. It contains a signal peptide at the amino terminus, an extracellular immunoglobulin-like variable region (IgV), a constant region (IgC), a transmembrane region and a cytoplasmic tail region comprising 45 amino acids (Tissue Antigens. 2007 August; 70 (2): 96-104). Currently, B7H3 mainly has two types of splicing forms, B7H3a and B7H3b. The extracellular segment of B7H3a is composed of two immunoglobulin domains, IgV-IgC, also known as 2IgB7H3, whereas the extracellular segment of B7H3b is composed of four immunoglobulin domains, IgV-IgC-IgV-IgC, also known as 4IgB7H3.

B7H3 protein is absent in normal tissues and cells, or expressed in normal tissues and cells at extremely low level; however, it is highly expressed in a variety of tumor tissues, and is closely related to tumor progression, patient survival and prognosis. It has been clinically reported that B7H3 is over-expressed in various cancer types, especially in non-small cell lung cancer, kidney cancer, urinary tract epithelial cancer, colorectal cancer, prostate cancer, glioblastoma multiforme, ovarian cancer and pancreatic cancer. (Lung Cancer. 2009 November; 66(2): 245-249; Clin Cancer Res. 2008 Aug. 15; 14(16): 5150-5157). In addition, it has also been reported in literatures that the expression intensity of B7H3 is positively correlated with clinically pathological malignancy in prostate cancer (such as tumor volume, invasion beyond the prostate or Gleason score), and is also correlated with cancer progression (Cancer Res. 2007 Aug. 15; 67 (16): 7893-7900). Similarly, the expression of B7H3 is negatively correlated with event-free survival in glioblastoma multiforme, and the expression of B7H3 is correlated with lymphatic metastasis and pathological progression in pancreatic cancer. Therefore, B7H3 is considered as a new tumor marker and potential therapeutic target.

SUMMARY OF THE INVENTION

The present disclosure provides antibodies or antigen-binding fragments thereof that can specifically bind to human CD3.

In one aspect, the present disclosure provides an antibody or antigen-binding fragment thereof specifically binding to human CD3, the antibody or antigen-binding fragment thereof comprising a heavy chain variable region and a light chain variable region, wherein the light chain variable region comprises LCDR1, LCDR2, and LCDR3 as shown in SEQ ID NOs: 48, 49, and 50, respectively, and
  the heavy chain variable region is any one selected from the group consisting of the following i) to v):
  i) a heavy chain variable region comprising HCDR1, HCDR2 and HCDR3 as shown in SEQ ID NOs: 37, 38 and 39, respectively;
  ii) a heavy chain variable region comprising HCDR1, HCDR2 and HCDR3 as shown in SEQ ID NOs: 37, 40 and 41, respectively;
  iii) a heavy chain variable region comprising HCDR1, HCDR2 and HCDR3 as shown in SEQ ID NOs: 37, 40 and 42, respectively;

iv) a heavy chain variable region comprising HCDR1, HCDR2 and HCDR3 as shown in SEQ ID NOs: 37, 40 and 43, respectively; and v) a heavy chain variable region comprising HCDR1, HCDR2 and HCDR3 as shown in SEQ ID NOs: 37, 47 and 45, respectively.

In some embodiments, the antibody or antigen-binding fragment thereof specifically binding to human CD3 is a humanized antibody or antigen-binding fragment thereof.

In some embodiments, the antibody or antigen-binding fragment thereof specifically binding to human CD3 comprises a light chain variable region of SEQ ID NO: 36 and/or a heavy chain variable region as shown in any one selected from the group consisting of SEQ ID NOs: 29,30,31,32 and 35.

In some embodiments, the antibody or antigen-binding fragment thereof specifically binding to human CD3 further comprises an antibody light chain constant region and/or a heavy chain constant region; optionally, the light chain constant region is a light chain constant region of a human kappa, lambda chain or variant thereof, and the heavy chain constant region is a heavy chain constant region of a human IgG1, IgG2, IgG3, IgG4 or variant thereof.

In some embodiments, the antigen-binding fragment is selected from Fab, Fab', F(ab')2, dimerized V region (diabody) and disulfide-stabilized V region (dsFv).

In another aspect, the present disclosure provides a single-chain antibody comprising the light chain variable region and the heavy chain variable region of the antibody or antigen-binding fragment thereof specifically binding to human CD3 as described above.

In some embodiments, the sequence of the single-chain antibody is as shown in SEQ ID NO: 55, 56, 57, 58, 61, 62, 63, 64, 65 or 68.

In another aspect, the present disclosure provides a multispecific antibody specifically binding to human CD3 and tumor-associated antigen(s) (TAA), the multispecific antibody comprising the single-chain antibody or the antibody or antigen-binding fragment thereof specifically binding to human CD3 as described above.

In some embodiments of the multispecific antibody, the tumor-associated antigen is selected from the group consisting of AFP, ALK, B7H3, BAGE protein, BCMA, BIRC5 (survivin), BIRC7, β-catenin, brc-abl, BRCA1, BORIS, CA9, CA125, carbonic anhydrase IX, caspase-8, CALR, CCR5, CD19, CD20(MS4A1), CD22, CD30, CD33, CD38, CD40, CD123, CD133, CD138, CDK4, CEA, Claudin 18.2, cyclin-B1, CYP1B1, EGFR, EGFRvIII, ErbB2/Her2, ErbB3, ErbB4, ETV6-AML, EpCAM, EphA2, Fra-1, FOLR1, GAGE protein (such as GAGE-1, -2), GD2, GD3, GloboH, Glypican-3, GM3, gp100, Her2, HLA/B-raf, HLA/k-ras, HLA/MAGE-A3, hTERT, IL13Rα2, LMP2, κ-Light, LeY, MAGE protein (such as MAGE-1, -2, -3, -4, -6 and -12), MART-1, mesothelin, ML-IAP, MOv-γ, Muc1, Muc2, Muc3, Muc4, Muc5, Muc16(CA-125, MUM1, NA17, NKG2D, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE protein, Ras, RGS5, Rho, ROR1, SART-1, SART-3, STEAP1, STEAP2, TAG-72, TGF-β, TMPRSS2, Thompson-nouvelle antigen (Tn), TRP-1, TRP-2, tyrosinase, uroplakin-3 and 5T4 (Trophoblast glycoprotein). Preferably, the tumor-associated antigen is selected from the group consisting of B7H3, BCMA, CEA, CD19, CD20, CD38, CD138, Claudin 18.2, PSMA and mesothelin.

In another aspect, the present disclosure provides a pharmaceutical composition comprising a therapeutically effective amount of the antibody or antigen-binding fragment thereof specifically binding to human CD3, the single chain antibody, or the multispecific antibody as described above, and one or more pharmaceutically acceptable carriers, diluents, buffers or excipients. In some embodiments, the therapeutically effective amount means that the composition comprises a unit dose of 0.1-3000 mg (more preferably 1-1000 mg) of the antibody or antigen-binding fragment thereof specifically binding to human CD3, the single-chain antibody, or the multispecific antibody as described above.

In another aspect, the present disclosure provides an isolated nucleic acid molecule, encoding the antibody or antigen-binding fragment thereof specifically binding to human CD3, encoding the single-chain antibody, or encoding the multispecific antibody as described above.

In another aspect, the present disclosure provides a recombinant vector comprising the isolated nucleic acid molecule as described above.

In another aspect, the present disclosure provides a host cell transformed with the aforementioned recombinant vector, and the host cell is selected from prokaryotic cell and eukaryotic cell, preferably eukaryotic cell, more preferably mammalian cell or insect cell.

In another aspect, the present disclosure provides a method for producing the antibody or antigen-binding fragment thereof specifically binding to human CD3, the single-chain antibody, or the multispecific antibody as described above, the method comprising culturing the host cell as described above in a culture medium to form and accumulate the antibody or antigen-binding fragment thereof specifically binding to human CD3, the single-chain antibody, or the multispecific antibody as described above, and recovering the antibody or antigen-binding fragment thereof, the single-chain antibody or the multispecific antibody from the culture.

In another aspect, the present disclosure provides the antibody or antigen-binding fragment thereof specifically binding to human CD3, the single-chain antibody, the multispecific antibody, the pharmaceutical composition, or the isolated nucleic acid molecule as described above, as a medicament. In some embodiments, the medicament is a medicament for the activation of T cells; In some embodiments, the medicament is a medicament for the treatment of cancer, autoimmune disease or inflammatory disease.

In another aspect, the present disclosure provides use of the antibody or antigen-binding fragment thereof specifically binding to human CD3, the single-chain antibody, the multispecific antibody, the pharmaceutical composition, or the isolated nucleic acid molecule as described above in the preparation of a medicament for the activation of T cells.

In another aspect, the present disclosure provides a method for activating T cells, the method comprising administering to a subject a therapeutically effective amount of the antibody or antigen-binding fragment thereof specifically binding to human CD3, the single-chain antibody, the multispecific antibody, the pharmaceutical composition, or the isolated nucleic acid molecule as described above. In some embodiments, the method comprises administering to a subject a composition comprising a unit dose of 0.1-3000 mg (more preferably 1-1000 mg) of the multispecific antibody as described above, or the pharmaceutical composition, or the isolated nucleic acid molecule as described above.

In another aspect, the present disclosure provides a method for the treatment of cancer, autoimmune disease or inflammatory disease, the method comprising administering to a subject a therapeutically effective amount of the antibody or antigen-binding fragment thereof specifically binding to human CD3, the single-chain antibody, the multispecific antibody, the pharmaceutical composition, or the isolated nucleic acid molecule as described above. In some embodiments, the method comprises administering to a subject a composition comprising a unit dose of 0.1-3000 mg (more preferably 1-1000 mg) of the multispecific antibody as described above, or the pharmaceutical composition, or the isolated nucleic acid molecule as described above.

In another aspect, the present disclosure provides use of the antibody or antigen-binding fragment thereof specifically binding to human CD3, the single-chain antibody, the multispecific antibody, the pharmaceutical composition, or the isolated nucleic acid molecule as described above in the preparation of a medicament for the treatment of cancer, autoimmune disease or inflammatory disease.

In some embodiments, the cancer described above is any one selected from the group consisting of carcinoma, lymphoma, blastoma, sarcoma, leukemia and lymphoid malignancies. More specific examples of the cancer include squamous cell carcinoma, myeloma, small cell lung cancer, non-small cell lung cancer (NSCLC), head and neck squamous cell carcinoma (HNSCC), glioma, Hodgkin's lymphoma, Non-Hodgkin's lymphoma, diffuse large B-cell lymphoma (DLBCL), follicular lymphoma, acute lymphoblastic leukemia (ALL), acute myeloid leukemia (AML), chronic lymphocytic leukemia (CLL), chronic myeloid leukemia (CML), primary mediastinal large B-cell lymphoma, mantle cell lymphoma (MCL), small lymphocytic lymphoma (SLL), T-cell/histocyte-rich large B-cell lymphoma, multiple myeloma, myeloid leukemia-protein 1 (Mcl-1), myelodysplastic syndrome (MDS), gastrointestinal (tract) cancer, kidney cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, gastric cancer, bone cancer, Ewing sarcoma, cervical cancer, brain cancer, gastric cancer, bladder cancer, hepatocellular tumor, breast cancer, colon cancer, hepatocellular cancer (HCC), clear cell renal cell carcinoma (RCC), head and neck cancer, pharyngolaryngeal cancer, hepatobiliary cancer, central nervous system cancer, esophagus cancer, malignant pleural mesothelioma, systemic light chain amyloidosis, lymphoplasmacytic lymphoma, myelodysplastic syndrome, myeloproliferative tumor, neuroendocrine tumor, Merkel cell cancel, testicular cancer, and skin cancer. In some embodiments, the cancer is B7-H3 positive cell-related cancer; preferably breast cancer, ovarian cancer, prostate cancer, pancreatic cancer, kidney cancer, lung cancer, liver cancer, gastric cancer, colon cancer, bladder cancer, esophagus cancer, cervical cancer, gallbladder cancer, glioblastoma or melanoma.

In some embodiments, the autoimmune disease or inflammatory disease described above is any one selected from the group consisting of rheumatoid arthritis, psoriasis, Crohn's disease, ankylosing spondylitis, multiple sclerosis, type I diabetes, hepatitis, myocarditis, Sjogren syndrome, autoimmune hemolytic anemia after transplant rejection, vesicular pemphigoid, Graves disease, Hashimoto thyroiditis, systemic lupus erythematosus (SLE), myasthenia gravis, pemphigus and pernicious anemia.

DESCRIPTION OF THE DRAWINGS

FIG. 1A is a schematic diagram of a bivalent bispecific antibody, and FIG. 1B is a schematic diagram of a monovalent bispecific antibody.

FIG. 2A shows the detection of the activity of various antibodies to bind to A498 cells expressing human B7H3; FIG. 2B shows the detection of the activity of various antibodies to bind to CT26 cells over-expressing human B7H3; FIG. 2C shows the detection of the activity of various antibodies to bind to CT26 cells which do not express human B7H3, and the results show that none of the antibodies bind to CT26 cells that do not express human B7H3; FIG. 2D shows the detection of the activity of various antibodies to bind to Jurkat recombinant cells expressing CD3. The vertical axis in FIG. 2A to FIG. 2D represents the geometric mean of the fluorescence signal.

FIG. 3A shows the killing activity of the B7H3 monovalent bispecific antibody. FIG. 3B shows the killing activity of the B7H3 bivalent bispecific antibody. All of the bispecific antibodies show obvious killing activity, regardless of B7H3 monovalent or bivalent, except 155, 156, 185 and 186 which have weaker killing activity against A498.

FIG. 4A shows a comparison of the killing activity between the B7H3 monovalent (181) and bivalent (131) bispecific antibodies comprising HRH1. FIG. 4B shows a comparison of the killing activity between the B7H3 monovalent (187) and bivalent (177) comprising HRH7. All of the experimental results show that the B7H3 bivalent bispecific antibodies have more obvious A498 killing activity compared to the B7H3 monovalent bispecific antibodies. At the same time, the B7H3 bivalent bispecific antibodies have significantly stronger killing activity than that of B7H3 monovalent bispecific antibodies.

FIG. 5A shows a comparison of the killing activity of the B7H3 bivalent bispecific antibodies comprising a first polypeptide chain comprising HRH2, wherein the first polypeptide chain is arranged in various orders (AFF1, AFF2, AFF3, AFF4). FIG. 5B shows a comparison of the killing activity of the B7H3 bivalent bispecific antibodies comprising a second polypeptide chain comprising HRH2, wherein the second polypeptide chain is arranged in various orders (AFF3, AFF3-B). The results show that all the B7H3 bivalent bispecific antibodies with the same sequence but with different arrangement of VH and VL have significant A498 cell killing activity, and the molecules with different arrangement orders have similar killing activity. FIG. 5C shows a comparison of the killing activity between the bispecific antibodies comprising the same B7H3 scFv and CD3 scFv, but with different structures. The three test bispecific antibodies 127, 201 and 202 all have the ability to kill A498 tumor cells, of which the bispecific antibody 127 exhibits killing activity superior to that of 201 and 202.

FIG. 6A shows the antibody-mediated B7H3 target-specific activation of Jurkat recombination cell, in the presence of A498 cells; FIG. 6B shows the antibody-mediated non-B7H3 target-specific activation of Jurkat recombination cell, in the absence of A498 cells. The same antibody legends are indicated in FIG. 6A to FIG. 6B.

FIG. 7A shows the antibody-mediated B7H3 target-specific activation of Jurkat recombination cell by the B7H3 mono/bivalent bispecific antibodies in the presence of A498 cells; FIG. 7B shows the antibody-mediated non-B7H3 target-specific activation of Jurkat recombination cell by the B7H3 mono/bivalent bispecific antibodies in the absence of A498 cells.

FIG. 8A shows a comparison of IFNγ secretion levels from PBMCs stimulated by various antibodies; FIG. 8B shows a comparison of TNFα secretion levels from PBMCs stimulated by various antibodies; and FIG. 8C shows a comparison of IL-2 secretion levels from PBMCs stimulated by various antibodies. FIG. 8A-FIG. 8C show that antibodies 118, 127 and 132 can significantly stimulate PBMC to produce B7H3 target-specific cytokine secretion. The same antibody legends are indicated in FIG. 8A to FIG. 8C.

FIG. 9A shows a comparison of IFNγ levels secreted from PBMCs stimulated by various antibodies; FIG. 9B shows a comparison of TNFα levels secreted from PBMCs stimulated by various antibodies; and FIG. 9C shows a comparison of IL-2 levels secreted from PBMCs stimulated by various antibodies. FIG. 9A-FIG. 9C show that antibodies 118, 127, and 132 cannot stimulate PBMC to produce non B7H3 target-specific cytokine secretion, and have better safety. The same antibody legends are indicated in FIG. 9A to FIG. 9C.

FIG. 10A to FIG. 10E: Detection of the anti-tumor efficacy of the bispecific antibodies in mouse A498 model reconstituted with human PBMC. FIG. 10A shows detection of the anti-tumor activity of the low-dose B7H3 bivalent bispecific antibodies. Both the low-dose antibodies 118 and 119 still show certain anti-tumor activity and show a certain degree of dose-dependency. FIG. 10B shows detection of the anti-tumor activity of the B7H3 bivalent bispecific antibodies at doses of 0.3 mpk and 0.6 mpk. The antibody 113 shows an in vivo dose-dependent tumor inhibitory activity. FIG. 10C shows detection of the anti-tumor activity of the B7H3 bivalent bispecific antibodies at doses of 0.12 mpk and 0.36 mpk. Antibody 118 shows significant anti-tumor activity at both doses. FIG. 10D shows detection of the anti-tumor activity of the B7H3 bivalent bispecific antibodies at a dose of 0.36 mpk. Antibodies 126, 127 and 128 all show significant anti-tumor activity. FIG. 10E shows the anti-tumor activity of antibody 127 at various doses and various dosing frequencies. In FIG. 10A to FIG. 10E, "Vehicle" represents a negative control group administered with PBS.

FIG. 11A to FIG. 11B: Anti-tumor efficacy of the bispecific antibodies in hCD3 KI mouse model. FIG. 11A and FIG. 11B show the anti-tumor effects of 118 and 132 in hCD3 KI mouse model, respectively.

DETAILED DESCRIPTION OF THE INVENTION

Terminology (Definition)

Figure 1A:
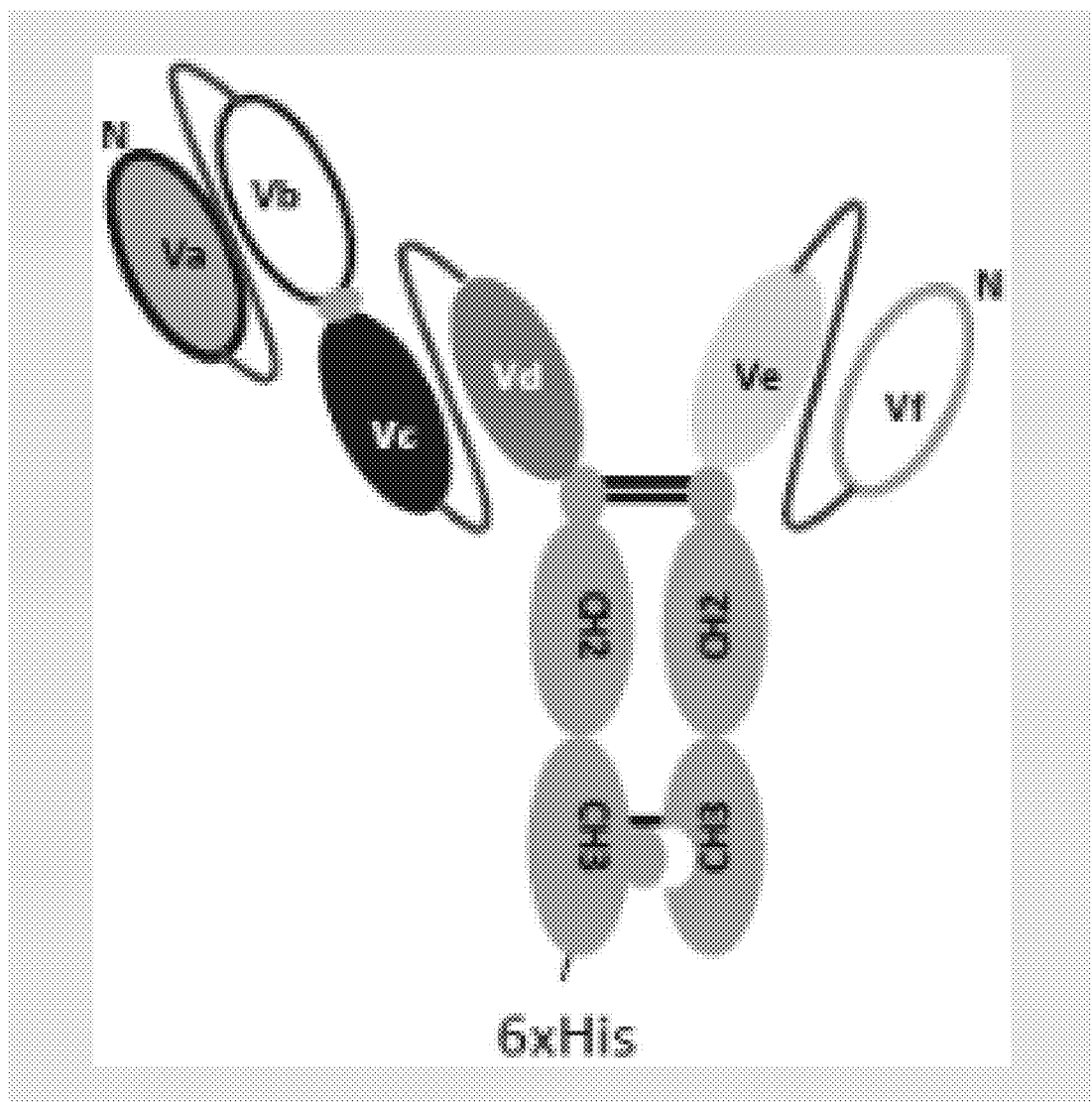
FIG. 1A and FIG. 1B.

Three-letter codes and one-letter codes for amino acids used in the present disclosure are as described in J. biol. chem, 243, p 3558(1968).

The term "multispecific protein molecule" refers to a protein molecule capable of specifically binding to two or more target antigens or target antigen epitopes. A protein molecule that can specifically bind to two target antigens or target antigen epitopes is named as bispecific protein molecule, including antibodies or antigen-binding fragments of the antibodies (such as single-chain antibodies). "Bispecific protein molecule" is interchangeable with "bispecific antibody" herein.

The term "binding region" for an antigen refers to a region or part that can specifically bind to an antigen in a multispecific protein molecule or antibody molecule. The antigen-binding region can be a ligand binding domain that can directly bind to the antigen, or can be a domain comprising a variable region of the antibody that can directly bind to the antigen.

The term "antibody (Ab)" includes any antigen binding molecule or molecular complex that includes at least one complementarity determining region (CDR) that specifically binds to or interacts with a specific antigen (e.g., CD3). The term "antibody" includes: four polypeptide chains connected to each other via disulfide bond(s), immunoglobulin molecules comprising two heavy (H) chains and two light (L) chains, and multimers thereof (e.g., IgM). Each heavy chain includes a heavy chain variable region (hereinafter abbreviated as HCVR or VH) and a heavy chain constant region. This heavy chain constant region comprises three regions (domains): CH1, CH2 and CH3. Each light chain includes a light chain variable region (hereinafter abbreviated as LCVR or VL) and a light chain constant region. The light chain constant region comprises one region (domain, CL1). VH and VL regions can be further subdivided into hypervariable regions, named as complementarity determining regions (CDRs), among which the more conservative regions are interspersed, named as framework regions (FRs). Each VH and VL are composed of three CDRs and four FRs, arranged from the amino terminus to the carboxyl terminus in the following order: FR1, CDR1, FR2, CDR2, FR3, CDR3, FR4. In various embodiments of the present disclosure, the FRs of the anti-CD3 antibodies (or antigen-binding portions thereof), anti-B7H3 antibodies (or antigen-binding portions thereof), or antibodies against other target antigens can be the same as the human germline sequence, or can be naturally or artificially modified. The antibodies can be antibodies of different subclasses, for example, IgG (e.g., IgG1, IgG2, IgG3 or IgG4 subclass), IgA1, IgA2, IgD, IgE, or IgM antibody.

The term "antibody" also encompasses antigen-binding fragments of the full antibody molecules. The terms "antigen-binding portion", "antigen-binding domain", "antigen-binding fragment", etc. of an antibody, as used herein, include any naturally occurring, enzymatically produced, synthetic or genetically engineered polypeptide or glycoprotein that specifically binds to an antigen to form a complex. Antigen-binding fragments of an antibody can be derived from, for example, the full antibody molecule by using any suitable standard technique, such as proteolytic digestion or recombinant genetic engineering techniques involving manipulation and expression of DNA encoding antibody variable regions and (optionally) constant regions. The DNA is known and/or can be easily obtained from, for example, commercially available sources, DNA databases (including, for example, phage-antibody databases), or can be synthesized. The DNA can be sequenced and manipulated chemically or by using molecular biotechnology, for example, by arranging one or more variable and/or constant regions into a suitable configuration, or by introducing codons, generating cysteine residues, modification, additon or deletion of amino acids, etc.

Non-limiting examples of antigen-binding fragments include: (i) Fab fragment; (ii) F(ab')2 fragment; (iii) Fd fragment; (iv) Fv fragment; (v) single-chain Fv (scFv) molecule; (vi) dAb fragment. Other engineered molecules, such as region-specific antibodies, single-domain antibodies, region-deleted antibodies, chimeric antibodies, CDR-grafted antibodies, diabodies, tribodies, tetrabodies, minibodies, nanobodies (e.g. monovalent nanobodies, bivalent nanobodies, etc.), Small Modular Immunopharmaceuticals (SMIP) and Shark Variable IgNAR regions are also included in the term "antigen-binding fragment" as used herein.

The antigen-binding fragment of an antibody will typically contain at least one variable region. The variable region can be a region of any size or amino acid composition and will generally comprise one or more CDRs adjacent to or within the framework sequences. In an antigen-binding fragment having a VH region associated with a VL region, the VH and VL regions can be located opposite to each other in any suitable arrangement. For example, the variable region can be dimerized and comprises VH-VL or VL-VH dimers.

In some embodiments, the antigen-binding fragment of the antibody is in any configuration of variable region and constant region, the variable region and the constant region can be directly connected to each other or can be connected through a complete or partial hinge or linker region. The hinge region can be composed of at least 2 (for example, 5, 10, 15, 20, 40, 60 or more) amino acids, so that a flexible or semi-flexible connection will be generated between the adjacent variable and/or constant regions in a single polypeptide molecule. Furthermore, the antigen-binding fragments of the antibodies of the present invention can include homodimers or heterodimers (or other multimers) in any configuration of variable region and constant region as indicated above, wherein the variable region and constant region can be non-covalently connected to each other and/or connected to one or more monomeric VH or VL regions (e.g., via disulfide bond(s)).

"Murine antibody" as used herein refers to mouse-derived monoclonal antibodies prepared according to the knowledge and skills in the art. During the preparation, test subjects are injected with an antigen, and then a hybridoma expressing the antibody which possesses desired sequence or functional characteristics is isolated. The resulting antibody will be a murine antibody if the injected test subjects are mice.

The "chimeric antibody", is an antibody by fusing the variable region of murine antibody together with the constant region of human antibody, and such antibody can alleviate the murine antibody-induced immune response. To establish a chimeric antibody, a hybridoma secreting specific murine monoclonal antibody is established firstly, and variable region gene is cloned from the murine hybridoma. Then constant region gene is cloned from human antibody according to the need. The murine variable region gene is connected to the human constant region gene to form a chimeric gene, which can be subsequently inserted into an expression vector. Finally the chimeric antibody molecule will be expressed in eukaryotic or prokaryotic system. In a preferable embodiment of the present disclosure, the antibody light chain of the chimeric antibody further comprises a light chain constant region of a human kappa, lambda chain or variant thereof. The antibody heavy chain of the chimeric antibody further comprises a heavy chain constant region of human IgG1, IgG2, IgG3, IgG4 or variant thereof, preferably comprises a heavy chain constant region of human IgG1, IgG2 or IgG4, or comprises a heavy chain constant region variant of human IgG1, IgG2 or IgG4 with amino acid mutations (such as YTE mutation or back mutation, L234A and/or L235A mutation, or S228P mutation).

The term "humanized antibody", including CDR-grafted antibody, refers to an antibody generated by grafting animal-derived antibody, e.g., murine antibody CDR sequences into human antibody variable region frameworks (i.e., framework regions). Humanized antibodies can conquer heterologous responses induced by chimeric antibodies which carry a large number of heterologous protein components. Such framework sequences can be obtained from public DNA database covering germline antibody gene sequences or published references. For example, germline DNA sequences of human heavy and light chain variable region genes can be found in "VBase" human germline sequence database, as well as in Kabat, E A, et al. 1991 Sequences of Proteins of Immunological Interest, 5th Ed. To avoid a decrease in activity caused by the decreased immunogenicity, the framework sequences in human antibody variable region can be subjected to minimal reverse mutations or back mutations to maintain the activity. The humanized antibody of the present disclosure also comprises humanized antibody on which CDR affinity maturation is performed by phage display.

Due to the residues contacted with an antigen, the grafting of CDR can result in a decreased affinity of an antibody or antigen binding fragment thereof to the antigen due to the framework residues contacted with the antigen. Such interactions can be resulted from highly somatic mutations. Therefore, it may still be necessary to graft the donor framework amino acids onto the humanized antibody framework. The amino acid residues involved in antigen binding and derived from non-human antibody or antigen binding fragment thereof can be identified by checking the sequence and structure of animal monoclonal antibody variable region. The donor CDR framework amino acid residues which are different from the germ lines can be considered as being related. If it is not possible to determine the most closely related germ line, the sequence can be compared to the consensus sequence shared by subtypes or the animal antibody sequence with high similarity percentage. Rare framework residues are thought to be the result of a high mutation in somatic cells, and play an important role in binding.

In an embodiment of the present disclosure, the antibody or antigen-binding fragment thereof can further comprises a light chain constant region of human or murine κ, λ chain or variant thereof, or further comprises a heavy chain constant region of human or murine IgG1, IgG2, IgG3, IgG4 or variant thereof.

"Human antibody" and "antibody derived from human" can be used interchangeably, and can be antibodies derived from human or antibodies obtained from a genetically modified organism which has been "engineered" and produced by any method known in the art to produce specific human antibodies in response to antigen stimulation. In some technologies, elements of human heavy and light chain loci are introduced into cell lines of organisms derived from embryonic stem cell lines, and the endogenous heavy and light chain loci in these cell lines are targeted and disrupted. The targeted endogenous heavy and light chain loci included in these cell lines are disrupted. Transgenic organisms can synthesize human antibodies specific for human antigens, and the organisms can be used to produce hybridomas that secrete human antibodies. A human antibody can also be such antibody in which the heavy and light chains are encoded by nucleotide sequences derived from one or more human DNA sources. Fully human antibodies can also be constructed by gene or chromosome transfection methods and phage display technology, or constructed from B cells activated in vitro, all of which are known in the art.

"Monoclonal antibody" refers to an antibody obtained from a population of substantially homogeneous antibodies, that is, the individual antibodies constituting the population are identical and/or bind to the same epitope, except for possible variant antibodies (for example, variants containing naturally occurring mutations or mutations produced during the manufacture of monoclonal antibody preparations, and the mutations are usually present in minimal amounts). Unlike polyclonal antibody preparations that usually contain different antibodies directed against different determinants (epitopes), each monoclonal antibody of a monoclonal antibody preparation (formulation) is directed against a single determinant on the antigen. Therefore, the modifier "monoclonal" indicates the characteristics of the antibody obtained from a substantially homogeneous antibody population, and should not be interpreted as requiring any specific method to manufacture the antibody. For example, monoclonal antibodies used in accordance with the present disclosure can be prepared by various techniques, including but not limited to hybridoma methods, recombinant DNA methods, phage display methods, and methods by using transgenic animals containing all or part of human immunoglobulin loci. Such methods and other exemplary methods for preparing monoclonal antibodies are described herein.

The terms "full-length antibody", "full antibody", "whole antibody" and "complete antibody" are used interchangeably herein and refer to an antibody in a substantially complete form, as distinguished from antigen-binding fragments defined below. The term specifically refers to an antibody of which the heavy chain contains Fc region.

In addition, the VL domain and VH domain of the Fv fragment are encoded by two separate genes, however, they can be linked by a synthetic linker by using recombinant methods, to generate a single protein chain in which a monovalent molecular is formed by pairing the VL and VH domain (referred to as single chain Fv (scFv); see, e.g., Bird et al. (1988): 423-426; Science 242 and Huston et al (1988) Proc. Natl. Acad. Sci USA 85:5879-5883). Such single chain antibodies are also intended to be included in the term of "antigen binding fragment" of an antibody. Such antibody fragments are obtained using conventional techniques known in the field, and are screened for functional fragments by using the same method as that for an intact antibody. Antigen binding portions can be produced by recombinant DNA technology or by enzymatic or chemical disruption of an intact immunoglobulin.

Antigen-binding fragments can also be incorporated into a single-chain molecule comprising a pair of tandem Fv fragments (VH-CH1-VH-CH1), and the pair of tandem Fv fragments forms a pair of antigen-binding regions together with complementary light chain polypeptides (Zapata et al., 1995 Protein Eng. 8(10): 1057-1062; and U.S. Pat. No. 5,641,870).

Fab is an antibody fragment obtained by treating an IgG antibody molecule with a papain (which cleaves the amino acid residue at position 224 of the H chain), and the antibody fragment has a molecular weight of about 50,000 Da and has antigen binding activity, in which about a half of the N-terminal side of H chain and the entire L chain are bound together through disulfide bond(s).

F(ab')2 is an antibody fragment having molecular weight of about 100,000 Da and having antigen binding activity and comprising two Fab regions which are bound at the hinge position, it can be produced by digesting the part downstream of the two disulfide bonds in the IgG hinge region with pepsin.

Fab' is an antibody fragment having a molecular weight of about 50,000 Da and having antigen binding activity, which is obtained by cleaving the disulfide bonds at the hinge region of the above-mentioned F(ab')2. Fab' can be produced by treating F(ab')2 that specifically recognizes and binds to an antigen with a reducing agent such as dithiothreitol.

Further, the Fab' can be produced by inserting DNA encoding Fab' of the antibody into a prokaryotic expression vector or eukaryotic expression vector and introducing the vector into a prokaryote or eukaryote to express the Fab'.

The term "single chain antibody", "single chain Fv" or "scFv" refers to a molecule comprising antibody heavy chain variable domain (or region; VH) connected to antibody light chain variable domain (or region; VL) by a linker. Such scFv molecules have general structure of NH$_2$-VL-linker-VH—COOH or NH$_2$-VH-linker-VL-COOH. Suitable linkers in the prior art consist of repeated GGGGS (SEQ ID No. 105) amino acid sequence or variant thereof, for example, variant with 1-4 (including 1, 2, 3 or 4) repeats (Holliger et al. (1993), Proc Natl Acad Sci USA. 90: 6444-6448). Other linkers useful for the present disclosure are described by Alfthan et al. (1995), Protein Eng. 8:725-731, Choi et al. (2001), Eur J Immuno. 31:94-106, Hu et al. (1996), Cancer Res. 56:3055-3061, Kipriyanov et al. (1999), J Mol Biol. 293:41-56 and Roovers et al. (2001), Cancer Immunol Immunother. 50:51-59.

"Multispecific antibody" refers to an antibody that comprises two or more antigen-binding domains and is capable of binding two or more different epitopes (for example, two, three, four or more different epitopes), and the epitope can be present on the same or different antigens. Examples of multispecific antibodies include "bispecific antibodies" that bind to two different epitopes.

The term "bivalent bispecific antibody" of a tumor-associated antigen refers to a bispecific antibody, in which two antigen-binding regions are directed against a tumor-associated antigen target. For example, B7H3 bivalent bispecific antibody refers to the bispecific antibody comprising two antigen-binding regions targeting B7H3. The term "monovalent bispecific antibody" refers to a bispecific antibody, in which only one antigen-binding region is directed against a certain target. For example, B7H3 monovalent bispecific antibody refers to the bispecific antibody comprising one antigen-binding region targeting B7H3.

"Linker" or "linking fragment" refers to "L1" located between two protein domains for connecting the two domains, also refers to a connecting peptide sequence used to connect protein domains. It usually has a certain degree of flexibility, and the use of linkers will not cause the protein domain to lose its original functions.

Diabody is an antibody fragment wherein the scFv is dimerized, and it is an antibody fragment having bivalent antigen binding activity. In the bivalent antigen binding activity, the two antigens can be the same or different.

dsFv is obtained by substituting one amino acid residue in each of VH and VL with a cysteine residue, and then connecting the substituted polypeptides via a disulfide bond between the two cysteine residues. The amino acid residues to be substituted with a cysteine residue can be selected based on three-dimensional structure prediction of the antibody in accordance with known methods (Protein Engineering, 7, 697 (1994)).

In some embodiments of the present disclosure, the antigen-binding fragment can be produced by the following steps: obtaining cDNAs encoding the monoclonal antibody VH and/or VL of the present disclosure that specifically recognizes and binds to the antigen, and cDNAs encoding the other domains as required; constructing DNA encoding the antigen-binding fragment; inserting the DNA into a prokaryotic or eukaryotic expression vector, and then introducing the expression vector into a prokaryote or eukaryote to express the antigen-binding fragment.

"Fc region" can be a naturally occurring sequence or a variant Fc region. The boundaries of the Fc region of an immunoglobulin heavy chain are variable; however, the Fc region of a human IgG heavy chain is usually defined as a region extending from the amino acid residue at position Cys226 or from Pro230 to carboxyl terminus. The numbering of residues in the Fc region is according to the EU index numbering in Kabat. Kabat et al., Sequences of Proteins of Immunological Interest, 5th Edition Public Health Service, National Institutes of Health, Bethesda, Md., 1991. The Fc region of immunoglobulin usually has two constant domains, CH2 and CH3. Herein, the "first Fc" is also referred to as "Fc1", and the second Fc is also referred to as "Fc2".

In "$V_a1$-L1-$V_b1$-L2-$V_c2$-L2-$V_d2$-L4-Fc1" and "$V_e3$-L5-$V_f3$-L6-Fc2", $V_a1$, $V_b1$, $V_c2$, $V_d2$, $V_e3$ and $V_f3$ represent an antibody light chain variable region or heavy chain variable region, $V_a1$ and $V_b1$ bind to the first epitope of the antigen, $V_c2$ and $V_d2$ bind to the second epitope of the antigen, and $V_e3$ and $V_f3$ bind to the third epitope. The first epitope, the second epitope and the third epitope can be the same or not.

Similar to "$VH_{TAA}$-L1-$VL_{TAA}$-L2-$VH_{CD3}$-L3-$VL_{CD3}$-L4-Fc1", $VH_{TAA}$ and $VL_{TAA}$ represent an antibody variable region binding to an epitope of the tumor-associated antigen, and $VH_{CD3}$ and $VL_{CD3}$ represent an antibody variable region binding to an epitope of CD3.

In the present disclosure, "knob-Fc" refers to a knob-like spatial structure formed by incorporating a point mutation T366W in the Fc region of an antibody. Correspondingly, "hole-Fc" refers to a hole-like spatial structure formed by incorporating point mutations T366S, L368A, and Y407V in the Fc region of an antibody. Knob-Fc and hole-Fc are more likely to form heterodimers due to steric hindrance. In order to further promote the formation of heterodimers, point mutations S354C and Y349C can be introduced into knob-Fc and hole-Fc, respectively, to further promote the formation of heterodimers via disulfide bonds. Meanwhile, in order to eliminate or alleviate the ADCC effect caused by antibody Fc, substitution mutations of 234A and 235A can also be introduced into Fc. For example, the preferred knob-Fc and hole-Fc of the present disclosure are shown in SEQ ID NOs: 69 and 70, respectively. In a bispecific antibody, knob-Fc or hole-Fc can be used as either the Fc region of the first polypeptide chain or the Fc region of the second polypeptide chain. For a single bispecific antibody, Fc regions of the first and the second polypeptide chain can not both be knob-Fc or hole-Fc.

The term "amino acid difference" or "amino acid mutation" refers to the amino acid changes or mutations in a protein or polypeptide variant when compared to the original protein or polypeptide, and involves insertion, deletion or substitution of one or more amino acid(s) on the basis of the original protein or polypeptide.

"Variable region" of an antibody refers to an antibody light chain variable region (VL) or antibody heavy chain variable region (VH), alone or in combination. As known in the field, each of the heavy and light chain variable regions consists of three complementarity determining regions (CDRs) (also named as hypervariable regions) connected to four framework regions (FRs). The CDRs in each chain are held tightly together by FRs and contribute to the formation of an antigen binding site of the antibody together with the CDRs from the other chain. There are at least two techniques for determining CDR: (1) a method based on cross-species sequence variability (i.e., Kabat et al. Sequences of Proteins of Immunological Interest, (5th edition, 1991, National Institutes of Health, Bethesda MD)); and (2) a method based on the crystallographic study of antigen-antibody complexes (Al-Lazikani et al., J. Molec. Biol. 273:927-948 (1997)). As used herein, CDRs can refer to those determined by either of or the combination of the two methods.

The term "antibody framework" or "FR region" refers to a part of the variable domain, either VL or VH, which serves as a scaffold for the antigen binding loops (CDRs) of this variable domain. Essentially, it is a variable domain without CDRs.

The term "CDR" refers to one of the six hypervariable regions present in the antibody variable domain that mainly contribute to antigen binding. One of the most commonly used definitions of the 6 CDRs is provided by Kabat E. A. et al. ((1991) Sequences of proteins of immunological interest. NIH Publication 91-3242). As used in some embodiments herein, CDRs can be defined according to Kabat criteria (Kabat et al. Sequences of Proteins of Immunological Interest, (5th edition, 1991, National Institutes of Health, Bethesda MD)), for the definition of the light chain variable domains CDR1, CDR2 and CDR3 (LCDR1, LCDR2 and LCDR3), and the heavy chain variable domains CDR1, CDR2 and CDR3 (HCDR1, HCDR2 and HCDR3), for example, for the definition of CD3 antibody CDRs of the present disclosure. In other embodiments, CDRs can also be defined according to IMGT criteria and the like. For example, the B7H3 antibody CDRs are defined according to IMGT criteria.

The term "tumor antigen" refers to a substance produced by tumor cells, optionally a protein, including "tumor-associated antigen" or "TAA" (which refers to a protein that is produced in tumor cells and is differentially expressed in cancers versus the corresponding normal tissues) and "tumor specific antigen" or "TSA" (which refers to a tumor antigen that is produced in tumor cells and is specifically expressed or abnormally expressed in cancers compared to the corresponding normal tissues).

Non-limiting examples of "tumor-associated antigen" include, for example, AFP, ALK, B7H3, BAGE protein, BCMA, BIRC5(survivin), BIRC7, β-catenin, brc-abl, BRCA1, BORIS, CA9, CA125, carbonic anhydrase IX, caspase-8, CALR, CCR5, CD19, CD20(MS4A1), CD22, CD30, CD33, CD38, CD40, CD123, CD133, CD138, CDK4, CEA, Claudin 18.2, cyclin-B1, CYP1B1, EGFR, EGFRvIII, ErbB2/Her2, ErbB3, ErbB4, ETV6-AML, EpCAM, EphA2, Fra-1, FOLR1, GAGE protein (such as GAGE-1, -2), GD2, GD3, GloboH, Glypican-3, GM3, gp100, Her2, HLA/B-raf, HLA/k-ras, HLA/MAGE-A3, hTERT, IL13Rα2, LMP2, κ-Light, LeY, MAGE protein (such as MAGE-1, -2, -3, -4, -6 and -12), MART-1, mesothelin, ML-IAP, MOv-γ, Muc1, Muc2, Muc3, Muc4, Muc5, Muc16 (CA-125), MUM1, NA17, NKG2D, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE protein, Ras, RGS5, Rho, ROR1, SART-1, SART-3, STEAP1, STEAP2, TAG-72, TGF-β, TMPRSS2, Thompson-nouvelle antigen (Tn), TRP-1, TRP-2, tyrosinase, uroplakin-3 and 5T4 (Trophoblast glycoprotein).

"CD3" refers to an antigen expressed on T cells as part of a multi-molecule T cell receptor (TCR), and it is a homodimer or heterodimer formed by two of the following four receptor chains: CD3-ε, CD3-δ, CD3-ζ and CD3-γ. Human CD3-ε (hCD3ε) comprises amino acid sequence described in UniProtKB/Swiss-Prot: P07766.2. Human CD3-δ (hCD3δ) comprises amino acid sequence described in UniProtKB/Swiss-Prot: P04234.1. Therefore, the term "CD3" refers to human CD3, unless specifically indicating that it is from a non-human species, such as "murine CD3", "monkey CD3", etc.

"Epitope" or "antigenic determinant" refers to a site on an antigen to which an immunoglobulin or antibody specifically binds. Epitopes usually include at least 3, 4, 5, 6, 7, 8, 9, 10, 11, 12, 13, 14, or 15 consecutive or non-consecutive amino acids in a unique spatial conformation. See, for example, Epitope Mapping Protocols in Methods in Molecular Biology, Vol. 66, G. E. Morris, Ed. (1996).

The term "specifically bind to", "selectively bind to", "selective binding" or "specific binding" refers to the binding of an antibody to a predetermined epitope on an antigen. Typically, the antibody binds with an affinity (KD) of less than about $10^{-8}$M, for example, less than about $10^{-9}$ M, $10^{-10}$ M or $10^{-11}$ M or even less. The term "affinity" refers to the strength of the interaction between an antibody and an antigen at a single epitope. Within each antigenic site, the variable region of the antibody "arm" interacts with the antigen at multiple amino acid sites via weak non-covalent forces; the greater the interaction, the stronger the affinity. As used herein, the term "high affinity" of an antibody or antigen-binding fragment thereof (e.g., Fab fragment) generally refers to an antibody or antigen-binding fragment with $K_D$ of $1E^{-9}$M or less (e.g., $K_D$ of $1E^{-10}$M or less, $K_D$ of $1E^{-11}$M or less, $K_D$ of $1E^{-12}$M or less, $K_D$ of $1E^{-13}$M or less, $K_D$ of $1E^{-14}$ M or less, etc.).

The term "KD" or "$K_D$" refers to a dissociation equilibrium constant for particular antibody-antigen interaction. Typically, the antibody binds to an antigen with a dissociation equilibrium constant (KD) of less than about $1E^{-8}$M, for example, less than about $1E^{-9}$M, $1E^{-10}$M or $1E^{-11}$M or even less, for example, as determined by Surface Plasma Resonance (SPR) technology in Biacore™ instrument. The smaller the KD value, the greater the affinity is.

The term "nucleic acid molecule" refers to DNA molecules and RNA molecules. The nucleic acid molecule can be single-stranded or double-stranded, but preferably is double-stranded DNA. A nucleic acid is "operably linked" when it is placed into a functional relationship with another nucleic acid sequence. For instance, a promoter or enhancer is operably linked to a coding sequence if it affects the transcription of the sequence.

The term "vector" means a construct capable of delivering one or more target genes or sequences, and preferably, expressing them in a host cell. Examples of vectors include, but are not limited to, viral vectors, naked DNA or RNA expression vectors, plasmids, cosmids or phage vectors, DNA or RNA expression vectors associated with cationic coagulants, DNA or RNA expression vectors encapsulated in liposomes, and certain eukaryotic cells such as producer cells.

Methods for producing and purifying antibodies and antigen-binding fragments are well known in the art, for example, Antibodies: A Laboratory Manual, Cold Spring Harbor, New York, chapters 5-8 and 15. For example, mice can be immunized with antigen or fragment thereof, and the resulting antibodies can then be renatured, purified, and sequenced for amino acid sequences by using conventional methods well known in the art. Antigen-binding fragments can also be prepared by conventional methods. The antibodies or antigen binding fragments of the present disclosure are engineered to incorporate one or more human framework regions onto the CDR regions derived from non-human antibody. Human FR germline sequences can be obtained from The Immunoglobulin Facts Book, 2001, ISBN 012441351, by aligning against IMGT human antibody variable germline gene database by MOE software.

The term "host cell" refers to a cell into which an expression vector has been introduced. Host cells can include bacterial, microbial, plant or animal cells. Bacteria that are easily transformed include members of enterobacteriaceae, such as *Escherichia coli* or *Salmonella* strains; Bacillaceae such as *Bacillus subtilis*; Pneumococcus; *Streptococcus* and *Haemophilus influenzae*. Suitable microorganisms include *Saccharomyces cerevisiae* and *Pichia pastoris*. Suitable animal host cell lines include CHO (Chinese Hamster Ovary cell line), HEK293 cells (non-limiting examples such as HEK293E cells), and NS0 cells.

The engineered antibodies or antigen-binding fragments can be prepared and purified by conventional methods. For example, the cDNA sequences encoding the heavy and light chains can be cloned and recombined into a GS expression vector. The recombinant immunoglobulin expression vector can be stably transfected into CHO cells. As an alternative prior art, mammalian expression systems can lead to glycosylation of antibodies, especially in the highly conserved N-terminal sites of the Fc region. Stable clones were obtained by expressing an antibody specifically binding to an antigen. Positive clones can be expanded in serum-free culture medium in bioreactors for antibody production. Culture medium, into which an antibody has been secreted, can be purified by conventional techniques. For example, purification can be performed on Protein A or Protein G Sepharose™ FF column comprising adjusting buffer. The nonspecific binding components are washed out. The bound antibody is eluted by pH gradient and antibody fragments are detected by SDS-PAGE, and then pooled. The antibodies can be filtered and concentrated using common techniques. Soluble mixtures and multimers can be effectively removed by common techniques, such as size exclusion or ion exchange. The resulting product is needed to be frozen immediately, such as at −70° C., or lyophilized.

"Administration" or "treatment," as it applies to an animal, human, experimental subject, cell, tissue, organ, or biological fluid, refers to contacting an exogenous pharmaceutical, therapeutic, diagnostic agent, or composition with the animal, human, subject, cell, tissue, organ, or biological fluid. "Administration" and "treatment" can refer, e.g., to therapeutic, pharmacokinetic, diagnostic, research, and experimental methods. The treatment of a cell encompasses contacting a reagent with the cell, as well as contacting a reagent with a fluid, where the fluid is in contact with the cell. "Administration" or "treatment" also means in vitro or ex vivo treatments, e.g., of a cell, with a reagent, diagnostic, binding compound, or with another cell. "Treatment", as it applies to a human, veterinary, or research subject, refers to therapeutic treatment, prophylactic or preventative measures, research and diagnostic applications.

"Treat" means to administer a therapeutic agent, such as a composition containing any of the compounds of the present disclosure, internally or externally to a patient having one or more disease symptoms for which the agent has known therapeutic activity. Typically, the agent is administered in an amount effectively to alleviate one or more disease symptoms in the patient or population to be treated, by inducing the regression of or inhibiting the progression of such symptom(s) by any clinically measurable degree. The amount of a therapeutic agent that is effective to alleviate any particular disease symptom (also referred to as the "therapeutically effective amount") may vary according to various factors such as the disease state, age, and body weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While the embodiment of the present disclosure (e.g., a treatment method or article of manufacture) may not be effective in alleviating the target disease symptom(s) in every patient, it should alleviate the target disease symptom(s) in a statistically significant number of patients as determined by any statistical test known in the art such as Student's t-test, chi-square test, U-test according to Mann and Whitney, Kruskal-Wallis test (H-test), Jonckheere-Terpstra-test and Wilcoxon-test.

"Amino acid conservative modification" or "amino acid conservative substitution" means that the amino acids in a protein or polypeptide are substituted by other amino acids with similar characteristics (such as charge, side chain size, hydrophobicity/hydrophilicity, backbone conformation and rigidity, etc.), such that the changes can frequently be made without altering the biological activity or other required characteristics (such as affinity and/or specificity to an antigen) of the protein or polypeptide. Those skilled in the art recognize that, in general, single amino acid substitution in non-essential regions of a polypeptide does not substantially alter the biological activity (see, e.g., Watson et al. (1987) Molecular Biology of the Gene, The Benjamin/Cummings Pub. Co., p. 224 (4th Ed.)). In addition, substitutions with structurally or functionally similar amino acids are less likely to disrupt biological activity. Exemplary conservative substitutions are set forth in the table below, "Exemplary Amino Acid Conservative Substitutions".

Exemplary Amino Acid Conservative Substitutions

| Original residue | Conservative substitution |
| --- | --- |
| Ala(A) | Gly; Ser |
| Arg(R) | Lys; His |
| Asn(N) | Gln; His; Asp |
| Asp(D) | Glu; Asn |
| Cys(C) | Ser; Ala; Val |
| Gln(Q) | Asn; Glu |
| Glu(E) | Asp; Gln |
| Gly(G) | Ala |
| His(H) | Asn; Gln |
| Ile(I) | Leu; Val |
| Leu(L) | Ile; Val |
| Lys(K) | Arg; His |
| Met(M) | Leu; Ile; Tyr |
| Phe(F) | Tyr; Met; Leu |
| Pro(P) | Ala |

Exemplary Amino Acid Conservative Substitutions

| Original residue | Conservative substitution |
| --- | --- |
| Ser(S) | Thr |
| Thr(T) | Ser |
| Trp(W) | Tyr; Phe |
| Tyr(Y) | Trp; Phe |
| Val(V) | Ile; Leu |

"Effective amount" or "effective dose" refers to the amount of a medicament, compound, or pharmaceutical composition necessary to obtain any one or more beneficial or desired results. For prophylactic applications, beneficial or desired results include elimination or reduction of risk, reduction of severity, or delay of the onset of the disease, including the biochemical, histological, and behavioral manifestations of the condition, its complications, and intermediate pathological phenotypes during the development of the condition. For therapeutic applications, beneficial or desired results include clinical results, such as reduction of the incidence of various conditions associated with target antigen of the present disclosure or improvement of one or more symptoms of the condition, reduction of the dosage of other agents required to treat the condition, enhancement of the efficacy of another agent, and/or delay of the progression of the condition associated with the target antigen of the present disclosure in patients.

"Exogenous" refers to substances produced outside organisms, cells, or humans according to circumstances. "Endogenous" refers to substances produced in cells, organisms, or human bodies according to circumstances.

"Homology" and "identity" are interchangeable herein and refer to the sequence similarity between two polynucleotide sequences or between two polypeptide sequences. When a position in both of the two sequences to be compared is occupied by the same base or amino acid monomer subunit, e.g., if a position in each of two DNA molecules is occupied by adenine, then the molecules are homologous at that position. The percentage of homology between two sequences is a function of the number of matching or homologous positions shared by the two sequences divided by the number of positions to be compared and then multiplied by 100. For example, when two sequences are optimally aligned, if 6 out of 10 positions in the two sequences are matched or homologous, then the two sequences are 60% homologous; if 95 out of 100 positions in the two sequences are matched or homologous, then the two sequences are 95% homologous. Generally, when two sequences are aligned, comparison is performed to give the maximum homology percentage. For example, the comparison can be performed by BLAST algorithm, in which the parameters of the algorithm are selected to give the maximum match between each sequence over the entire length of each reference sequence.

The following references relate to the BLAST algorithm frequently used for sequence analysis: BLAST algorithm (BLAST ALGORITHMS): Altschul, S F et al., (1990) J. Mol. Biol. 215:403-410; Gish, W. et al., (1993) Nature Genet. 3:266-272; Madden, T L et al., (1996) Meth. Enzymol. 266:131-141; Altschul, S F et al., (1997) Nucleic Acids Res. 25:3389-3402; Zhang, J. et al. (1997) Genome Res. 7:649-656. Other conventional BLAST algorithms such as those available from NCBI BLAST are also well known to those skilled in the art.

"Isolated" refers to a purified state, in which the designated molecule is substantially free of other biological molecules, such as nucleic acids, proteins, lipids, carbohydrates, or other materials, such as cell debris and growth medium. In general, the term "isolated" is not intended to mean the complete absence of these materials or the absence of water, buffers or salts, unless they are present in an amount that significantly interferes with the experimental or therapeutic use of the compound as described herein.

"Optional" or "optionally" means that the event or circumstance that follows may but does not necessarily occur, and the description includes the instances in which the event or circumstance does or does not occur. For example, "optionally contains 1-3 antibody heavy chain variable regions" means the antibody heavy chain variable region with specific sequence can be, but need not be, present.

"Pharmaceutical composition" refers to a mixture containing one or more compounds according to the present disclosure or a physiologically/pharmaceutically acceptable salt or produg thereof and other chemical components, such as physiologically/pharmaceutically acceptable carriers and excipients. The pharmaceutical composition aims at promoting the administration to an organism, facilitating the absorption of the active ingredient and thereby exerting a biological effect.

The term "pharmaceutically acceptable carrier" refers to any inactive substance suitable for use in a formulation for the delivery of antibodies or antigen-binding fragments. The carrier can be an anti-adhesive agent, adhesive agent, coating agent, disintegrating agent, filler or diluent, preservative (such as antioxidant, antibacterial or antifungal agent), sweetener, absorption delaying agent, wetting agent, emulsifier, buffer, and the like. Examples of suitable pharmaceutically acceptable carriers include water, ethanol, polyols (such as glycerol, propylene glycol, polyethylene glycol, and the like), dextrose, vegetable oil (such as olive oil), saline, buffer, buffered saline, and isotonic agent, such as sugars, polyols, sorbitol and sodium chloride.

The term "cancer", "cancerous" or "malignant" refers to or describes a physiological condition in mammals generally characterized by unregulated cell growth. Examples of cancer include, but are not limited to, carcinoma, lymphoma, blastoma, sarcoma, and leukemia or lymphoid malignancies. More specific examples of the cancer include squamous cell carcinoma, myeloma, small cell lung cancer, non-small cell lung cancer (NSCLC), head and neck squamous cell carcinoma (HNSCC), glioma, Hodgkin's lymphoma, Non-Hodgkin's lymphoma, diffuse large B-cell lymphoma (DLBCL), follicular lymphoma, acute lymphoblastic leukemia (ALL), acute myeloid leukemia (AML), chronic lymphocytic leukemia (CLL), chronic myeloid leukemia (CML), primary mediastinal large B-cell lymphoma, mantle cell lymphoma (MCL), small lymphocytic lymphoma (SLL), T-cell/histocyte-rich large B-cell lymphoma, multiple myeloma, myeloid leukemia-protein 1 (Mcl-1), myelodysplastic syndrome (MDS), gastrointestinal (tract) cancer, kidney cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, gastric cancer, bone cancer, Ewing sarcoma, cervical cancer, brain cancer, gastric cancer, bladder cancer, hepatocellular tumor, breast cancer, colon cancer, hepatocellular cancer (HCC), clear cell renal cell carcinoma (RCC), head and neck cancer, hepatobiliary cancer, central nervous system cancer, esophagus cancer, malignant pleural mesothelioma, systemic light chain amyloidosis, lymphoplasmacytic lymphoma, myelodysplastic syndrome, myeloproliferative tumor, neuroendocrine tumor, Merkel cell cancel, testicular cancer, and skin cancer.

"Inflammatory disorder" refers to any disease, disorder, or syndrome in which an excessive or unregulated inflammatory response results in excessive inflammatory symptoms, host tissue damage, or loss of tissue function. "Inflammatory disease" also refers to a pathological state mediated by the chemotaxis pooling of leukocytes or neutrophils.

"Inflammation" refers to a protective local response caused by tissue damage or destruction, and it is useful to destroy, alleviate or eliminate (isolate) harmful substances and injured tissues. Inflammation is significantly related to the chemotaxis pooling of leukocytes or neutrophils. Inflammation can be caused by pathogenic organisms and viruses, as well as non-infectious causes such as trauma, reperfusion after myocardial infarction, stroke, immune response to foreign antigens, and autoimmune response.

"Autoimmune disease" refers to any group of diseases in which tissue damage is related to the responses to body's own components mediated by humoral or cell immunity. Non-limiting examples of autoimmune diseases include rheumatoid arthritis, psoriasis, Crohn's disease, ankylosing spondylitis, multiple sclerosis, type I diabetes, hepatitis, myocarditis, Sjogren syndrome, autoimmune hemolytic anemia due to transplant rejection, vesicular pemphigoid, Graves disease, Hashimoto thyroiditis, systemic lupus erythematosus (SLE), myasthenia gravis, pemphigus, pernicious anemia, etc.

In addition, another aspect of the present disclosure relates to methods for immunodetection or determination of target antigens, reagents for immunodetection or determination of target antigens, methods for immunodetection or determination of cells expressing target antigens, and the diagnostic agents for diagnosing diseases associated with target antigen-positive cells, comprising the monoclonal antibodies or antibody fragments of the present disclosure that specifically recognize and bind to the target antigen as an active ingredient.

In the present disclosure, the method for detecting or measuring the amount of the target antigen can be any known method. For example, it includes immunoassay or immunodetection method.

The immunoassay or immunodetection method is a method of detecting or measuring the amount of an antibody or antigen with a labeled antigen or antibody. Examples of immunoassay or immunodetection methods include radioactive substance-labeled immunoantibody method (RIA), enzyme immunoassay (EIA or ELISA), fluorescence immunoassay (FIA), luminescence immunoassay, western blotting, physicochemical method, and the like.

The above-mentioned diseases related to the target antigen-positive cells can be diagnosed by detecting or measuring the target antigen-expressing cells using the antibodies or antibody fragments of the present disclosure.

Cells expressing the polypeptide can be detected by the known immunodetection methods, preferably by immunoprecipitation, fluorescent cell staining, immunotissue staining, and the like. In addition, the method such as fluorescent antibody staining method with the FMAT8100HTS system (Applied Biosystem) can be used.

In the present disclosure, samples to be detected or measured for the target antigen are not particularly limited, as long as they are possible to contain cells expressing the target antigen, such as tissue cells, blood, plasma, serum, pancreatic juice, urine, stool, tissue fluid or culture medium.

Dependent on the required diagnostic method, the diagnostic agent containing the monoclonal antibody or antibody fragment thereof of the present disclosure can also contain reagents for performing an antigen-antibody reaction or reagents for detecting the reaction. The reagents for performing an antigen-antibody reaction include buffers, salts and the like. The reagents for detection include agents commonly used in immunoassay or immunodetection methods, for example, a labeled secondary antibody that recognizes the monoclonal antibody, antibody fragment or conjugate thereof, and a substrate corresponding to the label.

The details of one or more embodiments of the present disclosure are set forth in the above specification. The preferred methods and materials are described below, although any method and material similar or identical to those described herein can be used in the practice or testing of the present disclosure. Through the specification and claims, other features, purposes and advantages of the present disclosure will become apparent. In the specification and claims, the singular forms include plural aspects unless the context clearly dictates otherwise. Unless otherwise defined explicitly herein, all technical and scientific terms used herein have the meaning commonly understood by those skilled in the art to which this disclosure belongs. All patents and publications cited in the specification are incorporated by reference. The following examples are presented to more fully illustrate the preferred embodiments of the present disclosure. These examples should not be construed as limiting the scope of the present disclosure in any way, and the scope of the present disclosure is defined by the claims.

EXAMPLES

Preparation and Screening of Antibodies

Methods of making monoclonal antibodies are known in the art. One of methods that can be used is the method as described in Kohler, G. et al. (1975) "Continuous Cultures Of Fused Cells Secreting Antibody Of Predefined Specificity," Nature 256:495-497 or the modified form thereof. Typically, monoclonal antibodies are generated in non-human species, such as mice. Generally, mice or rats are used for immunization, but other animals such as rabbits and alpacas can also be used. Antibodies are prepared by immunizing mice with immunogenic amounts of cells, cell extracts, or protein preparations containing human CD3 or other target antigens (such as human B7H3). The immunogen can be, but is not limited to, primary cells, cultured cell lines, cancerous cells, nucleic acids or tissues.

In one embodiment, monoclonal antibodies binding to the target antigen are obtained by using host cells that overexpress the target antigen as an immunogen. Such cells include, for example, but are not limited to, human T cells, cells over-expressing human B7H3.

In order to monitor the antibody response, a small amount of biological sample (e.g., blood) can be obtained from the animal and is tested for the titers of antibodies against the immunogen. The spleen and/or some large lymph nodes can be removed and dissociated into single cells. If desired, spleen cells can be selected by applying the cell suspension to an antigen-coated plate or well (after the non-specific adherent cells are removed). B cells expressing membrane-bound antigen-specific immunoglobulins will bind to the plate and will not be washed away by the remaining suspension. Subsequently, the resulting B cells or all dissociated spleen cells can be fused with myeloma cells (for example, X63-Ag8.653 and cells available from Salk Institute, Cell Distribution Center, San Diego, CA). Polyethylene glycol (PEG) can be used to fuse spleen or lymphocytes with myeloma cells to form hybridomas. The hybridomas are then cultured in a selective medium (for example, hypoxanthine, aminopterin, thymidine medium, otherwise referred to as "HAT medium"). Subsequently, the resulting hybridomas are seeded on the plate by limiting dilution, and the production of antibodies that specifically bind to the immunogen is analyzed by using, for example, FACS (Fluorescence Activated Cell Sorting) or Immunohistochemistry (IHC) screening. Subsequently, the selected monoclonal antibody-secreting hybridomas are cultured in vitro (e.g., in a tissue culture flask or hollow fiber reactor) or in vivo (e.g., as ascites in mice).

As another alternative to cell fusion technology, Epstein-Barr virus (EBV) immortalized B cells can be used to prepare the monoclonal antibodies of the present invention. If necessary, the hybridoma is proliferated and subcloned, and the anti-immunogen activity of the supernatant is analyzed by traditional analysis methods (for example, FACS, IHC, radioimmunoassay, enzyme immunoassay, fluorescent immunoassay, etc.).

In another alternative, the monoclonal antibodies against target antigens (such as CD3, B7H3) and any other equivalent antibodies can be sequenced and prepared recombinantly by any method known in the art (for example, humanization, preparation of fully human antibodies using transgenic mice, phage display technology, etc.). In one embodiment, the monoclonal antibodies against the target antigens (e.g., CD3, B7H3) are sequenced and then the polynucleotide sequences are cloned into a vector for expression or proliferation. The sequence encoding the antibody of interest can be maintained in a vector in the host cell and then the host cell can be proliferated and frozen for later use.

The polynucleotide sequences of the anti-CD3 monoclonal antibodies and any other equivalent antibody can be used for genetic manipulation to produce "humanized" antibodies to improve the affinity or other characteristics of the antibodies. The general principle of humanized antibodies includes retaining the basic sequence of the antigen-binding portion of the antibody, while the remaining non-human portion of the antibody is replaced with a human antibody sequence. Four steps are generally used for humanizing monoclonal antibodies. These steps are as follows: (1) determining the nucleotide sequences and the putative amino acid sequences of the light and heavy chain variable domains of an original antibody; (2) designing the humanized antibody, that is, determining which antibody framework region will be used in the process of humanization; (3) actual humanization methods/techniques and (4) transfection and expression of the humanized antibodies. See, for example, U.S. Pat. Nos. 4,816,567, 5,807,715, 5,866,692, and 6,331,415.

1. Preparation and Screening of B7H3 Antibodies

B cells were isolated by using human PBMCs, spleen, and lymph node tissues and RNAs were extracted to construct a library of natural single-stranded phage antibodies. The constructed natural single-chain phage antibody library was packaged to form phage particles, which were screened by panning using the liquid phase method. The phage was associated with the biotinylated B7H3 liquid phase, and was then separated by streptavidin magnetic beads. In order to obtain a positive sequence that binds to human B7H3, biotinylated human B7H3 was used for panning. Several monoclonal colonies were picked up and packaged into phage single-chain antibodies for phage ELISA test. The monoclonal phages were tested for their ability to bind to human B7H3 and murine B7H3, respectively, and B7H3 antibodies were obtained after screening.

The B7H3-related antigen used for detection are shown as follows:

Human B7H3 Antigen for Detection

Commercially available product (SinoBiological cat #11188-H08H)

The sequence is as follows:

SEQ ID NO: 1
LEVQVPEDPVVALVGTDATLCCSFSPEPGFSLAQL

NLIWQLTDTKQLVHSFAEGQDQGSAYANRTALFPD

LLAQGNASLRLQRVRVADEGSFTCFVSIRDFGSAA

VSLQVAAPYSKPSMTLEPNKDLRPGDTVTITCSSY

QGYPEAEVFWQDGQGVPLTGNVTTSQMANEQGLFD

VHSILRVVLGANGTYSCLVRNPVLQQDAHSSVTIT

PQRSPTGAVEVQVPEDPVVALVGTDATLRCSFSPE

PGFSLAQLNLIWQLTDTKQLVHSFTEGRDQGSAYA

NRTALFPDLLAQGNASLRLQRVRVADEGSFTCFVS

IRDFGSAAVSLQVAAPYSKPSMTLEPNKDLRPGDT

VTITCSSYRGYPEAEVFWQDGQGVPLTGNVTTSQM

ANEQGLFDVHSVLRVVLGANGTYSCLVRNPVLQQD

AHGSVTITGQPMT-*HHHHHH*

Note: The underlined portion represents the extracellular region of B7H3; the italics represent His-tag.

Monkey B7H3 Antigen for Detection

Commercially available product (SinoBiological cat #90806-C08H)

The sequence is as follows:

SEQ ID NO: 2
LEVQVPEDPVVALVGTDATLRCSFSPEPGFSLAQL

NLIWQLTDTKQLVHSFTEGRDQGSAYANRTALFLD

LLAQGNASLRLQRVRVADEGSFTCFVSIRDFGSAA

VSLQVAAPYSKPSMTLEPNKDLRPGDTVTITCSSY

RGYPEAEVFWQDGQGAPLTGNVTTSQMANEQGLFD

VHSVLRVVLGANGTYSCLVRNPVLQQDAHGSITIT

PQRSPTGAVEVQVPEDPVVALVGTDATLRCSFSPE

PGFSLAQLNLIWQLTDTKQLVHSFTEGRDQGSAYA

NRTALFLDLLAQGNASLRLQRVRVADEGSFTCFVS

IRDFGSAAVSLQVAAPYSKPSMTLEPNKDLRPGDT

VTITCSSYRGYPEAEVFWQDGQGAPLTGNVTTSQM

ANEQGLFDVHSVLRVVLGANGTYSCLVRNPVLQQD

AHGSVTITGQPMTFPPE-*HHHHHH*

Note: The underlined portion represents the extracellular region of B7H3; the italics represent His-tag.

Mouse B7H3 Antigen for Detection

Commercially available product (SinoBiological cat #50973-M08H)

The sequence is as follows:

SEQ ID NO: 3
VEVQVSEDPVVALVDTDATLRCSFSPEPGFSLAQL

NLIWQLTDTKQLVHSFTEGRDQGSAYSNRTALFPD

LLVQGNASLRLQRVRVTDEGSYTCFVSIQDFDSAA

VSLQVAAPYSKPSMTLEPNKDLRPGNIVIVTITCS

SYQGYPEAEVFWKDGQGVPLTGNVTTSQMANERGL

FDVHSVLRVVLGANGTYSCLVRNPVLQQDAHGSVT

ITGQPLTF-*HHHHHH*

Note: The underlined portion represents the extracellular region of B7H3; the italics represent His-tag.

| Human B7H3 full-length amino acid sequence |
| --- |
| SEQ ID NO: 4 |
| MLRRRGSPGMGVHVGAALGALWFCLTGA<u>LEVQVPEDPVVALVGTDATLCCSFSPE</u><br><br><u>PGFSLAQLNLIWQLTDTKQLVHSFAEGQDQGSAYANRTALFPDLLAQGNASLRLQR</u><br><br><u>VRVADEGSFTCFVSIRDFGSAAVSLQVAAPYSKPSMTLEPNKDLRPGDTVTITCSSY</u><br><br><u>QGYPEAEVFWQDGQGVPLTGNVTTSQMANEQGLFDVHSILRVVLGANGTYSCLV</u><br><br><u>RNPVLQQDAHSSVTITPQRSPTGAVEVQVPEDPVVALVGTDATLRCSFSPEPGFSLA</u><br><br><u>QLNLIWQLTDTKQLVHSFTEGRDQGSAYANRTALFPDLLAQGNASLRLQRVRVADE</u><br><br><u>GSFTCFVSIRDFGSAAVSLQVAAPYSKPSMTLEPNKDLRPGDTVTITCSSYRGYPEA</u><br><br><u>EVFWQDGQGVPLTGNVTTSQMANEQGLFDVHSVLRVVLGANGTYSCLVRNPVLQ</u><br><br><u>DAHGVSTITGQPMTFPPEALWVTVGLSVCLIALLVALAFV</u>*CWRKIKQSCEEENAGAE*<br>*DQDGEGEGSKTALQPLKHSDSKEDDGQEIA* |

Note: The double underlined portion represents the signal peptide (Signal peptide:1-28); The underlined portion represents the extracellular region of B7H3 (Extracellular domain: 29-466), wherein 29-139 refers to Ig-like V-type 1 Domain, 145-238 refers to Ig-like C2-type 1 Domain; 243-357 refers to Ig-like V-type 2 Domain, and 363-456 refers to Ig-like C2-type 2 Domain; The dotted line represents the transmembrane region (Transmembrane domain:467-487); The italics represent the intracellular region (Cytoplasmic domain:488-534).

Monkey B7H3 full-length amino acid sequence

SEQ ID NO: 5

MLHRRGSPGMGVHVGAALGALWFCLTGALEVQVPEDPVVALVGTDATLRCSFSP

EPGFSLAQLNLIWQLTDTKQLVHSFTEGRDQGSAYANRTALFLDLLAQGNASLRL

QRVRVADEGSFTCFVSIRDFGSAAVSLQVAAPYSKPSMTLEPNKDLRPGDTVTITC

SSYRGYPEAEVFWQDGQGAPLTGNVTTSQMANEQGLFDVHSVLRVVLGANGTYS

CLVRNPVLQQDAHGSITITPQRSPTGAVEVQVPEDPVVALVGTDATLRCSFSPEPGF

SLAQLNLIWQLTDTKQLVHSFTEGRDQGSAYANRTALFLDLLAQGNASLRLQRVR

VADEGSFTCFVSIRDFGSAAVSLQVAAPYSKPSMTLEPNKDLRPGDTVTITCSSYRG

YPEAEVFWQDGQGAPLTGNVTTSQMANEQGLFDVHSVLRVVLGANGTYSCLVRN

VLQQDAHGSVTITGQPMTFPPEALWVTGLSVCLVALLVALAFVCWRKIKQSCEEE
NAGAEDQDGEGEGSKTALQPLKHSDSKEDDGQLEA

Note:
The double underlined portion represents the signal peptide (Signal peptide:1-28);
The underlined portion represents the extracellular region of B7H3 (Extracellular domain: 29-466), wherein 29-139 refers to Ig-like V-type 1 Domain, 145-238 refers to Ig-like C2-type 1 Domain; 243-357 refers to Ig-like V-type 2 Domain, and 363-456 refers to Ig-like C2-type 2 Domain; The dotted line represents the transmembrane region (Transmembrane domain:467-487); The italics represent the intracellular region (Cytoplasmic domain:488-534).

>Mouse B7H3 full-length amino acid sequence

SEQ ID NO: 6

MLRGWGGPSVGVCVRTALGVLCLCLTGAVEVQVSEDPVVALVDTDATLRCSFSPEP

GFSLAQLNLIWQLTDTKQLVHSFTEGRDQGSAYSNRTALFPDLLVQGNASLRLQRV

RVTDEGSYTCFVSIQDFDSAAVSLQVAAPYSKPSMTLEPNKDLRPGNMVTITCSSYQ

GYPEAEVFWKDGQGVPLTGNVTTSQMANERGLFDVHSVLRVVLGANGTYSCLVR

NPVLQQDAHGSVTITGQPLTFPPEALWVTVGLSVCLVVLLVALAFVCWRKIKQSCEE
ENAGAEDQDGDGEGSKTALRPLKPSENKEDDGQEIA

Note:
The double underlined portion represents the signal peptide (Signal peptide:1-28); The underlined portion represents the extracellular region of B7H3 (Extracellular domain: 29-248); The dotted line represents the transmembrane region (Transmembrane domain:249-269); The italics represent the intracellular region (Cytoplasmic domain:270-316).

For B7H3 antibody h1702 obtained by screening, the sequences and CDR sequences defined by IMGT numbering criteria are as follows:

>h1702 VH

SEQ ID NO: 7

QVQLVQSGGGVVQPGTSLRLSCAASGFIFSSSAMHWVRQAPGK

GLEWVAVISYDGSNKYYVDSVKGRFTISRDNSKNTLYLQMNSL

RAEDTAVYYCARSARLYASFDYWGQGALVTVSS

-continued

>h1702 VL

SEQ ID NO: 8

QTVVTQEPSFSVSPGGTVTLTCGLSSGSVSTSHYPSWYQQTPG

QAPIVILIYNTNTRSSGVPDRFSGSILGNKAALTITGAQADDE

SDYYCAIHVDRDIWVFGGGTKLTVL

Note: Arranged in the order of FR1-CDR1-FR2-CDR2-FR3-CDR3-FR4, the italic sequences represent FRs, and the underlined sequences represent CDRs.

TABLE 1

Light chain and heavy chain CDR sequences of B7H3 antibody h1702

| Antibody | Heavy chain | | Light chain | |
|---|---|---|---|---|
| h1702 | HCDR1 | GFIFSSSA SEQ ID NO: 9 | LCDR1 | SGSVSTSHY SEQ ID NO: 12 |

TABLE 1-continued

Light chain and heavy chain CDR sequences of B7H3 antibody h1702

| Antibody | Heavy chain | Light chain |
|---|---|---|
| HCDR 2 | ISYDGSNK SEQ ID NO: 10 | LCDR2 NTN SEQ ID NO: 13 |
| HCDR 3 | ARSARLYASFDY SEQ ID NO: 11 | LCDR3 AIHVDRDIWV SEQ ID NO: 14 |

In order to further improve the performance of the bispecific antibodies, cysteine substitution mutations were carried out in the VH and VL of the B7H3 antibody h1702. Mutation G103C (according to natural amino acid sequence numbering, position 103 of SEQ ID NO: 16) was introduced into the light chain variable region, and mutation G44C (according to natural amino acid sequence numbering, position 44 of SEQ ID NO: 15) was introduced into the heavy chain variable region, such that a pair of disulfide bonds were formed. The heavy and light chain variable regions of the anti-B7H3 single-chain antibody after the mutation are as follows:

B7H3 VH44C:
SEQ ID NO: 15
QVQLVQSGGGVVQPGTSLRLSCAASGFIFSSSAMHWVRQAPGKC
LEWVAVISYDGSNKYYVDSVKGRFTISRDNSKNTLYLQMNSLRA
EDTAVYYCARSARLYASFDYWGQGALVTVSS

B7H3 VL103C:
SEQ ID NO: 16
QTVVTQEPSFSVSPGGTVTLTCGLSSGSVSTSHYPSWYQQTPGQ
APRMLIYNTNTRSSGVPDRFSGSILGNKAALTITGAQADDESDY
YCAIHVDRDIWVFCCGTKLTVL.

2. Preparation and Screening of CD3 Antibodies

Humanized CD3 antibodies can be obtained on the basis of murine CD3 antibodies by the methods such as mutation, library construction, humanization engineering and screening.

CD3 Antigen Related Sequence Information is as Follows

Human CD3 Antigen for Detection

Commercially available product (SinoBiological cat #CT038-H2508H)

The sequences are as follows:

Human CD3ε (Human CD3ε)
SEQ ID NO: 17
DGNEEMGGITQTPYKVSISGTTVILTCPQYPGSEILWQHNDKN
IGGDEDDKNIGSDEDHLSLKEFSELEQSGYYVCYPRGSKPEDA
NFYLYLRARVCENCMEMD-*HHHHHH*

Note:

The underlined portion represents the extracellular region of CD3ε (Extracellular domain: 23-126); the italics represent His tag.

Human CD3δ
SEQ ID NO: 18
FKIPIEELEDRVFVNCNTSITWVEGTVGTLLSDITRLDLGKR
ILDPRGIYRCNGTDIYKDKESTVQVHYRIVICQSCVELDPAT
VA *DYKDDDDK*

Note:

The underlined portion represents the extracellular region of CD3δ (Extracellular domain: 22-105); the italics represent the Flag tag.

Monkey CD3 Antigen for Detection

Commercially available product (Acro biosystem cat #CDD-C52W4-100 ug)

The sequences are as follows:

Monkey CD3ε
SEQ ID NO: 19
QDGNEEMGSITQTPYQVSISGTTVILTCSQHLGSEAQWQHNGKNKEDSG
DRLFLPEFSEMEQSGYYVCYPRGSNPEDASHHLYLKARVCENCMEMD
-*HHHHHH*

Note:

The underlined portion represents the extracellular region of CD3ε (Extracellular domain: 22-117); the italics represent His tag.

Monkey CD3δ
SEQ ID NO: 20
FKIPVEELEDRVFVKCNTSVTWVEGTVGTLLTNNTRLDLGKRILDPRGI
YRCNGTDIYKDKESAVQVHYRMCQNCVELDPATLA-*DYKDDDDK*

Note:

The underlined portion represents the extracellular region of CD3δ (Extracellular domain: 22-105); the italics represent the Flag tag.

Mouse CD3 Antigen for Detection

Commercially available product (SinoBiological cat #CT033-M2508H). The sequences are as follows:

Mouse CD3ε
SEQ ID NO: 21
DDAENIEYKVSISGTSVELTCPLDSDENLKWEKNGQELPQKHDKHLVLQ
DFSEVEDSGYYVCYTPASNKNTYLYLKARVCEYCVEVD-*HHHHHH*

Note:

The underlined portion represents the extracellular region of CD3ε (Extracellular domain: 22-108); the italics represent His tag.

Mouse CD3δ
SEQ ID NO: 22
FKIQVTEYEDKVFVTCNTSVMHLDGTVEGWFAKNKTLNLGKGVLDPRGI
YLCNGTEQLAKVVSSVQVHYRMCQNCVELDSGTMA *DYKDDDDK*

Note:

The underlined portion represents the extracellular region of CD3δ (Extracellular domain: 22-105); the italics represent the Flag tag.

| Human CD3ε full-length amino acid sequence |
|---|
| SEQ ID NO: 23 |
| MQSGTHWRVLGLCLLSVGVWGQDGNEEMGGITQTPYKVSISGTTVILTCPQYPGSE<br>ILWQHNDKNIGGDEDDKNIGSDEDHLSLKEFSELEQSGYYVCYPRGSKPEDANFYL<br>YLRARVCENCMEMDVMSVATIVIVDICITGGLLLLVYYWSKNRKAKAKPVTRGAGA<br>GGRQRGQNKERP PPVPNPDYEP IRKGQRDLYSGLNQRRI |

Note:

The double underlined portion represents the signal peptide (Signal peptide:1-28);

The underlined portion represents the extracellular region of CD3ε (Extracellular domain: 23-126), wherein 32-112 refers to Ig-like Domain; The dotted line represents the transmembrane region (Transmembrane domain:127-152); The italics represent the intracellular region (Cytoplasmic domain:153-207).

| Human CD3δ full-length amino acid sequence |
|---|
| SEQ ID NO: 24 |
| MEHSTFLSGLVLATLLSQVSPFKIPIEELEDRVFVNCNTSITWVEGTVGTLLSDITRLD<br>LGKRILDPRGIYRCNGTDIYKDKESTVQVHYRMCQSCVELDPATVAGIIVTDVIATL<br>LLALGVFCFAGHETGRLSGAADTQALLRNDQVYQPLRDRDDAQYSHLGGNWARNK |

Note:

The double underlined portion represents the signal peptide (Signal peptide:1-21);

The underlined portion represents the extracellular region of CD3δ (Extracellular domain: 22-105); The dotted line represents the transmembrane region (Transmembrane domain: 106-126); The italics represent the intracellular region (Cytoplasmic domain: 127-171).

| Monkey CD3ε full-length amino acid sequence |
|---|
| SEQ ID NO: 25 |
| MQSGTRWRVLGLCLLSIGVWGQDGNEEMGSITQTPYQVSISGTTVILTCSQHLGSE<br>AQWQHNGKNKEDSGDRLFLPEFSEMEQSGYYVCYPRGSNPEDASHHYLKARVC<br>ENCMEMDVMAVATIVIVDICITLGLLLLVYYWSKNRKAKAKPVTRGAGAGGRQRGQN<br>KERPPPVPNPDYEPIRKGQQDLYSGLNQRRI |

Note:

The double underlined portion represents the signal peptide (Signal peptide:1-21);

The underlined portion represents the extracellular region of CD3δ (Extracellular domain: 22-117); The dotted line represents the transmembrane region (Transmembrane domain: 118-138); The italics represent the intracellular region (Cytoplasmic domain:139-198).

| Monkey CD3δ full-length amino acid sequence |
|---|
| SEQ ID NO: 26 |
| MEHSTFLSGLVLATLLSQVSPFKIPVEELEDRVFVKCNTSVTWVEGTVGTLLTNNTR<br>LDLGKRILDPRGIYRCNGTDIYKDKESAVQVHYRMCQNCVELDPATLAGIIVTDVIA<br>TLLLALGVFCFAGHETGRLSGAADTQALLRNDQVYQPLRDRDDAQYSRLGGNWARNK |

Note:
The double underlined portion represents the signal peptide (Signal peptide:1-21);
The underlined portion represents the extracellular region of CD3δ (Extracellular domain: 22-105); The dotted line represents the transmembrane region (Transmembrane domain: 106-126); The italics represent the intracellular region (Cytoplasmic domain:127-171).

---

Mouse CD3ε full-length amino acid sequence

SEQ ID NO: 27

MRWNTFWGILCLSLLAVGTCQDDAENIEYKVSISGTSVELTCPLDSDENLKWEKNG
QELPQKHDKHLVLQDFSEVEDSGYYVCYTPASNKNTYLYLKARVCEYCVEVDLTA
VAIIIVDICITLGLLMVIYYWSKNRKAKAKPVTRGTGAGSRPRGQNKERPPPVPNPDY
EPIRKGQRDLYSGLNQRAV

---

Note:
The double underlined portion represents the signal peptide (Signal peptide:1-21);
The underlined portion represents the extracellular region of CD3δ (Extracellular domain: 22-108); The dotted line represents the transmembrane region (Transmembrane domain: 109-134); The italics represent the intracellular region (Cytoplasmic domain:135-189).

---

Mouse CD3δ full-length amino acid sequence

SEQ ID NO: 28

MEHSGILASLILIAVLPQGSPFKIQVTEYEDKVFVTCNTSVMHLDGTVEGWFAKNK
TLNLGKGVLDPRGIYLCNGTEQLAKVVSSVQVHYRMCQNCVELDSGTMAGVIFID
LIATLLLALGVYCFAGHETGRPSGAAEVQALLKNEQLYQPLRDREDTQYSRLGGNPR
NKKS

---

Note:
The double underlined portion represents the signal peptide (Signal peptide:1-21);
The underlined portion represents the extracellular region of CD3δ (Extracellular domain: 22-105); The dotted line represents the transmembrane region (Transmembrane domain: 106-126); The italics represent the intracellular region (Cytoplasmic domain:127-173).

After repeated analysis and optimization, a series of humanized anti-CD3 antibody sequences were obtained. The heavy chain variable region sequences are as follows:

TABLE 2

The heavy chain variable region sequence of CD3 humanized antibodies

| Name | SEQ ID NO: | Sequence |
|---|---|---|
| HRH-1 | 29 | EVQLVESGGGLVQPGGSLKLSCAASGFTFNKYAMNWVRQAPGKGLEW VARIRSKANNYATYYADSVKDRFTISRDDSKNTAYLQMNNLKTEDTA VYYCVRHGNFGNSYISYWAYWGQGTLVTVSS |
| HRH-2 | 30 | EVQLVESGGGLVQPGGSLKLSCAASGFTFNKYAMNWVRQAPGKGLEW VARIRSKYNNYATYYADSVKDRFTISRDDSKNTAYLQMNNLKTEDTA VYYCVRHGNFGNPYISYWAYWGQGTLVTVSS |
| HRH-3 | 31 | EVQLVESGGGLVQPGGSLKLSCAASGFTFNKYAMNWVRQAPGKGLEW VARIRSKYNNYATYYADSVKDRFTISRDDSKNTAYLQMNNLKTEDTA VYYCVRHGNFGNEYISYWAYWGQGTLVTVSS |
| HRH-4 | 32 | EVQLVESGGGLVQPGGSLKLSCAASGFTFNKYAMNWVRQAPGKGLEW VARIRSKYNNYATYYADSVKDRFTISRDDSKNTAYLQMNNLKTEDTA VYYCVRHGNFGNSYISYWDYWGQGTLVTVSS |
| HRH-5 | 33 | EVQLVESGGGLVQPGGSLKLSCAASGFTFNKYAMSWVRQAPGKGLEW VARIRSKYNNYATYYADSVKDRFTISRDDSKNTAYLQMNNLKTEDTA VYYCVRHGNFGNSYISYWAYWGQGTLVTVSS |
| HRH-6 | 34 | EVQLVESGGGLVQPGGSLKLSCAASGFTFNKYAMNWVRQAPGKGLEW VARIRNKYNNYATEYADSVKDRFTISRDDSKNTAYLQMNNLKTEDTA VYYCVRHGNFGNSYISYWAYWGQGTLVTVSS |

TABLE 2-continued

The heavy chain variable region sequence of CD3 humanized antibodies

| Name | SEQ ID NO: | Sequence |
|------|------------|----------|
| HRH-7 | 35 | *EVQLVESGGGLVQPGGSLKLSCAASGFTFN*KYAMN*WVRQAPGKGLEW VAR*IRSKYNNYATEYAASVKD*RFTISRDDSK*NTAYLQMNNLKTEDTA VYYCVR*HGNFGNSYISYWAY*WGQGTLVTVSS* |

The light chain variable region sequences are as follows:

>HRL
SEQ ID NO: 36
*QTVVTQEPSLTVSPGGTVTLTC*GSSTGAVTSGNYPN*WVQQKPGQAPRGL IG*GTKFLAP*GTPARFSGSLLGGKAALTLSGVQPEDEAEYYC*VLWYSNRW V*FGGGTKLTVL*

Note: Arranged in the order of FR1-CDR1-FR2-CDR2-FR3-CDR3-FR4, the italic sequences represent FRs, and the underlined sequences represent CDRs. The number and position of light and heavy chain variable region CDRs (LCDR1-LCDR3 and HCDR1-HCDR3) of the CD3 humanized antibodies listed herein and in table 3 below comply with the well-known Kabat numbering criteria.

TABLE 3

CDR sequences of CD3 antibodies

| Antibody variable region | Heavy chain CDR | | Antibody variable region | Light chain CDR | |
|---|---|---|---|---|---|
| HRH-1 | HCDR1 | KYAMN SEQ ID NO: 37 | HRL | LCDR1 | GSSTGAVTSGNYPN SEQ ID NO: 48 |
| | HCDR2 | RIRSKANNYATYYADSVKD SEQ ID NO: 38 | | LCDR2 | GTKFLAP SEQ ID NO: 49 |
| | HCDR3 | HGNFGNSYISYWAY SEQ ID NO: 39 | | LCDR3 | VLWYSNRWV SEQ ID NO: 50 |
| HRH-2 | HCDR1 | KYAMN SEQ ID NO: 37 | | | |
| | HCDR2 | RIRSKYNNYATYYADSVKD SEQ ID NO: 40 | | | |
| | HCDR3 | HGNFGNPYISYWAY SEQ ID NO: 41 | | | |
| HRH-3 | HCDR1 | KYAMN SEQ ID NO: 37 | | | |
| | HCDR2 | RIRSKYNNYATYYADSVKD SEQ ID NO: 40 | | | |
| | HCDR3 | HGNFGNEYISYWAY SEQ ID NO: 42 | | | |
| HRH-4 | HCDR1 | KYAMN SEQ ID NO: 37 | | | |
| | HCDR2 | RIRSKYNNYATYYADSVKD SEQ ID NO: 40 | | | |
| | HCDR3 | HGNFGNSYISYWDY SEQ ID NO: 43 | | | |
| HRH-5 | HCDR1 | KYAMS SEQ ID NO: 44 | | | |
| | HCDR2 | RIRSKYNNYATYYADSVKD SEQ ID NO: 40 | | | |
| | HCDR3 | HGNFGNSYISYWAY SEQ ID NO: 45 | | | |
| HRH-6 | HCDR1 | KYAMN SEQ ID NO: 37 | | | |
| | HCDR2 | RIRNKYNNYATEYADSVKD SEQ ID NO: 46 | | | |
| | HCDR3 | HGNFGNSYISYWAY SEQ ID NO: 45 | | | |
| HRH-7 | HCDR1 | KYAMN SEQ ID NO: 37 | | | |
| | HCDR2 | RIRSKYNNYATEYAASVKD SEQ ID NO: 47 | | | |
| | HCDR3 | HGNFGNSYISYWAY SEQ ID NO: 45 | | | |

Construction and Preparation of Single Chain Antibodies
scFvs against B7H3 and scFvs against CD3 were generated by connecting the light and heavy chain variable regions derived from the above-mentioned B7H3 antibodies, and by connecting the light and heavy chain variable regions derived from the CD3 antibody respectively, wherein the linker can be selected from those well-known in the art. Exemplary linker can be selected from: (GGGGS)n (SEQ ID No. 105-108) or (GGGGS)n GGG (SEQ ID No. 109-112), where n can be 1, 2, 3, or 4.

Exemplary anti-B7H3 scFvs are as follows:

TABLE 4

Sequence listing of various anti-B7H3 single chain antibodies (scFvs)

| Name of the Single chain antibody (structural form) | Sequence (SEQ ID NO:) |
|---|---|
| B7H3-scFv1 (VL$_{B7H3}$-linker-VH$_{B7H3}$) | QTVVTQEPSFSVSPGGTVTLTCGLSSGSVSTSHYPSWYQQTPGQAPRM LIYNTNTRSSGVPDRFSGSILGNKAALTITGAQADDESDYYCAIHVDR DIWVFGGGTKLTVL*GGGGSGGGGSGGGGS*QVQLVQSGGGVVQPGTSLR LSCAASGFIFSSSAMEIWVRQAPGKGLEWVAVISYDGSNKYYVDSVKG RFTISRDNSKNTLYLQMNSLRAEDTAVYYCARSARLYASFDYWGQGAL VTVSS (SEQ ID NO: 51) |
| B7H3-scFv2 (VH$_{B7H3}$-linker-VL$_{B7H3}$) | QVQLVQSGGGVVQPGTSLRLSCAASGFIFSSSAMEIWVRQAPGKGLEW VAVISYDGSNKYYVDSVKGRFTISRDNSKNTLYLQMNSLRAEDTAVYY CARSARLYASFDYWGQGALVTV*SSGGGGSGGGGSGGGGS*QTVVTQEPS FSVSPGGTVTLTCGLSSGSVSTSHYPSWYQQTPGQAPRMLIYNTNTRS SGVPDRFSGSILGNKAALTITGAQADDESDYYCAIHVDRDIWVFGGGT KLTVL (SEQ ID NO: 52) |
| B7H3-scFv3 (VL$_{B7H3}$-linker-VH$_{B7H3}$) | QTVVTQEPSFSVSPGGTVTLTCGLSSGSVSTSHYPSWYQQTPGQAPRM LIYNTNTRSSGVPDRFSGSILGNKAALTITGAQADDESDYYCAIHVDR DIWVFGCGTKLTVL*GGGGSGGGGSGGGGS*QVQLVQSGGGVVQPGTSLR LSCAASGFIFSSSAMEIWVRQAPGKCLEWVAVISYDGSNKYYVDSVKG RFTISRDNSKNTLYLQMNSLRAEDTAVYYCARSARLYASFDYWGQGAL VTVSS (SEQ ID NO: 53) |
| B7H3-scFv4 (VH$_{B7H3}$-linker-VL$_{B7H3}$) | QVQLVQSGGGVVQPGTSLRLSCAASGFIFSSSAMEIWVRQAPGKCLEW VAVISYDGSNKYYVDSVKGRFTISRDNSKNTLYLQMNSLRAEDTAVYY CARSARLYASFDYWGQGALVTV*SSGGGGSGGGGSGGGGS*QTVVTQEPS FSVSPGGTVTLTCGLSSGSVSTSHYPSWYQQTPGQAPRMLIYNTNTRS SGVPDRFSGSILGNKAALTITGAQADDESDYYCAIHVDRDIWVFGCGT KLTVL (SEQ ID NO: 54) |

Exemplary anti-CD3 scFvs are as follows:

TABLE 5

Sequence listing of various anti-CD3 single chain antibodies (scFvs)

| Name of anti-CD3 scFvs (structural form) | Sequence (SEQ ID NO:) |
|---|---|
| CD3-scFv1H (V$_{HCD3}$-linker-VL$_{CD3}$) | EVQLVESGGGLVQPGGSLKLSCAASGFTFNKYAMNWVRQAPGKGLEW VARIRSKANNYATYYADSVKDRFTISRDDSKNTAYLQMNNLKTEDTA VYYCVRHGNFGNSYISYWAYWGQGTLVTV*SSGGGGSGGGGSGGGGS*Q TVVTQEPSLTVSPGGTVTLTCGSSTGAVTSGNYPNWVQQKPGQAPRG LIGGTKFLAPGTPARFSGSLLGGKAALTLSGVQPEDEAEYYCVLWYS NRWVFGGGTKLTVL (SEQ ID NO: 55) |
| CD3-scFv2H VH$_{CD3}$-linker-VL$_{CD3}$ | EVQLVESGGGLVQPGGSLKLSCAASGFTFNKYAMNWVRQAPGKGLEW VARIRSKYNNYATYYADSVKDRFTISRDDSKNTAYLQMNNLKTEDTA VYYCVRHGNFGNPYISYWAYWGQGTLVTV*SSGGGGSGGGGSGGGGS*Q TVVTQEPSLTVSPGGTVTLTCGSSTGAVTSGNYPNWVQQKPGQAPRG LIGGTKFLAPGTPARFSGSLLGGKAALTLSGVQPEDEAEYYCVLWYS NRWVFGGGTKLTVL (SEQ ID NO: 56) |

TABLE 5-continued

Sequence listing of various anti-CD3
single chain antibodies (scFvs)

Name of
anti-CD3 scFvs
(structural form)   Sequence (SEQ ID NO:)

CD3-scFv3H
VH<sub>CD3</sub>-linker-VL<sub>CD3</sub>
EVQLVESGGGLVQPGGSLKLSCAASGFTFN<u>KYAMN</u>WVRQAPGKGLEW
VARIRSKYNNYATYYADSVKDRFTISRDD<u>SKNTAYL</u>QMNNLKTEDTA
VYYC<u>VRHGNFGNEYISYWAYW</u>GQGTLVTVSS*GGGGSGGGGSGGGGS*Q
TVVTQEPSLTVSPGGTVTLTC<u>GSSTGAVTSGNYPNW</u>VQQKPGQAPRG
LIG<u>GTKFLAP</u>GTPARFSGSLLGGKAALTLSGVQPEDEAEYYC<u>VLWYS</u>
<u>NRW</u>VFGGGTKLTVL
(SEQ ID NO: 57)

CD3-scFv4H
VH<sub>CD3</sub>-linker-VL<sub>CD3</sub>
EVQLVESGGGLVQPGGSLKLSCAASGFTFN<u>KYAMN</u>WVRQAPGKGLEW
VARIRSKYNNYATYYADSVKDRFTISRDD<u>SKNTAYL</u>QMNNLKTEDTA
VYYC<u>VRHGNFGNSYISYWDYW</u>GQGTLVTVSS*GGGGSGGGGSGGGGS*Q
TVVTQEPSLTVSPGGTVTLTC<u>GSSTGAVTSGNYPNW</u>VQQKPGQAPRG
LIG<u>GTKFLAP</u>GTPARFSGSLLGGKAALTLSGVQPEDEAEYYC<u>VLWYS</u>
<u>NRW</u>VFGGGTKLTVL
(SEQ ID NO: 58)

CD3-scFv5H
VH<sub>CD3</sub>-linker-VL<sub>CD3</sub>
*EVQLVESGGGLVQPGGSLKLSCAASGFTFN<u>KYAMS</u>WVRQAPGKGLEW*
*VARIRSKYNNYATYYADSVKDRFTISRDD<u>SKNTAYL</u>QMNNLKTEDTA*
*VYYC<u>VRHGNFGNSYISYWAYW</u>GQGTLVTVSSGGGGSGGGGSGGGGS*Q
TVVTQEPSLTVSPGGTVTLTC<u>GSSTGAVTSGNYPNW</u>VQQKPGQAPRG
LIG<u>GTKFLAP</u>GTPARFSGSLLGGKAALTLSGVQPEDEAEYYC<u>VLWYS</u>
<u>NRW</u>VFGGGTKLTVL
(SEQ ID NO: 59)

CD3-scFv6H
VH<sub>CD3</sub>-linker-VL<sub>CD3</sub>
EVQLVESGGGLVQPGGSLKLSCAASGFTFN<u>KYAMN</u>WVRQAPGKGLEW
VARIRNKYNNYATEYADSVKDRFTISRDD<u>SKNTAYL</u>QMNNLKTEDTA
VYYC<u>VRHGNFGNSYISYWAYW</u>GQGTLVTVSS*GGGGSGGGGSGGGGS*Q
TVVTQEPSLTVSPGGTVTLTC<u>GSSTGAVTSGNYPNW</u>VQQKPGQAPRG
LIG<u>GTKFLAP</u>GTPARFSGSLLGGKAALTLSGVQPEDEAEYYC<u>VLWYS</u>
<u>NRW</u>VFGGGTKLTVL
(SEQ ID NO: 60)

CD3-scFv7H
VH<sub>CD3</sub>-linker-VL<sub>CD3</sub>
EVQLVESGGGLVQPGGSLKLSCAASGFTFN<u>KYAMN</u>WVRQAPGKGLEW
VARIRSKYNNYATEYAASVKDRFTISRDD<u>SKNTAYL</u>QMNNLKTEDTA
VYYC<u>VRHGNFGNSYISYWAYW</u>GQGTLVTVSS*GGGGSGGGGSGGGGS*Q
TVVTQEPSLTVSPGGTVTLTC<u>GSSTGAVTSGNYPNW</u>VQQKPGQAPRG
LIG<u>GTKFLAP</u>GTPARFSGSLLGGKAALTLSGVQPEDEAEYYC<u>VLWYS</u>
<u>NRW</u>VFGGGTKLTVL
(SEQ ID NO: 61)

CD3-scFv1L
VL<sub>CD3</sub>-linker-VH<sub>CD3</sub>
QTVVTQEPSLTVSPGGTVTLTC<u>GSSTGAVTSGNYPNW</u>VQQKPGQAPR
GLIG<u>GTKFLAP</u>GTPARFSGSLLGGKAALTLSGVQPEDEAEYYC<u>VLWY</u>
<u>SNRW</u>VFGGGTKLTVL*GGGGSGGGGSGGGGS*EVQLVESGGGLVQPGGS
LKLSCAASGFTFN<u>KYAMN</u>WVRQAPGKGLEWVARIRSKANNYATYYAD
SVKDRFTISRDD<u>SKNTAYL</u>QMNNLKTEDTAVYYC<u>VRHGNFGNSYISY</u>
<u>WAYW</u>GQGTLVTVSS
(SEQ ID NO: 62)

CD3-scFv2L
VL<sub>CD3</sub>-linker-VH<sub>CD3</sub>
QTVVTQEPSLTVSPGGTVTLTC<u>GSSTGAVTSGNYPNW</u>VQQKPGQAPR
GLIG<u>GTKFLAP</u>GTPARFSGSLLGGKAALTLSGVQPEDEAEYYC<u>VLWY</u>
<u>SNRW</u>VFGGGTKLTVL*GGGGSGGGGSGGGGS*EVQLVESGGGLVQPGGS
LKLSCAASGFTFN<u>KYAMN</u>WVRQAPGKGLEWVARIRSKYNNYATYYAD
SVKDRFTISRDD<u>SKNTAYL</u>QMNNLKTEDTAVYYC<u>VRHGNFGNPYISY</u>
<u>WAYW</u>GQGTLVTVSS
(SEQ ID NO: 63)

CD3-scFv3L
VL<sub>CD3</sub>-linker-VH<sub>CD3</sub>
QTVVTQEPSLTVSPGGTVTLTC<u>GSSTGAVTSGNYPNW</u>VQQKPGQAPR
GLIG<u>GTKFLAP</u>GTPARFSGSLLGGKAALTLSGVQPEDEAEYYC<u>VLWY</u>
<u>SNRW</u>VFGGGTKLTVL*GGGGSGGGGSGGGGS*EVQLVESGGGLVQPGGS
LKLSCAASGFTFN<u>KYAMN</u>WVRQAPGKGLEWVARIRSKYNNYATYYAD
SVKDRFTISRDD<u>SKNTAYL</u>QMNNLKTEDTAVYYC<u>VRHGNFGNEYISY</u>
<u>WAYW</u>GQGTLVTVSS
(SEQ ID NO: 64)

CD3-scFv4L
VL<sub>CD3</sub>-linker-VH<sub>CD3</sub>
QTVVTQEPSLTVSPGGTVTLTC<u>GSSTGAVTSGNYPNW</u>VQQKPGQAPR
GLIG<u>GTKFLAP</u>GTPARFSGSLLGGKAALTLSGVQPEDEAEYYC<u>VLWY</u>
<u>SNRW</u>VFGGGTKLTVL*GGGGSGGGGSGGGGS*EVQLVESGGGLVQPGGS
LKLSCAASGFTFN<u>KYAMN</u>WVRQAPGKGLEWVARIRSKYNNYATYYAD
SVKDRFTISRDD<u>SKNTAYL</u>QMNNLKTEDTAVYYC<u>VRHGNFGNSYISY</u>
<u>WDYW</u>GQGTLVTVSS
(SEQ ID NO: 65)

TABLE 5-continued

Sequence listing of various anti-CD3 single chain antibodies (scFvs)

| Name of anti-CD3 scFvs (structural form) | Sequence (SEQ ID NO:) |
|---|---|
| CD3-scFv5L VL$_{CD3}$-linker-VH$_{CD3}$ | QTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWY SNRWVFGGGTKLTVL*GGGGSGGGGSGGGGS*EVQLVESGGGLVQPGGS LKLSCAASGFTFNKYAMSWVRQAPGKGLEWVARIRSKYNNYATYYAD SVKDRFTISRDDSKNTAYLQMNNLKTEDTAVYYCVRHGNFGNSYISY WAYWGQGTLVTVSS (SEQ ID NO: 66) |
| CD3-scFv6L VL$_{CD3}$-linker-VH$_{CD3}$ | QTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWY SNRWVFGGGTKLTVL*GGGGSGGGGSGGGGS*EVQLVESGGGLVQPGGS LKLSCAASGFTFNKYAMNWVRQAPGKGLEWVARIRNKYNNYATEYAD SVKDRFTISRDDSKNTAYLQMNNLKTEDTAVYYCVRHGNFGNSYISY WAYWGQGTLVTVSS (SEQ ID NO: 67) |
| CD3-scFv7L VL$_{CD3}$-linker-VH$_{CD3}$ | QTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWY SNRWVFGGGTKLTVLGGGGSGGGGSGGGGSEVQLVESGGGLVQPGGS LKLSCAASGFTFNKYAMNWVRQAPGKGLEWVARIRSKYNNYATEYAA SVKDRFTISRDDSKNTAYLQMNNLKTEDTAVYYCVRHGNFGNSYISY WAYWGQGTLVTVSS (SEQ ID NO: 68) |

Construction and Preparation of Bispecific Antibodies

B7H3 Bivalent Bispecific Antibodies and B7H3 Monovalent Bispecific Antibodies

Figure 1B:
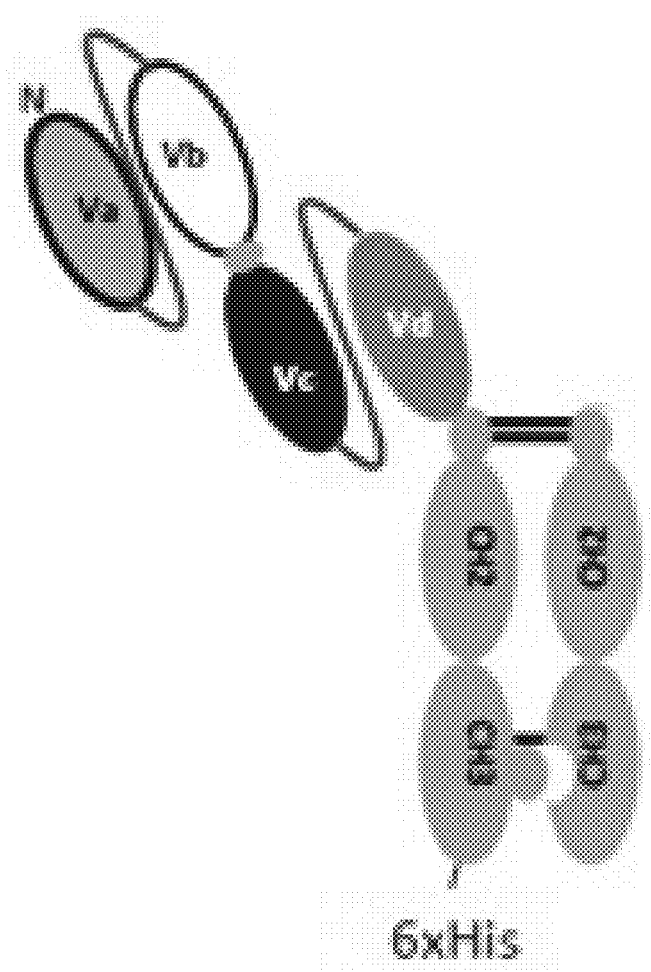

In some embodiments of the present disclosure, the structure of the B7H3 bivalent bispecific antibodies is shown in FIG. 1A, wherein the the C-terminus of the antibody can be or can not be labeled to His tag. Two B7H3 antigen-binding domains and one CD3 antigen-binding domain are configurated in a designed asymmetric structure of the two Fc-containing chains, wherein each B7H3 antigen-binding domain is on each of the two chains respectively, and the antigen-binding domains are all in the form of scFv. The Fc region can make the antibody maintain the normal half-life and favorable stability. The design of the two chains greatly reduces the probability of mismatches and improves the homogeneity of the sample and the yield of the target antibody. The specific molecular structure (Format) of the bispecific antibodies is shown in Table 6 below. In addition, the molecular structure of the B7H3 monovalent bispecific antibodies used in some embodiments of the present disclosure has Fc domain alone in the second polypeptide chain, without any antigen-binding domain, such structure is shown in FIG. 1B.

TABLE 6

Structural representation of the bispecific antibodies

| Name of the molecular structure | The arrangement order of the first polypeptide chain | The arrangement order of the second polypeptide chain |
|---|---|---|
| AFF1 | VH$_{B7H3}$-L1-VL$_{B7H3}$-L2-VH$_{CD3}$-L3-VL$_{CD3}$-L4-F$_c$1 | VL$_{B7H3}$-L5-VH$_{B7H3}$-L6-F$_c$2 |
| AFF2 | VH$_{B7H3}$-L1-VL$_{B7H3}$-L2-VL$_{CD3}$-L3-VH$_{CD3}$-L4-F$_c$1 | VL$_{B7H3}$-L5-VH$_{B7H3}$-L6-F$_c$2 |
| AFF3 | VL$_{B7H3}$-L1-VH$_{B7H3}$-L2-VH$_{CD3}$-L3-VL$_{CD3}$-L4-F$_c$1 | VL$_{B7H3}$-L5-VH$_{B7H3}$-L6-F$_c$2 |
| AFF4 | VL$_{B7H3}$-L1-VH$_{B7H3}$-L2-VL$_{CD3}$-L3-VH$_{CD3}$-L4-F$_c$1 | VL$_{B7H3}$-L5-VH$_{B7H3}$-L6-F$_c$2 |
| AFF5 | VH$_{CD3}$-L1-VL$_{CD3}$-L2-VH$_{B7H3}$-L3-VL$_{B7H3}$-L4-F$_c$1 | VL$_{B7H3}$-L5-VH$_{B7H3}$-L6-F$_c$2 |
| AFF6 | VH$_{CD3}$-L1-VL$_{CD3}$-L2-VL$_{B7H3}$-L3-VH$_{B7H3}$-L4-F$_c$1 | VL$_{B7H3}$-L5-VH$_{B7H3}$-L6-F$_c$2 |
| AFF7 | VL$_{CD3}$-L1-VH$_{CD3}$-L2-VH$_{B7H3}$-L3-VL$_{B7H3}$-L4-F$_c$1 | VL$_{B7H3}$-L5-VH$_{B7H3}$-L6-F$_c$2 |
| AFF8 | VL$_{CD3}$-L1-VH$_{CD3}$-L2-VL$_{B7H3}$-L3-VH$_{B7H3}$-L4-F$_c$1 | VL$_{B7H3}$-L5-VH$_{B7H3}$-L6-F$_c$2 |
| AFF1-B | VH$_{B7H3}$-L1-VL$_{B7H3}$-L2-VH$_{CD3}$-L3-VL$_{CD3}$-L4-F$_c$1 | VH$_{B7H3}$-L5-VL$_{B7H3}$-L6-F$_c$2 |
| AFF2-B | VH$_{B7H3}$-L1-VL$_{B7H3}$-L2-VL$_{CD3}$-L3-VH$_{CD3}$-L4-F$_c$1 | VH$_{B7H3}$-L5-VL$_{B7H3}$-L6-F$_c$2 |
| AFF3-B | VL$_{B7H3}$-L1-VH$_{B7H3}$-L2-VH$_{CD3}$-L3-VL$_{CD3}$-L4-F$_c$1 | VH$_{B7H3}$-L5-VL$_{B7H3}$-L6-F$_c$2 |
| AFF4-B | VL$_{B7H3}$-L1-VH$_{B7H3}$-L2-VL$_{CD3}$-L3-VH$_{CD3}$-L4-F$_c$1 | VH$_{B7H3}$-L5-VL$_{B7H3}$-L6-F$_c$2 |
| AFF5-B | VH$_{CD3}$-L1-VL$_{CD3}$-L2-VH$_{B7H3}$-L3-VL$_{B7H3}$-L4-F$_c$1 | VH$_{B7H3}$-L5-VL$_{B7H3}$-L6-F$_c$2 |
| AFF6-B | VH$_{CD3}$-L1-VL$_{CD3}$-L2-VL$_{B7H3}$-L3-VH$_{B7H3}$-L4-F$_c$1 | VH$_{B7H3}$-L5-VL$_{B7H3}$-L6-F$_c$2 |
| AFF7-B | VL$_{CD3}$-L1-VH$_{CD3}$-L2-VH$_{B7H3}$-L3-VL$_{B7H3}$-L4-F$_c$1 | VH$_{B7H3}$-L5-VL$_{B7H3}$-L6-F$_c$2 |
| AFF8-B | VL$_{CD3}$-L1-VH$_{CD3}$-L2-VL$_{B7H3}$-L3-VH$_{B7H3}$-L4-F$_c$1 | VH$_{B7H3}$-L5-VL$_{B7H3}$-L6-F$_c$2 |
| AF1 | VH$_{B7H3}$-L1-VL$_{B7H3}$-L2-VH$_{CD3}$-L3-VL$_{CD3}$-L4-F$_c$1 | Fc2 |
| AF2 | VH$_{B7H3}$-L1-VL$_{B7H3}$-L2-VL$_{CD3}$-L3-VH$_{CD3}$-L4-F$_c$1 | Fc2 |

TABLE 6-continued

Structural representation of the bispecific antibodies

| Name of the molecular structure | The arrangement order of the first polypeptide chain | The arrangement order of the second polypeptide chain |
|---|---|---|
| AF3 | $VL_{B7H3}$-L1-$VH_{B7H3}$-L2-$VH_{CD3}$-L3-$VL_{CD3}$-L4-$F_C1$ | Fc2 |
| AF4 | $VL_{B7H3}$-L1-$VH_{B7H3}$-L2-$VL_{CD3}$-L3-$VH_{CD3}$-L4-$F_C1$ | Fc2 |
| AF5 | $VH_{CD3}$-L1-$VL_{CD3}$-L2-$VH_{B7H3}$-L3-$VL_{B7H3}$-L4-$F_C1$ | Fc2 |
| AF6 | $VH_{CD3}$-L1-$VL_{CD3}$-L2-$VL_{B7H3}$-L3-$VH_{B7H3}$-L4-$F_C1$ | Fc2 |
| AF7 | $VL_{CD3}$-L1-$VH_{CD3}$-L2-$VH_{B7H3}$-L3-$VL_{B7H3}$-L4-$F_C1$ | Fc2 |
| AF8 | $VL_{CD3}$-L1-$VH_{CD3}$-L2-$VL_{B7H3}$-L3-$VH_{B7H3}$-L4-$F_C1$ | Fc2 |

Note:
In this table, the carboxyl terminus of the first or the second polypeptide chain can be or can not be labeled to the His tag. L1, L2, L3, L4, L5, and L6 represent linkers for connecting each antigen-binding domain and the Fc region.

TABLE 7

Selection of linker sequence

| Linker | Structure or sequence |
|---|---|
| L1 | (GGGGS)n (SEQ ID NO: 106–107) or (GGGGS)n GGG (SEQ ID NO: 110–111) |
| L2 | (GGGGS)n (SEQ ID NO: 105–106) |
| L3 | (GGGGS)n (SEQ ID NO: 107) |
| L4 | GGGDKTHTCPPCP (SEQ ID NO: 98) |
| L5 | (GGGGS)n (SEQ ID NO: 107) |
| L6 | GGGDKTHTCPPCP (SEQ ID NO: 98) |

Wherein n is selected from 1, 2, 3 or 4; preferably, n in L1 is 2 or 3, more preferably 3; n in L2 is 1 or 2, more preferably 1; n in L3 or L5 is 3. Optionally, the linker used to connect the antigen-binding domain and the Fc region can be selected from any other linker that can be used to connect the antibody functional domains, and is not limited to the linkers defined by the above sequences.

The Fc1 and Fc2 indicated in Table 6 above can be Fc with the same sequence, or can be knob-Fc and hole-Fc respectively, or hole-Fc and knob-Fc respectively. In some embodiments of the present disclosure, the sequences of knob-Fc and hole-Fc are preferably as shown in Table 8.

TABLE 8

Sequence listing of various Fcs

| Name | SEQ ID NO | Sequence |
|---|---|---|
| knob-Fc | 69 | APEAAGGPSVFLFPPKPKDTLMISRTPEVTCVVVDVSHEDPEVKFNWY VDGVEVHNAKTKPREEQYNSTYRVVSVLTVLHQDWLNGKEYKCKVSNK ALPAPIEKTISKAKGQPREPQVYTLPPCREEMTKNQVSLWCLVKGFYP SDIAVEWESNGQPENNYKTTPPVLDSDGSFFLYSKLTVDKSRWQQGNV FSCSVMHEALHNHYTQKSLSLSPGK |
| hole-Fc | 70 | APEAAGGPSVFLFPPKPKDTLMISRTPEVTCVVVDVSHEDPEVKFNWY VDGVEVHNAKTKPREEQYNSTYRVVSVLTVLHQDWLNGKEYKCKVSNK ALPAPIEKTISKAKGQPREPQVCTLPPSREEMTKNQVSLSCAVKGFYP SDIAVEWESNGQPENNYKTTPPVLDSDGSFFLVSKLTVDKSRWQQGNV FSCSVMHEALHNHYTQKSLSLSPGK |

For the above-mentioned light and heavy chain variable regions, single-chain antibodies, and bispecific antibodies, DNAs encoding the above-mentioned polypeptides or antigen-binding fragments can be constructed on the basis of the cDNAs encoding the VH and/or VL and other required domains, and the DNAs are inserted into prokaryotic expression vector(s) or eukaryotic expression vector(s), and then the expression vector(s) is(are) introduced into a prokaryotic or eukaryotic organism to express the polypeptides or antigen-binding fragments.

Example 1. Preparation of Bispecific Antibody Molecules, Positive Control Molecules, and Negative Control Molecules According to the method for designing bispecific antibody molecules of the present disclosure, specific bispecific antibody molecules were designed and prepared. Exemplary amino acid sequences of the molecules are shown in Table 9 below:

TABLE 9

Sequence listing of the bispecific antibodies

| Antibody name (structure name) | The first polypeptide chain (SEQ ID NO) | The second polypeptide chain (SEQ ID NO) |
|---|---|---|
| 113 (AFF 3-2) | QTVVTQEPSFSVSPGGTVTLTCGLSSGSVSTSHYPSWYQQTPGQAPRMLIYNTNTRSSGVPDRFSGSILGNKAALTITGAQADDESDYYCAIHVDRDIWVFGGGTKLTVLGGGGSGGGGSGGGGSQVQLVQSGGGVVQPGTSLRLSCAASGFIFSSSAMHWVRQAPGKGLEWVAVISYDGSNKYYVDSVKGRFTISRDNSKNTLYLQMNSLRAEDTAVYYCARSARLYASFDYWGQGALVTVSSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNPYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVLGGGDKTHTCPPCPAPE*AA*GGPSVFLFPPKPKDTLMISTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSL*W*CLVKGFYPSDIAVEWESNGQPENNYKTTPPVLDSDGSFFLYSKLTVDKSRWQQGNVFSCSVMHEALHNHYTQKSLSPGKHHHHHH | QTVVTQEPSESVSPGGTVTLTCGLSSGSVSTSHYPSWYQQTPGQAPRMLIYNTNTRSSGVPDRFSGSILGNKAALTITGAQADDESDYYCAIHVDRDIWVFGGGTKLTVL*GGGGSGGGGSGGGGS*QVQLVQSGGGVVQPGTSLRLSCAASGFIFSSAMHWVRQAPGKGLEWVAVISYDGSNKYYVDSVKGRFTISRDNSKNTLYLQMNSLRAEDTAVYYCARSARLYASFDYWGQGALVTVSSGGGDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| 118 (AFF 6-3) | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNEYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVLGGGGSQTVVTQEPSFSVSPGGTVTLTCGLSSGSVSTSHYPSWYQQTPGQAPRMLIYNTNTRSSGVPDRFSGSILGNKAALTITGAQADDESDYYCAIHVDRDIWVFGGGTKLTVLGGGGSGGGGSGGGGSQVQLVQSGGGVVQPGTSLRLSCAASGFIFSSSAMHWVRQAPGKGLEWVAVISYDGSNKYYVDSVKGRFTISRDNSKNTLYLQMNSLRAEDTAVYYCARSARLYASFDYWGQGALVTVSSGGGDKTHTCPPCPAPE*AA*GGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSL*W*CLVKGFYPSDIAVEWESNGQPENNYKTTPPVLDSDGSFFLYSKLTVDKSRWQQGNVFSCSVMHEALHNHYTQKSLSLSPGKHHHHHH | |

TABLE 9-continued

Sequence listing of the bispecific antibodies

| Antibody name (structure name) | The first polypeptide chain (SEQ ID NO) | The second polypeptide chain (SEQ ID NO) |
|---|---|---|
| 119 (AFF6-3L1D(GS)) | EVQLVESGGGLVQPGGSLKLSCAASGFTFNKYA MNWVRQAPGKGLEWVARIRSKYNNYATYYAD SVKDRFTISRDDSKNTAYLQMNNLKTEDTAVYY CVRHGNFGNEYISYWAYWGQGTLVTVSSGGGG SGGGGSGGGQTVVTQEPSLTVSPGGTVTLTCGS STGAVTSGNYPNWVQQKPGQAPRGLIGGTKFL APGTPARFSGSLLGGKAALTLSGVQPEDEAEYY CVLWYSNRWVFGGGTKLTVLGGGGSQTVVTQE PSFSVSPGGTVTLTCGLSSGSVSTSHYPSWYQQT PGQAPRMLIYNTNTRSSGVPDRFSGSILGNKAA LTITGAQADDESDYYCAIHVDRDIWVFGGGTKL TVLGGGGSGGGGSGGGGSQVQLVQSGGGVVQ PGTSLRLSCAASGFIFSSSAMHWVRQAPGKGLE WVAVISYDGSNKYYVDSVKGRFTISRDNSKNTL YLQMNSLRAEDTAVYYCARSARLYASFDYWGQ GALVTVSSGGGDKTHTCPPCPAPEAAGGPSVFLF PPKPKDTLMISRTPEVTCVVVDVSHEDPEVKFNWY VDGVEVHNAKTKPREEQYNSTYRVVSVTVLHQD WLNGKEYKCKVSNKALPAPIEKTISKAKGQPREPQ VYTLPPCREEMTKNQVSLWCLVKGFYPSDIAVEWE SNGQPENNYKTTPPVLDSDGSFFLYSKLTVDKSRW QQGNVFSCSVMHEALHNHYTQSLSLSPGKHHHH HH | |
| 126 (AFF6-2) | EVQLVESGGGLVQPGGSLKLSCAASGFTFNKYA MNWVRQAPGKGLEWVARIRSKYNNYATYYAD SVKDRFTISRDDSKNTAYLQMNNLKTEDTAVYY CVRHGNFGNPYISYWAYWGQGTLVTVSSGGGG SGGGGSGGGGQTVVTQEPSLTVSPGGTVTLTC GSSTGAVTSGNYPNWVQQKPGQAPRGLIGGTK FLAPGTPARFSGSLLGGKAALTLSGVQPEDEAE YYCVLWYSNRWVFGGGTKLTVLGGGGSQTVV TQEPSFSVSPGGTVTLTCGLSSGSVSTSHYPSWY QQTPGQAPRMLIYNTNTRSSGVPDRFSGSILGN KAALTITGAQADDESDYYCAIHVDRDIWVFGG GTKLTVLGGGGSGGGGSGGGGSQVQLVQSGGG VVQPGTSLRLSCAASGFIFSSSAMHWVRQAPGK GLEWVAVISYDGSNKYYVDSVKGRFTISRDNSK NTLYLQMNSLRAEDTAVYYCARSARLYASFDY WGQGALVTVSSGGGDKTHTCPPCPAPEAAGGPS VFLFPPKPKDTLMISRTPEVTCVVVDVSHEDPEVK FNWYVDGVEHNAKTKPREEQYNSTYRVVSVLTVL HQDWLNGKEYKCKVSNKALPAPIEKTISKAKGQPR EPQVYTLPPCREEMTKNQVSLWCLVKGFYPSDIAV EWESNGQPENNYKTTPPVLDSDGSFFLYSKLTVDK SRWQQGNVFSCSVMHEALHNHYTQSLSLSPGKH HHHHH | |
| 127 (AFF3-3) | QTVVTQEPSFSVSPGGTVTLTCGLSSGSVSTSHY PSWYQQTPGQAPRMLIYNTNTRSSGVPDRFSGS ILGNKAALTITGAQADDESDYYCAIHVDRDIWV FGGGTKLTVLGGGGSGGGGSGGGGSQVQLVQS GGGVVQPGTSLRLSCAASGFIFSSSAMHWVRQ APGKGLEWVAVISYDGSNKYYVDSVKGRFTISR DNSKNTLYLQMNSLRAEDTAVYYCARSARLYAS FDYWGQGALVTVSSGGGGSEVQLVESGGGLVQ PGGSLKLSCAASGFTFNKYAMNWVRQAPGKGL EWVARIRSKYNNYATYYADSVKDRFTISRDDSK NTAYLQMNNLKTEDTAVYYCVRHGNFGNEYIS YWAYWGQGTLVTVSSGGGGSGGGGSGGGGSQ TVVTQEPSLTVSPGGTVTLTCGSSTGAVTSGNYP NWVQQKPGQAPRGLIGGTKFLAPQTPARFSGLS LGGKAALTLSGVQPEDEAEYYCVLWYSNRWVF GGGTKLTVLGGGDKTHTCPPCPAPEAAGGPSVF LFPPKPKDTLMISRTPEVTCVVVDVSHEDPEVKFN WYVDGVEVHNAKTKPREEQYNSTYRVVSVLTVHQ DWLNGKEYKCKVSNKALPAPIEKTISKAKGQPREP QVYTLPPCREEMTKNQVSLWCLVKGFYPSDIAVEW ESNGQPENNYKTTPPVLDSDGSFFLYSKLTVDKSR WQQGNVFSCSVMHEALHNHYTQSLSLSPGKHH HHH | |

TABLE 9-continued

Sequence listing of the bispecific antibodies

| Antibody name (structure name) | The first polypeptide chain (SEQ ID NO) | The second polypeptide chain (SEQ ID NO) |
|---|---|---|
| 128 (AFF3-2(L2)₂) | QTVVTQEPSFSVSPGGTVTLTCGLSSGSVSTSHY<br>PSWYQQTPGQAPRMLIYNTNTRSSGVPDRFSGS<br>ILNKAALTITGAQADDESDYYCAIHVDRDIWV<br>FGGGTKLTVLGGGGSGGGGSGGGGSQVQLQS<br>GGGVVQPGTSLRLSCAASGFIFSSSAMHWVRQ<br>APGKGLEWVAVISYDGSNKYYVDSVKGRFTISR<br>DNSKNTLYLQMNSLRAEDTAVYYCARSARLYAS<br>FDYWGQGALVTVSSGGGGSGGGGSEVQLVESG<br>GGLVQPGGSLKLSCAASGFTFNKYAMNWVRQA<br>PGKGLEWVARIRSKYNNYATYYADSVKDRFTIS<br>RDDSKNTAYLQMNNLKTEDTAVYYCVRHGNFG<br>NPYISYWAYWGQGTLVTVSSGGGGSGGGGSGG<br>GGSQTVVTQEPSLTVSPGGTVTLTCGSSTGAVTS<br>GNYPNWVQQKPGQAPRGLIGGTKFLAPGTPAR<br>FSGSLLGGKAALTLSGVQPEDEAEYYCVLWYS<br>NRWVFGGGTKLTVLGGGDKTHTCPPCPAPEAA<br>*GGPSVFLFPPKPKDTLMISRTPEVTCVVVDVSHED*<br>*PEVKFNWYVDGVEVHNAKTKPREEQYNSTYRVVS*<br>*VLTVLHQDWLNGKEYKCKVSNKALPAPIEKTISKA*<br>*KGQPREPQVYTLPPCREEMTKNQVSLWCLVKGFY*<br>*PSDIAVEWESNGQPENNYKTTPPVLDSDGSFFLYS*<br>*KLTVDKSRWQQGNVFSCSVMHEALHNHYTQKSLS*<br>*LSPGK*HHHHHH | |
| 132 (AFF3-3SS) | QTVVTQEPSFSVSPGGTVTLTCGLSSGSVSTSHY<br>PSWYQQTPGQAPRMLIYNTNTRSSGVPDRFSGS<br>ILGNKAALTITGAQADDESDYYCAIHVDRDIWV<br>FGCGTKLTVLGGGGSGGGGSGGGGSQVQLVQS<br>GGGVVQPGTSLRLSCAASGFIFSSSAMHWVRQ<br>APGKCLEWVAVISYDGSNKYYVDSVKGRFTISR<br>DNSKNTLYLQMNSLRAEDTAVYYCARSARLYAS<br>FDYWGQGALVTVSSGGGGSEVQLVESGGGLVQ<br>PGGSLKLSCAASGFTFNKYAMNWVRQAPGKGL<br>EWVARIRSKYNNYATYYADSVKDRFTISRDDSK<br>NTAYLQMNNLKTEDTAVYYCVRHGNFGNEYIS<br>YWAYWGQGTLVTVSSGGGGSGGGGSGGGGSQ<br>TVVTQEPSLTVSPGGTVTLTCGSSTGAVTSGNYP<br>NWVQQKPGQAPRGLIGGTKFLAPGTPARFSGSL<br>LGGKAALTLSGVQPEDEAEYYCVLWYSNRWVF<br>GGGTKLTVLGGGDKTHTCPPCPAPEAAGGPSVF<br>*LFPPKPKDTLMISRTPEVTCVVVDVSHEDPEVKFN*<br>*WYVDGVEVHNAKTKPREEQYNSTYRVVSVLTVLHQ*<br>*DWLNGKEYKCKVSNKALPAPIEKTISKAKGQPREP*<br>*QVYTLPPCREEMTKNQVSLWCLVKGFYPSDIAVEW*<br>*ESNGQPENNYKTTPPVLDSDGSFFLYSKLTVDKSR*<br>*WQQGNVFSCSVMHEALHNHYTQKSLSLSPGK*HH<br>HHHH | |
| 131 (AFF3-1) | QTVVTQEPSFSVSPGGTVTLTCGLSSGSVSTSHY<br>PSWYQQTPGQAPRMLIYNTNTRSSGVPDRFSGS<br>ILGNKAALTITGAQADDESDYYCAIHVDRDIWV<br>FGCGTKLTVLGGGGSGGGGSGGGGSQVQLVQS<br>GGGVVQPGTSLRLSCAASGFIFSSSAMHWVRQ<br>APGKCLEWVAVISYDGSNKYYVDSVKGRFTISR<br>DNSKNTLYLQMNSLRAEDTAVYYCARSARLYAS<br>FDYWGQGALVTVSSGGGGSEVQLVESGGGLVQ<br>PGGSLKLSCAASGFTFNKYAMNWVRQAPGKGL<br>EWVARIRSKYNNYATYYADSVKDRFTISRDDSK<br>NTAYLQMNNLKTEDTAVYYCVRHGNFGNEYIS<br>YWAYWGQGTLVTVSSGGGGSGGGGSGGGGSQ<br>TVVTQEPSLTVSPGGTVTLTCGSSTGAVTSGNYP<br>NWVQQKPGQAPRGLIGGTKFLAPGTPARFSGSL<br>LGGKAALTLSGVQPEDEAEYYCVLWYSNRWVF<br>GGGTKLTVLGGGDKTHTCPPCPAPEAAGGPSVF<br>*LFPPKPKDTLMISRTPEVTCVVVDVSHEDPEVKFN*<br>*WYVDGVEVHNAKTKPREEQYNSTYRVVSVLTVLHQ*<br>*DWLNGKEYKCKVSNKALPAPIEKTISKAKGQPREP*<br>*QVYTLPPCREEMTKNQVSLWCLVKGFYPSDIAVEW*<br>*ESNGQPENNYKTTPPVLDSDGSFFLYSKLTVDKSR*<br>*WQQGNVFSCSVMHEALHNHYTQKSLSLSPGK*HH<br>HHH | |

TABLE 9-continued

Sequence listing of the bispecific antibodies

| Antibody name (structure name) | The first polypeptide chain (SEQ ID NO) | The second polypeptide chain (SEQ ID NO) |
|---|---|---|
| 154 (AFF3-4) | QTVVTQEPSFSVSPGGTVTLTCGLSSGSVSTSHY PSWYQQTPGQAPRMLIYNTNTRSSGVPDRFSGS ILGNKAALTITGAQADDESDYYCAIHVDRDIWV FGCGTKLTVLGGGGSGGGGSGGGGSQVQLVQS GGGVVQPGTSLRLSCAASGFIFSSSAMHWVRQ APGKCLEWVAVISYDGSNKYYVDSVKGRFTISR DNSKNTLYLQMNSLRAEDTAVYYCARSARLYAS FDYWGQGALVTVSSGGGGSEVQLVESGGGLVQ PGGSLKLSCAASGFTFNKYAMNWVRQAPGKGL EWVARIRSKYNNYATYYADSVKDRFTISRDDSK NTAYLQMNNLKTEDTAVYYCVRHGNFGNEYIS YWAYWGQGTLVTVSSGGGGSGGGGSGGGGSQ TVVTQEPSLTVSPGGTVTLTCGSSTGAVTSGNYP NWVQQKPGQAPRGLIGGTKFLAPGTPARFSGSL LGGKAALTLSGVQPEDEAEYYCVLWYSNRWVF GGGTKLTVLGGGDKTHTCPPCPAPEAAGGPSVF LFPPKPKDTLMISRTPEVTCVVVDVSHEDPEVKFN WYVDGVEVHNAKTKPREEQYNSTYRVVSVLTVLHQ DWLNGKEYKCKVSNKALPAPIEKTISKAKGQPREP QVYTLPPCREEMTKNQVSLWCLVKGFYPSDIAVEW ESNGQPENNYKTTPPVLDSDGSFFLYSKLTVDKSR WQQGNVFSCSVMHEALHNHYTQKSLSLSPGKHH HHHH | |
| 156 (AFF3-6) | QTVVTQEPSFSVSPGGTVTLTCGLSSGSVSTSHY PSWYQQTPGQAPRMLIYNTNTRSSGVPDRFSGS ILGNKAALTITGAQADDESDYYCAIHVDRDIWV FGCGTKLTVLGGGGSGGGGSGGGGSQVQLVQS GGGVVQPGTSLRLSCAASGFIFSSSAMHWVRQ APGKCLEWVAVISYDGSNKYYVDSVKGRFTISR DNSKNTLYLQMNSLRAEDTAVYYCARSARLYAS FDYWGQGALVTVSSGGGGSEVQLVESGGGLVQ PGGSLKLSCAASGFTFNKYAMNWVRQAPGKGL EWVARIRSKYNNYATYYADSVKDRFTISRDDSK NTAYLQMNNLKTEDTAVYYCVRHGNFGNEYIS YWAYWGQGTLVTVSSGGGGSGGGGSGGGGSQ TVVTQEPSLTVSPGGTVTLTCGSSTGAVTSGNYP NWVQQKPGQAPRGLIGGTKFLAPGTPARFSGSL LGGKAALTLSGVQPEDEAEYYCVLWYSNRWVF GGGTKLTVLGGGDKTHTCPPCPAPEAAGGPSVF LFPPKPKDTLMISRTPEVTCVVVDVSHEDPEVKFN WYVDGVEVHNAKTKPREEQYNSTYRVVSVLTVLHQ DWLNGKEYKCKVSNKALPAPIEKTISKAKGQPREP QVYTLPPCREEMTKNQVSLWCLVKGFYPSDIAVEW ESNGQPENNYKTTPPVLDSDGSFFLYSKLTVDKSR WQQGNVFSCSVMHEALHNHYTQKSLSLSPGKHH HHHH | |
| 155 (AFF3-5) | QTVVTQEPSFSVSPGGTVTLTCGLSSGSVSTSHY PSWYQQTPGQAPRMLIYNTNTRSSGVPDRFSGS ILGNKAALTITGAQADDESDYYCAIHVDRDIWV FGCGTKLTVLGGGGSGGGGSGGGGSQVQLVQS GGGVVQPGTSLRLSCAASGFIFSSSAMHWVRQ APGKCLEWVAVISYDGSNKYYVDSVKGRFTISR DNSKNTLYLQMNSLRAEDTAVYYCARSARLYAS FDYWGQGALVTVSSGGGGSEVQLVESGGGLVQ PGGSLKLSCAASGFTFNKYAMNWVRQAPGKGL EWVARIRSKYNNYATYYADSVKDRFTISRDDSK NTAYLQMNNLKTEDTAVYYCVRHGNFGNEYIS YWAYWGQGTLVTVSSGGGGSGGGGSGGGGSQ TVVTQEPSLTVSPGGTVTLTCGSSTGAVTSGNYP NWVQQKPGQAPRGLIGGTKFLAPGTPARFSGSL LGGKAALTLSGVQPEDEAEYYCVLWYSNRWVF GGGTKLTVLGGGDKTHTCPPCPAPEAAGGPSVF LFPPKPKDTLMISRTPEVTCVVVDVSHEDPEVKFN WYVDGVEVHNAKTKPREEQYNSTYRVVSVLTVLHQ DWLNGKEYKCKVSNKALPAPIEKTISKAKGQPREP QVYTLPPCREEMTKNQVSLWCLVKGFYPSDIAVEW ESNGQPENNYKTTPPVLDSDGSFFLYSKLTVDKSR WQQGNVFSCSVMHEALHNHYTQKSLSLSPGKHH HHHH | |

TABLE 9-continued

Sequence listing of the bispecific antibodies

| Antibody name (structure name) | The first polypeptide chain (SEQ ID NO) | The second polypeptide chain (SEQ ID NO) |
|---|---|---|
| 177 (AFF3-7) | QTVVTQEPSFSVSPGGTVTLTCGLSSGSVSTSHY PSWYQQTPGQAPRMLIYNTNTRSSGVPDRFSGS ILGNKAALTITGAQADDESDYYCAIHVDRDIWV FGGGTKLTVLGGGGSGGGGSGGGGSQVQLVQS GGGVVQPGTSLRLSCAASGFIFSSSAMHWVRQ APGKGLEWVAVISYDGSNKYYVDSVKGRFTISR DNSKNTLYLQMNSLRAEDTAVYYCARSARLYAS FDYWGQGALVTVSSGGGGSEVQLVESGGGLVQ PGGSLKLSCAASGFTFNKYAMNWVRQAPGKGL EWVARIRSKYNNYATEYAASVKDRFTISRDDSK NTAYLQMNNLKTEDTAVYYCVRHGNFGNSYIS YWAYWGQGTLVTVSSGGGGSGGGGSGGGGSQ TVVTQEPSLTVSPGGTVTLTCGSSTGAVTSGNYP NWVQQKPGQAPRGLIGGTKFLAPGTPARFSGSL LGGKAALTLSGVQPEDEAEYYCVLWYSNRWVF GGGTKLTVLGGGDKTHTCPPCPAPEAAGGPSVF LFPPKPKDTLMISRTPEVTCVVVDVSHEDPEVKFN WYVDGVEVHNAKTKPREEQYNSTYRVVSVLTVLHQ DWLLNGKEYKCKVSNKALPAPIEKTISKAKGQPREP QVYTLPPCREEMTKNQVSLWCLVKGFYPSDIAVEW ESNGQPENNYKTTPPVLDSDGSFFLYSKLTVDKSR WQQGNVFSCSVMHEALHNHYTQKSLSLSPGKHH HHHH | |
| 172 (AFF2-3) | QVQLVQSGGGVVQPGTSLRLSCAASGFIFSSSA MHWVRQAPGKGLEWVAVISYDGSNKYYVDSV KGRFTISRDNSKNTLYLQMNSLRAEDTAVYYCA RSARLYASFDYWGQGALVTVSSGGGGSGGGGS GGGGSQTVVTQEPSFSVSPGGTVTLTCGLSSGS VSTSHYPSWYQQTPGQAPRMLIYNTNTRSSGVP DRFSGSILGNKAALTITGAQADDESDYYCAIHV DRDIWVFGGGTKLTVLGGGGSQTVVTQEPSLTV SPGGTVTLTCGSSTGAVTSGNYPNWVQQKPGQ APRGLIGGTKFLAPGTPARFSGSLLGGKAALTLS GVQPEDEAEYYCVLWYSNRWVFGGGTKLTVLG GGGSGGGGSGGGGSEVQLVESGGGLVQPGGSL KLSCAASGFTFNKYAMNWVRQAPGKGLEWVA RIRSKYNNYATYYADSVKDRFTISRDDSKNTAYL QMNNLKTEDTAVYYCVRHGNFGNEYISYWAY WGQGTLVTVSSGGGDKTHTCPPCPAPEAAGGPS VFLFPPKPKDTLMISRTPEVTCVVVDVSHEDPEVK FNWYVDGVEVHNAKTKPREEQYNSTYRVVSVLTVL HQDWLNGKEYKCKVSNKALPAPIEKTISKAKGQPR EPQVYTLPPCREEMTKNQVSLWCLVGFYSDIAV EWESNGQPENNYKTTPPVLDSDGSFFLYSKLTVDK SRWQQGNVFSCSVMHEALHNHYTQKSLSLSPGKH HHHHH | |
| 171 (AFF1-3) | QVQLVQSGGGVVQPGTSLRLSCAASGFIFSSSA MHWVRQAPGKGLEWVAVISYDGSNKYYVDSV KGRFTISRDNSKNTLYLQMNSLRAEDTAVYYCA RSARLYASFDYWGQGALVTVSSGGGGSGGGGS GGGGSQTVVTQEPSFSVSPGGTVTLTCGLSSGS VSTSHYPSWYQQTPGQAPRMLIYNTNTRSSGVP DRFSGSILGNKAALTITGAQADDESDYYCAIHV DRDIWVFGGGTKLTVLGGGGSEVQLVESGGGL VQPGGSLKLSCAASGFTFNKYAMNWVRQAPGK GLEWVARIRSKYNNYATYYADSVKDRFTISRDD SKNTAYLQMNNLKTEDTAVYYCVRHGNFGNEY ISYWAYWGQGTLVTVSSGGGGSGGGGSGGGGS QTVVTQEPSLTVSPGGTVTLTCGSSTGAVTSGNY PNWVQQKPGQAPRGLIGGTKFLAPGTPARFSGS LLGGKAALTLSGVQPEDEAEYYCVLWYSNRWV FGGGTKLTVLGGGDKTHTCPPCPAPEAAGGPSV FLFPPKPKDTLMISRTPEVTCVVVDVSHEDPEVKF NWYVDGVEVHNAKTKPREEQYNSTYRVVSVLTVLH QDWLNGKEYKCKVSNKALPAPIEKTISKAKGQPRE PQVYTLPPCREEMTKNQVSLWCLVKGFYPSDIAVE WESNGQPENNYKTTPPVLDSDGSFFLYSKLTVDKS RWQQGNVFSCSVMHEALHNHYTQKSLSLSPGKHH HHHH | |

TABLE 9-continued

Sequence listing of the bispecific antibodies

| Antibody name (structure name) | The first polypeptide chain (SEQ ID NO) | The second polypeptide chain (SEQ ID NO) |
|---|---|---|
| 161 (AFF1-2) | QVQLVQSGGGVVQPGTSLRLSCAASGFIFSSSA MHWVRQAPGKGLEWVAVISYDGSNKYYVDSV KGRFTISRDNSKNTLYLQMNSLRAEDTAVYYCA RSARLYASFDYWGQGALVTVSSGGGGSGGGGS GGGGSQTVVTQEPSFSVSPGGTVTLTCGLSSGS VSTSHYPSWYQQTPGQAPRMLIYNTNTRSSGVP DRFSGSILGNKAALTITGAQADDESDYYCAIHV DRDIWVFGGGTKLTVLGGGGSEVQLVESGGGL VQPGGSLKLSCAASGFTFNKYAMNWVRQAPGK GLEWVARIRSKYNNYATYYADSVKDRFTISRDD SKNTAYLQMNNLKTEDTAVYYCVRHGNFGNPY ISYWAYWGQGTLVTVSSGGGGSGGGGSGGGGS QTVVTQEPSLTVSPGGTVLTLCGSSTGAVTSGNY PNWVQQKPGQAPRGLIGGTKFLAPGTPARFSGS LLGGKAALTLSGVQPEDEAEYYCVLWYSNRWV FGGGTKLTVLGGGDKTHTCPPCPAPEAAGGPSV FLFPPKPKDTLMISRTPEVTCVVVDVSHEDPEVKF NWYVDGVEVHNAKTKPREEQYNSTYRVVSVLTVLH QDWLNGKEYKCKVSNKALPAPIEKTISKAKGQPRE PQVYTLPPCREEMTKNQVSLWCLVKGFYPSDIAVE WESNGQPENNYKTTPPVLDSDGSFFLYSKLTVDKS RWQQGNVFSCSVMHEALHNHYTQKSLSLSPGKHH HHHH | |
| 162 (AFF2-2) | QVQLVQSGGGVVQPGTSLRLSCAASGFIFSSSA MHWVRQAPGKGLEWVAVISYDGSNKYYVDSV KGRFTISRDNSKNTLYLQMNSLRAEDTAVYYCA RSARLYASFDYWGQGALVTVSSGGGGSGGGGS GGGGSQTVVTQEPSFSVSPGGTVTLTCGLSSGS VSTSHYPSWYQQTPGQAPRMLIYNTNTRSSGVP DRFSGSILGNKAALTITGAQADDESDYYCAIHV DRDIWVFGGGTKLTVLGGGGSQTVVTQEPSLTV SPGGTVTLTCGSSTGAVTSGNYPNWVQQKPGQ APRGLIGGTKFLAPGTPARFSGSLLGGKAALTLS GVQPEDEAEYYCVLWYSNRWVFGGGTKLTVLG GGGSGGGGSGGGGSEVQLVESGGGLVQPGGSL KLSCAASGFTFNKYAMNWVRQAPGKGLEWVA RIRSKYNNYATYYADSVKDRFTISRDDSKNTAYL QMNNLKTEDTAVYYCVRHGNFGNPYISYWAY WGQGTLVTVSSGGGDKTHTCPPCPAPEAAGGPS VFLFPPKPKDTLMISRTPEVTCVVVDVSHEDPEVK FNWYVDGVEVHNAKTKPREEQYNSTYRVVSVLTVL HQDWLNGKEYKCKVSNKALPAPIEKTISKAKGQPR EPQVYTLPPCREEMTKNQVSLWCLVKGFYPSDIAV EWESNGQPENNYKTTPPVLDSDGSFFLYSKLTVDK SRWQQGNVFSCSVMHEALHNHYTQKSLSLSPGKH HHHHH | |

TABLE 9-continued

Sequence listing of the bispecific antibodies

| Antibody name (structure name) | The first polypeptide chain (SEQ ID NO) | The second polypeptide chain (SEQ ID NO) |
| --- | --- | --- |
| 142 (AFF3-3B) | QTVVTQEPSFSVSPGGTVTLTCGLSSGSVSTSHY PSWYQQTPGQAPRMLIYNTNTRSSGVPDRFSGS ILGNKAALTITGAQADDESDYYCAIHVDRDIWV FGGGTKLTVLGGGSGGGGSGGGGSQVQLVQS GGGVVQPGTSLRLSCAASGFIFSSSAMHWVRQ APGKGLEWVAVISYDGSNKYYVDSVKGRFTISR DNSKNTLYLQMNSLRAEDTAVYYCARSARLYAS FDYWGQGALVTVSSGGGGS*EVQLVESGGGLVQ PGGSLKLSCAASGFTFNKY*AMNWVRQAPGKGL EWVARIRSKYNNYATEYAASVKDRFTISRDDSK NTAYLQMNNLKTEDTAVYYCVRHGNFGNEYIS YWAYWGQGTLVTVSSGGGGSGGGGSGGGGSQ TVVTQEPSLTVSPGGTVTLTCGSSTGAVTSGNYP NWVQQKPGQAPRGLIGGTKFLAPGTPARFSGSL LGGKAALTLSGVQPEDEAEYYCVLWYSNRWVF GGGTKLTVLGGGDKTHTCPPCPAPEAAGGPSVF LFPPKPKDTLMISRTPEVTCVVVDVSHEDPEVKFN WYVDGVEVHNAKTKPREEQYNSTYRVVSVLTVLHQ DWLLNGKEYKCKVSNKALPAPIEKTISKAKGQPREP QVYTLPPCREEMTKNQVSLWCLVKGFYPSDIAVEW ESNGQPENNYKTTPPVLDSDGSFFLYSKLTVDKSR WQQGNVFSCSVMHEALHNHYTQKSLSLSPGKHH HHHH | *QVQLVQSGGG VVQPGTSLRL SCAASGFIFS SSAMHWVRQA PGKGLEWVAV ISYDGSNKYY VDSVKGRFTI SRDNSKNTLY LQMNSLRAED TAVYYCARSA RLYASFDYWG QGALVTVSSG* GGGSGGGGSG GGGSQTVVTQ EPSFSVSPGG TVTLTCGLSS GSVSTSHYPS WYQQTPGQAP RMLIYNTNTR SSGVPDRFSG SILGNKAALT ITGAQADDES DYYCAIHVDR DIWVFGGGTK LTVLGGGDKT HTCPPCPAPE AAGGPSVFL FPPKPKDTL MISRTPEVT CVVVDVSHE DPEVKFNWY VDGVEVHNA KTKPREEQY NSTYRVVSV LTVLHQDWL NGKEYKCKV SNKALPAPI EKTISKAKG QPREPQVCT LPPSREEMT KNQVSLSCA VKGFYPSDI AVEWESNGQ PENNYKTTP PVLDSDGSF FLVSKLTVD KSRWQQGNV FSCSVMHEA LHNHYTQKS LSLSPGK |
| 143 (AFF3-2B) | QTVVTQEPSFSVSPGGTVTLTCGLSSGSVSTSHY PSWYQQTPGQAPRMLIYNTNTRSSGVPDRFSGS ILGNKAALTITGAQADDESDYYCAIHVDRDIWV FGGGTKLTVLGGGSGGGGSGGGGSQVQLVQS GGGVVQPGTSLRLSCAASGFIFSSSAMHWVRQ APGKGLEWVAVISYDGSNKYYVDSVKGRFTISR DNSKNTLYLQMNSLRAEDTAVYYCARSARLYAS FDYWGQGALVTVSSGGGGS*EVQLVESGGGLVQ PGGSLKLSCAASGFTFNKY*AMNWVRQAPGKGL EWVARIRSKYNNYATEYAASVKDRFTISRDDSK NTAYLQMNNLKTEDTAVYYCVRHGNFGNEYIS YWAYWGQGTLVTVSSGGGGSGGGGSGGGGSQ TVVTQEPSLTVSPGGTVTLTCGSSTGAVTSGNYP NWVQQKPGQAPRGLIGGTKFLAPGTPARFSGSL LGGKAALTLSGVQPEDEAEYYCVLWYSNRWVF GGGTKLTVLGGGDKTHTCPPCPAPEAAGGPSVF LFPPKPKDTLMISRTPEVTCVVVDVSHEDPEVKFN WYVDGVEVHNAKTKPREEQYNSTYRVVSVLTVLHQ DWLNGKEYKCKVSNKALPAPIEKTISKAKGQPREP QVYTLPPCREEMTKNQVSLWCLVKGFYPSDIAVEW ESNGQPENNYKTTPPVLDSDGSFFLYSKLTVDKSR WQQGNVFSCSVMHEALHNHYTQKSLSLSPGKHH HHHH | |

TABLE 9-continued

Sequence listing of the bispecific antibodies

| Antibody name (structure name) | The first polypeptide chain (SEQ ID NO) | The second polypeptide chain (SEQ ID NO) |
|---|---|---|
| 181 (AF3-1) | SEQ ID NO: 79 | |
| 182 (AF3-2) | SEQ ID NO: 72 | |
| 183 (AF3-3) | SEQ ID NO: 76 | |
| 184 (AF3-4) | SEQ ID NO: 80 | |
| 185 (AF3-5) | SEQ ID NO: 82 | |
| 186 (AF3-6) | Seq ID No: 81 | |
| 187 (AF3-7) | Seq ID NO: 83 | |

Note:
The second polypeptide chains of the B7H3 bivalent bispecific antibody molecules 113, 118, 119, 126, 127, 128, 131, 132, 154, 155, 156, 161, 162, 171, 172 and 177 indicated in the above table are $VL_{B7H3}$-L5-$VH_{B7H3}$-L6-hole-Fc, as shown in SEQ ID NO: 71; and the second polypeptide chains of the B7H3 monovalent bispecific antibody molecules 181-187 are hole-Fc, as shown in SEQ ID NO: 70.

The amino acid sequences of the negative control (NC1, NC2, NC3) and the positive control (MGD009) bispecific antibodies used in this disclosure are as follows:

NC1: The B7H3 binding domain is replaced with a non-related antibody (anti-fluorescein antibody, anti-fluorescein), but the CD3 binding domain is retained. Reference literature for its amino acid sequence is: The anti-fluorescein antibody used to form the control DART diabody was antibody 4-4-20 (Gruber. M. et al. (1994)).

Chain 1 ($VH_{CD3}$-$VL_{CD3}$-$VL_{ctrl}$-$VH_{ctrl}$-knob-Fc)

SEQ ID NO: 89

EVQLVESGGGLVQPGGSLKLSCAASGFTFNKYAMNWVRQAPGKGLEWVA

RIRSKYNNYATYYADSVKDRFTISRDDSKNTAYLQMNNLKTEDTAVYYC

VRHGNFGNEYISYWAYWGQGTLVTVSSGGGGSGGGGSGGGGSQTVVTQE

PSLTVSPGGTVTLTCGSSTGAVTSGNYPNWVQQKPGQAPRGLIGGTKFL

APGTPARFSGSLLGGKAALTLSGVQPEDEAEYYCVLWYSNRWVFGGGTK

LTVLGGGGSDIQMTQSPSSVSASVGDRVTITCRASQDIANYLSWYQQKP

GKSPKLLIYGTSNLEVGVPSRFSGSRSGTDFTLTISSLQPEDFATYYCL

QDKEFPRTFGGGTKVEIKGGGGSGGGGSGGGGSEVQLVESGGGLVQPGG

SLRLSCAASGFTFSHYYMAWVRQAPGKGLEWVTSISYEGDITYYGDSVK

GRFTISRDNSKNTLYLQMNSLRAEDTATYYCASQTLRESFDYWGQGTLV

TVSSGGGDKTHTCPPCPAPEAAGGPSVFLFPPKPKDTLMISRTPEVTCV

VVDVSHEDPEVKFNWYVDGVEVHNAKTKPREEQYNSTYRVVSVLTVLHQ

DWLNGKEYKCKVSNKALPAPIEKTISKAKGQPREPQVYTLPPCREEMTK

NQVSLWCLVKGFYPSDIAVEWESNGQPENNYKTTPPVLDSDGSFFLYSK

LTVDKSRWQQGNVFSCSVMHEALHNHYTQKSLSLSPGKHHHHHH

Chain 2 ($VL_{ctrl}$-$VH_{ctrl}$-hole-Fc)

SEQ ID NO: 90

DIQMTQSPSSVSASVGDRVTITCRASQDIANYLSWYQQKPGKSPKLLIY

GTSNLEVGVPSRFSGSRSGTDFTLTISSLQPEDFATYYCLQDKEFPRTF

GGGTKVEIKGGGGSGGGGSGGGGSEVQLVESGGGLVQPGGSLRLSCAAS

GFTFSHYYMAWVRQAPGKGLEWVTSISYEGDITYYGDSVKGRFTISRDN

SKNTLYLQMNSLRAEDTATYYCASQTLRESFDYWGQGTLVTVSSGGGDK

THTCPPCPAPEAAGGPSVFLFPPKPKDTLMISRTPEVTCVVVDVSHEDP

EVKFNWYVDGVEVHNAKTKPREEQYNSTYRVVSVLTVLHQDWLNGKEYK

CKVSNKALPAPIEKTISKAKGQPREPQVCTLPPSREEMTKNQVSLSCAV

KGFYPSDIAVEWESNGQPENNYKTTPPVLDSDGSFFLVSKLTVDKSRWQ

QGNVFSCSVMHEALHNHYTQKSLSLSPGK

NC2: The B7H3 binding domain is retained, only the CD3 binding domain is replaced with a non-related antibody, anti-fluorescein.

Chain 1 ($VH_{ctrl}$ $VL_{ctrl}$-$VL_{B7H3}$-$VH_{B7H3}$-knob-Fc)

SEQ ID NO: 91

EVQLVESGGGLVQPGGSLRLSCAASGFTFSHYYMAWVRQAPGKGLEWVT

SISYEGDITYYGDSVKGRFTISRDNSKNTLYLQMNSLRAEDTATYYCAS

QTLRESFDYWGQGTLVTVSSGGGGSGGGGSGGGGSDIQMTQSPSSVSAS

VGDRVTITCRASQDIANYLSWYQQKPGKSPKLLIYGTSNLEVGVPSRFS

GSRSGTDFTLTISSLQPEDFATYYCLQDKEFPRTFGGGTKVEIKGGGGS

QTVVTQEPSFSVSPGGTVTLTCGLSSGSVSTSHYPSWYQQTPGQAPRML

IYNTNTRSSGVPDRFSGSILGNKAALTITGAQADDESDYYCAIHVDRDI

-continued

WVFGGGTKLTVL*GGGGSGGGGSGGGGS*QVQLVQSGGGVVQPGTSLRLSC

AASGFIFSSSAMHWVRQAPGKGLEWVAVISYDGSNKYYVDSVKGRFTIS

RDNSKNTLYLQMNSLRAEDTAVYYCARSARLYASFDYWGQGALVTVSSG

GGDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNG

KEYKCKVSNKALPAPIEKTISKAKGQPREPQVYTLPPCREEMTKNQVSL

WCLVKGFYPSDIAVEWESNGQPENNYKTTPPVLDSDGSFFLYSKLTVDK

SRWQQGNVFSCSVMHEALHNHYTQKSLSLSPGKHEIHHHH

Chain 2
SEQ ID NO: 92
QTVVTQEPSFSVSPGGTVTLTCGLSSGSVSTSHYPSWYQQTPGQAPRML

IYNTNTRSSGVPDRFSGSILGNKAALTITGAQADDESDYYCAIHVDRDI

WVFGGGTKLTVLGGGGSGGGGSGGGGSQVQLVQSGGGVVQPGTSLRLSC

AASGFIFSSSAMHWVRQAPGKGLEWVAVISYDGSNKYYVDSVKGRFTIS

RDNSKNTLYLQMNSLRAEDTAVYYCARSARLYASFDYWGQGALVTVSSG

GGDKTHTCPPCP*APEAAGGPSVFLEPPKPKDTLMISRTPEVTCVVVDVS*

*HEDPEVKFNWYVDGVEVHNAKTKPREEQYNSTYRVVSVLTVLHQDWLNG*

*KEYKCKVSNKALPAPIEKTISKAKGQPREPQVCTLPPSREEMTKNQVSL*

*SCAVKGFYPSDIAVEWESNGQPENNYKTTPPVLDSDGSFFLVSKLTVDK*

*SRWQQGNVFSCSVMHEALHNHYTQKSLSLSPGK*

Note:
The arrangement order is VLB7H3-linker-VHB7H3-
linker-Fc. The underlined sequences represent the
B7H3 antibody sequences, and the italics
represent the hole-Fc sequence.

NC3

Chain 1 (VL$_{ctrl}$-VH$_{ctrl}$-VH$_{CD3}$-VL$_{CD3}$-knob-Fc-His tag)
SEQ ID NO: 93
DIQMTQSPSSVSASVGDRVTITCRASQDIANYLSWYQQKPGKSPKLLIY

GTSNLEVGVPSRFSGSRSGTDFTLTISSLQPEDFATYYCLQDKEFPRTF

GGGTKVEIKGGGSGGGGSGGGGSEVQLVESGGGLVQPGGSLRLSCAAS

GFTFSHYYMAWVRQAPGKGLEWVTSISYEGDITYYGDSVKGRFTISRDN

SKNTLYLQMNSLRAEDTATYYCASQTLRESFDYWGQGTLVTVSSGGGGS

EVQLVESGGGLVQPGGSLKLSCAASGFTFNKYAMNWVRQAPGKGLEWVA

RIRSKYNNYATYYADSVKDRFTISRDDSKNTAYLQMNNLKTEDTAVYYC

VRHGNFGNEYISYWAYWGQGTLVTVSSGGGGSGGGGSGGGGSQTVVTQE

PSLTVSPGGTVTLTCGSSTGAVTSGNYPNWVQQKPGQAPRGLIGGTKFL

APGTPARFSGSLLGKAALTLSGVQPEDEAEYYCVLWYSNRWVFGGGTK

LTVLGGGDKTHTCPPCPAPEAAGGPSVFLFPPKPKDTLMISRTPEVTCV

VVDVSHEDPEVKFNWYVDGVEVHNAKTKPREEQYNSTYRVVSVLTVLHQ

DWLNGKEYKCKVSNKALPAPIEKTISKAKGQPREPQVYTLPPCREEMTK

NQVSLWCLVKGFYPSDIAVEWESNGQPENNYKTTPPVLDSDGSFFLYSK

LTVDKSRWQQGNVFSCSVMHEALHNHYTQKSLSLSPGKHEIHHHH

Chain 2 (VL$_{ctrl}$-VH$_{ctrl}$-hole-Fc)
SEQ ID NO: 94
DIQMTQSPSSVSASVGDRVTITCRASQDIANYLSWYQQKPGKSPKLLIY

GTSNLEVGVPSRFSGSRSGTDFTLTISSLQPEDFATYYCLQDKEFPRTF

GGGTKVEIKGGGSGGGGSGGGGSEVQLVESGGGLVQPGGSLRLSCAAS

GFTFSHYYMAWVRQAPGKGLEWVTSISYEGDITYYGDSVKGRFTISRDN

SKNTLYLQMNSLRAEDTATYYCASQTLRESFDYWGQGTLVTVSSGGGDK

THTCPPCPAPEAAGGPSVFLFPPKPKDTLMISRTPEVTCVVVDVSHEDP

EVKFNWYVDGVEVHNAKTKPREEQYNSTYRVVSVLTVLHQDWLNGKEYK

CKVSNKALPAPIEKTISKAKGQPREPQVCTLPPSREEMTKNQVSLSCAV

KGFYPSDIAVEWESNGQPENNYKTTPPVLDSDGSFFLVSKLTVDKSRWQ

QGNVFSCSVMHEALHNHYTQKSLSLSPGK

The positive control MGD009 comprises three chains, and the preparation and amino acid sequences can be found in the published patent application WO2017030926A1. Its amino acid sequences are as follows:

Chain 1 (B7H3VL-CD3VH-Fc)
SEQ ID NO: 95
DIQLTQSPSFLSASVGDRVTITCKASQNVDTNVAWYQQKPGKAPKALIY

SASYRYSGVPSRFSGSGSGTDFTLTISSLQPEDFATYYCQQYNNYPFTF

GQGTKLEIKGGGSGGGGEVQLVESGGGLVQPGGSLRLSCAASGFTFSTY

AMNWVRQAPGKGLEWVGRIRSKYNNYATYYADSVKDRFTISRDDSKNSL

YLQMNSLKTEDTAVYYCVRHGNFGNSYVSWFAYWGQGTLVTVSSGGCGG

GEVAALEKEVAALEKEVAALEKEVAALEKGGGDKTHTCPPCPAPEAAGG

PSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKT

ISKAKGQPREPQVYTLPPSREEMTKNQVSLWCLVKGFYPSDIAVEWESN

GQPENNYKTTPPVLDSDGSFFLYSKLTVDKSRWQQGNVFSCSVMHEALH

NHYTQKSLSLSPGK

Chain 2 (CD3VL-B7H3VH)
SEQ ID NO: 96
QAVVTQEPSLTVSPGGTVTLTCRSSTGAVTTSNYANWVQQKPGQAPRGL

IGGTNKRAPWTPARFSGSLLGGKAALTITGAQAEDEADYYCALWYSNLW

VFGGGTKLTVLGGGGSGGGGEVQLVESGGGLVQPGGSLRLSCAASGFTF

SSFGIVIRWVRQAPGKGLEWVAYISSDSSAIYYADTVKGRFTISRDNAK

NSLYLQMNSLRDEDTAVYYCGRGRENIYYGSRLDYWGQGTTVTVSSGGC

GGGKVAALKEKVAALKEKVAALKEKVAALKE

Chain 3 (Fc)
SEQ ID NO: 97
DKTHTCPPCPAPEAAGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLSC

AVKGFYPSDIAVEWESNGQPENNYKTTPPVLDSDGSFFLVSKLTVDKSR
WQQGNVFSCSVMHEALHNRYTQKSLSLSPGK 201 (DART-Fc Three-Chain Structure) 201 chain 1
(B7H3VL-CD3VH-E-Fc)

SEQ ID NO: 99

QTVVTQEPSFSVSPGGTVTLTCGLSSGSVSTSHYPSWYQQTPGQAPRML
IYNTNTRSSGVPDRFSGSILGNKAALTITGAQADDESDYYCAIHVDRDI
WVFGGGTKLTVLGGGSGGGGEVQLVESGGGLVQPGGSLKLSCAASGFTF
NKYAMNWVRQAPGKGLEWVARIRSKYNNYATYYADSVKDRFTISRDDSK
NTAYLQMNNLKTEDTAVYYCVRHGNFGNEYISYWAYWGQGTLVTVSSGG
CGGGEVAALEKEVAALEKEVAALEKEVAALEKGGGDKTHTCPPCPAPEA
AGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPI
EKTISKAKGQPREPQVYTLPPSREEMTKNQVSLWCLVKGFYPSDIAVEW
ESNGQPENNYKTTPPVLDSDGSFFLYSKLTVDKSRWQQGNVFSCSVMHE
ALHNHYTQKSLSLSPGKHEIREIHH 201 chain 2 (CD3VL-B7H3VH-K)

SEQ ID NO: 100

QTVVTQEPSLTVSPGGTVTLTCGSSTGAVTSGNYPNWVQQKPGQAPRGL
IGGTKFLAPGTPARFSGSLLGGKAALTLSGVQPEDEAEYYCVLWYSNRW
VFGGGTKLTVLGGGSGGGGQVQLVQSGGGVVQPGTSLRLSCAASGFIF
SSSAMEIWVRQAPGKGLEWVAVISYDGSNKYYVDSVKGRFTISRDNSKN
TLYLQMNSLRAEDTAVYYCARSARLYASFDYWGQGALVTVSSGGCGGGK
VAALKEKVAALKEKVAALKEKVAALKE

201 Chain 3

SEQ ID NO: 97

DKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLSC
AVKGFYPSDIAVEWESNGQPENNYKTTPPVLDSDGSFFLVSKLTVDKSR
WQQGNVFSCSVMHEALHNRYTQKSLSLSPGK 202 (Four-Chain Structure, where the mass ratio of the four chains Is Chain 1: Chain 2: Chain 3: Chain 4=1:2:1:1)

202 chain 1 (B7H3VH-CH1-Fc)

SEQ ID NO: 101

QVQLVQSGGGVVQPGTSLRLSCAASGFIFSSSAMHWVRQAPGKGLEWVA
VISYDGSNKYYVDSVKGRFTISRDNSKNTLYLQMNSLRAEDTAVYYCAR
SARLYASFDYWGQGALVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPEAAGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPCREEMTKNQVSLWCLVKGFYPSDIAVEWESNGQPENN
YKTTPPVLDSDGSFFLYSKLTVDKSRWQQGNVFSCSVMHEALHNHYTQK
SLSLSPGKHEIHEIHH 202 chain 2 (B7H3VL-CL)

SEQ ID NO: 102

QTVVTQEPSFSVSPGGTVTLTCGLSSGSVSTSHYPSWYQQTPGQAPRML
IYNTNTRSSGVPDRFSGSILGNKAALTITGAQADDESDYYCAIHVDRDI
WVFGGGTKLTVLRTVAAPSVFIFPPSDEQLKSGTASVVCLLNNFYPREA
KVQWKVDNALQSGNSQESVTEQDSKDSTYSLSSTLTLSKADYEKHKVYA
CEVTHQGLSSPVTKSFNRGEC 202 chain 3 (B7H3 VH-CH1-CD3VH-CL)

SEQ ID NO: 103

QVQLVQSGGGVVQPGTSLRLSCAASGFIFSSSAMHWVRQAPGKGLEWVA
VISYDGSNKYYVDSVKGRFTISRDNSKNTLYLQMNSLRAEDTAVYYCAR
SARLYASFDYWGQGALVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDGGGGSGGGGSEVQLVESGGGLV
QPGGSLKLSCAASGFTFNKYAMNWVRQAPGKGLEWVARIRSKYNNYATY
YADSVKDRFTISRDDSKNTAYLQMNNLKTEDTAVYYCVRHGNFGNEYIS
YWAYWGQGTLVTVSSASVAAPSVFIFPPSDEQLKSGTASVVCLLNNFYP
REAKVQWKVDNALQSGNSQESVTEQDSKDSTYSLSSTLTLSKADYEKHK
VYACEVTHQGLSSPVTKSFNRGECDKTHTCPPCPAPEAAGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQP
REPQVCTLPPSREEMTKNQVSLSCAVKGFYPSDIAVEWESNGQPENNYK
TTPPVLDSDGSFFLVSKLTVDKSRWQQGNVFSCSVMHEALHNHYTQKSL
SLSPGK 202 chain 4 (CD3VL-CH1)

SEQ ID NO: 104

QTVVTQEPSLTVSPGGTVTLTCGSSTGAVTSGNYPNWVQQKPGQAPRGL
IGGTKFLAPGTPARFSGSLLGGKAALTLSGVQPEDEAEYYCVLWYSNRW
VFGGGTKLTVLSSASTKGPSVFPLAPSSKSTSGGTAALGCLVKDYFPEP
VTVSWNSGALTSGVHTFPAVLQSSGLYSLSSVVTVPSSSLGTQTYICNV
NHKPSNTKVDKKVEPKSC.

Example 2. Expression and Purification of CD3-B7H3 Bispecific Antibodies

HEK293E cells were transfected with the plasmid expressing the bispecific antibody (chain 1: chain 2 is 1:1), the expression supernatant was collected 6 days later, and the impurities were removed by high-speed centrifugation. The clarified supernatant was purified on a Ni Sepharose™ excel column (GE Healthcare). The column was washed with PBS until the A280 reading dropped to the baseline, and then the column was washed with PBS+10 mM imidazole to remove non-specifically bound impurity proteins, and the effluent was collected. Finally, the target protein was eluted with PBS solution containing 300 mM imidazole, and the elution peaks were collected. The eluate samples were properly concentrated and then were further purified with the gel chromatography Superdex™200 (GE) pre-equilibrated with 550 buffer (10 mM acetic acid, pH5.5, 135 mM NaCl). The target peak was collected. The sample was equilibrated against 559 buffer (10 mM acetic acid, pH5.5, 9% sucrose) through a desalting column or ultrafiltration centrifuge tube, and aliquoted and stored at −80° C.

Test Example 1. Affinity of the Bispecific Antibodies to B7H3 and CD3 Detected by BIAcore™ Assay The detection of antibody affinity to B7H3 and CD3 was performed in the form of capture antibody. BsAb was captured by CM5 biosensor chip (Cat. #BR-1005-30, GE) or Protein A (Cat. #29127556, GE) biosensor chip coupled with Anti-Human IgG Antibody (Cat. #BR-1008-39, Lot. #10260416, GE), and then each antigen flowed through the surface of the chip. The reaction signals were detected in real time with the Biacore™ T200 instrument to obtain the binding and dissociation curves. After the dissociation of each experimental cycle was completed, the chip was washed and regenerated with regeneration buffer Glycine1.5 (Cat #BR100354, GE) or 3 M MgCl$_2$ (from Human antibody capture kit, Cat. #BR100839, GE). The data were fitted with the (1:1) Langmuir model using GE Biacore™ T200 Evaluation version 3.0 software, and the affinity values were obtained.

With the arrangement order unchanged, the affinity of the bispecific antibodies to CD3 was slightly changed, when the sequences of CD3 antibody VH varied. When HRH-6 and HRH-5 sequences were used, the affinity of the antibody to CD3 was the weakest, and the binding to CD3 was not detectable by Biacore™.

TABLE 10

Biacore assay results of the antigen-binding affinity of the bispecific antibodies with AFF3 structure

| Bispecific antibody | CD3 VH involved | BIAcore KD(M) |
| --- | --- | --- |
| 131 | HRH-1 | 4.07E−08 |
| 113 | HRH-2 | 7.72E−08 |
| 127 | HRH-3 | 9.72E−08 |
| 154 | HRH-4 | 6.97E−08 |
| 156 | HRH-6 | No binding |
| 155 | HRH-5 | No binding |
| 177 | HRH-7 | 1.62E−07 |

As an example, antibodies comprising HRH3 as the heavy chain variable region of the CD3 antigen-binding domain were selected for the assay. Among the selected antibodies, the test antibodies 118, 127 and 132 have an affinity to human B7H3 and human CD3 at levels of $10^{-9}$ and $10^{-8}$M, respectively, which are comparable to those of MGD009. These antibodies all have strong cross-binding activity to both monkey (cyno) B7H3 and human CD3.

TABLE 11

Biacore assay results of the antigen-binding affinity of the bispecific antibodies comprising HRH3 arranged in different orders

| | Affinity (M) | | | |
| --- | --- | --- | --- | --- |
| Antibody | Human B7H3 | Monkey B7H3 | Human CD3 | Monkey CD3 |
| MGD009 | 1.96E−09 | 2.65E−09 | 7.81E−08 | 4.94E−09 |
| 118 | 5.33E−09 | 7.31E−09 | 6.61E−08 | 1.59E−09 |
| 127 | 4.29E−09 | 5.61E−09 | 8.47E−08 | 1.24E−09 |
| 132 | 5.35E−09 | 6.90E−09 | 8.53E−08 | 8.13E−10 |

Test Example 2. Determination of the Antibody Binding Ability at Cell Level

The ability of bispecific antibodies to bind to cell surface antigens was detected by FACS method. A498 (ATCC™, HTB-44), CT26/hB7H3 (a recombinant cell line over-expressing human B7H3 in mouse cell CT26, constructed in-house, CT26 was obtained from the Cell Bank of Chinese Academy of Sciences, TCM37) and Jurkat recombinant cell lines (Jurkat cells were obtained from ATCC™, PTS-TIB-152; the recombinant cell line was obtained on the basis of Jurkat cells by over-expressing luciferase gene and inserting NFAT response element upstream of the gene) were separately used for binding to antigens B7H3 and CD3 on cell surface.

FACS buffer (98% PBS, 2% FBS) was added into a 96-well U-shaped bottom plate (corning, 3795) to resuspend the cells, the serially diluted antibodies were added, incubated at 4° C. for 1 hour, and the plate was washed with FACS buffer twice. Then APC anti-human IgG Fc Antibody (biolegend, Cat #409306, dilution at 1:50) was added into each well, incubated at 4° C. for 30 minutes, washed twice, the cells were resuspended in FACS buffer, and finally the fluorescence signal values were read by FACS Canto™II (BD).

Figure 2A:
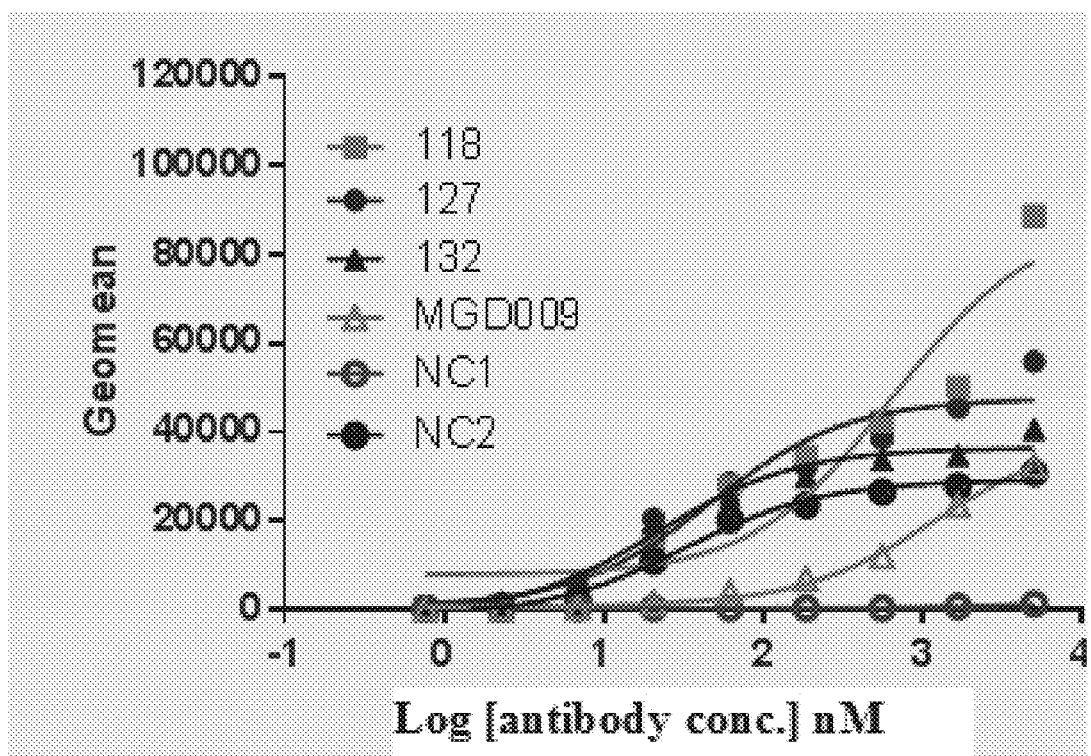
FIG. 2A to FIG. 2D: Detection of the antibodies by flowcytometry for the activity of binding to cells with the expression of or without the expression of corresponding antigen.
Figure 2B:
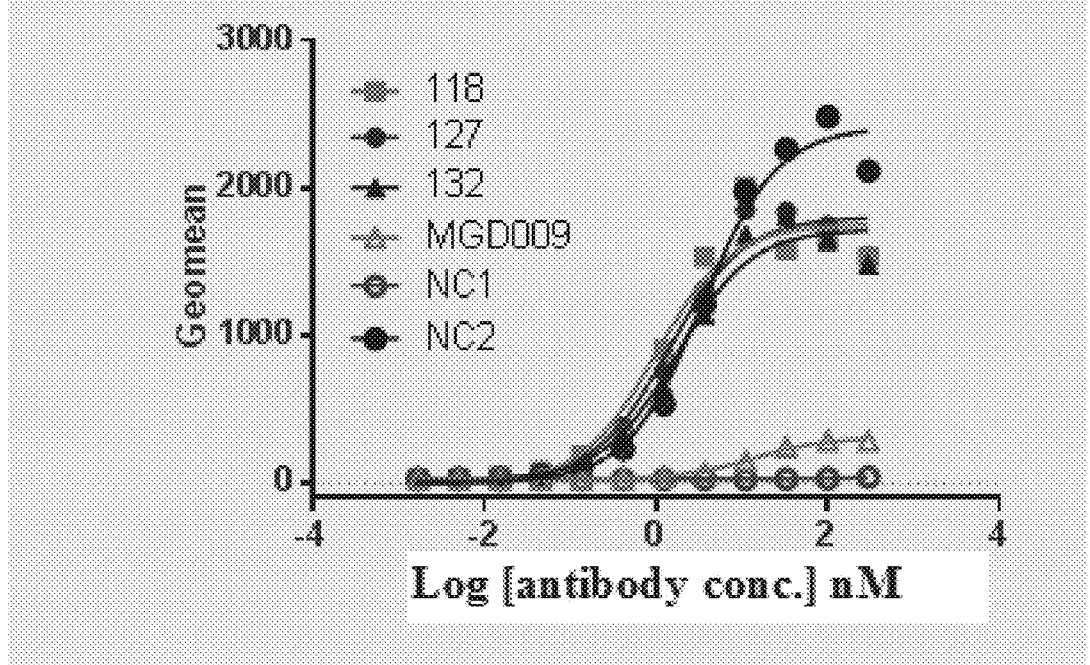
Figure 2C:
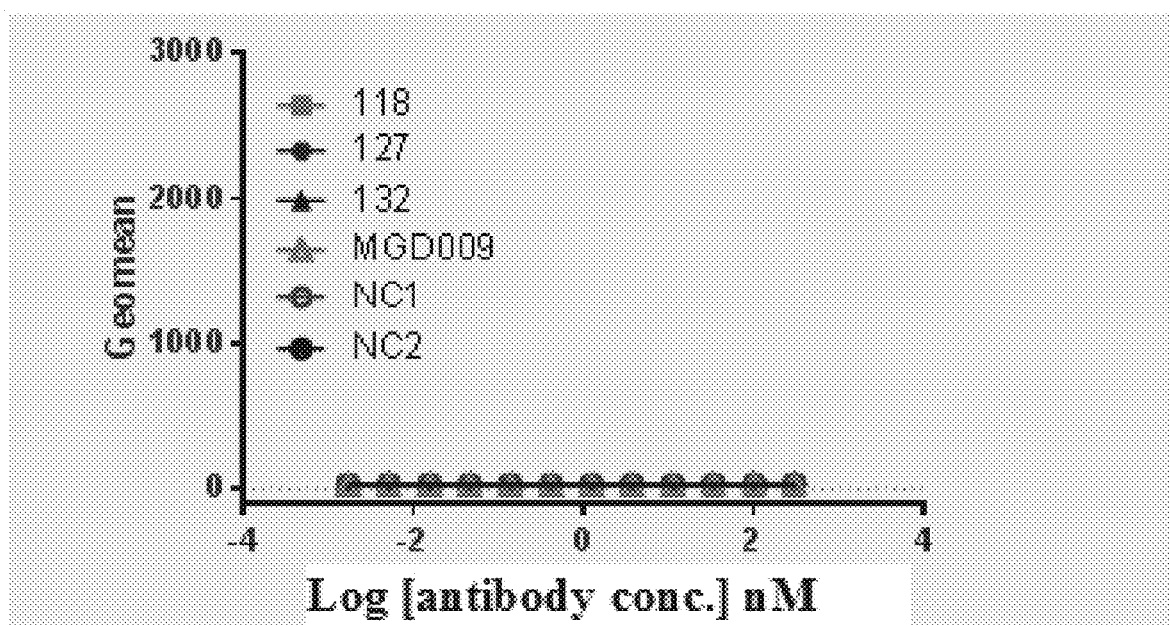

The results show that the B7H3 bivalent bispecific antibodies 118, 127, and 132 and the negative control antibody NC2 (in which the B7H3 binding domain was retained, and the CD3 binding domain was replaced with an unrelated antibody) are capable of binding to the A498 cell line (which highly expresses B7H3) (See FIG. 2A), showing a gradient-dependent effect, with binding capacity stronger than that of MGD009, and specific for the B7H3 target. The negative control antibody NC1 (in which the B7H3 binding domain was replaced with a non-related antibody, but the CD3 binding domain was retained) does not bind to A498. Similarly, the bispecific antibodies 118, 127 and 132, MGD009 and NC2 strongly bind to CT26/hB7H3 (see FIG. 2B), but do not bind to the CT26 cell line that does not express B7H3 (see FIG. 2C), which also fully demonstrates that the test bispecific antibodies specifically bind to the B7H3 target on the cell membrane surface. The antibodies 118, 127 and 132 exhibit different binding ability from that of MGD009, such difference in binding ability is much significant on B7H3 over-expressing CT26/hB7H3 cell line than that on A498 cell line, indicating that the B7H3 bivalent bispecific antibodies have a more significant advantage for binding to B7H3 highly-expressing cells, and will have a better safety window compared to the B7H3 monovalent bispecific antibody MGD009.

Figure 2D:
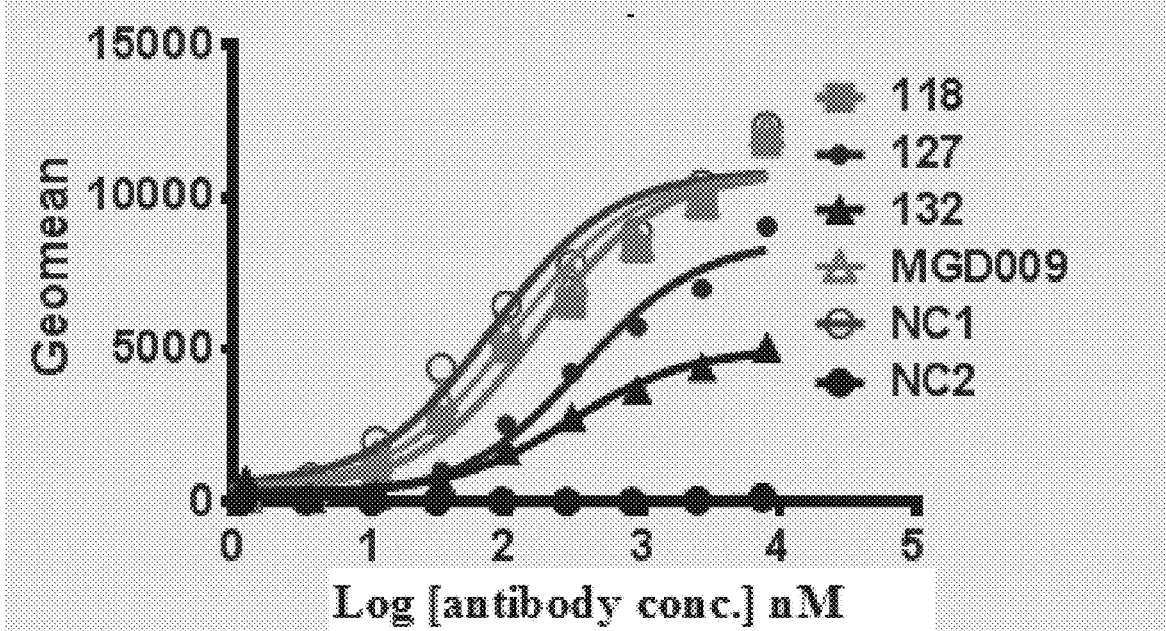

The bispecific antibodies 118, 127 and 132 and the negative control antibody NC1 can bind to the Jurkat recombinant cell line (see FIG. 2D), showing a gradient-dependent effect. Among these antibodies, 118 and NC1 have a Jurkat recombinant cell binding ability equivalent to that of MGD009, whereas 127 and 132 show a lightly weaker binding ability. This can be because that the CD3 binding domain is located between the B7H3 binding domain and FC, and a certain steric hindrance may affect the binding to Jurkat recombinant cells. The negative control antibody NC2 without the CD3 binding domain does not bind to Jurkat recombinant cells, indicating that the binding of the bispecific antibodies to Jurkat is specific for the CD3 target.

Test Example 3. In Vitro PBMC Killing Assay

Bispecific antibody-mediated PBMC killing assay on tumor cells was achieved by quantitatively detecting cell proliferation. The content of ATP, an indicator of the metabolism of living cells and being directly proportional to the number of cells in the culture, was detected by using Cell Titer-Glo® in cells.

Four different target cells (T), including three tumor cell lines with different expression levels of B7H3 (A498, U87 (Cell Bank of Chinese Academy of Sciences, TCHu138), Detroit562 (ATCC™, CCL-138)), and one negative control cell line CHOK1 that does not express B7H3 (ATCC™, CCL-61) were used. Effector cells (E) were PBMCs obtained from healthy volunteers. The target cells were inoculated in a 96-well plate, cultured overnight, and equal amounts of freshly extracted PBMCs and serially diluted test bispecific antibodies (the highest final concentration was 300 nM, diluted at 1:3), or PBS (control, with effector cells and target cells, without antibody) was added to each well on the next day. Blank controls (blank, medium only, without cells or antibodies) were set. The ratios of E:T were 10:1, 5:1, 5:1 and 5:1, respectively, for A498, U87, Detroit562 and CHOK1 cells. The cells were incubated for 48 hours and detected with Cell Titer-Glo® (refer to the instruction manual). The signal values were read on a microplate reader, and finally converted into the inhibition rate. The data were processed and analyzed by using Graphpad Prism 5.

Inhibition rate % (Inhibition %)=100%−(signal value $_{sample}$−signal value $_{blank}$)/(signal value $_{control}$−signal value $_{blank}$).

Figure 3A:
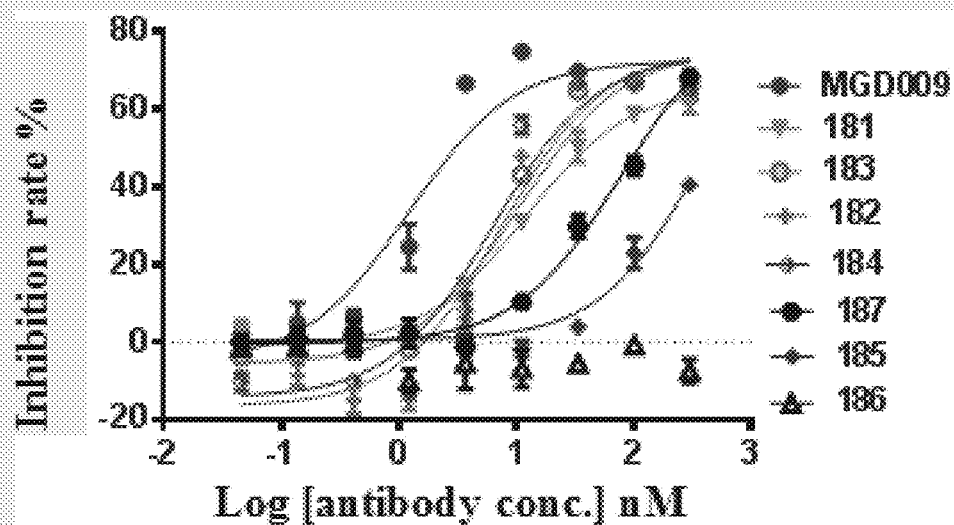
FIG. 3A to FIG. 3B: Detection of the activity of bispecific antibodies comprising various CD3 scFvs in killing A498.
Figure 3B:
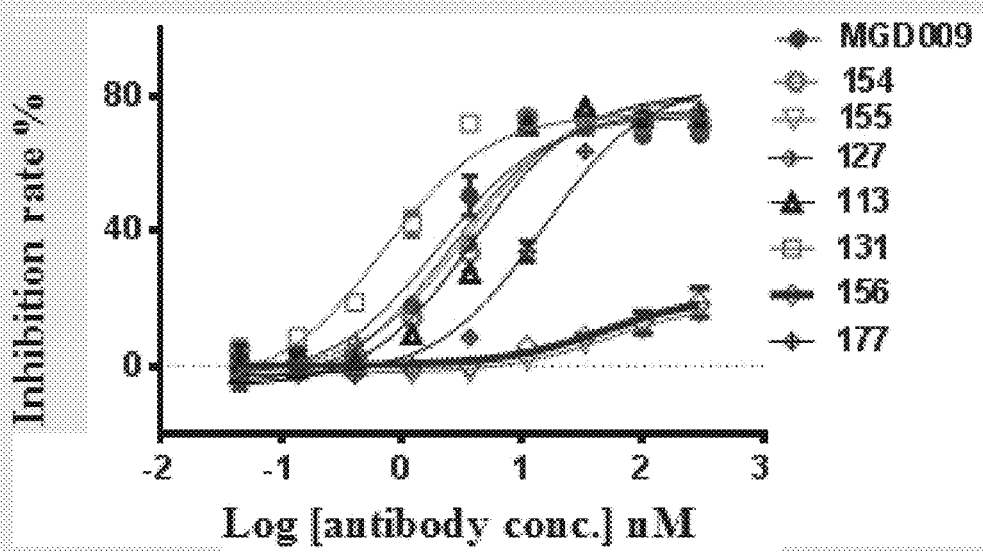

3.1 Comparison of Antibodies Comprising Different CD3 Antigen-Binding Domain with Varying Affinity CD3 scFvs with different affinities were used to construct various bispecific antibodies, which show different in vitro target cell killing effects (see FIG. 3A and FIG. 3B). The bispecific antibodies 155, 156, 185 and 186 comprising HRH5 and HRH6, respectively show the weakest killing effect, which is consistent with the results of the Biacore™ affinity assay.

3.2 Comparison of B7H3 Monovalent and Bivalent Bispecific Antibodies

Figures 4A, 4B:
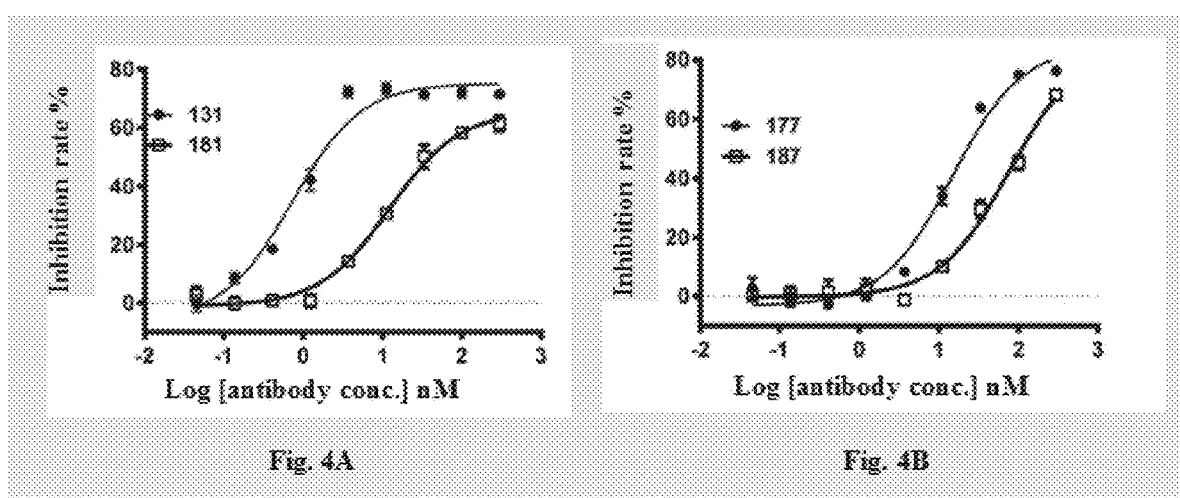
FIG. 4A to FIG. 4B: Comparison of the killing activity against A498 between B7H3 mono- and bi-valent bispecific antibodies comprising the same CD3 scFv.

The comparison of the structure AFF3 (131 and 177 were used as exemplary antibodies of this structure) and AF3 (181 and 187 were used as exemplary antibodies of this structure) was performed as an illustrative example for the bispecific antibodies constructed from scFvs containing different anti-CD3 antibody heavy chain variable regions (see FIG. 4A and FIG. 4B). The B7H3 bivalent bispecific antibodies with AFF3 structure of CD3-B7H3 have significantly enhanced in vitro cell killing activity compared to the B7H3 monovalent bispecific antibodies with the AF3 structure. This applies for all bispecific antibodies containing different CD3 VHs.

TABLE 12

Antibody arrangement order

| Name of the structure | First polypeptide chain | Second polypeptide chain |
|---|---|---|
| AFF3 | $VL_{B7H3}$-L1-$VH_{B7H3}$-L2-$VH_{CD3}$-L3-$VL_{CD3}$-L4-$F_C$1 | $VL_{B7H3}$-L5-$VH_{B7H3}$-L6-$F_C$2 |
| AF3 | $VL_{B7H3}$-L1-$VH_{B7H3}$-L2-$VH_{CD3}$-L3-$VL_{CD3}$-L4-$F_C$1 | Fc2 |

Figure 5A:
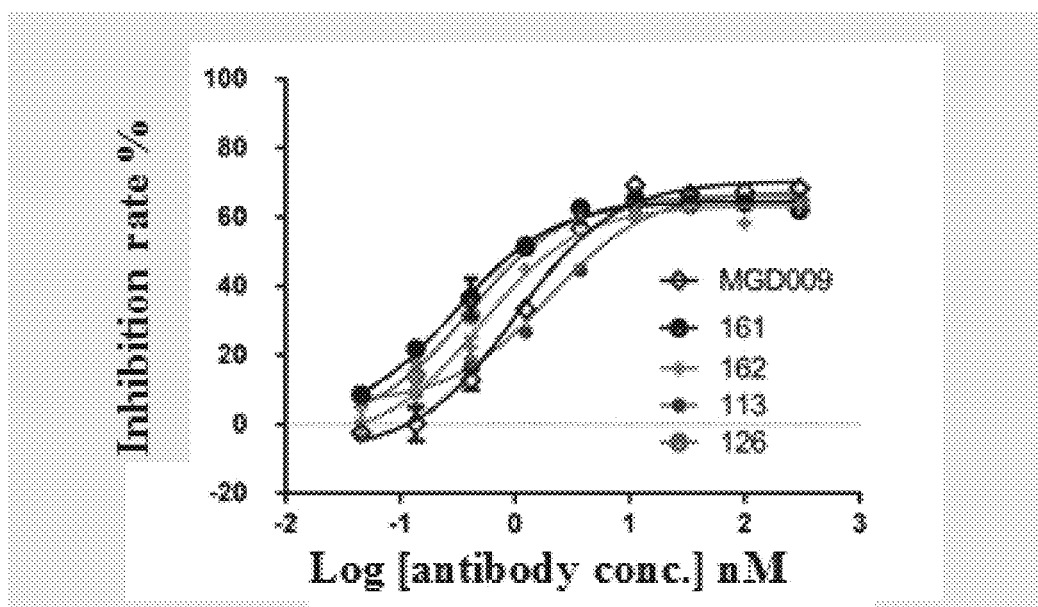
FIG. 5A to FIG. 5C: Detection of the killing activity against A498 of B7H3 bivalent bispecific antibodies comprising the same CD3 heavy chain variable region, but with different arrangement orders.
Figure 5B:
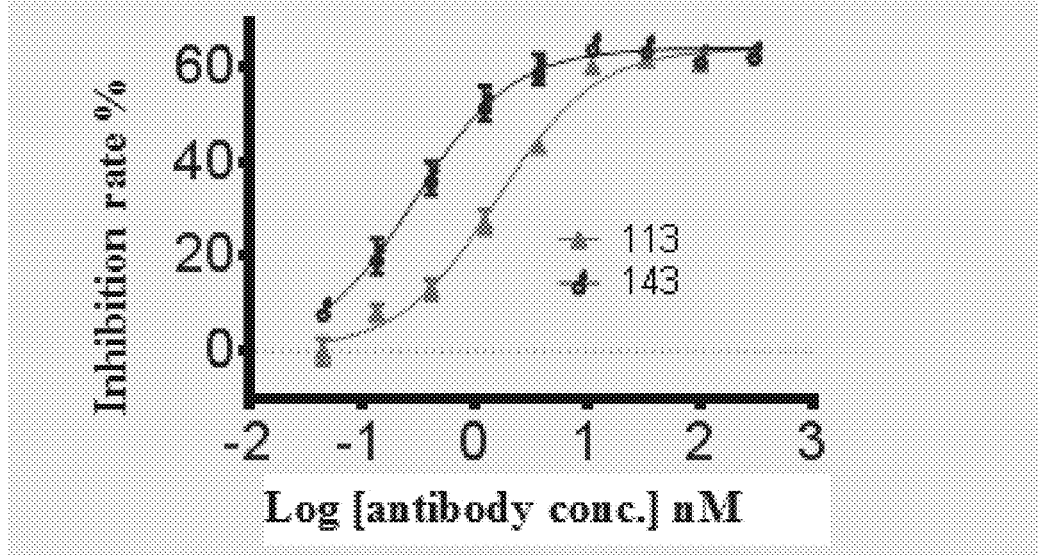

3.3 the Effect of Different Molecular Structures of the B7H3 Bivalent Bispecific Antibodies on Tumor Killing Activity The B7H3 bivalent bispecific antibody molecules 161, 162, 113 and 126 (see FIG. 5A) and 113 and 143 (see FIG. 5B) that share the same antigen-binding domain components but different arrangement orders, were tested in parallel for tumor cell killing activity. All the above molecules have HRH2 as the heavy chain variable region of the CD3 antigen-binding domain. The results show that the B7H3 bivalent specific antibody molecules with different arrangement orders all have significant killing effects on A498 cells. Among these antibodies, the 161, 162, 113 and 126 have a killing activity equivalent or slightly superior to that of MGD009. The arrangement order of the different structures has little effect on the tumor cell killing activity of the B7H3 bivalent bispecific antibodies.

TABLE 13

Comparison of the structure of the different test antibodies

| Antibody | Name of the structure | First polypeptide chain | Second polypeptide chain |
|---|---|---|---|
| 161 | AFF1-2 | $VH_{B7H3}$-L1-$VL_{B7H3}$-L2-$VH_{CD3}$(HRH2)-L3-$VL_{CD3}$-L4-Fc1 | $VL_{B7H3}$-L5-$VH_{B7H3}$-L6-Fc2 |
| 162 | AFF2-2 | $VH_{B7H3}$-L1-$VL_{B7H3}$-L2-$VL_{CD3}$-L3-$VH_{CD3}$(HRH2)-L4-Fcl | $VL_{B7H3}$-L5-$VH_{B7H3}$-L6-Fc2 |
| 113 | AFF3-2 | $VL_{B7H3}$-L1-$VH_{B7H3}$-L2-$VH_{CD3}$(HRH2)-L3-$VL_{CD3}$-L4-Fc1 | $VL_{B7H3}$-L5-$VH_{B7H3}$-L6-Fc2 |
| 126 | AFF6-2 | $VH_{CD3}$(HRH2)-L1-$VL_{CD3}$-L2-$VL_{B7H3}$-L3-$VH_{B7H3}$-L4-FC1 | $VL_{B7H3}$-L5-$VH_{B7H3}$-L6-Fc2 |
| 143 | AFF3-2B | $VL_{B7H3}$-L1-$VH_{B7H3}$-L2-$VH_{CD3}$(HRH2)-L3-$VL_{CD3}$-L4-Fc1 | $VH_{B7H3}$-L5-$VL_{B7H3}$-L6-Fc2 |

3.4 Bispecific Antibodies have Killing Effects on Tumor Cell Lines with Different Expression Levels of B7H13

The three test bispecific antibodies 118, 127 and 132 were tested for the in vitro killing effects on A498, U87 and Detroit562 tumor cell lines. The killing effect is positively correlated with the expression level of B7H3. For example, the 118 has EC50 of 0.34, 2.4 and 14.5 nM for A498, U87 and Detroit 562, respectively. All the three antibody molecules show this tendency. None of the bispecific antibodies have killing effect on the B7H3-negative control cell line CHOK1, and the negative control bispecific antibody NC1 did not have killing effect on any of the target cell lines. Together, these two aspects indicate that the cell killing is a target-specific killing, which requires redirecting the effector cells towards the B7H3 positive target cells by the bispecific antibodies.

TABLE 14

Redirection of PBMCs mediated by the test bispecific antibodies towards killing of different target cell lines

| Cell line | B7H3 expression | 118 | | 127 | | 132 | | NC1 | |
|---|---|---|---|---|---|---|---|---|---|
| | | IC50 (nM) | Emax (%) | IC50 (nM) | Emax (%) | IC50 (nM) | Emax (%) | IC50 (nM) | Emax (%) |
| A498 | high | 0.34 | 65.9 | 2.4 | 67.5 | 2.94 | 66.4 | >300 | 20.9 |
| U87 | intermediate | 2.4 | 67.2 | 8.2 | 69.5 | 11.9 | 67.6 | >300 | 3.8 |
| Detroit562 | low | 14.5 | 39.24 | 15.8 | 26.46 | 15.7 | 15.23 | >300 | 0.95 |
| CHOK1 | Negative | >300 | 1.83 | >300 | 3.91 | >300 | 0.00 | >300 | 0.81 |

Figure 5C:
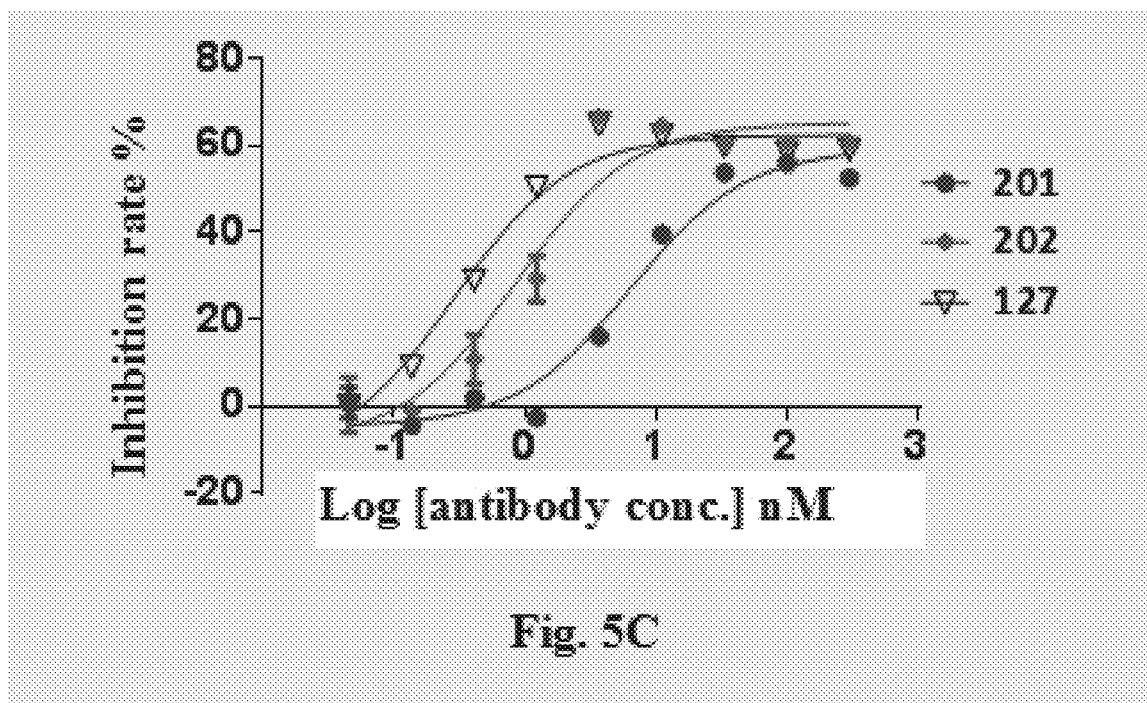

3.5 Comparison of the Killing Effects of Bispecific Antibodies with Different Structures on A498 Cells The three test bispecific antibodies 127, 201 and 202 were tested for the in vitro killing effects on A498 tumor cell lines. The results show (see FIG. 5C) that the bispecific antibodies with the three structures all have tumor killing activity, among which, the bispecific antibody 127 has a killing activity superior to that of 201 or 202.

Test Example 4. In Vitro T Cell Activation Assay

In order to detect the activation function of the bispecific antibodies on T cells, the expression of the NFAT-driven luciferase reporter gene after Jurkat's activation was measured using the Jurkat recombinant cell line, in the presence or absence of the A498 tumor cell line.

A498 cells were inoculated into a 96-well cell culture plate ($1\times10^5$/ml, 100 μL/well), and placed in a 37° C., 5% $CO_2$ incubator for 20-24 h. On the next day, after the cell culture supernatant was removed, 90 μl of Jurkat recombinant cell suspension ($5.5\times10^5$/ml) and 10 μl of serially diluted test bispecific antibody (with the highest final concentration of 500 nM, 1: 3 gradient dilution) were added into each well, and a negative control (which has A498 and Jurkat recombinant cells, without antibodies) and blank control (which has medium, without cells or antibodies) were set, and incubated at a 37° C., 5% $CO_2$ incubator for 5-6 hours. For the non-tumor cell-specific activation of Jurkat recombinant cells, Jurkat recombinant cells and the test antibodies were directly added into a blank 96-well culture plate. After the co-cultivation, 100 μl of Bright-Glo Reagent (Bright-Glo™ Luciferase Assay System, Promega, Cat #: E2620) was added to each well, placed at room temperature for 5-10 minutes, and the chemiluminescence signal values were read on a multifunctional microplate. The fluorescence fold increase was calculated according to the formula:

Fold increase=($Signal_{sample}$−$Signal_{blank}$)/($Signal_{control}$−$Signal_{blank}$).

Figure 6A:
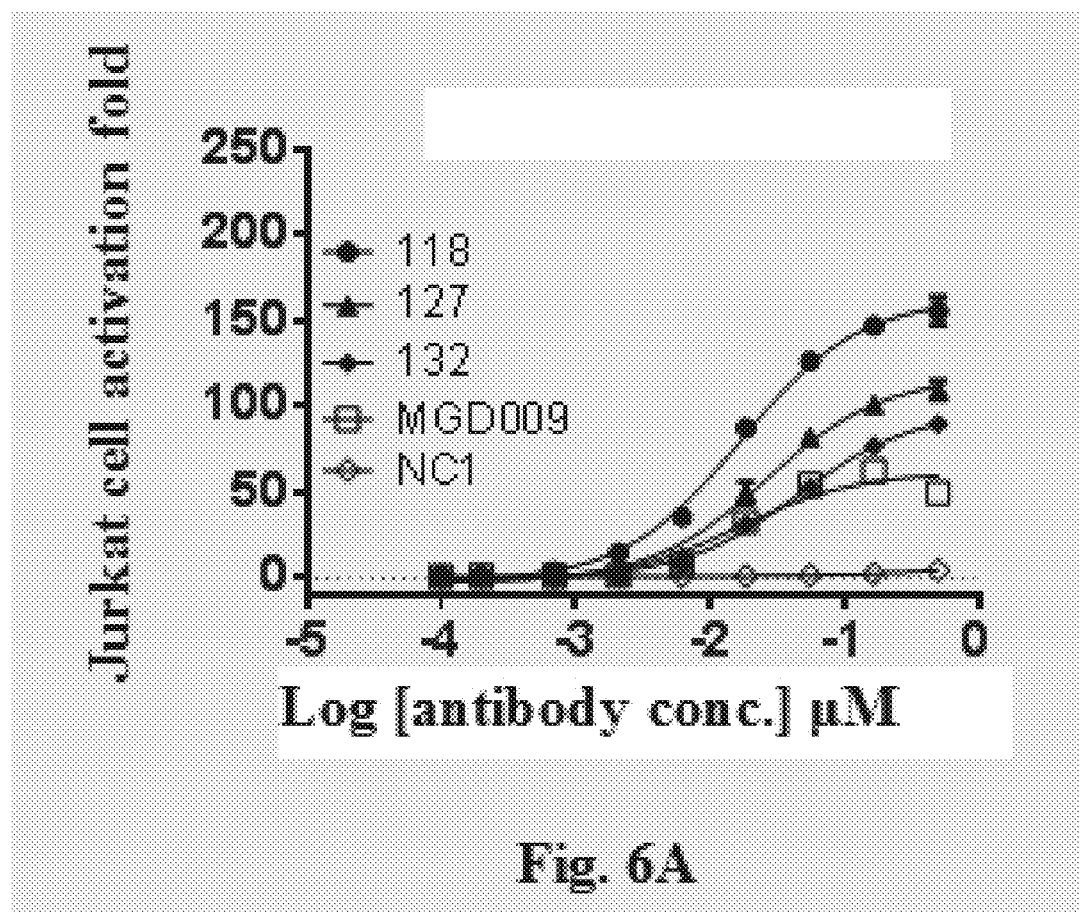
FIG. 6A to FIG. 6B: Detection of the activation of Jurkat recombinant cells by different antibodies.
Figure 6B:
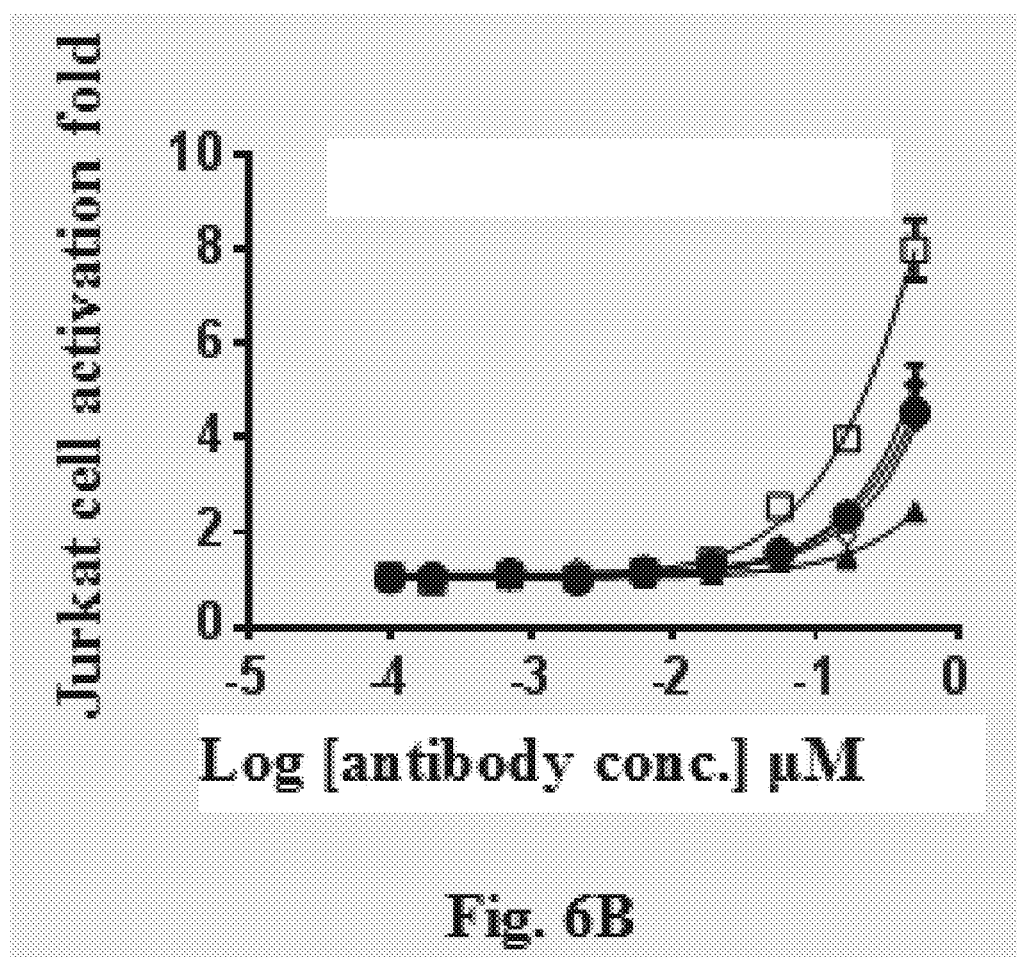

4.1 B7H3 Bivalent Molecules with Different Arrangement Orders can all Effectively Activate T Cells The B7H3 bivalent bispecific antibodies 118, 127, and 132 were tested for the activation of Jurkat recombinant cells in the presence or absence of A498 to verify the specific and non-specific activation effects of the bispecific antibodies on T cells. The results show that the B7H3 bivalent bispecific antibodies 118, 127 and 132 with different arrangement orders can effectively activate the Jurkat recombinant cell line and significantly induce the expression of luciferase, in the presence of the tumor cell line A498 (see FIG. 6A). It demonstrates that the activation of Jurkat recombinant cells is specific to the B7H3 target, because the negative control antibody NC1 cannot induce the expression of luciferase. Co-recruitment of both Jurkat recombinant cells expressing CD3 and tumor cells expressing B7H3 through bispecific antibodies is required for the activation of Jurkat recombinant cells. In the case that Jurkat recombinant cells are present alone with the absence of A498 cells (see FIG. 6B), the expression of luciferase is very low, and only a few weak signals can be detected at the several highest antibody concentration points.

TABLE 15

Antibody arrangement order

| Antibody | First polypeptide chain | Second polypeptide chain |
|---|---|---|
| 118 | $VH_{CD3}$(HRH3)-L1-$VL_{CD3}$-L2-$VL_{B7H3}$-L3-$VH_{B7H3}$-L4-Fc | $VL_{B7H3}$-L5-$VH_{B7H3}$-L6-Fc |
| 127 | $VL_{B7H3}$-L1-$VH_{B7H3}$-L2-$VH_{CD3}$(HRH3)-L3-$VL_{CD3}$-L4-Fc | $VL_{B7H3}$-L5-$VH_{B7H3}$-L6-Fc |
| 132 | $VL_{B7H3}$-L1-$VH_{B7H3}$-L2-$VH_{CD3}$(HRH3)-L3-$VL_{CD3}$-L4-Fc | $VL_{B7H3}$-L5-$VH_{B7H3}$-L5-Fc |

4.2 Comparison of B7H3 Monovalent and Bivalent Bispecific Antibodies

Figure 7A:
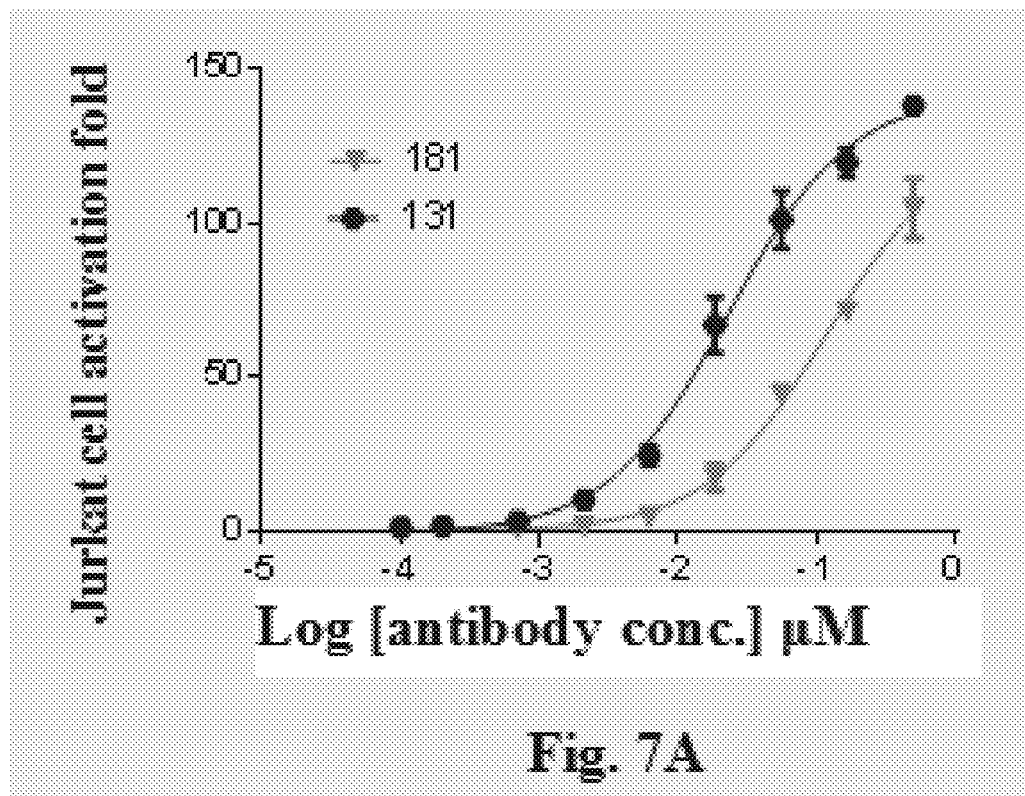
FIG. 7A to FIG. 7B: Detection of the activation of Jurkat recombinant cells by the bispecific antibodies comprising the same CD3scFv, but with different valences.
Figure 7B:
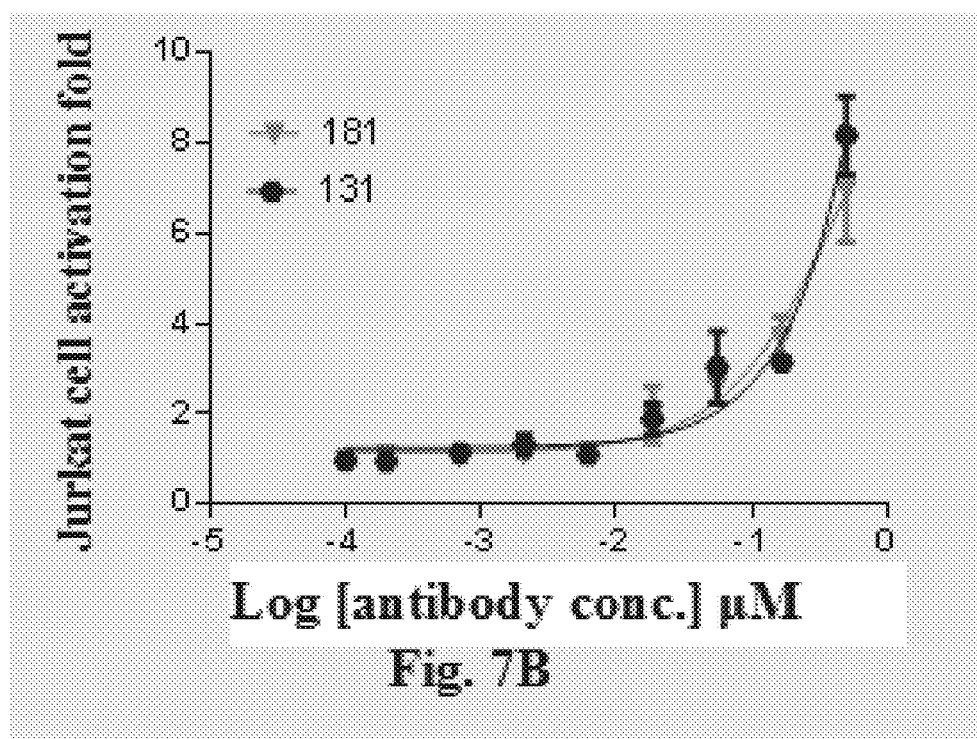

The bivalent CD3-B7H3 bispecific antibodies have significantly enhanced target-specific T cell activation compared to the B7H3 monovalent bispecific antibodies, which is consistent with the enhanced in vitro tumor killing ability of the B7H3 bivalent molecules compared to the B7H3 monovalent molecules as indicated in Test Example 3. Meanwhile, the non-target-specific T cell activation remains unchanged. Therefore, the B7H3 bivalent molecule (131) has stronger efficacy than the B7H3 monovalent molecule (181) (see FIG. 7A), whereas the side effects caused by the non-specific activation of T cells are not enhanced (see FIG. 7B).

TABLE 16

Antibody structure

| Antibody | First polypeptide chain | Second polypeptide chain |
|---|---|---|
| 131 | $VL_{B7H3}$-L1-$VH_{B7H3}$-L2-$VH_{CD3}$-L3-$VL_{CD3}$-L4-$F_C$1 | $VL_{B7H3}$-L5-$VH_{B7H3}$-L6-$F_C$2 |
| 181 | $VL_{B7H3}$-L1-$VH_{B7H3}$-L2-$VH_{CD3}$-L3-$VL_{CD3}$-L4-$F_C$1 | Fc2 |

Test Example 5. An In Vitro Cytokine Secretion Assay

The effector cells are redirected against the target cells under the mediation of the bispecific antibody, and release cytokines while killing the target cells. The cytokine secretion was analyzed by quantitatively detecting the content of the cytokines (including IL2, IFNγ, and TNFα) in the cell culture supernatant, by ELISA.

The experimental design and the antibodies used were the same as those described in Test Example 4. The cell culture supernatant was collected at the end of the in vitro killing assay and added into a 96-well plate (Corning #3795), and stored at −20° C. for later use. For ELISA assay, the frozen culture supernatant was taken out, thawed at room temperature, centrifuged at 3500 rpm for 10 minutes, and the supernatant was collected for the ELISA assay. The procedures for ELISA followed the instructions supplied in the kit (Human IL-2 ELISA kit, Human IFN-γ ELISA Kit, Human TNF-α ELISA kit, Neobioscience, Cat #EHC003.96, EHC102g.96, EHC103a.96).

Figure 8A:
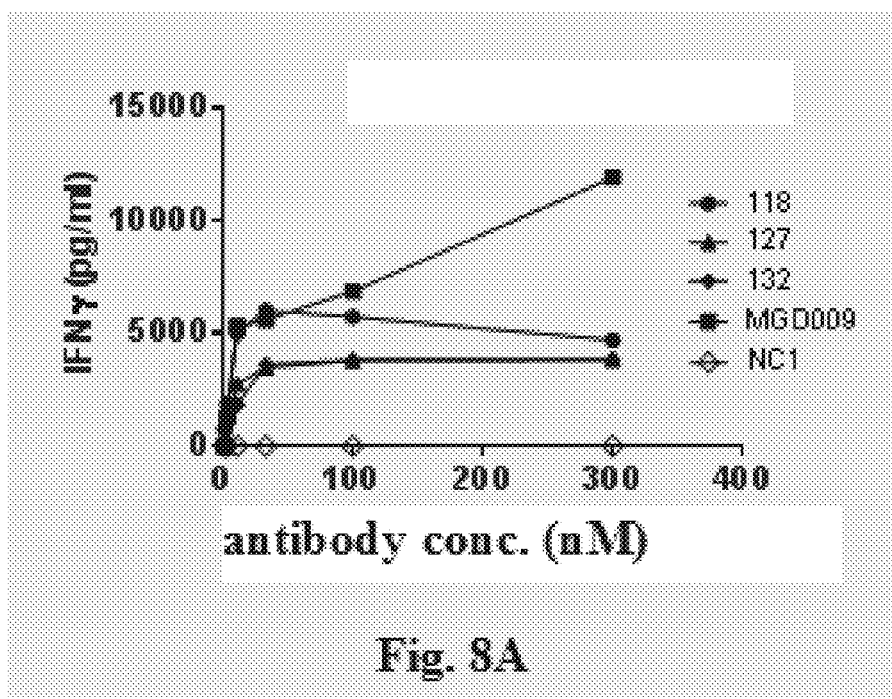
FIG. 8A to FIG. 8C: Various antibodies are tested, in the presence of A498 cells, for the stimulation of PBMCs to produce B7H3 target-specific cytokine secretion.
Figure 8B:
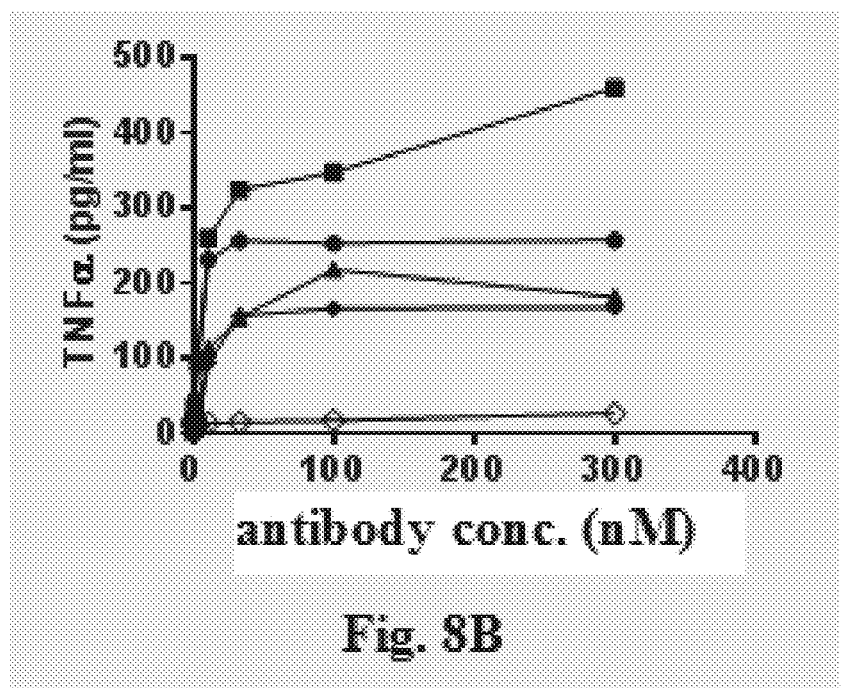
Figure 8C:
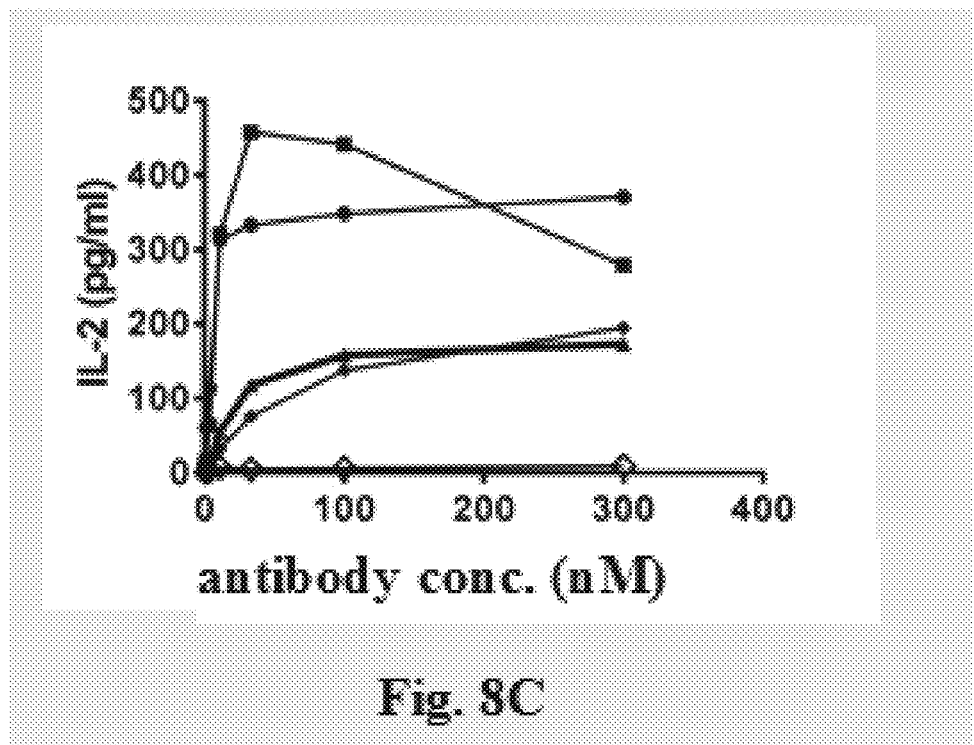
Figure 9A:
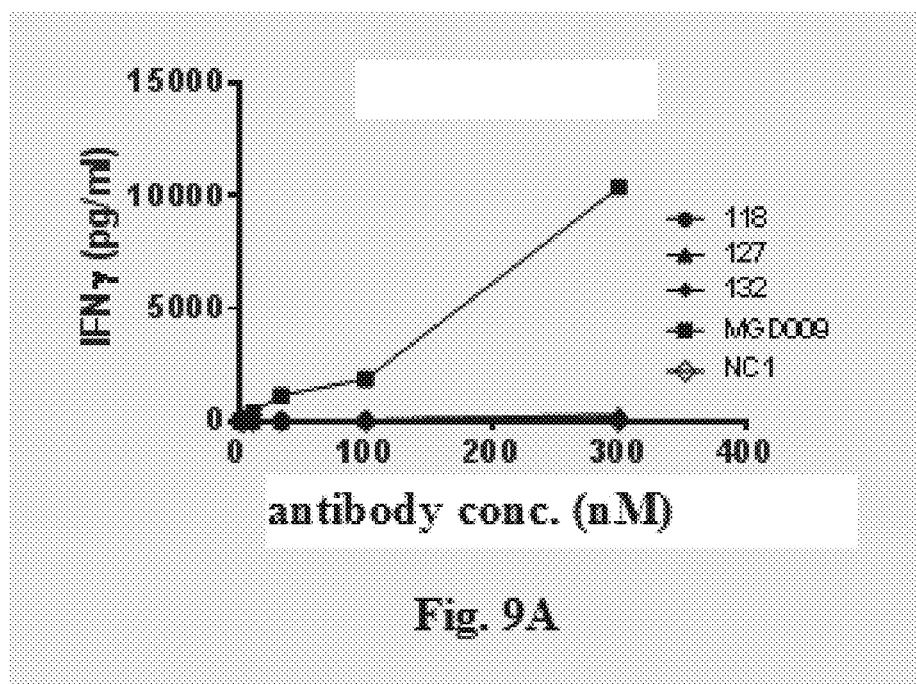
FIG. 9A to FIG. 9C: Various antibodies are tested, in the presence of CHOK1 cells (without the expression of B7H3), for the stimulation of PBMCs to produce non B7H3 target-specific cytokine secretion.
Figure 9B:
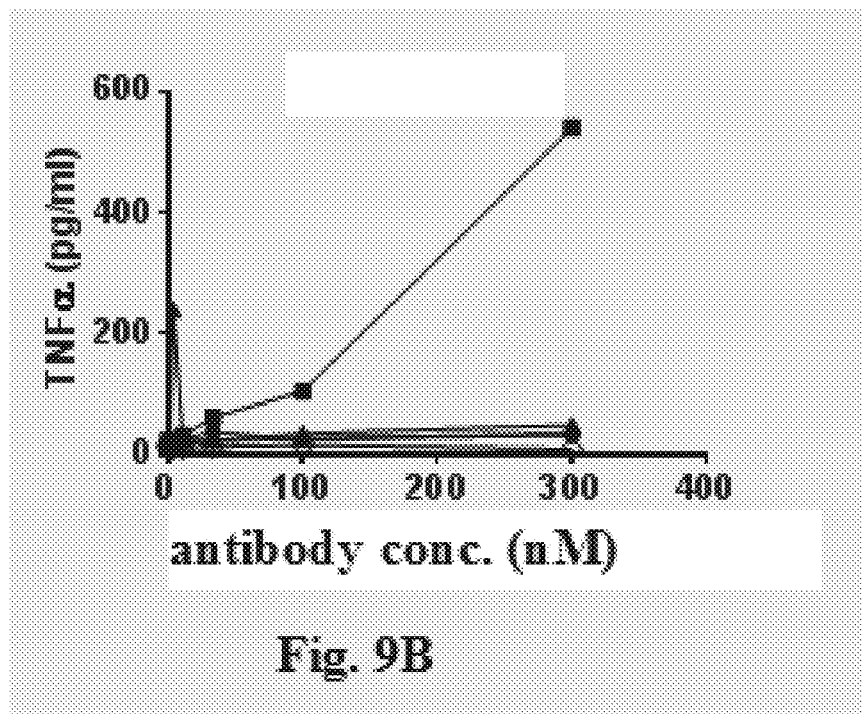
Figure 9C:
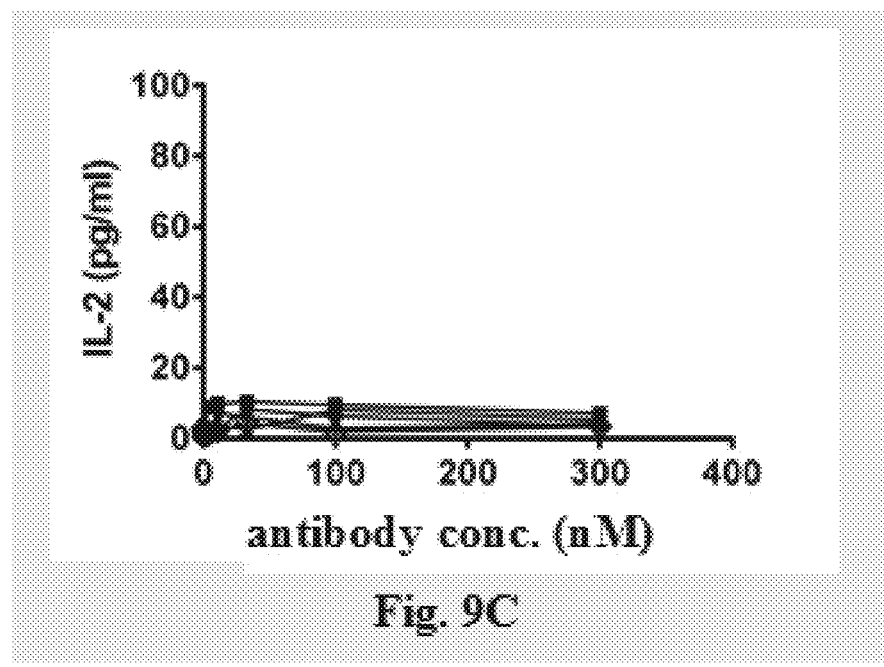

The results show that the test bispecific antibodies can effectively induce PBMC to secrete IL2, IFNγ and TNFα in the presence of both PBMC and B7H3-positive target cells A498 (see FIGS. 8A-8C), among these antibodies, MGD009 and 118 induce the highest secretion level of cytokines, followed by 127 and 132, and the negative control antibody NC1 induces the secretion of cytokine at a level beyond the range of detection sensitivity. MGD009 can significantly induce the release of IFNγ and TNFα at the three highest concentration points in the presence of both PBMC and B7H3-negative cell CHOK1 (see FIG. 9A-FIG. 9C), whereas the three test bispecific antibodies 118, 127 and 132 cannot induce the release of IFNγ and TNFα, indicating that the three test bispecific antibodies have better safety than MGD009, in terms of the secretion of non-target-specific cytokines.

Test Example 6. Pharmacodynamic Test in Mouse A498 Model Reconstructed with Human PBMCs In this test example, the anti-tumor efficacy of the test CD3-B7H3 bispecific antibodies of the present invention in mice was evaluated by using the NOG mouse (Beijing Charles River Experimental Animal Co., Ltd.) A498 model (ATCC™) reconstructed with human PBMCs.

$5 \times 10^6$ cells/mouse/100 µl (containing 50% Matrigel®) of A498 cells were inoculated subcutaneously into the right flank of NOG mice. When the tumor volume in the tumor-bearing mice reached about 130-150 mm$^3$, the mice were randomly grouped, with 5-6 animals per group, and the day of grouping was defined as day 0 of the experiment. On day 0 or day 1, the PBMCs freshly extracted from two volunteers were mixed at a ratio of 1:1, and $5 \times 10^6$ cells/100 µl was injected intraperitoneally in NOG mice, and each antibody was injected intraperitoneally, twice a week, a total of 6 doses. Tumor volumes and animal weights were monitored twice a week and data were recorded. Vehicle means a negative control group administrated with PBS buffer, instead of antibody.

Figure 10A:
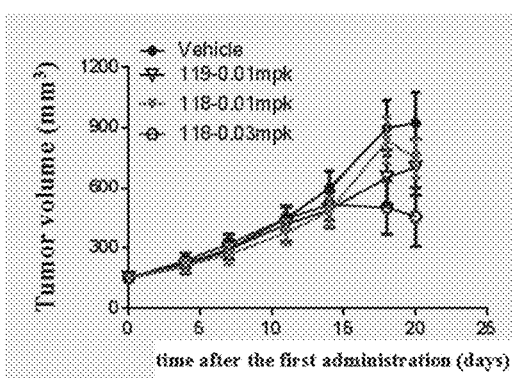

Antibodies 118 and 119 showed certain anti-tumor efficacy at lower doses (FIG. 10A), and exhibited a dose-dependent effect. Antibody 118 had tumor inhibition rate (TGI) of 22.17% and 60.39% at the doses of 0.01 mpk and 0.03 mpk, respectively, at the end of the experiment (day 20).

Figure 10B:
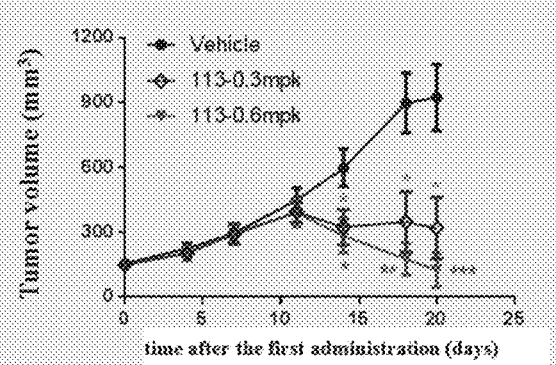

Antibody 113 showed a certain anti-tumor effect on day 14, and the tumor inhibition rates in 0.6 mpk and 0.3 mpk dose groups reached 70.05% (p<0.05) and 60.78% (p<0.05), respectively (FIG. 10B). On 20 day, the anti-tumor effects kept increasing in a dose-dependent manner, and the anti-tumor rates are greater than 100% (p<0.001) and 77.92% (p<0.05), respectively.

Figure 10C:
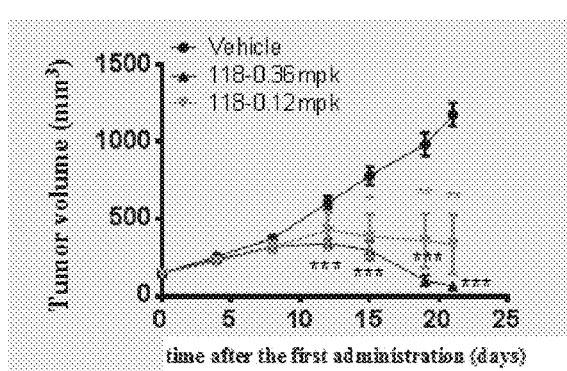

Under the conditions of 0.12 mpk and 0.36 mpk dosed (FIG. 10C), antibody 118 showed tumor inhibition rate of 39.18% and 57.44% (p<0.001) at the doses of 0.12 mpk and 0.36 mpk respectively on day 12, and the tumor inhibition rates reached 81.72% (p<0.01) and greater than 100% (p<0.001), respectively on day 21. Among the results, at the dose of 0.36 mpk, one mouse even exhibited complete tumor regression (⅙).

Figure 10D:
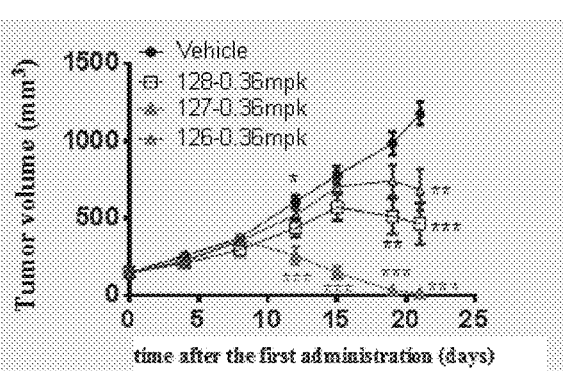

At the dose of 0.36 mpk (FIG. 10D), antibody 126 had the tumor inhibition rate of 47.78% on day 21 (p<0.01). Antibody 128 showed a significant anti-tumor effect on day 19 (TGI=56.37%). By Day 21, the tumor-inhibition rate was increased to 69.28% (p<0.001). Antibody 127 exhibited a tumor inhibition rate of 76.20% on day 12 (p<0.001), and the tumor-inhibitory effect kept increasing on day 21, and the tumor inhibition rate is greater than 100% (p<0.001). In 3 out of the 5 animals, the tumor volumes were regressed compared to those on the day of grouping, and the tumor volumes in the other 2 animals were completely regressed.

The anti-tumor activity of antibody 127 was repeated in another experiment (FIG. 10E). The tumor inhibition rate reached 90.6% on day 14 (p<0.001), and it is increased to 95.80% on day 17 (p<0.001). 127 was still effective at lower dose (0.12 mpk) and at lower administration frequency (once a week, 127-0.36 mpk-qw), with the tumor inhibition rates on day 17 reached 51.37% (p<0.001) and 96.20% (p<0.001) respectively.

Test Example 7. Pharmacodynamic Test in hCD3 KI Mouse Model

In this experiment, Balb/c-hCD3 mice were subcutaneously inoculated with CT26-hB7H3 tumor cell line (CT26 cells were derived from the Cell Bank of the Chinese Academy of Sciences, TCM37, and CT26-hB7H3 cells were obtained by expressing hB7H3) to evaluate the inhibitory effect of the CD3-B7H3 bispecific antibodies of the present invention on tumor growth in mice.

Female hCD3E Balb/c transgenic mice were purchased from Model Animal Research Center of Nanjing University (Certificate Number 201801374/5/6, license SCXK (Jiangsu) 2015-0001).

$8 \times 10^5$ cells/mouse/100 µl of CT26-hB7H3 cells were inoculated subcutaneously into the right flank of hCD3 mice. When the tumor volumes in the tumor-bearing mice reached about 80-120 mm$^3$, the mice were randomly divided into different groups, 7 mice per group. The day of grouping was defined as day 0 of the experiment, and the intraperitoneal injection of each antibody was performed, twice a week, for a total of 5 doses. The tumor volumes and animal weights were monitored twice a week and the data were recorded. Vehicle means a negative control group administrated with PBS buffer instead of the antibody.

The results show that antibody 118 showed strong efficacy after the initial administration at a dose of 1 mpk (FIG. 11A), and the tumor inhibition rate reached 38.34% on day 13 (p<0.05).

Antibody 132 had a tendency to inhibit tumor growth at a dose of 3.6 mpk (FIG. 11B), and the tumor inhibition rate reached 26.35% on day 13.

Test Example 8. PK Experiment in Rats

In this experiment, the CD3-B7H3 bispecific antibodies were injected into the tail vein of SD rats, and the antibody concentrations in the rat's serum at different time points were detected to evaluate the metabolism of the CD3-B7H3 bispecific antibodies in SD rats.

The test drugs were injected into the tail vein of the rats with 3 mg/kg, and the administration volume was 5 mL/kg. Blood was collected at various time points, i.e., before administration and 5 min, 8 h, 1 d, 2 d, 4 d, 7 d, 10 d, 14 d, 21 d, 28 d after administration. The antibody concentrations in serum were detected by ELISA method. Two different ELISA methods were used, wherein B7H3 antigen (1 μg/mL) or CD3 antigen (1 μg/mL) were plated, and anti-human Fc-HRP (abeam, ab98624) was used as the secondary antibody. The pharmacokinetic parameters of the test drugs were calculated with Winnolin software, and the resulting main pharmacokinetic parameters are shown in Table 17.

The antibodies 118, 127 and 132 have a half-life of 4.9-8.1 days in terms of the B7H3 antigen-binding region, slightly longer than that of MGD009 and reaching the level of ordinary IgG antibodies; and a half-life of 3.2-5.6 days in terms of the CD3 antigen-binding region. Wherein, the kinetic parameters of two different antigen-binding regions for B7H3 and CD3 in antibody 118 are not much different, indicating that the integrity of the molecule in vivo is favorable, and the half-lives are 4.9 and 4.4 days, respectively. The antibody 127 has half-lives of 4.9 and 3.2 days, respectively, in terms of the two different antigen-binding regions for B7H3 and CD3. The differences in exposure amount and clearance rate are obvious, with the CD3 part inferior to the B7H3 part. This is more likely to be caused by weakening of the binding ability of CD3 rather than by molecular breakage, since the CD3 part is inside the molecular structure. Antibody 132 was obtained by incorporating a pair of disulfide bonds into B7H3 scFv, on the basis of the molecular sequence of antibody 127. This modification greatly increases the half-life of the molecule (65-75%), and also greatly improves the exposure amount and clearance rate.

TABLE 17

| | Main pharmacokinetic parameters in rats | | | | | | |
|---|---|---|---|---|---|---|---|
| | 118 | | 127 | | 132 | | MGD009 |
| Statistics | B7H3 Coated | CD3 Coated | B7H3 Coated | CD3 Coated | B7H3 Coated | CD3 Coated | B7H3 Coated |
| $AUC_{0-\infty}$ (μg/ml*h) | 4797 ± 603 | 3059 ± 227 | 3328 ± 171 | 437 ± 37 | 5182 ± 122 | 1634 ± 654 | 2994 ± 244 |
| $t_{1/2}$ (h) | 117 ± 16 | 106 ± 11 | 118 ± 6 | 76 ± 5 | 196 ± 5 | 134 ± 13 | 94.7 ± 11.1 |
| $t_{1/2}$ (d) | 4.9 ± 0.7 | 4.4 ± 0.4 | 4.9 ± 0.3 | 3.2 ± 0.2 | 8.1 ± 0.2 | 5.6 ± 0.5 | 3.95 ± 0.46 |

What is claimed is:

1. An antibody or antigen-binding fragment thereof specifically binding to human CD3, the antibody or antigen-binding fragment thereof comprising a heavy chain variable region and a light chain variable region, wherein:
   the light chain variable region comprises LCDR1, LCDR2 and LCDR3 as shown in SEQ ID NOs: 48, 49 and 50, respectively, and
   the heavy chain variable region is any one selected from the group consisting of the following i) to v):
   i) a heavy chain variable region comprising HCDR1, HCDR2 and HCDR3 as shown in SEQ ID NOs: 37, 40 and 42, respectively;
   ii) a heavy chain variable region comprising HCDR1, HCDR2 and HCDR3 as shown in SEQ ID NOs: 37, 47 and 45, respectively;
   iii) a heavy chain variable region comprising HCDR1, HCDR2 and HCDR3 as shown in SEQ ID NOs: 37, 38 and 39, respectively;
   iv) a heavy chain variable region comprising HCDR1, HCDR2 and HCDR3 as shown in SEQ ID NOs: 37, 40 and 43, respectively; and
   v) a heavy chain variable region comprising HCDR1, HCDR2 and HCDR3 as shown in SEQ ID NOs: 37, 40 and 41, respectively.

2. The antibody or antigen-binding fragment thereof specifically binding to human CD3 according to claim 1, wherein the antibody or antigen-binding fragment thereof is a humanized antibody or antigen-binding fragment thereof.

3. The antibody or antigen-binding fragment thereof specifically binding to human CD3 according to claim 2, comprising a light chain variable region as shown in SEQ ID NO: 36, and/or a heavy chain variable region as shown in any one selected from the group consisting of SEQ ID NOs: 29, 30, 31, 32, and 35.

4. The antibody or antigen-binding fragment thereof specifically binding to human CD3 according to claim 3, further comprising an antibody light chain constant region and/or a heavy chain constant region;
   optionally, the light chain constant region is a light chain constant region of a human kappa, lambda chain or variant thereof, and the heavy chain constant region is a heavy chain constant region of a human IgG1, IgG2, IgG3, IgG4 or variant thereof.

5. The antibody or antigen-binding fragment thereof specifically binding to human CD3 according to claim 1, wherein the antigen-binding fragment is selected from Fab, Fab', F(ab')2, dimerized V region (diabody) and disulfide-stabilized V region (dsFv).

6. A single-chain antibody, comprising the light chain variable region and the heavy chain variable region of the antibody or antigen-binding fragment thereof specifically binding to human CD3 according to claim 1.

7. The single-chain antibody according to claim 6, wherein the sequence of the single-chain antibody is as shown in SEQ ID NO: 55, 56, 57, 58, 61, 62, 63, 64, 65 or 68.

8. A multispecific antibody specifically binding to human CD3 and tumor-associated antigen(s), the multispecific antibody comprising the single-chain antibody according to claim 6.

9. The multispecific antibody according to claim 8, wherein the tumor-associated antigen is selected from the group consisting of AFP, ALK, B7H3, BAGE protein, BCMA, BIRC5, BIRC7, β-catenin, brc-abl, BRCA1, BORIS, CA9, CA125, carbonic anhydrase IX, caspase-8, CALR, CCR5, CD19, CD20, CD22, CD30, CD33, CD38, CD40, CD123, CD133, CD138, CDK4, CEA, Claudin 18.2, cyclin-B1, CYP1B1, EGFR, EGFRvIII, ErbB2/Her2, ErbB3, ErbB4, ETV6-AML, EpCAM, EphA2, Fra-1, FOLR1, GAGE protein, GD2, GD3, GloboH, Glypican-3, GM3, gp100, Her2, HLA/B-raf, HLA/k-ras, HLA/MAGE-A3, hTERT, IL13Rα2, LMP2, κ-Light, LeY, MAGE protein, MART-1, Mesothelin, ML-IAP, MOv-γ, Muc1, Muc2, Muc3, Muc4, Muc5, CA-125, MUM1, NA17, NKG2D, NY-BR1, NY-BR62, NY-BR85, NY-ESO1, OX40, p15, p53, PAP, PAX3, PAX5, PCTA-1, PLAC1, PRLR, PRAME, PSMA, RAGE protein, Ras, RGS5, Rho, ROR1, SART-1, SART-3, STEAP1, STEAP2, TAG-72, TGF-β, TMPRSS2, Thompson-nouvelle antigen, TRP-1, TRP-2, tyrosinase, uroplakin-3 and 5T4.

10. A pharmaceutical composition, comprising a therapeutically effective amount of the antibody or antigen-binding fragment thereof specifically binding to human CD3 according to claim 1, and one or more pharmaceutically acceptable carriers, diluents, buffers or excipients.

11. An isolated nucleic acid molecule, encoding the antibody or antigen-binding fragment thereof specifically binding to human CD3 according to claim 1.

12. A recombinant vector, comprising the isolated nucleic acid molecule according to claim 11.

13. A host cell transformed with the recombinant vector of claim 12, wherein said host cell is a prokaryotic cell or a eukaryotic cell.

14. A method for producing the antibody or antigen-binding fragment thereof specifically binding to human CD3 according to claim 1, the method comprising transforming the recombinant vector into a host cell and culturing a host cell in a culture medium to express and accumulate the antibody or antigen-binding fragment thereof specifically binding to human CD3, and recovering the antibody or antigen-binding fragment thereof.

* * * * *

SEQUENCE LISTING

```
<160> NUMBER OF SEQ ID NOS: 112

<210> SEQ ID NO 1
<211> LENGTH: 439
<212> TYPE: PRT
<213> ORGANISM: Artificial Sequence
<220> FEATURE:
<221> NAME/KEY: PEPTIDE
<223> OTHER INFORMATION: human B7H3 antigen for detection

<400> SEQUENCE: 1

Leu Glu Val Gln Val Pro Glu Asp Pro Val Val Ala Leu Val Gly Thr
1               5                   10                  15

Asp Ala Thr Leu Cys Cys Ser Phe Ser Pro Glu Pro Gly Phe Ser Leu
                20                  25                  30

Ala Gln Leu Asn Leu Ile Trp Gln Leu Thr Asp Thr Lys Gln Leu Val
            35                  40                  45

His Ser Phe Ala Glu Gly Gln Asp Gln Gly Ser Ala Tyr Ala Asn Arg
        50                  55                  60

Thr Ala Leu Phe Pro Asp Leu Leu Ala Gln Gly Asn Ala Ser Leu Arg
65                  70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
                100                 105                 110

Pro Tyr Ser Lys Pro Ser Met Thr Leu Glu Pro Asn Lys Asp Leu Arg
            115                 120                 125

Pro Gly Asp Thr Val Thr Ile Thr Cys Ser Ser Tyr Gln Gly Tyr Pro
```

-continued

```
            130                 135                 140
Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Ile Leu Arg Val Val Leu Gly Ala Asn Gly Thr Tyr Ser Cys
            180                 185                 190

Leu Val Arg Asn Pro Val Leu Gln Gln Asp Ala His Ser Ser Val Thr
        195                 200                 205

Ile Thr Pro Gln Arg Ser Pro Thr Gly Ala Val Glu Val Gln Val Pro
210                 215                 220

Glu Asp Pro Val Val Ala Leu Val Gly Thr Asp Ala Thr Leu Arg Cys
225                 230                 235                 240

Ser Phe Ser Pro Glu Pro Gly Phe Ser Leu Ala Gln Leu Asn Leu Ile
                245                 250                 255

Trp Gln Leu Thr Asp Thr Lys Gln Leu Val His Ser Phe Thr Glu Gly
            260                 265                 270

Arg Asp Gln Gly Ser Ala Tyr Ala Asn Arg Thr Ala Leu Phe Pro Asp
        275                 280                 285

Leu Leu Ala Gln Gly Asn Ala Ser Leu Arg Leu Gln Arg Val Arg Val
290                 295                 300

Ala Asp Glu Gly Ser Phe Thr Cys Phe Val Ser Ile Arg Asp Phe Gly
305                 310                 315                 320

Ser Ala Ala Val Ser Leu Gln Val Ala Ala Pro Tyr Ser Lys Pro Ser
                325                 330                 335

Met Thr Leu Glu Pro Asn Lys Asp Leu Arg Pro Gly Asp Thr Val Thr
            340                 345                 350

Ile Thr Cys Ser Ser Tyr Arg Gly Tyr Pro Glu Ala Glu Val Phe Trp
        355                 360                 365

Gln Asp Gly Gln Gly Val Pro Leu Thr Gly Asn Val Thr Thr Ser Gln
370                 375                 380

Met Ala Asn Glu Gln Gly Leu Phe Asp Val His Ser Val Leu Arg Val
385                 390                 395                 400

Val Leu Gly Ala Asn Gly Thr Tyr Ser Cys Leu Val Arg Asn Pro Val
                405                 410                 415

Leu Gln Gln Asp Ala His Gly Ser Val Thr Ile Thr Gly Gln Pro Met
            420                 425                 430

Thr His His His His His His
        435
```

<210> SEQ ID NO 2
<211> LENGTH: 443
<212> TYPE: PRT
<213> ORGANISM: Artificial Sequence
<220> FEATURE:
<221> NAME/KEY: PEPTIDE
<223> OTHER INFORMATION: monkey B7H3 antigen for detection

<400> SEQUENCE: 2

```
Leu Glu Val Gln Val Pro Glu Asp Pro Val Val Ala Leu Val Gly Thr
1

```
His Ser Phe Thr Glu Gly Arg Asp Gln Gly Ser Ala Tyr Ala Asn Arg
 50                  55                  60

Thr Ala Leu Phe Leu Asp Leu Leu Ala Gln Gly Asn Ala Ser Leu Arg
 65                  70                  75                  80

Leu Gln Arg Val Arg Val Ala Asp Glu Gly Ser Phe Thr Cys Phe Val
                 85                  90                  95

Ser Ile Arg Asp Phe Gly Ser Ala Ala Val Ser Leu Gln Val Ala Ala
                100                 105                 110

Pro Tyr Ser Lys Pro Ser Met Thr Leu Glu Pro Asn Lys Asp Leu Arg
            115                 120                 125

Pro Gly Asp Thr Val Thr Ile Thr Cys Ser Ser Tyr Arg Gly Tyr Pro
130                 135                 140

Glu Ala Glu Val Phe Trp Gln Asp Gly Gln Gly Ala Pro Leu Thr Gly
145                 150                 155                 160

Asn Val Thr Thr Ser Gln Met Ala Asn Glu Gln Gly Leu Phe Asp Val
                165                 170                 175

His Ser Val Leu Arg Val Val Leu Gly Ala Asn Gly Thr Tyr Ser Cys
            180                 185                 190

Leu Val Arg Asn Pro Val Leu Gln Gln Asp Ala His Gly Ser Ile Thr
            195                 200                 205

Ile Thr Pro Gln Arg Ser Pro Thr Gly Ala Val Glu Val Gln Val Pro
210                 215                 220

Glu Asp Pro Val Val Ala Leu Val Gly Thr Asp Ala Thr Leu Arg Cys
225                 230                 235                 240

Ser Phe Ser Pro Glu Pro Gly Phe Ser Leu Ala Gln Leu Asn Leu Ile
                245                 250                 255

Trp Gln Leu Thr Asp Thr Lys Gln Leu Val His Ser Phe Thr Glu Gly
            260                 265                 270

Arg Asp Gln Gly Ser Ala Tyr Ala Asn Arg Thr Ala Leu Phe Leu Asp
            275                 280                 285

Leu Leu Ala Gln Gly Asn Ala Ser Leu Arg Leu Gln Arg Val Arg Val
            290                 295                 300

Ala Asp Glu Gly Ser Phe Thr Cys Phe Val Ser Ile Arg Asp Phe Gly
305                 310                 315                 320

Ser Ala Ala Val Ser Leu Gln Val Ala Ala Pro Tyr Ser Lys Pro Ser
                325                 330                 335

Met Thr Leu Glu Pro Asn Lys Asp Leu Arg Pro Gly Asp Thr Val Thr
            340                 345                 350

Ile Thr Cys Ser Ser Tyr Arg Gly Tyr Pro Glu Ala Glu Val Phe Trp
            355                 360                 365

Gln Asp Gly Gln Gly Ala Pro Leu Thr Gly Asn Val Thr Thr Ser Gln
370                 375                 380

Met Ala Asn Glu Gln Gly Leu Phe Asp Val His Ser Val Leu Arg Val
385                 390                 395                 400

Val Leu Gly Ala Asn Gly Thr Tyr Ser Cys Leu Val Arg Asn Pro Val
                405                 410                 415

Leu Gln Gln Asp Ala His Gly Ser Val Thr Ile Thr Gly Gln Pro Met
            420                 425                 430

Thr Phe Pro Pro Glu His His His His His
            435                 440

<210> SEQ ID NO 3
<211> LENGTH: 222
<212> TYPE: PRT
```

```
<213> ORGANISM: Artificial Sequence
<220> FEATURE:
<221> NAME/KEY: PEPTIDE
<223> OTHER INFORMATION: murine B7H3 antigen for detection

<400> SEQUENCE: 3
```

Val Glu Val Gln Val Ser Glu Asp Pro Val Ala Leu Val Asp Thr
1               5                  10                  15

Asp Ala Thr Leu Arg Cys Ser Phe Ser Pro Glu Pro Gly Phe Ser Leu
            20                  25                  30

Ala Gln Leu Asn Leu Ile Trp Gln Leu Thr Asp Thr Lys Gln Leu Val
        35                  40                  45

His Ser Phe Thr Glu Gly Arg Asp Gln Gly Ser Ala Tyr Ser Asn Arg
    50                  55                  60

Thr Ala Leu Phe Pro Asp Leu Leu Val Gln Gly Asn Ala Ser Leu Arg
65                  70                  75                  80

Leu Gln Arg Val Arg Val Thr Asp Glu Gly Ser Tyr Thr Cys Phe Val
                85                  90                  95

Ser Ile Gln Asp Phe Asp Ser Ala Ala Val Ser Leu Gln Val Ala Ala
            100                 105                 110

Pro Tyr Ser Lys Pro Ser Met Thr Leu Glu Pro Asn Lys Asp Leu Arg
        115                 120                 125

Pro Gly Asn Met Val Thr Ile Thr Cys Ser Ser Tyr Gln Gly Tyr Pro
130                 135                 140

Glu Ala Glu Val Phe Trp Lys Asp Gly Gln Gly Val Pro Leu Thr Gly
145                 150                 155                 160

Asn Val Thr Thr Ser Gln Met Ala Asn Glu Arg Gly Leu Phe Asp Val
                165                 170                 175

His Ser Val Leu Arg Val Val Leu Gly Ala Asn Gly Thr Tyr Ser Cys
            180                 185                 190

Leu Val Arg Asn Pro Val Leu Gln Gln Asp Ala His Gly Ser Val Thr
        195                 200                 205

Ile Thr Gly Gln Pro Leu Thr Phe His His His His His His
    210                 215                 220

```
<210> SEQ ID NO 4
<211> LENGTH: 534
<212> TYPE: PRT
<213> ORGANISM: Artificial Sequence
<220> FEATURE:
<221> NAME/KEY: PEPTIDE
<223> OTHER INFORMATION: human B7H3 full-length amino acid sequence

<400> SEQUENCE: 4
```

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val

```
                100             105             110
Arg Val Ala Asp Glu Gly Ser Phe Thr Cys Phe Val Ser Ile Arg Asp
            115             120             125

Phe Gly Ser Ala Ala Val Ser Leu Gln Val Ala Ala Pro Tyr Ser Lys
            130             135             140

Pro Ser Met Thr Leu Glu Pro Asn Lys Asp Leu Arg Pro Gly Asp Thr
145             150             155             160

Val Thr Ile Thr Cys Ser Ser Tyr Gln Gly Tyr Pro Glu Ala Glu Val
            165             170             175

Phe Trp Gln Asp Gly Gln Gly Val Pro Leu Thr Gly Asn Val Thr Thr
            180             185             190

Ser Gln Met Ala Asn Glu Gln Gly Leu Phe Asp Val His Ser Ile Leu
            195             200             205

Arg Val Val Leu Gly Ala Asn Gly Thr Tyr Ser Cys Leu Val Arg Asn
            210             215             220

Pro Val Leu Gln Gln Asp Ala His Ser Ser Val Thr Ile Thr Pro Gln
225             230             235             240

Arg Ser Pro Thr Gly Ala Val Glu Val Gln Val Pro Glu Asp Pro Val
            245             250             255

Val Ala Leu Val Gly Thr Asp Ala Thr Leu Arg Cys Ser Phe Ser Pro
            260             265             270

Glu Pro Gly Phe Ser Leu Ala Gln Leu Asn Leu Ile Trp Gln Leu Thr
            275             280             285

Asp Thr Lys Gln Leu Val His Ser Phe Thr Glu Gly Arg Asp Gln Gly
            290             295             300

Ser Ala Tyr Ala Asn Arg Thr Ala Leu Phe Pro Asp Leu Leu Ala Gln
305             310             315             320

Gly Asn Ala Ser Leu Arg Leu Gln Arg Val Arg Val Ala Asp Glu Gly
            325             330             335

Ser Phe Thr Cys Phe Val Ser Ile Arg Asp Phe Gly Ser Ala Ala Val
            340             345             350

Ser Leu Gln Val Ala Ala Pro Tyr Ser Lys Pro Ser Met Thr Leu Glu
            355             360             365

Pro Asn Lys Asp Leu Arg Pro Gly Asp Thr Val Thr Ile Thr Cys Ser
370             375             380

Ser Tyr Arg Gly Tyr Pro Glu Ala Glu Val Phe Trp Gln Asp Gly Gln
385             390             395             400

Gly Val Pro Leu Thr Gly Asn Val Thr Thr Ser Gln Met Ala Asn Glu
            405             410             415

Gln Gly Leu Phe Asp Val His Ser Val Leu Arg Val Val Leu Gly Ala
            420             425             430

Asn Gly Thr Tyr Ser Cys Leu Val Arg Asn Pro Val Leu Gln Gln Asp
            435             440             445

Ala His Gly Ser Val Thr Ile Thr Gly Gln Pro Met Thr Phe Pro Pro
            450             455             460

Glu Ala Leu Trp Val Thr Val Gly Leu Ser Val Cys Leu Ile Ala Leu
465             470             475             480

Leu Val Ala Leu Ala Phe Val Cys Trp Arg Lys Ile Lys Gln Ser Cys
            485             490             495

Glu Glu Glu Asn Ala Gly Ala Glu Asp Gln Asp Gly Glu Gly Glu Gly
            500             505             510

Ser Lys Thr Ala Leu Gln Pro Leu Lys His Ser Asp Ser Lys Glu Asp
            515             520             525
```

Asp Gly Gln Glu Ile Ala
      530

<210> SEQ ID NO 5
<211> LENGTH: 534
<212> TYPE: PRT
<213> ORGANISM: Artificial Sequence
<220> FEATURE:
<221> NAME/KEY: PEPTIDE
<223> OTHER INFORMATION: monkey B7H3 full-length amino acid sequence

<400> SEQUENCE: 5

Met Leu His Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Arg Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Thr
65                  70                  75                  80

Glu Gly Arg Asp Gln Gly Ser Ala Tyr Ala Asn Arg Thr Ala Leu Phe
                85                  90                  95

Leu Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Ala Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Ile Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Leu Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val

```
            340                 345                 350
Ser Leu Gln Val Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Ala Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Val Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
        515                 520                 525

Asp Gly Gln Glu Leu Ala
    530

<210> SEQ ID NO 6
<211> LENGTH: 316
<212> TYPE: PRT
<213> ORGANISM: Artificial Sequence
<220> FEATURE:
<221> NAME/KEY: PEPTIDE
<223> OTHER INFORMATION: murine B7H3 full-length amino acid sequence

<400> SEQUENCE: 6

Met Leu Arg Gly Trp Gly Gly Pro Ser Val Gly Val Cys Val Arg Thr
1               5                   10                  15

Ala Leu Gly Val Leu Cys Leu Cys Leu Thr Gly Ala Val Glu Val Gln
            20                  25                  30

Val Ser Glu Asp Pro Val Val Ala Leu Val Asp Thr Asp Ala Thr Leu
        35                  40                  45

Arg Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Thr
65                  70                  75                  80

Glu Gly Arg Asp Gln Gly Ser Ala Tyr Ser Asn Arg Thr Ala Leu Phe
                85                  90                  95

Pro Asp Leu Leu Val Gln Gly Asn Ala Ser Leu Arg Leu Gln Arg Val
            100                 105                 110

Arg Val Thr Asp Glu Gly Ser Tyr Thr Cys Phe Val Ser Ile Gln Asp
        115                 120                 125

Phe Asp Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asn Met
145                 150                 155                 160
```

-continued

```
Val Thr Ile Thr Cys Ser Ser Tyr Gln Gly Tyr Pro Glu Ala Glu Val
                165                 170                 175

Phe Trp Lys Asp Gly Gln Gly Val Pro Leu Thr Gly Asn Val Thr Thr
        180                 185                 190

Ser Gln Met Ala Asn Glu Arg Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Leu Thr Phe Pro Pro Glu Ala Leu Trp Val Thr Val Gly Leu Ser
                245                 250                 255

Val Cys Leu Val Val Leu Leu Val Ala Leu Ala Phe Val Cys Trp Arg
                260                 265                 270

Lys Ile Lys Gln Ser Cys Glu Glu Asn Ala Gly Ala Glu Asp Gln
                275                 280                 285

Asp Gly Asp Gly Glu Gly Ser Lys Thr Ala Leu Arg Pro Leu Lys Pro
        290                 295                 300

Ser Glu Asn Lys Glu Asp Asp Gly Gln Glu Ile Ala
305                 310                 315

<210> SEQ ID NO 7
<211> LENGTH: 119
<212> TYPE: PRT
<213> ORGANISM: Artificial Sequence
<220> FEATURE:
<221> NAME/KEY: DOMAIN
<223> OTHER INFORMATION: h1702 VH

<400> SEQUENCE: 7

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Arg Leu Tyr Ala Ser Phe Asp Tyr Trp Gly Gln Gly
            100                 105                 110

Ala Leu Val Thr Val Ser Ser
        115

<210> SEQ ID NO 8
<211> LENGTH: 110
<212> TYPE: PRT
<213> ORGANISM: Artificial Sequence
<220> FEATURE:
<221> NAME/KEY: DOMAIN
<223> OTHER INFORMATION: h1702 VL

<400> SEQUENCE: 8

Gln Thr Val Val Thr Gln Glu Pro Ser Phe Ser Val Ser Pro Gly Gly
1               5                   10                  15
```

```
Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
            35                  40                  45

Leu Ile Tyr Asn Thr Asn Thr Arg Ser Ser Gly Val Pro Asp Arg Phe
            50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu
            100                 105                 110

<210> SEQ ID NO 9
<211> LENGTH: 8
<212> TYPE: PRT
<213> ORGANISM: Artificial Sequence
<220> FEATURE:
<221> NAME/KEY: DOMAIN
<223> OTHER INFORMATION: h1702 HCDR1

<400> SEQUENCE: 9

Gly Phe Ile Phe Ser Ser Ser Ala
1               5

<210> SEQ ID NO 10
<211> LENGTH: 8
<212> TYPE: PRT
<213> ORGANISM: Artificial Sequence
<220> FEATURE:
<221> NAME/KEY: DOMAIN
<223> OTHER INFORMATION: h1702 HCDR2

<400> SEQUENCE: 10

Ile Ser Tyr Asp Gly Ser Asn Lys
1               5

<210> SEQ ID NO 11
<211> LENGTH: 12
<212> TYPE: PRT
<213> ORGANISM: Artificial Sequence
<220> FEATURE:
<221> NAME/KEY: DOMAIN
<223> OTHER INFORMATION: h1702 HCDR3

<400> SEQUENCE: 11

Ala Arg Ser Ala Arg Leu Tyr Ala Ser Phe Asp Tyr
1               5                   10

<210> SEQ ID NO 12
<211> LENGTH: 9
<212> TYPE: PRT
<213> ORGANISM: Artificial Sequence
<220> FEATURE:
<221> NAME/KEY: DOMAIN
<223> OTHER INFORMATION: h1702 LCDR1

<400> SEQUENCE: 12

Ser Gly Ser Val Ser Thr Ser His Tyr
1               5

<210> SEQ ID NO 13
<211> LENGTH: 3
<212> TYPE: PRT
<213> ORGANISM: Artificial Sequence
```

```
<220> FEATURE:
<221> NAME/KEY: DOMAIN
<223> OTHER INFORMATION: h1702 LCDR2

<400> SEQUENCE: 13

Asn Thr Asn
1

<210> SEQ ID NO 14
<211> LENGTH: 10
<212> TYPE: PRT
<213> ORGANISM: Artificial Sequence
<220> FEATURE:
<221> NAME/KEY: DOMAIN
<223> OTHER INFORMATION: h1702 LCDR3

<400> SEQUENCE: 14

Ala Ile His Val Asp Arg Asp Ile Trp Val
1               5                   10

<210> SEQ ID NO 15
<211> LENGTH: 119
<212> TYPE: PRT
<213> ORGANISM: Artificial Sequence
<220> FEATURE:
<221> NAME/KEY: DOMAIN
<223> OTHER INFORMATION: B7H3 VH44C

<400> SEQUENCE: 15

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Cys Leu Glu Trp Val
        35                  40                  45

Ala Val Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Arg Leu Tyr Ala Ser Phe Asp Tyr Trp Gly Gln Gly
            100                 105                 110

Ala Leu Val Thr Val Ser Ser
        115

<210> SEQ ID NO 16
<211> LENGTH: 110
<212> TYPE: PRT
<213> ORGANISM: Artificial Sequence
<220> FEATURE:
<221> NAME/KEY: DOMAIN
<223> OTHER INFORMATION: B7H3 VL103C

<400> SEQUENCE: 16

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
```

```
                    50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Ala Ile His Val Asp Arg
                    85                  90                  95

Asp Ile Trp Val Phe Gly Cys Gly Thr Lys Leu Thr Val Leu
                100                 105                 110

<210> SEQ ID NO 17
<211> LENGTH: 110
<212> TYPE: PRT
<213> ORGANISM: Artificial Sequence
<220> FEATURE:
<221> NAME/KEY: PEPTIDE
<223> OTHER INFORMATION: Human CD3 epsilon

<400> SEQUENCE: 17

Asp Gly Asn Glu Glu Met Gly Gly Ile Thr Gln Thr Pro Tyr Lys Val
 1               5                  10                  15

Ser Ile Ser Gly Thr Thr Val Ile Leu Thr Cys Pro Gln Tyr Pro Gly
                20                  25                  30

Ser Glu Ile Leu Trp Gln His Asn Asp Lys Asn Ile Gly Gly Asp Glu
                35                  40                  45

Asp Asp Lys Asn Ile Gly Ser Asp Glu Asp His Leu Ser Leu Lys Glu
            50                  55                  60

Phe Ser Glu Leu Glu Gln Ser Gly Tyr Tyr Val Cys Tyr Pro Arg Gly
 65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp His His His His His His
                100                 105                 110

<210> SEQ ID NO 18
<211> LENGTH: 92
<212> TYPE: PRT
<213> ORGANISM: Artificial Sequence
<220> FEATURE:
<221> NAME/KEY: DOMAIN
<223> OTHER INFORMATION: Human CD3 delta

<400> SEQUENCE: 18

Phe Lys Ile Pro Ile Glu Glu Leu Glu Asp Arg Val Phe Val Asn Cys
 1               5                  10                  15

Asn Thr Ser Ile Thr Trp Val Glu Gly Thr Val Gly Thr Leu Leu Ser
                20                  25                  30

Asp Ile Thr Arg Leu Asp Leu Gly Lys Arg Ile Leu Asp Pro Arg Gly
            35                  40                  45

Ile Tyr Arg Cys Asn Gly Thr Asp Ile Tyr Lys Asp Lys Glu Ser Thr
        50                  55                  60

Val Gln Val His Tyr Arg Met Cys Gln Ser Cys Val Glu Leu Asp Pro
 65                  70                  75                  80

Ala Thr Val Ala Asp Tyr Lys Asp Asp Asp Lys
                85                  90

<210> SEQ ID NO 19
<211> LENGTH: 102
<212> TYPE: PRT
<213> ORGANISM: Artificial Sequence
<220> FEATURE:
<221> NAME/KEY: PEPTIDE
```

<223> OTHER INFORMATION: monkey CD3 epsilon

<400> SEQUENCE: 19

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
            20                  25                  30

Gly Ser Glu Ala Gln Trp Gln His Asn Gly Lys Asn Lys Glu Asp Ser
        35                  40                  45

Gly Asp Arg Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
                85                  90                  95

His His His His His His
            100

<210> SEQ ID NO 20
<211> LENGTH: 92
<212> TYPE: PRT
<213> ORGANISM: Artificial Sequence
<220> FEATURE:
<221> NAME/KEY: DOMAIN
<223> OTHER INFORMATION: monkey CD3 delta

<400> SEQUENCE: 20

Phe Lys Ile Pro Val Glu Glu Leu Glu Asp Arg Val Phe Val Lys Cys
1               5                   10                  15

Asn Thr Ser Val Thr Trp Val Glu Gly Thr Val Gly Thr Leu Leu Thr
            20                  25                  30

Asn Asn Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Ala
    50                  55                  60

Val Gln Val His Tyr Arg Met Cys Gln Asn Cys Val Glu Leu Asp Pro
65                  70                  75                  80

Ala Thr Leu Ala Asp Tyr Lys Asp Asp Asp Lys
                85                  90

<210> SEQ ID NO 21
<211> LENGTH: 93
<212> TYPE: PRT
<213> ORGANISM: Artificial Sequence
<220> FEATURE:
<221> NAME/KEY: PEPTIDE
<223> OTHER INFORMATION: murine CD3 epsilon

<400> SEQUENCE: 21

Asp Asp Ala Glu Asn Ile Glu Tyr Lys Val Ser Ile Ser Gly Thr Ser
1               5                   10                  15

Val Glu Leu Thr Cys Pro Leu Asp Ser Asp Glu Asn Leu Lys Trp Glu
            20                  25                  30

Lys Asn Gly Gln Glu Leu Pro Gln Lys His Asp Lys His Leu Val Leu
        35                  40                  45

Gln Asp Phe Ser Glu Val Glu Asp Ser Gly Tyr Tyr Val Cys Tyr Thr
    50                  55                  60

Pro Ala Ser Asn Lys Asn Thr Tyr Leu Tyr Leu Lys Ala Arg Val Cys
65                  70                  75                  80

```
Glu Tyr Cys Val Glu Val Asp His His His His His
                85                  90
```

```
<210> SEQ ID NO 22
<211> LENGTH: 92
<212> TYPE: PRT
<213> ORGANISM: Artificial Sequence
<220> FEATURE:
<221> NAME/KEY: PEPTIDE
<223> OTHER INFORMATION: murine CD3 delta

<400> SEQUENCE: 22

Phe Lys Ile Gln Val Thr Glu Tyr Glu Asp Lys Val Phe Val Thr Cys
1               5                   10                  15

Asn Thr Ser Val Met His Leu Asp Gly Thr Val Glu Gly Trp Phe Ala
            20                  25                  30

Lys Asn Lys Thr Leu Asn Leu Gly Lys Gly Val Leu Asp Pro Arg Gly
        35                  40                  45

Ile Tyr Leu Cys Asn Gly Thr Glu Gln Leu Ala Lys Val Val Ser Ser
    50                  55                  60

Val Gln Val His Tyr Arg Met Cys Gln Asn Cys Val Glu Leu Asp Ser
65                  70                  75                  80

Gly Thr Met Ala Asp Tyr Lys Asp Asp Asp Lys
                85                  90
```

```
<210> SEQ ID NO 23
<211> LENGTH: 207
<212> TYPE: PRT
<213> ORGANISM: Artificial Sequence
<220> FEATURE:
<221> NAME/KEY: PEPTIDE
<223> OTHER INFORMATION: human CD3 epsilon full-length amino acid
      sequence

<400> SEQUENCE: 23

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
```

-continued

```
                180                 185                 190
Lys Gly Gln Arg Asp Leu Tyr Ser Gly Leu Asn Gln Arg Arg Ile
            195                 200                 205

<210> SEQ ID NO 24
<211> LENGTH: 171
<212> TYPE: PRT
<213> ORGANISM: Artificial Sequence
<220> FEATURE:
<221> NAME/KEY: PEPTIDE
<223> OTHER INFORMATION: human CD3 delta full-length amino acid sequence

<400> SEQUENCE: 24

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 25
<211> LENGTH: 198
<212> TYPE: PRT
<213> ORGANISM: Artificial Sequence
<220> FEATURE:
<221> NAME/KEY: PEPTIDE
<223> OTHER INFORMATION: monkey CD3 epsilon full-length amino acid
      sequence

<400> SEQUENCE: 25

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95
```

```
Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp
        115                 120                 125

Ile Cys Ile Thr Leu Gly Leu Leu Leu Val Tyr Tyr Trp Ser Lys
130                 135                 140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Val Pro Asn
                165                 170                 175

Pro Asp Tyr Glu Pro Ile Arg Lys Gly Gln Gln Asp Leu Tyr Ser Gly
        180                 185                 190

Leu Asn Gln Arg Arg Ile
            195

<210> SEQ ID NO 26
<211> LENGTH: 171
<212> TYPE: PRT
<213> ORGANISM: Artificial Sequence
<220> FEATURE:
<221> NAME/KEY: PEPTIDE
<223> OTHER INFORMATION: monkey CD3 delta full-length amino acid
      sequence

<400> SEQUENCE: 26

Met Glu His Ser Thr Phe Leu Ser Gly Leu Val Leu Ala Thr Leu Leu
1               5                   10                  15

Ser Gln Val Ser Pro Phe Lys Ile Pro Val Glu Glu Leu Glu Asp Arg
            20                  25                  30

Val Phe Val Lys Cys Asn Thr Ser Val Thr Trp Val Glu Gly Thr Val
        35                  40                  45

Gly Thr Leu Leu Thr Asn Asn Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Ala Val Gln Val His Tyr Arg Met Cys Gln Asn Cys
                85                  90                  95

Val Glu Leu Asp Pro Ala Thr Leu Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser Arg Leu Gly Gly Asn Trp Ala Arg Asn Lys
                165                 170

<210> SEQ ID NO 27
<211> LENGTH: 189
<212> TYPE: PRT
<213> ORGANISM: Artificial Sequence
<220> FEATURE:
<221> NAME/KEY: PEPTIDE
<223> OTHER INFORMATION: murine CD3 epsilon full-length amino acid
      sequence

<400> SEQUENCE: 27

Met Arg Trp Asn Thr Phe Trp Gly Ile Leu Cys Leu Ser Leu Leu Ala
```

```
1               5                   10                  15
Val Gly Thr Cys Gln Asp Asp Ala Glu Asn Ile Glu Tyr Lys Val Ser
                20                  25                  30

Ile Ser Gly Thr Ser Val Glu Leu Thr Cys Pro Leu Asp Ser Asp Glu
                35                  40                  45

Asn Leu Lys Trp Glu Lys Asn Gly Gln Glu Leu Pro Gln Lys His Asp
50                  55                  60

Lys His Leu Val Leu Gln Asp Phe Ser Glu Val Glu Asp Ser Gly Tyr
65                  70                  75                  80

Tyr Val Cys Tyr Thr Pro Ala Ser Asn Lys Asn Thr Tyr Leu Tyr Leu
                85                  90                  95

Lys Ala Arg Val Cys Glu Tyr Cys Val Glu Val Asp Leu Thr Ala Val
                100                 105                 110

Ala Ile Ile Ile Ile Val Asp Ile Cys Ile Thr Leu Gly Leu Leu Met
                115                 120                 125

Val Ile Tyr Tyr Trp Ser Lys Asn Arg Lys Ala Lys Ala Lys Pro Val
130                 135                 140

Thr Arg Gly Thr Gly Ala Gly Ser Arg Pro Arg Gly Gln Asn Lys Glu
145                 150                 155                 160

Arg Pro Pro Pro Val Pro Asn Pro Asp Tyr Glu Pro Ile Arg Lys Gly
                165                 170                 175

Gln Arg Asp Leu Tyr Ser Gly Leu Asn Gln Arg Ala Val
                180                 185

<210> SEQ ID NO 28
<211> LENGTH: 173
<212> TYPE: PRT
<213> ORGANISM: Artificial Sequence
<220> FEATURE:
<221> NAME/KEY: PEPTIDE
<223> OTHER INFORMATION: murine CD3 delta full-length amino acid
      sequence

<400> SEQUENCE: 28

Met Glu His Ser Gly Ile Leu Ala Ser Leu Ile Leu Ile Ala Val Leu
1               5                   10                  15

Pro Gln Gly Ser Pro Phe Lys Ile Gln Val Thr Glu Tyr Glu Asp Lys
                20                  25                  30

Val Phe Val Thr Cys Asn Thr Ser Val Met His Leu Asp Gly Thr Val
                35                  40                  45

Glu Gly Trp Phe Ala Lys Asn Lys Thr Leu Asn Leu Gly Lys Gly Val
50                  55                  60

Leu Asp Pro Arg Gly Ile Tyr Leu Cys Asn Gly Thr Glu Gln Leu Ala
65                  70                  75                  80

Lys Val Val Ser Ser Val Gln Val His Tyr Arg Met Cys Gln Asn Cys
                85                  90                  95

Val Glu Leu Asp Ser Gly Thr Met Ala Gly Val Ile Phe Ile Asp Leu
                100                 105                 110

Ile Ala Thr Leu Leu Leu Ala Leu Gly Val Tyr Cys Phe Ala Gly His
                115                 120                 125

Glu Thr Gly Arg Pro Ser Gly Ala Ala Glu Val Gln Ala Leu Leu Lys
                130                 135                 140

Asn Glu Gln Leu Tyr Gln Pro Leu Arg Asp Arg Glu Asp Thr Gln Tyr
145                 150                 155                 160

Ser Arg Leu Gly Gly Asn Trp Pro Arg Asn Lys Lys Ser
                165                 170
```

<210> SEQ ID NO 29
<211> LENGTH: 125
<212> TYPE: PRT
<213> ORGANISM: Artificial Sequence
<220> FEATURE:
<221> NAME/KEY: DOMAIN
<223> OTHER INFORMATION: HRH-1

<400> SEQUENCE: 29

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Ala Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125
```

<210> SEQ ID NO 30
<211> LENGTH: 125
<212> TYPE: PRT
<213> ORGANISM: Artificial Sequence
<220> FEATURE:
<221> NAME/KEY: DOMAIN
<223> OTHER INFORMATION: HRH-2

<400> SEQUENCE: 30

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Pro Tyr Ile Ser Tyr Trp
            100                 105                 110

Ala Tyr Trp Gly Gln Gly Thr Leu Val Thr Val Ser Ser
        115                 120                 125
```

<210> SEQ ID NO 31
<211> LENGTH: 125
<212> TYPE: PRT
<213> ORGANISM: Artificial Sequence
<220> FEATURE:
<221> NAME/KEY: DOMAIN
<223> OTHER INFORMATION: HRH-3

<400> SEQUENCE: 31

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Glu Tyr Ile Ser Tyr Trp
            100                 105                 110

Ala Tyr Trp Gly Gln Gly Thr Leu Val Thr Val Ser Ser
            115                 120                 125

<210> SEQ ID NO 32
<211> LENGTH: 125
<212> TYPE: PRT
<213> ORGANISM: Artificial Sequence
<220> FEATURE:
<221> NAME/KEY: DOMAIN
<223> OTHER INFORMATION: HRH-4

<400> SEQUENCE: 32

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Asp Tyr Trp Gly Gln Gly Thr Leu Val Thr Val Ser Ser
            115                 120                 125

<210> SEQ ID NO 33
<211> LENGTH: 125
<212> TYPE: PRT
<213> ORGANISM: Artificial Sequence
<220> FEATURE:
<221> NAME/KEY: DOMAIN
<223> OTHER INFORMATION: HRH-5

<400> SEQUENCE: 33

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

```
Ala Met Ser Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125
```

<210> SEQ ID NO 34
<211> LENGTH: 125
<212> TYPE: PRT
<213> ORGANISM: Artificial Sequence
<220> FEATURE:
<221> NAME/KEY: DOMAIN
<223> OTHER INFORMATION: HRH-6

<400> SEQUENCE: 34

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Asn Lys Tyr Asn Asn Tyr Ala Thr Glu Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125
```

<210> SEQ ID NO 35
<211> LENGTH: 125
<212> TYPE: PRT
<213> ORGANISM: Artificial Sequence
<220> FEATURE:
<221> NAME/KEY: DOMAIN
<223> OTHER INFORMATION: HRH-7

<400> SEQUENCE: 35

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Glu Tyr Ala Ala
        50                  55                  60

Ser Val Lys Asp Arg Phe Thr Ile Ser Arg Asp Asp Ser Lys Asn Thr
65                  70                  75                  80
```

Ala Tyr Leu Gln Met Asn Asn Leu Lys Thr Glu Asp Thr Ala Val Tyr
            85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125

<210> SEQ ID NO 36
<211> LENGTH: 109
<212> TYPE: PRT
<213> ORGANISM: Artificial Sequence
<220> FEATURE:
<221> NAME/KEY: DOMAIN
<223> OTHER INFORMATION: HRL

<400> SEQUENCE: 36

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 37
<211> LENGTH: 5
<212> TYPE: PRT
<213> ORGANISM: Artificial Sequence
<220> FEATURE:
<221> NAME/KEY: DOMAIN
<223> OTHER INFORMATION: HRH-1 HCDR1

<400> SEQUENCE: 37

Lys Tyr Ala Met Asn
1               5

<210> SEQ ID NO 38
<211> LENGTH: 19
<212> TYPE: PRT
<213> ORGANISM: Artificial Sequence
<220> FEATURE:
<221> NAME/KEY: DOMAIN
<223> OTHER INFORMATION: HRH-1 HCDR2

<400> SEQUENCE: 38

Arg Ile Arg Ser Lys Ala Asn Asn Tyr Ala Thr Tyr Tyr Ala Asp Ser
1               5                   10                  15

Val Lys Asp

<210> SEQ ID NO 39
<211> LENGTH: 14
<212> TYPE: PRT
<213> ORGANISM: Artificial Sequence
<220> FEATURE:
<221> NAME/KEY: DOMAIN
<223> OTHER INFORMATION: HRH-1 HCDR3

<400> SEQUENCE: 39

His Gly Asn Phe Gly Asn Ser Tyr Ile Ser Tyr Trp Ala Tyr
1               5                   10

<210> SEQ ID NO 40
<211> LENGTH: 19
<212> TYPE: PRT
<213> ORGANISM: Artificial Sequence
<220> FEATURE:
<221> NAME/KEY: DOMAIN
<223> OTHER INFORMATION: HRH-2 HCDR2

<400> SEQUENCE: 40

Arg Ile Arg Ser Lys Tyr Asn Asn Tyr Ala Thr Tyr Tyr Ala Asp Ser
1               5                   10                  15

Val Lys Asp

<210> SEQ ID NO 41
<211> LENGTH: 14
<212> TYPE: PRT
<213> ORGANISM: Artificial Sequence
<220> FEATURE:
<221> NAME/KEY: DOMAIN
<223> OTHER INFORMATION: HRH-2 HCDR3

<400> SEQUENCE: 41

His Gly Asn Phe Gly Asn Pro Tyr Ile Ser Tyr Trp Ala Tyr
1               5                   10

<210> SEQ ID NO 42
<211> LENGTH: 14
<212> TYPE: PRT
<213> ORGANISM: Artificial Sequence
<220> FEATURE:
<221> NAME/KEY: DOMAIN
<223> OTHER INFORMATION: HRH-3 HCDR3

<400> SEQUENCE: 42

His Gly Asn Phe Gly Asn Glu Tyr Ile Ser Tyr Trp Ala Tyr
1               5                   10

<210> SEQ ID NO 43
<211> LENGTH: 14
<212> TYPE: PRT
<213> ORGANISM: Artificial Sequence
<220> FEATURE:
<221> NAME/KEY: DOMAIN
<223> OTHER INFORMATION: HRH-4 HCDR3

<400> SEQUENCE: 43

His Gly Asn Phe Gly Asn Ser Tyr Ile Ser Tyr Trp Asp Tyr
1               5                   10

<210> SEQ ID NO 44
<211> LENGTH: 5
<212> TYPE: PRT
<213> ORGANISM: Artificial Sequence
<220> FEATURE:
<221> NAME/KEY: DOMAIN
<223> OTHER INFORMATION: HRH-5 HCDR1

<400> SEQUENCE: 44

Lys Tyr Ala Met Ser
1               5

```
<210> SEQ ID NO 45
<211> LENGTH: 14
<212> TYPE: PRT
<213> ORGANISM: Artificial Sequence
<220> FEATURE:
<221> NAME/KEY: DOMAIN
<223> OTHER INFORMATION: HRH-5 HCDR3

<400> SEQUENCE: 45

His Gly Asn Phe Gly Asn Ser Tyr Ile Ser Tyr Trp Ala Tyr
1               5                   10

<210> SEQ ID NO 46
<211> LENGTH: 19
<212> TYPE: PRT
<213> ORGANISM: Artificial Sequence
<220> FEATURE:
<221> NAME/KEY: DOMAIN
<223> OTHER INFORMATION: HRH-6 HCDR2

<400> SEQUENCE: 46

Arg Ile Arg Asn Lys Tyr Asn Asn Tyr Ala Thr Glu Tyr Ala Asp Ser
1               5                   10                  15

Val Lys Asp

<210> SEQ ID NO 47
<211> LENGTH: 19
<212> TYPE: PRT
<213> ORGANISM: Artificial Sequence
<220> FEATURE:
<221> NAME/KEY: DOMAIN
<223> OTHER INFORMATION: HRH-7 HCDR2

<400> SEQUENCE: 47

Arg Ile Arg Ser Lys Tyr Asn Asn Tyr Ala Thr Glu Tyr Ala Ala Ser
1               5                   10                  15

Val Lys Asp

<210> SEQ ID NO 48
<211> LENGTH: 14
<212> TYPE: PRT
<213> ORGANISM: Artificial Sequence
<220> FEATURE:
<221> NAME/KEY: DOMAIN
<223> OTHER INFORMATION: HRL LCDR1

<400> SEQUENCE: 48

Gly Ser Ser Thr Gly Ala Val Thr Ser Gly Asn Tyr Pro Asn
1               5                   10

<210> SEQ ID NO 49
<211> LENGTH: 7
<212> TYPE: PRT
<213> ORGANISM: Artificial Sequence
<220> FEATURE:
<221> NAME/KEY: DOMAIN
<223> OTHER INFORMATION: HRL LCDR2

<400> SEQUENCE: 49

Gly Thr Lys Phe Leu Ala Pro
1               5

<210> SEQ ID NO 50
<211> LENGTH: 9
<212> TYPE: PRT
<213> ORGANISM: Artificial Sequence
<220> FEATURE:
```

<221> NAME/KEY: DOMAIN
<223> OTHER INFORMATION: HRL LCDR3

<400> SEQUENCE: 50

Val Leu Trp Tyr Ser Asn Arg Trp Val
1               5

<210> SEQ ID NO 51
<211> LENGTH: 244
<212> TYPE: PRT
<213> ORGANISM: Artificial Sequence
<220> FEATURE:
<221> NAME/KEY: PEPTIDE
<223> OTHER INFORMATION: B7H3-scFv1

<400> SEQUENCE: 51

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
                20                  25                  30

His Tyr Pro Ser Trp Tyr Gln Gln Thr Pro Gly Gln Ala Pro Arg Met
            35                  40                  45

Leu Ile Tyr Asn Thr Asn Thr Arg Ser Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gly
            100                 105                 110

Gly Gly Ser Gly Gly Gly Gly Ser Gly Gly Gly Gly Ser Gln Val Gln
        115                 120                 125

Leu Val Gln Ser Gly Gly Gly Val Val Gln Pro Gly Thr Ser Leu Arg
    130                 135                 140

Leu Ser Cys Ala Ala Ser Gly Phe Ile Phe Ser Ser Ser Ala Met His
145                 150                 155                 160

Trp Val Arg Gln Ala Pro Gly Lys Gly Leu Glu Trp Val Ala Val Ile
                165                 170                 175

Ser Tyr Asp Gly Ser Asn Lys Tyr Tyr Val Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Arg Ser
    210                 215                 220

Ala Arg Leu Tyr Ala Ser Phe Asp Tyr Trp Gly Gln Gly Ala Leu Val
225                 230                 235                 240

Thr Val Ser Ser

<210> SEQ ID NO 52
<211> LENGTH: 244
<212> TYPE: PRT
<213> ORGANISM: Artificial Sequence
<220> FEATURE:
<221> NAME/KEY: PEPTIDE
<223> OTHER INFORMATION: B7H3-scFv2

<400> SEQUENCE: 52

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Arg Leu Tyr Ala Ser Phe Asp Tyr Trp Gly Gln Gly
            100                 105                 110

Ala Leu Val Thr Val Ser Ser Gly Gly Gly Ser Gly Gly Gly Gly
            115                 120                 125

Ser Gly Gly Gly Gly Ser Gln Thr Val Val Thr Gln Glu Pro Ser Phe
130                 135                 140

Ser Val Ser Pro Gly Gly Thr Val Thr Leu Thr Cys Gly Leu Ser Ser
145                 150                 155                 160

Gly Ser Val Ser Thr Ser His Tyr Pro Ser Trp Tyr Gln Gln Thr Pro
            165                 170                 175

Gly Gln Ala Pro Arg Met Leu Ile Tyr Asn Thr Asn Thr Arg Ser Ser
            180                 185                 190

Gly Val Pro Asp Arg Phe Ser Gly Ser Ile Leu Gly Asn Lys Ala Ala
            195                 200                 205

Leu Thr Ile Thr Gly Ala Gln Ala Asp Asp Glu Ser Asp Tyr Tyr Cys
            210                 215                 220

Ala Ile His Val Asp Arg Asp Ile Trp Val Phe Gly Gly Gly Thr Lys
225                 230                 235                 240

Leu Thr Val Leu

<210> SEQ ID NO 53
<211> LENGTH: 244
<212> TYPE: PRT
<213> ORGANISM: Artificial Sequence
<220> FEATURE:
<221> NAME/KEY: PEPTIDE
<223> OTHER INFORMATION: B7H3-scFv3

<400> SEQUENCE: 53

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
            35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Cys Gly Thr Lys Leu Thr Val Leu Gly Gly
            100                 105                 110

Gly Gly Ser Gly Gly Gly Gly Ser Gly Gly Gly Gly Ser Gln Val Gln
            115                 120                 125

```
Leu Val Gln Ser Gly Gly Val Val Gln Pro Gly Thr Ser Leu Arg
        130             135             140

Leu Ser Cys Ala Ala Ser Gly Phe Ile Phe Ser Ser Ala Met His
145             150             155             160

Trp Val Arg Gln Ala Pro Gly Lys Cys Leu Glu Trp Val Ala Ile
                165             170             175

Ser Tyr Asp Gly Ser Asn Lys Tyr Tyr Val Asp Ser Val Lys Gly Arg
            180             185             190

Phe Thr Ile Ser Arg Asp Asn Ser Lys Asn Thr Leu Tyr Leu Gln Met
            195             200             205

Asn Ser Leu Arg Ala Glu Asp Thr Ala Val Tyr Tyr Cys Ala Arg Ser
    210             215             220

Ala Arg Leu Tyr Ala Ser Phe Asp Tyr Trp Gly Gln Gly Ala Leu Val
225             230             235             240

Thr Val Ser Ser
```

<210> SEQ ID NO 54
<211> LENGTH: 244
<212> TYPE: PRT
<213> ORGANISM: Artificial Sequence
<220> FEATURE:
<221> NAME/KEY: PEPTIDE
<223> OTHER INFORMATION: B7H3-scFv4

<400> SEQUENCE: 54

```
Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Cys Leu Glu Trp Val
        35                  40                  45

Ala Val Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Arg Leu Tyr Ala Ser Phe Asp Tyr Trp Gly Gln Gly
            100                 105                 110

Ala Leu Val Thr Val Ser Ser Gly Gly Gly Gly Ser Gly Gly Gly Gly
        115                 120                 125

Ser Gly Gly Gly Gly Ser Gln Thr Val Val Thr Gln Glu Pro Ser Phe
    130                 135                 140

Ser Val Ser Pro Gly Gly Thr Val Thr Leu Thr Cys Gly Leu Ser Ser
145                 150                 155                 160

Gly Ser Val Ser Thr Ser His Tyr Pro Ser Trp Tyr Gln Gln Thr Pro
                165                 170                 175

Gly Gln Ala Pro Arg Met Leu Ile Tyr Asn Thr Asn Thr Arg Ser Ser
            180                 185                 190

Gly Val Pro Asp Arg Phe Ser Gly Ser Ile Leu Gly Asn Lys Ala Ala
        195                 200                 205

Leu Thr Ile Thr Gly Ala Gln Ala Asp Asp Glu Ser Asp Tyr Tyr Cys
    210                 215                 220

Ala Ile His Val Asp Arg Asp Ile Trp Val Phe Gly Cys Gly Thr Lys
225                 230                 235                 240
```

Leu Thr Val Leu

<210> SEQ ID NO 55
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv1H

<400> SEQUENCE: 55

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Ala Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 56
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv2H

<400> SEQUENCE: 56

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
         35                  40                  45

Ala Arg Ile Arg Ser Lys Tyr Asn Asn Tyr Ala Thr Tyr Tyr Ala Asp
     50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Pro Tyr Ile Ser Tyr Trp
                100                 105                 110

Ala Tyr Trp Gly Gln Gly Thr Leu Val Thr Val Ser Ser Gly Gly Gly
         115                 120                 125

Gly Ser Gly Gly Gly Gly Ser Gly Gly Gly Gly Ser Gln Thr Val Val
     130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly
         180                 185                 190

Thr Lys Phe Leu Ala Pro Gly Thr Pro Ala Arg Phe Ser Gly Ser Leu
         195                 200                 205

Leu Gly Gly Lys Ala Ala Leu Thr Leu Ser Gly Val Gln Pro Glu Asp
         210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 57
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv3H

<400> SEQUENCE: 57

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Lys Tyr
             20                  25                  30

Ala Met Asn Trp Val Arg Gln Ala Pro Gly Lys Gly Leu Glu Trp Val
         35                  40                  45

Ala Arg Ile Arg Ser Lys Tyr Asn Asn Tyr Ala Thr Tyr Tyr Ala Asp
     50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Glu Tyr Ile Ser Tyr Trp
                100                 105                 110

Ala Tyr Trp Gly Gln Gly Thr Leu Val Thr Val Ser Ser Gly Gly Gly
         115                 120                 125

Gly Ser Gly Gly Gly Gly Ser Gly Gly Gly Gly Ser Gln Thr Val Val
     130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 58
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv4H

<400> SEQUENCE: 58

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Asp Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu

-continued

```
              245

<210> SEQ ID NO 59
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv5H

<400> SEQUENCE: 59

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Ser Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 60
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv6H

<400> SEQUENCE: 60

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
```

-continued

```
            35                  40                  45
Ala Arg Ile Arg Asn Lys Tyr Asn Asn Tyr Ala Thr Glu Tyr Ala Asp
 50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Phe Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245
```

<210> SEQ ID NO 61
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv7H

<400> SEQUENCE: 61

```
Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Lys Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Glu Tyr Ala Ala
 50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
        130                 135                 140
```

```
Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Phe Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
        210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245
```

```
<210> SEQ ID NO 62
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv1L

<400> SEQUENCE: 62

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Asn Lys Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Ala Asn Asn Tyr Ala Thr Tyr Tyr Ala Asp Ser Val Lys Asp
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Gly Asn Phe Gly Asn Ser Tyr Ile Ser Tyr Trp Ala Tyr Trp Gly
225                 230                 235                 240

Gln Gly Thr Leu Val Thr Val Ser Ser
                245
```

<210> SEQ ID NO 63
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv2L

<400> SEQUENCE: 63

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Asn Lys Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Gly Asn Phe Gly Asn Pro Tyr Ile Ser Tyr Trp Ala Tyr Trp Gly
225                 230                 235                 240

Gln Gly Thr Leu Val Thr Val Ser Ser
                245
```

<210> SEQ ID NO 64
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv3L

<400> SEQUENCE: 64

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45
```

```
Leu Ile Gly Gly Thr Lys Phe Leu Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Val Leu Trp Tyr Ser Asn
                 85                  90                  95

Arg Trp Val Phe Gly Gly Gly Thr Lys Leu Thr Val Leu Gly Gly Gly
                100                 105                 110

Gly Ser Gly Gly Gly Gly Ser Gly Gly Gly Gly Ser Glu Val Gln Leu
            115                 120                 125

Val Glu Ser Gly Gly Gly Leu Val Gln Pro Gly Gly Ser Leu Lys Leu
        130                 135                 140

Ser Cys Ala Ala Ser Gly Phe Thr Phe Asn Lys Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
                180                 185                 190

Arg Phe Thr Ile Ser Arg Asp Asp Ser Lys Asn Thr Ala Tyr Leu Gln
            195                 200                 205

Met Asn Asn Leu Lys Thr Glu Asp Thr Ala Val Tyr Tyr Cys Val Arg
        210                 215                 220

His Gly Asn Phe Gly Asn Glu Tyr Ile Ser Tyr Trp Ala Tyr Trp Gly
225                 230                 235                 240

Gln Gly Thr Leu Val Thr Val Ser Ser
                245

<210> SEQ ID NO 65
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv4L

<400> SEQUENCE: 65

Gln Thr Val Val Thr Gln Glu Pro Ser Leu Thr Val Ser Pro Gly Gly
 1                   5                  10                  15

Thr Val Thr Leu Thr Cys Gly Ser Ser Thr Gly Ala Val Thr Ser Gly
                 20                  25                  30

Asn Tyr Pro Asn Trp Val Gln Gln Lys Pro Gly Gln Ala Pro Arg Gly
                 35                  40                  45

Leu Ile Gly Gly Thr Lys Phe Leu Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Val Leu Trp Tyr Ser Asn
                 85                  90                  95

Arg Trp Val Phe Gly Gly Gly Thr Lys Leu Thr Val Leu Gly Gly Gly
                100                 105                 110

Gly Ser Gly Gly Gly Gly Ser Gly Gly Gly Gly Ser Glu Val Gln Leu
            115                 120                 125

Val Glu Ser Gly Gly Gly Leu Val Gln Pro Gly Gly Ser Leu Lys Leu
        130                 135                 140

Ser Cys Ala Ala Ser Gly Phe Thr Phe Asn Lys Tyr Ala Met Asn Trp
```

```
                145                 150                 155                 160
Val Arg Gln Ala Pro Gly Lys Gly Leu Glu Trp Val Arg Ile Arg
                165                 170                 175

Ser Lys Tyr Asn Asn Tyr Ala Thr Tyr Tyr Ala Asp Ser Val Lys Asp
                180                 185                 190

Arg Phe Thr Ile Ser Arg Asp Asp Ser Lys Asn Thr Ala Tyr Leu Gln
                195                 200                 205

Met Asn Asn Leu Lys Thr Glu Asp Thr Ala Val Tyr Tyr Cys Val Arg
                210                 215                 220

His Gly Asn Phe Gly Asn Ser Tyr Ile Ser Tyr Trp Asp Tyr Trp Gly
225                 230                 235                 240

Gln Gly Thr Leu Val Thr Val Ser Ser
                245

<210> SEQ ID NO 66
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv5L

<400> SEQUENCE: 66

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
                20                  25                  30

Asn Tyr Pro Asn Trp Val Gln Gln Lys Pro Gly Gln Ala Pro Arg Gly
                35                  40                  45

Leu Ile Gly Gly Thr Lys Phe Leu Ala Pro Gly Thr Pro Ala Arg Phe
        50                  55                  60

Ser Gly Ser Leu Leu Gly Gly Lys Ala Ala Leu Thr Leu Ser Gly Val
65              70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu Gly Gly Gly
                100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Lys Leu
        130                 135                 140

Ser Cys Ala Ala Ser Gly Phe Thr Phe Asn Lys Tyr Ala Met Ser Trp
145                 150                 155                 160

Val Arg Gln Ala Pro Gly Lys Gly Leu Glu Trp Val Arg Ile Arg
                165                 170                 175

Ser Lys Tyr Asn Asn Tyr Ala Thr Tyr Tyr Ala Asp Ser Val Lys Asp
                180                 185                 190

Arg Phe Thr Ile Ser Arg Asp Asp Ser Lys Asn Thr Ala Tyr Leu Gln
                195                 200                 205

Met Asn Asn Leu Lys Thr Glu Asp Thr Ala Val Tyr Tyr Cys Val Arg
                210                 215                 220

His Gly Asn Phe Gly Asn Ser Tyr Ile Ser Tyr Trp Ala Tyr Trp Gly
225                 230                 235                 240

Gln Gly Thr Leu Val Thr Val Ser Ser
                245
```

<210> SEQ ID NO 67
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv6L

<400> SEQUENCE: 67

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu Gly Gly Gly
            100                 105                 110

Gly Ser Gly Gly Gly Gly Ser Gly Gly Gly Ser Glu Val Gln Leu
        115                 120                 125

Val Glu Ser Gly Gly Gly Leu Val Gln Pro Gly Gly Ser Leu Lys Leu
    130                 135                 140

Ser Cys Ala Ala Ser Gly Phe Thr Phe Asn Lys Tyr Ala Met Asn Trp
145                 150                 155                 160

Val Arg Gln Ala Pro Gly Lys Gly Leu Glu Trp Val Ala Arg Ile Arg
                165                 170                 175

Asn Lys Tyr Asn Asn Tyr Ala Thr Glu Tyr Ala Asp Ser Val Lys Asp
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Gly Asn Phe Gly Asn Ser Tyr Ile Ser Tyr Trp Ala Tyr Trp Gly
225                 230                 235                 240

Gln Gly Thr Leu Val Thr Val Ser Ser
                245

<210> SEQ ID NO 68
<211> LENGTH: 249
<212> TYPE: PRT
<213> ORGANISM: Artificial Sequence
<220> FEATURE:
<221> NAME/KEY: PEPTIDE
<223> OTHER INFORMATION: CD3-scFv7L

<400> SEQUENCE: 68

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
50              55                  60

Ser Gly Ser Leu Leu Gly Gly Lys Ala Ala Leu Thr Leu Ser Gly Val
65              70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu Gly Gly Gly
            100                 105                 110

Gly Ser Gly Gly Gly Gly Ser Gly Gly Gly Ser Glu Val Gln Leu
            115                 120                 125

Val Glu Ser Gly Gly Gly Leu Val Gln Pro Gly Gly Ser Leu Lys Leu
130             135                 140

Ser Cys Ala Ala Ser Gly Phe Thr Phe Asn Lys Tyr Ala Met Asn Trp
145             150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Glu Tyr Ala Ala Ser Val Lys Asp
            180                 185                 190

Arg Phe Thr Ile Ser Arg Asp Asp Ser Lys Asn Thr Ala Tyr Leu Gln
            195                 200                 205

Met Asn Asn Leu Lys Thr Glu Asp Thr Ala Val Tyr Tyr Cys Val Arg
210             215                 220

His Gly Asn Phe Gly Asn Ser Tyr Ile Ser Tyr Trp Ala Tyr Trp Gly
225             230                 235                 240

Gln Gly Thr Leu Val Thr Val Ser Ser
                245

<210> SEQ ID NO 69
<211> LENGTH: 217
<212> TYPE: PRT
<213> ORGANISM: Artificial Sequence
<220> FEATURE:
<221> NAME/KEY: PEPTIDE
<223> OTHER INFORMATION: knob-Fc

<400> SEQUENCE: 69

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
50              55                  60

Gln Tyr Asn Ser Thr Tyr Arg Val Val Ser Val Leu Thr Val Leu His
65              70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Cys Arg Glu Glu Met
            115                 120                 125

Thr Lys Asn Gln Val Ser Leu Trp Cys Leu Val Lys Gly Phe Tyr Pro
130             135                 140

Ser Asp Ile Ala Val Glu Trp Glu Ser Asn Gly Gln Pro Glu Asn Asn
145             150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 70
<211> LENGTH: 217
<212> TYPE: PRT
<213> ORGANISM: Artificial Sequence
<220> FEATURE:
<221> NAME/KEY: PEPTIDE
<223> OTHER INFORMATION: hole-Fc

<400> SEQUENCE: 70

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 71
<211> LENGTH: 474
<212> TYPE: PRT
<213> ORGANISM: Artificial Sequence
<220> FEATURE:
<221> NAME/KEY: PEPTIDE
<223> OTHER INFORMATION: 113 second polypeptide chain

<400> SEQUENCE: 71

Gln Thr Val Val Thr Gln Glu Pro Ser Phe Ser Val Ser Pro Gly Gly
1               5                   10                  15

```
Thr Val Thr Leu Thr Cys Gly Leu Ser Ser Gly Ser Val Thr Ser
             20                  25                  30

His Tyr Pro Ser Trp Tyr Gln Gln Thr Pro Gly Gln Ala Pro Arg Met
             35                  40                  45

Leu Ile Tyr Asn Thr Asn Thr Arg Ser Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Ala Ile His Val Asp Arg
                 85                  90                  95

Asp Ile Trp Val Phe Gly Gly Thr Lys Leu Thr Val Leu Gly Gly
            100                 105                 110

Gly Gly Ser Gly Gly Gly Ser Gly Gly Gly Gly Ser Gln Val Gln
            115                 120                 125

Leu Val Gln Ser Gly Gly Val Val Gln Pro Gly Thr Ser Leu Arg
130                 135                 140

Leu Ser Cys Ala Ala Ser Gly Phe Ile Phe Ser Ser Ala Met His
145                 150                 155                 160

Trp Val Arg Gln Ala Pro Gly Lys Gly Leu Glu Trp Val Ala Val Ile
                165                 170                 175

Ser Tyr Asp Gly Ser Asn Lys Tyr Tyr Val Asp Ser Val Lys Gly Arg
            180                 185                 190

Phe Thr Ile Ser Arg Asp Asn Ser Lys Asn Thr Leu Tyr Leu Gln Met
            195                 200                 205

Asn Ser Leu Arg Ala Glu Asp Thr Ala Val Tyr Tyr Cys Ala Arg Ser
210                 215                 220

Ala Arg Leu Tyr Ala Ser Phe Asp Tyr Trp Gly Gln Gly Ala Leu Val
225                 230                 235                 240

Thr Val Ser Ser Gly Gly Gly Asp Lys Thr His Thr Cys Pro Pro Cys
                245                 250                 255

Pro Ala Pro Glu Ala Ala Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Cys Thr Leu Pro Pro Ser Arg Glu Glu
370                 375                 380

Met Thr Lys Asn Gln Val Ser Leu Ser Cys Ala Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430
```

-continued

```
Leu Val Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 72
<211> LENGTH: 734
<212> TYPE: PRT
<213> ORGANISM: Artificial Sequence
<220> FEATURE:
<221> NAME/KEY: PEPTIDE
<223> OTHER INFORMATION: 113  first polypeptide chain

<400> SEQUENCE: 72

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gly
            100                 105                 110

Gly Gly Ser Gly Gly Gly Ser Gly Gly Gly Ser Gln Val Gln
            115                 120                 125

Leu Val Gln Ser Gly Gly Val Val Gln Pro Gly Thr Ser Leu Arg
130                 135                 140

Leu Ser Cys Ala Ala Ser Gly Phe Ile Phe Ser Ser Ala Met His
145                 150                 155                 160

Trp Val Arg Gln Ala Pro Gly Lys Gly Leu Glu Trp Val Ala Val Ile
                165                 170                 175

Ser Tyr Asp Gly Ser Asn Lys Tyr Tyr Val Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Arg Ser
    210                 215                 220

Ala Arg Leu Tyr Ala Ser Phe Asp Tyr Trp Gly Gln Gly Ala Leu Val
225                 230                 235                 240

Thr Val Ser Ser Gly Gly Gly Ser Glu Val Gln Leu Val Glu Ser
            245                 250                 255

Gly Gly Gly Leu Val Gln Pro Gly Gly Ser Leu Lys Leu Ser Cys Ala
        260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320
```

```
Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Pro Tyr Ile Ser Tyr Trp Ala Tyr Trp Gly Gln Gly Thr
        355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Asp Lys Thr His Thr Cys Pro Pro Cys Pro Ala
            500                 505                 510

Pro Glu Ala Ala Gly Gly Pro Ser Val Phe Leu Phe Pro Pro Lys Pro
        515                 520                 525

Lys Asp Thr Leu Met Ile Ser Arg Thr Pro Glu Val Thr Cys Val Val
    530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
            580                 585                 590

Asp Trp Leu Asn Gly Lys Glu Tyr Lys Cys Lys Val Ser Asn Lys Ala
        595                 600                 605

Leu Pro Ala Pro Ile Glu Lys Thr Ile Ser Lys Ala Lys Gly Gln Pro
    610                 615                 620

Arg Glu Pro Gln Val Tyr Thr Leu Pro Pro Cys Arg Glu Glu Met Thr
625                 630                 635                 640

Lys Asn Gln Val Ser Leu Trp Cys Leu Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
        675                 680                 685

Ser Lys Leu Thr Val Asp Lys Ser Arg Trp Gln Gln Gly Asn Val Phe
    690                 695                 700

Ser Cys Ser Val Met His Glu Ala Leu His Asn His Tyr Thr Gln Lys
705                 710                 715                 720

Ser Leu Ser Leu Ser Pro Gly Lys His His His His His
                725                 730
```

```
<210> SEQ ID NO 73
<211> LENGTH: 734
<212> TYPE: PRT
<213> ORGANISM: Artificial Sequence
<220> FEATURE:
<221> NAME/KEY: PEPTIDE
<223> OTHER INFORMATION: 118  first polypeptide chain

<400> SEQUENCE: 73

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Glu Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Gly Gly Gly Ser Gln Thr
                245                 250                 255

Val Val Thr Gln Glu Pro Ser Phe Ser Val Ser Pro Gly Gly Thr Val
            260                 265                 270

Thr Leu Thr Cys Gly Leu Ser Ser Gly Ser Val Ser Thr Ser His Tyr
        275                 280                 285

Pro Ser Trp Tyr Gln Gln Thr Pro Gly Gln Ala Pro Arg Met Leu Ile
    290                 295                 300

Tyr Asn Thr Asn Thr Arg Ser Ser Gly Val Pro Asp Arg Phe Ser Gly
305                 310                 315                 320

Ser Ile Leu Gly Asn Lys Ala Ala Leu Thr Ile Thr Gly Ala Gln Ala
                325                 330                 335

Asp Asp Glu Ser Asp Tyr Tyr Cys Ala Ile His Val Asp Arg Asp Ile
            340                 345                 350

Trp Val Phe Gly Gly Gly Thr Lys Leu Thr Val Leu Gly Gly Gly Gly
        355                 360                 365
```

Ser Gly Gly Gly Gly Ser Gly Gly Gly Ser Gln Val Gln Leu Val
        370             375             380

Gln Ser Gly Gly Gly Val Val Gln Pro Gly Thr Ser Leu Arg Leu Ser
385             390             395             400

Cys Ala Ala Ser Gly Phe Ile Phe Ser Ser Ala Met His Trp Val
            405             410             415

Arg Gln Ala Pro Gly Lys Gly Leu Glu Trp Val Ala Val Ile Ser Tyr
            420             425             430

Asp Gly Ser Asn Lys Tyr Tyr Val Asp Ser Val Lys Gly Arg Phe Thr
        435             440             445

Ile Ser Arg Asp Asn Ser Lys Asn Thr Leu Tyr Leu Gln Met Asn Ser
450             455             460

Leu Arg Ala Glu Asp Thr Ala Val Tyr Tyr Cys Ala Arg Ser Ala Arg
465             470             475             480

Leu Tyr Ala Ser Phe Asp Tyr Trp Gly Gln Gly Ala Leu Val Thr Val
            485             490             495

Ser Ser Gly Gly Gly Asp Lys Thr His Thr Cys Pro Pro Cys Pro Ala
        500             505             510

Pro Glu Ala Ala Gly Gly Pro Ser Val Phe Leu Phe Pro Pro Lys Pro
        515             520             525

Lys Asp Thr Leu Met Ile Ser Arg Thr Pro Glu Val Thr Cys Val Val
530             535             540

Val Asp Val Ser His Glu Asp Pro Glu Val Lys Phe Asn Trp Tyr Val
545             550             555             560

Asp Gly Val Glu Val His Asn Ala Lys Thr Lys Pro Arg Glu Glu Gln
            565             570             575

Tyr Asn Ser Thr Tyr Arg Val Val Ser Val Leu Thr Val Leu His Gln
        580             585             590

Asp Trp Leu Asn Gly Lys Glu Tyr Lys Cys Lys Val Ser Asn Lys Ala
        595             600             605

Leu Pro Ala Pro Ile Glu Lys Thr Ile Ser Lys Ala Lys Gly Gln Pro
610             615             620

Arg Glu Pro Gln Val Tyr Thr Leu Pro Pro Cys Arg Glu Glu Met Thr
625             630             635             640

Lys Asn Gln Val Ser Leu Trp Cys Leu Val Lys Gly Phe Tyr Pro Ser
            645             650             655

Asp Ile Ala Val Glu Trp Glu Ser Asn Gly Gln Pro Glu Asn Asn Tyr
            660             665             670

Lys Thr Thr Pro Pro Val Leu Asp Ser Asp Gly Ser Phe Phe Leu Tyr
        675             680             685

Ser Lys Leu Thr Val Asp Lys Ser Arg Trp Gln Gln Gly Asn Val Phe
690             695             700

Ser Cys Ser Val Met His Glu Ala Leu His Asn His Tyr Thr Gln Lys
705             710             715             720

Ser Leu Ser Leu Ser Pro Gly Lys His His His His His
            725             730

<210> SEQ ID NO 74
<211> LENGTH: 732
<212> TYPE: PRT
<213> ORGANISM: Artificial Sequence
<220> FEATURE:
<221> NAME/KEY: PEPTIDE
<223> OTHER INFORMATION: 119 first polypeptide chain

<400> SEQUENCE: 74

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Glu Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gln Thr Val Val Thr Gln
    130                 135                 140

Glu Pro Ser Leu Thr Val Ser Pro Gly Gly Thr Val Thr Leu Thr Cys
145                 150                 155                 160

Gly Ser Ser Thr Gly Ala Val Thr Ser Gly Asn Tyr Pro Asn Trp Val
                165                 170                 175

Gln Gln Lys Pro Gly Gln Ala Pro Arg Gly Leu Ile Gly Gly Thr Lys
            180                 185                 190

Phe Leu Ala Pro Gly Thr Pro Ala Arg Phe Ser Gly Ser Leu Leu Gly
        195                 200                 205

Gly Lys Ala Ala Leu Thr Leu Ser Gly Val Gln Pro Glu Asp Glu Ala
    210                 215                 220

Glu Tyr Tyr Cys Val Leu Trp Tyr Ser Asn Arg Trp Val Phe Gly Gly
225                 230                 235                 240

Gly Thr Lys Leu Thr Val Leu Gly Gly Gly Ser Gln Thr Val Val
                245                 250                 255

Thr Gln Glu Pro Ser Phe Ser Val Ser Pro Gly Gly Thr Val Thr Leu
            260                 265                 270

Thr Cys Gly Leu Ser Ser Gly Ser Val Ser Thr Ser His Tyr Pro Ser
        275                 280                 285

Trp Tyr Gln Gln Thr Pro Gly Gln Ala Pro Arg Met Leu Ile Tyr Asn
    290                 295                 300

Thr Asn Thr Arg Ser Ser Gly Val Pro Asp Arg Phe Ser Gly Ser Ile
305                 310                 315                 320

Leu Gly Asn Lys Ala Ala Leu Thr Ile Thr Gly Ala Gln Ala Asp Asp
                325                 330                 335

Glu Ser Asp Tyr Tyr Cys Ala Ile His Val Asp Arg Asp Ile Trp Val
            340                 345                 350

Phe Gly Gly Gly Thr Lys Leu Thr Val Leu Gly Gly Gly Gly Ser Gly
        355                 360                 365

Gly Gly Gly Ser Gly Gly Gly Gly Ser Gln Val Gln Leu Val Gln Ser
    370                 375                 380

Gly Gly Gly Val Val Gln Pro Gly Thr Ser Leu Arg Leu Ser Cys Ala
385                 390                 395                 400

Ala Ser Gly Phe Ile Phe Ser Ser Ser Ala Met His Trp Val Arg Gln
                405                 410                 415
```

```
Ala Pro Gly Lys Gly Leu Glu Trp Val Ala Val Ile Ser Tyr Asp Gly
                420                 425                 430

Ser Asn Lys Tyr Tyr Val Asp Ser Val Lys Gly Arg Phe Thr Ile Ser
            435                 440                 445

Arg Asp Asn Ser Lys Asn Thr Leu Tyr Leu Gln Met Asn Ser Leu Arg
450                 455                 460

Ala Glu Asp Thr Ala Val Tyr Tyr Cys Ala Arg Ser Ala Arg Leu Tyr
465                 470                 475                 480

Ala Ser Phe Asp Tyr Trp Gly Gln Gly Ala Leu Val Thr Val Ser Ser
                485                 490                 495

Gly Gly Gly Asp Lys Thr His Thr Cys Pro Pro Cys Pro Ala Pro Glu
                500                 505                 510

Ala Ala Gly Gly Pro Ser Val Phe Leu Phe Pro Pro Lys Pro Lys Asp
            515                 520                 525

Thr Leu Met Ile Ser Arg Thr Pro Glu Val Thr Cys Val Val Val Asp
530                 535                 540

Val Ser His Glu Asp Pro Glu Val Lys Phe Asn Trp Tyr Val Asp Gly
545                 550                 555                 560

Val Glu Val His Asn Ala Lys Thr Lys Pro Arg Glu Glu Gln Tyr Asn
                565                 570                 575

Ser Thr Tyr Arg Val Val Ser Val Leu Thr Val Leu His Gln Asp Trp
            580                 585                 590

Leu Asn Gly Lys Glu Tyr Lys Cys Lys Val Ser Asn Lys Ala Leu Pro
        595                 600                 605

Ala Pro Ile Glu Lys Thr Ile Ser Lys Ala Lys Gly Gln Pro Arg Glu
610                 615                 620

Pro Gln Val Tyr Thr Leu Pro Pro Cys Arg Glu Glu Met Thr Lys Asn
625                 630                 635                 640

Gln Val Ser Leu Trp Cys Leu Val Lys Gly Phe Tyr Pro Ser Asp Ile
                645                 650                 655

Ala Val Glu Trp Glu Ser Asn Gly Gln Pro Glu Asn Asn Tyr Lys Thr
            660                 665                 670

Thr Pro Pro Val Leu Asp Ser Asp Gly Ser Phe Phe Leu Tyr Ser Lys
        675                 680                 685

Leu Thr Val Asp Lys Ser Arg Trp Gln Gln Gly Asn Val Phe Ser Cys
690                 695                 700

Ser Val Met His Glu Ala Leu His Asn His Tyr Thr Gln Lys Ser Leu
705                 710                 715                 720

Ser Leu Ser Pro Gly Lys His His His His His His
                725                 730

<210> SEQ ID NO 75
<211> LENGTH: 734
<212> TYPE: PRT
<213> ORGANISM: Artificial Sequence
<220> FEATURE:
<221> NAME/KEY: PEPTIDE
<223> OTHER INFORMATION: 126 first polypeptide

<400> SEQUENCE: 75

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
                20                  25                  30

Ala Met Asn Trp Val Arg Gln Ala Pro Gly Lys Gly Leu Glu Trp Val
```

35                  40                  45
Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Pro Tyr Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Gly Gly Gly Ser Gln Thr
                245                 250                 255

Val Val Thr Gln Glu Pro Ser Phe Ser Val Ser Pro Gly Gly Thr Val
            260                 265                 270

Thr Leu Thr Cys Gly Leu Ser Ser Gly Ser Val Ser Thr Ser His Tyr
        275                 280                 285

Pro Ser Trp Tyr Gln Gln Thr Pro Gly Gln Ala Pro Arg Met Leu Ile
290                 295                 300

Tyr Asn Thr Asn Thr Arg Ser Ser Gly Val Pro Asp Arg Phe Ser Gly
305                 310                 315                 320

Ser Ile Leu Gly Asn Lys Ala Ala Leu Thr Ile Thr Gly Ala Gln Ala
                325                 330                 335

Asp Asp Glu Ser Asp Tyr Tyr Cys Ala Ile His Val Asp Arg Asp Ile
            340                 345                 350

Trp Val Phe Gly Gly Gly Thr Lys Leu Thr Val Leu Gly Gly Gly Gly
        355                 360                 365

Ser Gly Gly Gly Gly Ser Gly Gly Gly Ser Gln Val Gln Leu Val
    370                 375                 380

Gln Ser Gly Gly Gly Val Val Gln Pro Gly Thr Ser Leu Arg Leu Ser
385                 390                 395                 400

Cys Ala Ala Ser Gly Phe Ile Phe Ser Ser Ser Ala Met His Trp Val
                405                 410                 415

Arg Gln Ala Pro Gly Lys Gly Leu Glu Trp Val Ala Val Ile Ser Tyr
            420                 425                 430

Asp Gly Ser Asn Lys Tyr Tyr Val Asp Ser Val Lys Gly Arg Phe Thr
        435                 440                 445

Ile Ser Arg Asp Asn Ser Lys Asn Thr Leu Tyr Leu Gln Met Asn Ser
        450                 455                 460

```
Leu Arg Ala Glu Asp Thr Ala Val Tyr Tyr Cys Ala Arg Ser Ala Arg
465                 470                 475                 480

Leu Tyr Ala Ser Phe Asp Tyr Trp Gly Gln Gly Ala Leu Val Thr Val
                485                 490                 495

Ser Ser Gly Gly Gly Asp Lys Thr His Thr Cys Pro Pro Cys Pro Ala
            500                 505                 510

Pro Glu Ala Ala Gly Gly Pro Ser Val Phe Leu Phe Pro Pro Lys Pro
            515                 520                 525

Lys Asp Thr Leu Met Ile Ser Arg Thr Pro Glu Val Thr Cys Val Val
        530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
            580                 585                 590

Asp Trp Leu Asn Gly Lys Glu Tyr Lys Cys Lys Val Ser Asn Lys Ala
            595                 600                 605

Leu Pro Ala Pro Ile Glu Lys Thr Ile Ser Lys Ala Lys Gly Gln Pro
        610                 615                 620

Arg Glu Pro Gln Val Tyr Thr Leu Pro Pro Cys Arg Glu Glu Met Thr
625                 630                 635                 640

Lys Asn Gln Val Ser Leu Trp Cys Leu Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
        675                 680                 685

Ser Lys Leu Thr Val Asp Lys Ser Arg Trp Gln Gln Gly Asn Val Phe
690                 695                 700

Ser Cys Ser Val Met His Glu Ala Leu His Asn His Tyr Thr Gln Lys
705                 710                 715                 720

Ser Leu Ser Leu Ser Pro Gly Lys His His His His His
                725                 730

<210> SEQ ID NO 76
<211> LENGTH: 734
<212> TYPE: PRT
<213> ORGANISM: Artificial Sequence
<220> FEATURE:
<221> NAME/KEY: PEPTIDE
<223> OTHER INFORMATION: 127 first polypeptide

<400> SEQUENCE: 76

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
```

```
                    85                  90                  95
Asp Ile Trp Val Phe Gly Gly Thr Lys Leu Thr Val Leu Gly Gly
                   100                 105                 110

Gly Gly Ser Gly Gly Gly Ser Gly Gly Gly Ser Gln Val Gln
            115                 120                 125

Leu Val Gln Ser Gly Gly Val Val Gln Pro Gly Thr Ser Leu Arg
        130                 135                 140

Leu Ser Cys Ala Ala Ser Gly Phe Ile Phe Ser Ser Ala Met His
145                 150                 155                 160

Trp Val Arg Gln Ala Pro Gly Lys Gly Leu Glu Trp Val Ala Ile
                165                 170                 175

Ser Tyr Asp Gly Ser Asn Lys Tyr Tyr Val Asp Ser Val Lys Gly Arg
            180                 185                 190

Phe Thr Ile Ser Arg Asp Asn Ser Lys Asn Thr Leu Tyr Leu Gln Met
                195                 200                 205

Asn Ser Leu Arg Ala Glu Asp Thr Ala Val Tyr Tyr Cys Ala Arg Ser
        210                 215                 220

Ala Arg Leu Tyr Ala Ser Phe Asp Tyr Trp Gly Gln Gly Ala Leu Val
225                 230                 235                 240

Thr Val Ser Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
        260                 265                 270

Ala Ser Gly Phe Thr Phe Asn Lys Tyr Ala Met Asn Trp Val Arg Gln
    275                 280                 285

Ala Pro Gly Lys Gly Leu Glu Trp Val Ala Arg Ile Arg Ser Lys Tyr
290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Glu Tyr Ile Ser Tyr Trp Ala Tyr Trp Gly Gln Gly Thr
        355                 360                 365

Leu Val Thr Val Ser Ser Gly Gly Gly Ser Gly Gly Gly Ser
        370                 375                 380

Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Lys Pro Gly
            420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Thr Lys Leu Thr
                485                 490                 495

Val Leu Gly Gly Gly Asp Lys Thr His Thr Cys Pro Pro Cys Pro Ala
            500                 505                 510
```

Pro Glu Ala Ala Gly Gly Pro Ser Val Phe Leu Phe Pro Lys Pro
            515                 520                 525

Lys Asp Thr Leu Met Ile Ser Arg Thr Pro Glu Val Thr Cys Val Val
530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
                580                 585                 590

Asp Trp Leu Asn Gly Lys Glu Tyr Lys Cys Lys Val Ser Asn Lys Ala
            595                 600                 605

Leu Pro Ala Pro Ile Glu Lys Thr Ile Ser Lys Ala Lys Gly Gln Pro
            610                 615                 620

Arg Glu Pro Gln Val Tyr Thr Leu Pro Pro Cys Arg Glu Glu Met Thr
625                 630                 635                 640

Lys Asn Gln Val Ser Leu Trp Cys Leu Val Lys Gly Phe Tyr Pro Ser
                645                 650                 655

Asp Ile Ala Val Glu Trp Glu Ser Asn Gly Gln Pro Glu Asn Asn Tyr
                660                 665                 670

Lys Thr Thr Pro Pro Val Leu Asp Ser Asp Gly Ser Phe Phe Leu Tyr
            675                 680                 685

Ser Lys Leu Thr Val Asp Lys Ser Arg Trp Gln Gln Gly Asn Val Phe
            690                 695                 700

Ser Cys Ser Val Met His Glu Ala Leu His Asn His Tyr Thr Gln Lys
705                 710                 715                 720

Ser Leu Ser Leu Ser Pro Gly Lys His His His His His His
                725                 730

<210> SEQ ID NO 77
<211> LENGTH: 739
<212> TYPE: PRT
<213> ORGANISM: Artificial Sequence
<220> FEATURE:
<221> NAME/KEY: PEPTIDE
<223> OTHER INFORMATION: 128 first polypeptide

<400> SEQUENCE: 77

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
                20                  25                  30

His Tyr Pro Ser Trp Tyr Gln Gln Thr Pro Gly Gln Ala Pro Arg Met
            35                  40                  45

Leu Ile Tyr Asn Thr Asn Thr Arg Ser Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gly
                100                 105                 110

Gly Gly Ser Gly Gly Gly Gly Ser Gly Gly Gly Gly Ser Gln Val Gln
            115                 120                 125

Leu Val Gln Ser Gly Gly Gly Val Val Gln Pro Gly Thr Ser Leu Arg

-continued

```
                130                 135                 140
Leu Ser Cys Ala Ala Ser Gly Phe Ile Phe Ser Ser Ala Met His
145                 150                 155                 160

Trp Val Arg Gln Ala Pro Gly Lys Gly Leu Glu Trp Val Ala Ile
                165                 170                 175

Ser Tyr Asp Gly Ser Asn Lys Tyr Tyr Val Asp Ser Val Lys Gly Arg
            180                 185                 190

Phe Thr Ile Ser Arg Asp Asn Ser Lys Asn Thr Leu Tyr Leu Gln Met
            195                 200                 205

Asn Ser Leu Arg Ala Glu Asp Thr Ala Val Tyr Tyr Cys Ala Arg Ser
210                 215                 220

Ala Arg Leu Tyr Ala Ser Phe Asp Tyr Trp Gly Gln Gly Ala Leu Val
225                 230                 235                 240

Thr Val Ser Ser Gly Gly Gly Gly Ser Gly Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Met
275                 280                 285

Asn Trp Val Arg Gln Ala Pro Gly Lys Gly Leu Glu Trp Val Ala Arg
290                 295                 300

Ile Arg Ser Lys Tyr Asn Asn Tyr Ala Thr Tyr Tyr Ala Asp Ser Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350

Val Arg His Gly Asn Phe Gly Asn Pro Tyr Ile Ser Tyr Trp Ala Tyr
            355                 360                 365

Trp Gly Gln Gly Thr Leu Val Thr Val Ser Ser Gly Gly Gly Gly Ser
            370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Gly Ser Ser Thr Gly Ala Val Ser Gly Asn Tyr Pro Asn Trp Val
            420                 425                 430

Gln Gln Lys Pro Gly Gln Ala Pro Arg Gly Leu Ile Gly Gly Thr Lys
            435                 440                 445

Phe Leu Ala Pro Gly Thr Pro Ala Arg Phe Ser Gly Ser Leu Leu Gly
450                 455                 460

Gly Lys Ala Ala Leu Thr Leu Ser Gly Val Gln Pro Glu Asp Glu Ala
465                 470                 475                 480

Glu Tyr Tyr Cys Val Leu Trp Tyr Ser Asn Arg Trp Val Phe Gly Gly
                485                 490                 495

Gly Thr Lys Leu Thr Val Leu Gly Gly Gly Asp Lys Thr His Thr Cys
            500                 505                 510

Pro Pro Cys Pro Ala Pro Glu Ala Ala Gly Gly Pro Ser Val Phe Leu
            515                 520                 525

Phe Pro Pro Lys Pro Lys Asp Thr Leu Met Ile Ser Arg Thr Pro Glu
            530                 535                 540

Val Thr Cys Val Val Val Asp Val Ser His Glu Asp Pro Glu Val Lys
545                 550                 555                 560
```

```
Phe Asn Trp Tyr Val Asp Gly Val Glu Val His Asn Ala Lys Thr Lys
                565                 570                 575
Pro Arg Glu Glu Gln Tyr Asn Ser Thr Tyr Arg Val Val Ser Val Leu
            580                 585                 590
Thr Val Leu His Gln Asp Trp Leu Asn Gly Lys Glu Tyr Lys Cys Lys
        595                 600                 605
Val Ser Asn Lys Ala Leu Pro Ala Pro Ile Glu Lys Thr Ile Ser Lys
610                 615                 620
Ala Lys Gly Gln Pro Arg Glu Pro Gln Val Tyr Thr Leu Pro Pro Cys
625                 630                 635                 640
Arg Glu Glu Met Thr Lys Asn Gln Val Ser Leu Trp Cys Leu Val Lys
                645                 650                 655
Gly Phe Tyr Pro Ser Asp Ile Ala Val Glu Trp Glu Ser Asn Gly Gln
            660                 665                 670
Pro Glu Asn Asn Tyr Lys Thr Thr Pro Pro Val Leu Asp Ser Asp Gly
        675                 680                 685
Ser Phe Phe Leu Tyr Ser Lys Leu Thr Val Asp Lys Ser Arg Trp Gln
690                 695                 700
Gln Gly Asn Val Phe Ser Cys Ser Val Met His Glu Ala Leu His Asn
705                 710                 715                 720
His Tyr Thr Gln Lys Ser Leu Ser Leu Ser Pro Gly Lys His His His
                725                 730                 735
His His His

<210> SEQ ID NO 78
<211> LENGTH: 734
<212> TYPE: PRT
<213> ORGANISM: Artificial Sequence
<220> FEATURE:
<221> NAME/KEY: PEPTIDE
<223> OTHER INFORMATION: 132 first polypeptide

<400> SEQUENCE: 78

Gln Thr Val Val Thr Gln Glu Pro Ser Phe Ser Val Ser Pro Gly Gly
1               5                   10                  15
Thr Val Thr Leu Thr Cys Gly Leu Ser Ser Gly Ser Val Ser Thr Ser
            20                  25                  30
His Tyr Pro Ser Trp Tyr Gln Gln Thr Pro Gly Gln Ala Pro Arg Met
        35                  40                  45
Leu Ile Tyr Asn Thr Asn Thr Arg Ser Ser Gly Val Pro Asp Arg Phe
    50                  55                  60
Ser Gly Ser Ile Leu Gly Asn Lys Ala Ala Leu Thr Ile Thr Gly Ala
65                  70                  75                  80
Gln Ala Asp Asp Glu Ser Asp Tyr Tyr Cys Ala Ile His Val Asp Arg
                85                  90                  95
Asp Ile Trp Val Phe Gly Cys Gly Thr Lys Leu Thr Val Leu Gly Gly
            100                 105                 110
Gly Gly Ser Gly Gly Gly Gly Ser Gly Gly Gly Gly Ser Gln Val Gln
        115                 120                 125
Leu Val Gln Ser Gly Gly Val Val Gln Pro Gly Thr Ser Leu Arg
    130                 135                 140
Leu Ser Cys Ala Ala Ser Gly Phe Ile Phe Ser Ser Ala Met His
145                 150                 155                 160
Trp Val Arg Gln Ala Pro Gly Lys Cys Leu Glu Trp Val Ala Val Ile
                165                 170                 175
```

```
Ser Tyr Asp Gly Ser Asn Lys Tyr Tyr Val Asp Ser Val Lys Gly Arg
            180                 185                 190
Phe Thr Ile Ser Arg Asp Asn Ser Lys Asn Thr Leu Tyr Leu Gln Met
        195                 200                 205
Asn Ser Leu Arg Ala Glu Asp Thr Ala Val Tyr Tyr Cys Ala Arg Ser
    210                 215                 220
Ala Arg Leu Tyr Ala Ser Phe Asp Tyr Trp Gly Gln Gly Ala Leu Val
225                 230                 235                 240
Thr Val Ser Ser Gly Gly Gly Ser Glu Val Gln Leu Val Glu Ser
                245                 250                 255
Gly Gly Gly Leu Val Gln Pro Gly Gly Ser Leu Lys Leu Ser Cys Ala
            260                 265                 270
Ala Ser Gly Phe Thr Phe Asn Lys Tyr Ala Met Asn Trp Val Arg Gln
        275                 280                 285
Ala Pro Gly Lys Gly Leu Glu Trp Val Ala Arg Ile Arg Ser Lys Tyr
    290                 295                 300
Asn Asn Tyr Ala Thr Tyr Tyr Ala Asp Ser Val Lys Asp Arg Phe Thr
305                 310                 315                 320
Ile Ser Arg Asp Asp Ser Lys Asn Thr Ala Tyr Leu Gln Met Asn Asn
                325                 330                 335
Leu Lys Thr Glu Asp Thr Ala Val Tyr Tyr Cys Val Arg His Gly Asn
            340                 345                 350
Phe Gly Asn Glu Tyr Ile Ser Tyr Trp Ala Tyr Trp Gly Gln Gly Thr
        355                 360                 365
Leu Val Thr Val Ser Ser Gly Gly Gly Ser Gly Gly Gly Gly Ser
    370                 375                 380
Gly Gly Gly Gly Ser Gln Thr Val Val Thr Gln Glu Pro Ser Leu Thr
385                 390                 395                 400
Val Ser Pro Gly Gly Thr Val Thr Leu Thr Cys Gly Ser Ser Thr Gly
                405                 410                 415
Ala Val Thr Ser Gly Asn Tyr Pro Asn Trp Val Gln Gln Lys Pro Gly
            420                 425                 430
Gln Ala Pro Arg Gly Leu Ile Gly Gly Thr Lys Phe Leu Ala Pro Gly
        435                 440                 445
Thr Pro Ala Arg Phe Ser Gly Ser Leu Leu Gly Gly Lys Ala Ala Leu
    450                 455                 460
Thr Leu Ser Gly Val Gln Pro Glu Asp Glu Ala Glu Tyr Tyr Cys Val
465                 470                 475                 480
Leu Trp Tyr Ser Asn Arg Trp Val Phe Gly Gly Thr Lys Leu Thr
                485                 490                 495
Val Leu Gly Gly Gly Asp Lys Thr His Thr Cys Pro Pro Cys Pro Ala
            500                 505                 510
Pro Glu Ala Ala Gly Gly Pro Ser Val Phe Leu Phe Pro Pro Lys Pro
        515                 520                 525
Lys Asp Thr Leu Met Ile Ser Arg Thr Pro Glu Val Thr Cys Val Val
    530                 535                 540
Val Asp Val Ser His Glu Asp Pro Glu Val Lys Phe Asn Trp Tyr Val
545                 550                 555                 560
Asp Gly Val Glu Val His Asn Ala Lys Thr Lys Pro Arg Glu Glu Gln
                565                 570                 575
Tyr Asn Ser Thr Tyr Arg Val Val Ser Val Leu Thr Val Leu His Gln
            580                 585                 590
```

Asp Trp Leu Asn Gly Lys Glu Tyr Lys Cys Lys Val Ser Asn Lys Ala
            595                 600                 605

Leu Pro Ala Pro Ile Glu Lys Thr Ile Ser Lys Ala Lys Gly Gln Pro
    610                 615                 620

Arg Glu Pro Gln Val Tyr Thr Leu Pro Pro Cys Arg Glu Glu Met Thr
625                 630                 635                 640

Lys Asn Gln Val Ser Leu Trp Cys Leu Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
    675                 680                 685

Ser Lys Leu Thr Val Asp Lys Ser Arg Trp Gln Gln Gly Asn Val Phe
690                 695                 700

Ser Cys Ser Val Met His Glu Ala Leu His Asn His Tyr Thr Gln Lys
705                 710                 715                 720

Ser Leu Ser Leu Ser Pro Gly Lys His His His His His His
                725                 730

<210> SEQ ID NO 79
<211> LENGTH: 734
<212> TYPE: PRT
<213> ORGANISM: Artificial Sequence
<220> FEATURE:
<221> NAME/KEY: PEPTIDE
<223> OTHER INFORMATION: 131 first polypeptide

<400> SEQUENCE: 79

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gly
            100                 105                 110

Gly Gly Ser Gly Gly Gly Gly Ser Gly Gly Gly Gly Ser Gln Val Gln
        115                 120                 125

Leu Val Gln Ser Gly Gly Gly Val Val Gln Pro Gly Thr Ser Leu Arg
    130                 135                 140

Leu Ser Cys Ala Ala Ser Gly Phe Ile Phe Ser Ser Ser Ala Met His
145                 150                 155                 160

Trp Val Arg Gln Ala Pro Gly Lys Gly Leu Glu Trp Val Ala Val Ile
                165                 170                 175

Ser Tyr Asp Gly Ser Asn Lys Tyr Tyr Val Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Arg Ser
    210                 215                 220

```
Ala Arg Leu Tyr Ala Ser Phe Asp Tyr Trp Gly Gln Gly Ala Leu Val
225                 230                 235                 240

Thr Val Ser Ser Gly Gly Gly Ser Glu Val Gln Leu Val Glu Ser
            245                 250                 255

Gly Gly Gly Leu Val Gln Pro Gly Gly Ser Leu Lys Leu Ser Cys Ala
        260                 265                 270

Ala Ser Gly Phe Thr Phe Asn Lys Tyr Ala Met Asn Trp Val Arg Gln
    275                 280                 285

Ala Pro Gly Lys Gly Leu Glu Trp Val Ala Arg Ile Arg Ser Lys Ala
290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
            325                 330                 335

Leu Lys Thr Glu Asp Thr Ala Val Tyr Tyr Cys Val Arg His Gly Asn
        340                 345                 350

Phe Gly Asn Ser Tyr Ile Ser Tyr Trp Ala Tyr Trp Gly Gln Gly Thr
    355                 360                 365

Leu Val Thr Val Ser Ser Gly Gly Gly Ser Gly Gly Gly Gly Ser
370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
            405                 410                 415

Ala Val Thr Ser Gly Asn Tyr Pro Asn Trp Val Gln Gln Lys Pro Gly
        420                 425                 430

Gln Ala Pro Arg Gly Leu Ile Gly Gly Thr Lys Phe Leu Ala Pro Gly
    435                 440                 445

Thr Pro Ala Arg Phe Ser Gly Ser Leu Leu Gly Gly Lys Ala Ala Leu
450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
            485                 490                 495

Val Leu Gly Gly Gly Asp Lys Thr His Thr Cys Pro Pro Cys Pro Ala
        500                 505                 510

Pro Glu Ala Ala Gly Gly Pro Ser Val Phe Leu Phe Pro Pro Lys Pro
    515                 520                 525

Lys Asp Thr Leu Met Ile Ser Arg Thr Pro Glu Val Thr Cys Val Val
530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
            565                 570                 575

Tyr Asn Ser Thr Tyr Arg Val Val Ser Val Leu Thr Val Leu His Gln
        580                 585                 590

Asp Trp Leu Asn Gly Lys Glu Tyr Lys Cys Lys Val Ser Asn Lys Ala
    595                 600                 605

Leu Pro Ala Pro Ile Glu Lys Thr Ile Ser Lys Ala Lys Gly Gln Pro
610                 615                 620

Arg Glu Pro Gln Val Tyr Thr Leu Pro Pro Cys Arg Glu Glu Met Thr
625                 630                 635                 640
```

```
Lys Asn Gln Val Ser Leu Trp Cys Leu Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
            675                 680                 685

Ser Lys Leu Thr Val Asp Lys Ser Arg Trp Gln Gln Gly Asn Val Phe
        690                 695                 700

Ser Cys Ser Val Met His Glu Ala Leu His Asn His Tyr Thr Gln Lys
705                 710                 715                 720

Ser Leu Ser Leu Ser Pro Gly Lys His His His His His His
                725                 730
```

<210> SEQ ID NO 80
<211> LENGTH: 734
<212> TYPE: PRT
<213> ORGANISM: Artificial Sequence
<220> FEATURE:
<221> NAME/KEY: PEPTIDE
<223> OTHER INFORMATION: 154 first polypeptide

<400> SEQUENCE: 80

```
Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gly
            100                 105                 110

Gly Gly Ser Gly Gly Gly Gly Ser Gly Gly Gly Gly Ser Gln Val Gln
        115                 120                 125

Leu Val Gln Ser Gly Gly Val Val Gln Pro Gly Thr Ser Leu Arg
    130                 135                 140

Leu Ser Cys Ala Ala Ser Gly Phe Ile Phe Ser Ser Ala Met His
145                 150                 155                 160

Trp Val Arg Gln Ala Pro Gly Lys Gly Leu Glu Trp Val Ala Val Ile
                165                 170                 175

Ser Tyr Asp Gly Ser Asn Lys Tyr Tyr Val Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Arg Ser
    210                 215                 220

Ala Arg Leu Tyr Ala Ser Phe Asp Tyr Trp Gly Gln Gly Ala Leu Val
225                 230                 235                 240

Thr Val Ser Ser Gly Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270
```

```
Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
                340                 345                 350

Phe Gly Asn Ser Tyr Ile Ser Tyr Trp Asp Tyr Trp Gly Gln Gly Thr
                355                 360                 365

Leu Val Thr Val Ser Ser Gly Gly Gly Ser Gly Gly Gly Gly Ser
    370                 375                 380

Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
        450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Asp Lys Thr His Thr Cys Pro Pro Cys Pro Ala
            500                 505                 510

Pro Glu Ala Ala Gly Gly Pro Ser Val Phe Leu Phe Pro Pro Lys Pro
        515                 520                 525

Lys Asp Thr Leu Met Ile Ser Arg Thr Pro Glu Val Thr Cys Val Val
    530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
                580                 585                 590

Asp Trp Leu Asn Gly Lys Glu Tyr Lys Cys Lys Val Ser Asn Lys Ala
        595                 600                 605

Leu Pro Ala Pro Ile Glu Lys Thr Ile Ser Lys Ala Lys Gly Gln Pro
    610                 615                 620

Arg Glu Pro Gln Val Tyr Thr Leu Pro Pro Cys Arg Glu Glu Met Thr
625                 630                 635                 640

Lys Asn Gln Val Ser Leu Trp Cys Leu Val Lys Gly Phe Tyr Pro Ser
                645                 650                 655

Asp Ile Ala Val Glu Trp Glu Ser Asn Gly Gln Pro Glu Asn Asn Tyr
                660                 665                 670

Lys Thr Thr Pro Pro Val Leu Asp Ser Asp Gly Ser Phe Phe Leu Tyr
            675                 680                 685
```

-continued

Ser Lys Leu Thr Val Asp Lys Ser Arg Trp Gln Gln Gly Asn Val Phe
    690             695                 700

Ser Cys Ser Val Met His Glu Ala Leu His Asn His Tyr Thr Gln Lys
705                 710                 715                 720

Ser Leu Ser Leu Ser Pro Gly Lys His His His His His His
                725                 730

<210> SEQ ID NO 81
<211> LENGTH: 734
<212> TYPE: PRT
<213> ORGANISM: Artificial Sequence
<220> FEATURE:
<221> NAME/KEY: PEPTIDE
<223> OTHER INFORMATION: 156 first polypeptide

<400> SEQUENCE: 81

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
                20                  25                  30

His Tyr Pro Ser Trp Tyr Gln Gln Thr Pro Gly Gln Ala Pro Arg Met
            35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65              70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gly
            100                 105                 110

Gly Gly Ser Gly Gly Gly Ser Gly Gly Gly Ser Gln Val Gln
            115                 120                 125

Leu Val Gln Ser Gly Gly Val Val Gln Pro Gly Thr Ser Leu Arg
    130                 135                 140

Leu Ser Cys Ala Ala Ser Gly Phe Ile Phe Ser Ser Ala Met His
145                 150                 155                 160

Trp Val Arg Gln Ala Pro Gly Lys Gly Leu Glu Trp Val Ala Val Ile
                165                 170                 175

Ser Tyr Asp Gly Ser Asn Lys Tyr Tyr Val Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Arg Ser
    210                 215                 220

Ala Arg Leu Tyr Ala Ser Phe Asp Tyr Trp Gly Gln Gly Ala Leu Val
225                 230                 235                 240

Thr Val Ser Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Asn Lys Tyr
    290                 295                 300

Asn Asn Tyr Ala Thr Glu Tyr Ala Asp Ser Val Lys Asp Arg Phe Thr
305                 310                 315                 320

```
Ile Ser Arg Asp Asp Ser Lys Asn Thr Ala Tyr Leu Gln Met Asn Asn
            325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
            355                 360                 365

Leu Val Thr Val Ser Ser Gly Gly Gly Ser Gly Gly Gly Gly Ser
            370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Asp Lys Thr His Thr Cys Pro Pro Cys Pro Ala
            500                 505                 510

Pro Glu Ala Ala Gly Gly Pro Ser Val Phe Leu Phe Pro Pro Lys Pro
            515                 520                 525

Lys Asp Thr Leu Met Ile Ser Arg Thr Pro Glu Val Thr Cys Val Val
            530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
                580                 585                 590

Asp Trp Leu Asn Gly Lys Glu Tyr Lys Cys Lys Val Ser Asn Lys Ala
            595                 600                 605

Leu Pro Ala Pro Ile Glu Lys Thr Ile Ser Lys Ala Lys Gly Gln Pro
            610                 615                 620

Arg Glu Pro Gln Val Tyr Thr Leu Pro Pro Cys Arg Glu Glu Met Thr
625                 630                 635                 640

Lys Asn Gln Val Ser Leu Trp Cys Leu Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
            675                 680                 685

Ser Lys Leu Thr Val Asp Lys Ser Arg Trp Gln Gln Gly Asn Val Phe
    690                 695                 700

Ser Cys Ser Val Met His Glu Ala Leu His Asn His Tyr Thr Gln Lys
705                 710                 715                 720

Ser Leu Ser Leu Ser Pro Gly Lys His His His His His His
                725                 730
```

```
<210> SEQ ID NO 82
<211> LENGTH: 734
<212> TYPE: PRT
<213> ORGANISM: Artificial Sequence
<220> FEATURE:
<221> NAME/KEY: PEPTIDE
<223> OTHER INFORMATION: 155 first polypeptide

<400> SEQUENCE: 82
```

| | | | | | | | | | | | | | | |
|---|---|---|---|---|---|---|---|---|---|---|---|---|---|---|
| Gln | Thr | Val | Val | Thr | Gln | Glu | Pro | Ser | Phe | Ser | Val | Ser | Pro | Gly | Gly |
| 1 | | | | 5 | | | | | 10 | | | | | 15 | |
| Thr | Val | Thr | Leu | Thr | Cys | Gly | Leu | Ser | Ser | Gly | Ser | Val | Ser | Thr | Ser |
| | | | 20 | | | | | 25 | | | | | 30 | | |
| His | Tyr | Pro | Ser | Trp | Tyr | Gln | Gln | Thr | Pro | Gly | Gln | Ala | Pro | Arg | Met |
| | | | 35 | | | | | 40 | | | | | 45 | | |
| Leu | Ile | Tyr | Asn | Thr | Asn | Thr | Arg | Ser | Ser | Gly | Val | Pro | Asp | Arg | Phe |
| | 50 | | | | | 55 | | | | | 60 | | | | |
| Ser | Gly | Ser | Ile | Leu | Gly | Asn | Lys | Ala | Ala | Leu | Thr | Ile | Thr | Gly | Ala |
| 65 | | | | | 70 | | | | | 75 | | | | | 80 |
| Gln | Ala | Asp | Asp | Glu | Ser | Asp | Tyr | Tyr | Cys | Ala | Ile | His | Val | Asp | Arg |
| | | | | 85 | | | | | 90 | | | | | 95 | |
| Asp | Ile | Trp | Val | Phe | Gly | Gly | Thr | Lys | Leu | Thr | Val | Leu | Gly | Gly | Gly |
| | | | 100 | | | | | 105 | | | | | 110 | | |
| Gly | Gly | Ser | Gly | Gly | Gly | Gly | Ser | Gly | Gly | Gly | Gly | Ser | Gln | Val | Gln |
| | | 115 | | | | | 120 | | | | | 125 | | | |
| Leu | Val | Gln | Ser | Gly | Gly | Gly | Val | Val | Gln | Pro | Gly | Thr | Ser | Leu | Arg |
| | 130 | | | | | 135 | | | | | 140 | | | | |
| Leu | Ser | Cys | Ala | Ala | Ser | Gly | Phe | Ile | Phe | Ser | Ser | Ser | Ala | Met | His |
| 145 | | | | | 150 | | | | | 155 | | | | | 160 |
| Trp | Val | Arg | Gln | Ala | Pro | Gly | Lys | Gly | Leu | Glu | Trp | Val | Ala | Val | Ile |
| | | | | 165 | | | | | 170 | | | | | 175 | |
| Ser | Tyr | Asp | Gly | Ser | Asn | Lys | Tyr | Tyr | Val | Asp | Ser | Val | Lys | Gly | Arg |
| | | | 180 | | | | | 185 | | | | | 190 | | |
| Phe | Thr | Ile | Ser | Arg | Asp | Asn | Ser | Lys | Asn | Thr | Leu | Tyr | Leu | Gln | Met |
| | | 195 | | | | | 200 | | | | | 205 | | | |
| Asn | Ser | Leu | Arg | Ala | Glu | Asp | Thr | Ala | Val | Tyr | Tyr | Cys | Ala | Arg | Ser |
| | 210 | | | | | 215 | | | | | 220 | | | | |
| Ala | Arg | Leu | Tyr | Ala | Ser | Phe | Asp | Tyr | Trp | Gly | Gln | Gly | Ala | Leu | Val |
| 225 | | | | | 230 | | | | | 235 | | | | | 240 |
| Thr | Val | Ser | Ser | Gly | Gly | Gly | Gly | Ser | Glu | Val | Gln | Leu | Val | Glu | Ser |
| | | | | 245 | | | | | 250 | | | | | 255 | |
| Gly | Gly | Gly | Leu | Val | Gln | Pro | Gly | Gly | Ser | Leu | Lys | Leu | Ser | Cys | Ala |
| | | | 260 | | | | | 265 | | | | | 270 | | |
| Ala | Ser | Gly | Phe | Thr | Phe | Asn | Lys | Tyr | Ala | Met | Ser | Trp | Val | Arg | Gln |
| | | 275 | | | | | 280 | | | | | 285 | | | |
| Ala | Pro | Gly | Lys | Gly | Leu | Glu | Trp | Val | Ala | Arg | Ile | Arg | Ser | Lys | Tyr |
| | 290 | | | | | 295 | | | | | 300 | | | | |
| Asn | Asn | Tyr | Ala | Thr | Tyr | Tyr | Ala | Asp | Ser | Val | Lys | Asp | Arg | Phe | Thr |
| 305 | | | | | 310 | | | | | 315 | | | | | 320 |
| Ile | Ser | Arg | Asp | Asp | Ser | Lys | Asn | Thr | Ala | Tyr | Leu | Gln | Met | Asn | Asn |
| | | | | 325 | | | | | 330 | | | | | 335 | |
| Leu | Lys | Thr | Glu | Asp | Thr | Ala | Val | Tyr | Cys | Val | Arg | His | Gly | Asn |
| | | | 340 | | | | | 345 | | | | | 350 | | |
| Phe | Gly | Asn | Ser | Tyr | Ile | Ser | Tyr | Trp | Ala | Tyr | Trp | Gly | Gln | Gly | Thr |
| | | 355 | | | | | 360 | | | | | 365 | | | |

```
Leu Val Thr Val Ser Ser Gly Gly Gly Gly Gly Gly Gly Ser
        370                 375                 380

Gly Gly Gly Gly Ser Gln Thr Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
                435                 440                 445

Thr Pro Ala Arg Phe Ser Gly Ser Leu Leu Gly Gly Lys Ala Ala Leu
            450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Asp Lys Thr His Thr Cys Pro Pro Cys Pro Ala
            500                 505                 510

Pro Glu Ala Ala Gly Gly Pro Ser Val Phe Leu Phe Pro Pro Lys Pro
                515                 520                 525

Lys Asp Thr Leu Met Ile Ser Arg Thr Pro Glu Val Thr Cys Val Val
530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
            580                 585                 590

Asp Trp Leu Asn Gly Lys Glu Tyr Lys Cys Lys Val Ser Asn Lys Ala
                595                 600                 605

Leu Pro Ala Pro Ile Glu Lys Thr Ile Ser Lys Ala Lys Gly Gln Pro
            610                 615                 620

Arg Glu Pro Gln Val Tyr Thr Leu Pro Pro Cys Arg Glu Glu Met Thr
625                 630                 635                 640

Lys Asn Gln Val Ser Leu Trp Cys Leu Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
        675                 680                 685

Ser Lys Leu Thr Val Asp Lys Ser Arg Trp Gln Gln Gly Asn Val Phe
        690                 695                 700

Ser Cys Ser Val Met His Glu Ala Leu His Asn His Tyr Thr Gln Lys
705                 710                 715                 720

Ser Leu Ser Leu Ser Pro Gly Lys His His His His His
                725                 730
```

<210> SEQ ID NO 83
<211> LENGTH: 734
<212> TYPE: PRT
<213> ORGANISM: Artificial Sequence
<220> FEATURE:
<221> NAME/KEY: PEPTIDE
<223> OTHER INFORMATION: 177 first polypeptide

<400> SEQUENCE: 83

```
Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gly
            100                 105                 110

Gly Gly Ser Gly Gly Gly Gly Ser Gly Gly Gly Gly Ser Gln Val Gln
            115                 120                 125

Leu Val Gln Ser Gly Gly Val Val Gln Pro Gly Thr Ser Leu Arg
    130                 135                 140

Leu Ser Cys Ala Ala Ser Gly Phe Ile Phe Ser Ser Ser Ala Met His
145                 150                 155                 160

Trp Val Arg Gln Ala Pro Gly Lys Gly Leu Glu Trp Val Ala Val Ile
                165                 170                 175

Ser Tyr Asp Gly Ser Asn Lys Tyr Tyr Val Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Arg Ser
    210                 215                 220

Ala Arg Leu Tyr Ala Ser Phe Asp Tyr Trp Gly Gln Gly Ala Leu Val
225                 230                 235                 240

Thr Val Ser Ser Gly Gly Gly Ser Glu Val Gln Leu Val Glu Ser
                245                 250                 255

Gly Gly Gly Leu Val Gln Pro Gly Gly Ser Leu Lys Leu Ser Cys Ala
            260                 265                 270

Ala Ser Gly Phe Thr Phe Asn Lys Tyr Ala Met Asn Trp Val Arg Gln
        275                 280                 285

Ala Pro Gly Lys Gly Leu Glu Trp Val Ala Arg Ile Arg Ser Lys Tyr
    290                 295                 300

Asn Asn Tyr Ala Thr Glu Tyr Ala Ala Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
        355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415
```

```
Ala Val Thr Ser Gly Asn Tyr Pro Asn Trp Val Gln Gln Lys Pro Gly
                420                 425                 430

Gln Ala Pro Arg Gly Leu Ile Gly Gly Thr Lys Phe Leu Ala Pro Gly
            435                 440                 445

Thr Pro Ala Arg Phe Ser Gly Ser Leu Leu Gly Lys Ala Ala Leu
450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Thr Lys Leu Thr
                485                 490                 495

Val Leu Gly Gly Gly Asp Lys Thr His Thr Cys Pro Pro Cys Pro Ala
            500                 505                 510

Pro Glu Ala Ala Gly Gly Pro Ser Val Phe Leu Phe Pro Pro Lys Pro
        515                 520                 525

Lys Asp Thr Leu Met Ile Ser Arg Thr Pro Glu Val Thr Cys Val Val
530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
            580                 585                 590

Asp Trp Leu Asn Gly Lys Glu Tyr Lys Cys Lys Val Ser Asn Lys Ala
        595                 600                 605

Leu Pro Ala Pro Ile Glu Lys Thr Ile Ser Lys Ala Lys Gly Gln Pro
610                 615                 620

Arg Glu Pro Gln Val Tyr Thr Leu Pro Pro Cys Arg Glu Glu Met Thr
625                 630                 635                 640

Lys Asn Gln Val Ser Leu Trp Cys Leu Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
        675                 680                 685

Ser Lys Leu Thr Val Asp Lys Ser Arg Trp Gln Gln Gly Asn Val Phe
690                 695                 700

Ser Cys Ser Val Met His Glu Ala Leu His Asn His Tyr Thr Gln Lys
705                 710                 715                 720

Ser Leu Ser Leu Ser Pro Gly Lys His His His His His His
                725                 730

<210> SEQ ID NO 84
<211> LENGTH: 734
<212> TYPE: PRT
<213> ORGANISM: Artificial Sequence
<220> FEATURE:
<221> NAME/KEY: PEPTIDE
<223> OTHER INFORMATION: 172 first polypeptide

<400> SEQUENCE: 84

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Gly Leu Glu Trp Val
```

```
             35                  40                  45
Ala Val Ile Ser Tyr Asp Gly Ser Asn Lys Tyr Val Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Ser Ala Arg Leu Tyr Ala Ser Phe Asp Tyr Trp Gly Gln Gly
                100                 105                 110
Ala Leu Val Thr Val Ser Ser Gly Gly Gly Ser Gly Gly Gly Gly
                115                 120                 125
Ser Gly Gly Gly Gly Ser Gln Thr Val Val Thr Gln Glu Pro Ser Phe
130                 135                 140
Ser Val Ser Pro Gly Gly Thr Val Thr Leu Thr Cys Gly Leu Ser Ser
145                 150                 155                 160
Gly Ser Val Ser Thr Ser His Tyr Pro Ser Trp Tyr Gln Gln Thr Pro
                165                 170                 175
Gly Gln Ala Pro Arg Met Leu Ile Tyr Asn Thr Asn Thr Arg Ser Ser
                180                 185                 190
Gly Val Pro Asp Arg Phe Ser Gly Ser Ile Leu Gly Asn Lys Ala Ala
                195                 200                 205
Leu Thr Ile Thr Gly Ala Gln Ala Asp Asp Glu Ser Asp Tyr Tyr Cys
210                 215                 220
Ala Ile His Val Asp Arg Asp Ile Trp Val Phe Gly Gly Gly Thr Lys
225                 230                 235                 240
Leu Thr Val Leu Gly Gly Gly Gly Ser Gln Thr Val Val Thr Gln Glu
                245                 250                 255
Pro Ser Leu Thr Val Ser Pro Gly Gly Thr Val Thr Leu Thr Cys Gly
                260                 265                 270
Ser Ser Thr Gly Ala Val Thr Ser Gly Asn Tyr Pro Asn Trp Val Gln
                275                 280                 285
Gln Lys Pro Gly Gln Ala Pro Arg Gly Leu Ile Gly Gly Thr Lys Phe
                290                 295                 300
Leu Ala Pro Gly Thr Pro Ala Arg Phe Ser Gly Ser Leu Leu Gly Gly
305                 310                 315                 320
Lys Ala Ala Leu Thr Leu Ser Gly Val Gln Pro Glu Asp Glu Ala Glu
                325                 330                 335
Tyr Tyr Cys Val Leu Trp Tyr Ser Asn Arg Trp Val Phe Gly Gly Gly
                340                 345                 350
Thr Lys Leu Thr Val Leu Gly Gly Gly Gly Ser Gly Gly Gly Gly Ser
                355                 360                 365
Gly Gly Gly Gly Ser Glu Val Gln Leu Val Glu Ser Gly Gly Gly Leu
                370                 375                 380
Val Gln Pro Gly Gly Ser Leu Lys Leu Ser Cys Ala Ala Ser Gly Phe
385                 390                 395                 400
Thr Phe Asn Lys Tyr Ala Met Asn Trp Val Arg Gln Ala Pro Gly Lys
                405                 410                 415
Gly Leu Glu Trp Val Ala Arg Ile Arg Ser Lys Tyr Asn Asn Tyr Ala
                420                 425                 430
Thr Tyr Tyr Ala Asp Ser Val Lys Asp Arg Phe Thr Ile Ser Arg Asp
                435                 440                 445
Asp Ser Lys Asn Thr Ala Tyr Leu Gln Met Asn Asn Leu Lys Thr Glu
                450                 455                 460
```

```
Asp Thr Ala Val Tyr Tyr Cys Val Arg His Gly Asn Phe Gly Asn Glu
465                 470                 475                 480

Tyr Ile Ser Tyr Trp Ala Tyr Trp Gly Gln Gly Thr Leu Val Thr Val
                485                 490                 495

Ser Ser Gly Gly Gly Asp Lys Thr His Thr Cys Pro Pro Cys Pro Ala
            500                 505                 510

Pro Glu Ala Ala Gly Gly Pro Ser Val Phe Leu Phe Pro Pro Lys Pro
        515                 520                 525

Lys Asp Thr Leu Met Ile Ser Arg Thr Pro Glu Val Thr Cys Val Val
    530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
                580                 585                 590

Asp Trp Leu Asn Gly Lys Glu Tyr Lys Cys Lys Val Ser Asn Lys Ala
            595                 600                 605

Leu Pro Ala Pro Ile Glu Lys Thr Ile Ser Lys Ala Lys Gly Gln Pro
        610                 615                 620

Arg Glu Pro Gln Val Tyr Thr Leu Pro Pro Cys Arg Glu Glu Met Thr
625                 630                 635                 640

Lys Asn Gln Val Ser Leu Trp Cys Leu Val Lys Gly Phe Tyr Pro Ser
                645                 650                 655

Asp Ile Ala Val Glu Trp Glu Ser Asn Gly Gln Pro Glu Asn Asn Tyr
                660                 665                 670

Lys Thr Thr Pro Pro Val Leu Asp Ser Asp Gly Ser Phe Phe Leu Tyr
            675                 680                 685

Ser Lys Leu Thr Val Asp Lys Ser Arg Trp Gln Gln Gly Asn Val Phe
        690                 695                 700

Ser Cys Ser Val Met His Glu Ala Leu His Asn His Tyr Thr Gln Lys
705                 710                 715                 720

Ser Leu Ser Leu Ser Pro Gly Lys His His His His His
                725                 730

<210> SEQ ID NO 85
<211> LENGTH: 734
<212> TYPE: PRT
<213> ORGANISM: Artificial Sequence
<220> FEATURE:
<221> NAME/KEY: PEPTIDE
<223> OTHER INFORMATION: 171 first polypeptide

<400> SEQUENCE: 85

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                         85                  90                  95
Ala Arg Ser Ala Arg Leu Tyr Ala Ser Phe Asp Tyr Trp Gly Gln Gly
                100                 105                 110

Ala Leu Val Thr Val Ser Ser Gly Gly Gly Ser Gly Gly Gly Gly
                115                 120                 125

Ser Gly Gly Gly Ser Gln Thr Val Val Thr Gln Glu Pro Ser Phe
    130                 135                 140

Ser Val Ser Pro Gly Gly Thr Val Thr Leu Thr Cys Gly Leu Ser Ser
145                 150                 155                 160

Gly Ser Val Ser Thr Ser His Tyr Pro Ser Trp Tyr Gln Gln Thr Pro
                165                 170                 175

Gly Gln Ala Pro Arg Met Leu Ile Tyr Asn Thr Asn Thr Arg Ser Ser
                180                 185                 190

Gly Val Pro Asp Arg Phe Ser Gly Ser Ile Leu Gly Asn Lys Ala Ala
                195                 200                 205

Leu Thr Ile Thr Gly Ala Gln Ala Asp Asp Glu Ser Asp Tyr Tyr Cys
                210                 215                 220

Ala Ile His Val Asp Arg Asp Ile Trp Val Phe Gly Gly Gly Thr Lys
225                 230                 235                 240

Leu Thr Val Leu Gly Gly Gly Ser Glu Val Gln Leu Val Glu Ser
                245                 250                 255

Gly Gly Gly Leu Val Gln Pro Gly Gly Ser Leu Lys Leu Ser Cys Ala
                260                 265                 270

Ala Ser Gly Phe Thr Phe Asn Lys Tyr Ala Met Asn Trp Val Arg Gln
                275                 280                 285

Ala Pro Gly Lys Gly Leu Glu Trp Val Ala Arg Ile Arg Ser Lys Tyr
                290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
                340                 345                 350

Phe Gly Asn Glu Tyr Ile Ser Tyr Trp Ala Tyr Trp Gly Gln Gly Thr
                355                 360                 365

Leu Val Thr Val Ser Ser Gly Gly Gly Ser Gly Gly Gly Gly Ser
                370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
                420                 425                 430

Gln Ala Pro Arg Gly Leu Ile Gly Gly Thr Lys Phe Leu Ala Pro Gly
                435                 440                 445

Thr Pro Ala Arg Phe Ser Gly Ser Leu Leu Gly Gly Lys Ala Ala Leu
                450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Asp Lys Thr His Thr Cys Pro Pro Cys Pro Ala
                500                 505                 510
```

Pro Glu Ala Ala Gly Gly Pro Ser Val Phe Leu Phe Pro Pro Lys Pro
        515                 520                 525

Lys Asp Thr Leu Met Ile Ser Arg Thr Pro Glu Val Thr Cys Val Val
    530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
            580                 585                 590

Asp Trp Leu Asn Gly Lys Glu Tyr Lys Cys Lys Val Ser Asn Lys Ala
        595                 600                 605

Leu Pro Ala Pro Ile Glu Lys Thr Ile Ser Lys Ala Lys Gly Gln Pro
    610                 615                 620

Arg Glu Pro Gln Val Tyr Thr Leu Pro Pro Cys Arg Glu Glu Met Thr
625                 630                 635                 640

Lys Asn Gln Val Ser Leu Trp Cys Leu Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
        675                 680                 685

Ser Lys Leu Thr Val Asp Lys Ser Arg Trp Gln Gln Gly Asn Val Phe
    690                 695                 700

Ser Cys Ser Val Met His Glu Ala Leu His Asn His Tyr Thr Gln Lys
705                 710                 715                 720

Ser Leu Ser Leu Ser Pro Gly Lys His His His His His His
                725                 730

<210> SEQ ID NO 86
<211> LENGTH: 734
<212> TYPE: PRT
<213> ORGANISM: Artificial Sequence
<220> FEATURE:
<221> NAME/KEY: PEPTIDE
<223> OTHER INFORMATION: 161 first polypeptide

<400> SEQUENCE: 86

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Arg Leu Tyr Ala Ser Phe Asp Tyr Trp Gly Gln Gly
            100                 105                 110

Ala Leu Val Thr Val Ser Ser Gly Gly Gly Ser Gly Gly Gly Gly
        115                 120                 125

Ser Gly Gly Gly Gly Ser Gln Thr Val Val Thr Gln Glu Pro Ser Phe

-continued

```
            130                 135                 140
Ser Val Ser Pro Gly Gly Thr Val Thr Leu Thr Cys Gly Leu Ser Ser
145                 150                 155                 160

Gly Ser Val Ser Thr Ser His Tyr Pro Ser Trp Tyr Gln Gln Thr Pro
                165                 170                 175

Gly Gln Ala Pro Arg Met Leu Ile Tyr Asn Thr Asn Thr Arg Ser Ser
            180                 185                 190

Gly Val Pro Asp Arg Phe Ser Gly Ser Ile Leu Gly Asn Lys Ala Ala
        195                 200                 205

Leu Thr Ile Thr Gly Ala Gln Ala Asp Asp Glu Ser Asp Tyr Tyr Cys
    210                 215                 220

Ala Ile His Val Asp Arg Asp Ile Trp Val Phe Gly Gly Gly Thr Lys
225                 230                 235                 240

Leu Thr Val Leu Gly Gly Gly Ser Glu Val Gln Leu Val Glu Ser
                245                 250                 255

Gly Gly Gly Leu Val Gln Pro Gly Gly Ser Leu Lys Leu Ser Cys Ala
                260                 265                 270

Ala Ser Gly Phe Thr Phe Asn Lys Tyr Ala Met Asn Trp Val Arg Gln
            275                 280                 285

Ala Pro Gly Lys Gly Leu Glu Trp Val Ala Arg Ile Arg Ser Lys Tyr
        290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
                340                 345                 350

Phe Gly Asn Pro Tyr Ile Ser Tyr Trp Ala Tyr Trp Gly Gln Gly Thr
            355                 360                 365

Leu Val Thr Val Ser Ser Gly Gly Gly Ser Gly Gly Gly Ser
    370                 375                 380

Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu Gly Gly Gly Asp Lys Thr His Thr Cys Pro Pro Cys Pro Ala
                500                 505                 510

Pro Glu Ala Ala Gly Gly Pro Ser Val Phe Leu Phe Pro Pro Lys Pro
            515                 520                 525

Lys Asp Thr Leu Met Ile Ser Arg Thr Pro Glu Val Thr Cys Val Val
        530                 535                 540

Val Asp Val Ser His Glu Asp Pro Glu Val Lys Phe Asn Trp Tyr Val
545                 550                 555                 560
```

Asp Gly Val Glu Val His Asn Ala Lys Thr Lys Pro Arg Glu Glu Gln
            565                 570                 575

Tyr Asn Ser Thr Tyr Arg Val Val Ser Val Leu Thr Val Leu His Gln
            580                 585                 590

Asp Trp Leu Asn Gly Lys Glu Tyr Lys Cys Lys Val Ser Asn Lys Ala
            595                 600                 605

Leu Pro Ala Pro Ile Glu Lys Thr Ile Ser Lys Ala Lys Gly Gln Pro
            610                 615                 620

Arg Glu Pro Gln Val Tyr Thr Leu Pro Pro Cys Arg Glu Glu Met Thr
625                 630                 635                 640

Lys Asn Gln Val Ser Leu Trp Cys Leu Val Lys Gly Phe Tyr Pro Ser
            645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
            675                 680                 685

Ser Lys Leu Thr Val Asp Lys Ser Arg Trp Gln Gln Gly Asn Val Phe
            690                 695                 700

Ser Cys Ser Val Met His Glu Ala Leu His Asn His Tyr Thr Gln Lys
705                 710                 715                 720

Ser Leu Ser Leu Ser Pro Gly Lys His His His His His His
            725                 730

<210> SEQ ID NO 87
<211> LENGTH: 734
<212> TYPE: PRT
<213> ORGANISM: Artificial Sequence
<220> FEATURE:
<221> NAME/KEY: PEPTIDE
<223> OTHER INFORMATION: 162 first polypeptide

<400> SEQUENCE: 87

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Val Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ser Ala Arg Leu Tyr Ala Ser Phe Asp Tyr Trp Gly Gln Gly
            100                 105                 110

Ala Leu Val Thr Val Ser Ser Gly Gly Gly Gly Ser Gly Gly Gly Gly
            115                 120                 125

Ser Gly Gly Gly Gly Ser Gln Thr Val Val Thr Gln Glu Pro Ser Phe
130                 135                 140

Ser Val Ser Pro Gly Gly Thr Val Thr Leu Thr Cys Gly Leu Ser Ser
145                 150                 155                 160

Gly Ser Val Ser Thr Ser His Tyr Pro Ser Trp Tyr Gln Gln Thr Pro
            165                 170                 175

Gly Gln Ala Pro Arg Met Leu Ile Tyr Asn Thr Asn Thr Arg Ser Ser

```
                    180                 185                 190
Gly Val Pro Asp Arg Phe Ser Gly Ser Ile Leu Gly Asn Lys Ala Ala
            195                 200                 205
Leu Thr Ile Thr Gly Ala Gln Ala Asp Asp Glu Ser Asp Tyr Tyr Cys
            210                 215                 220
Ala Ile His Val Asp Arg Asp Ile Trp Val Phe Gly Gly Gly Thr Lys
225                 230                 235                 240
Leu Thr Val Leu Gly Gly Gly Ser Gln Thr Val Val Thr Gln Glu
                245                 250                 255
Pro Ser Leu Thr Val Ser Pro Gly Gly Thr Val Thr Leu Thr Cys Gly
            260                 265                 270
Ser Ser Thr Gly Ala Val Thr Ser Gly Asn Tyr Pro Asn Trp Val Gln
            275                 280                 285
Gln Lys Pro Gly Gln Ala Pro Arg Gly Leu Ile Gly Gly Thr Lys Phe
            290                 295                 300
Leu Ala Pro Gly Thr Pro Ala Arg Phe Ser Gly Ser Leu Leu Gly Gly
305                 310                 315                 320
Lys Ala Ala Leu Thr Leu Ser Gly Val Gln Pro Glu Asp Glu Ala Glu
                325                 330                 335
Tyr Tyr Cys Val Leu Trp Tyr Ser Asn Arg Trp Val Phe Gly Gly Gly
            340                 345                 350
Thr Lys Leu Thr Val Leu Gly Gly Gly Ser Gly Gly Gly Gly Ser
            355                 360                 365
Gly Gly Gly Gly Ser Glu Val Gln Leu Val Glu Ser Gly Gly Gly Leu
            370                 375                 380
Val Gln Pro Gly Gly Ser Leu Lys Leu Ser Cys Ala Ala Ser Gly Phe
385                 390                 395                 400
Thr Phe Asn Lys Tyr Ala Met Asn Trp Val Arg Gln Ala Pro Gly Lys
                405                 410                 415
Gly Leu Glu Trp Val Ala Arg Ile Arg Ser Lys Tyr Asn Asn Tyr Ala
            420                 425                 430
Thr Tyr Tyr Ala Asp Ser Val Lys Asp Arg Phe Thr Ile Ser Arg Asp
            435                 440                 445
Asp Ser Lys Asn Thr Ala Tyr Leu Gln Met Asn Asn Leu Lys Thr Glu
            450                 455                 460
Asp Thr Ala Val Tyr Tyr Cys Val Arg His Gly Asn Phe Gly Asn Pro
465                 470                 475                 480
Tyr Ile Ser Tyr Trp Ala Tyr Trp Gly Gln Gly Thr Leu Val Thr Val
                485                 490                 495
Ser Ser Gly Gly Gly Asp Lys Thr His Thr Cys Pro Pro Cys Pro Ala
            500                 505                 510
Pro Glu Ala Ala Gly Gly Pro Ser Val Phe Leu Phe Pro Pro Lys Pro
            515                 520                 525
Lys Asp Thr Leu Met Ile Ser Arg Thr Pro Glu Val Thr Cys Val Val
            530                 535                 540
Val Asp Val Ser His Glu Asp Pro Glu Val Lys Phe Asn Trp Tyr Val
545                 550                 555                 560
Asp Gly Val Glu Val His Asn Ala Lys Thr Lys Pro Arg Glu Glu Gln
                565                 570                 575
Tyr Asn Ser Thr Tyr Arg Val Val Ser Val Leu Thr Val Leu His Gln
            580                 585                 590
Asp Trp Leu Asn Gly Lys Glu Tyr Lys Cys Lys Val Ser Asn Lys Ala
            595                 600                 605
```

```
Leu Pro Ala Pro Ile Glu Lys Thr Ile Ser Lys Ala Lys Gly Gln Pro
    610                 615                 620

Arg Glu Pro Gln Val Tyr Thr Leu Pro Pro Cys Arg Glu Glu Met Thr
625                 630                 635                 640

Lys Asn Gln Val Ser Leu Trp Cys Leu Val Lys Gly Phe Tyr Pro Ser
                645                 650                 655

Asp Ile Ala Val Glu Trp Glu Ser Asn Gly Gln Pro Glu Asn Asn Tyr
                660                 665                 670

Lys Thr Thr Pro Pro Val Leu Asp Ser Asp Gly Ser Phe Phe Leu Tyr
            675                 680                 685

Ser Lys Leu Thr Val Asp Lys Ser Arg Trp Gln Gln Gly Asn Val Phe
        690                 695                 700

Ser Cys Ser Val Met His Glu Ala Leu His Asn His Tyr Thr Gln Lys
705                 710                 715                 720

Ser Leu Ser Leu Ser Pro Gly Lys His His His His His His
                725                 730
```

<210> SEQ ID NO 88
<211> LENGTH: 474
<212> TYPE: PRT
<213> ORGANISM: Artificial Sequence
<220> FEATURE:
<221> NAME/KEY: PEPTIDE
<223> OTHER INFORMATION: 142 second polypeptide

<400> SEQUENCE: 88

```
Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Arg Leu Tyr Ala Ser Phe Asp Tyr Trp Gly Gln Gly
                100                 105                 110

Ala Leu Val Thr Val Ser Ser Gly Gly Gly Ser Gly Gly Gly Gly
            115                 120                 125

Ser Gly Gly Gly Gly Ser Gln Thr Val Thr Gln Glu Pro Ser Phe
        130                 135                 140

Ser Val Ser Pro Gly Gly Thr Val Thr Leu Thr Cys Gly Leu Ser Ser
145                 150                 155                 160

Gly Ser Val Ser Thr Ser His Tyr Pro Ser Trp Tyr Gln Gln Thr Pro
                165                 170                 175

Gly Gln Ala Pro Arg Met Leu Ile Tyr Asn Thr Asn Thr Arg Ser Ser
                180                 185                 190

Gly Val Pro Asp Arg Phe Ser Gly Ser Ile Leu Gly Asn Lys Ala Ala
            195                 200                 205

Leu Thr Ile Thr Gly Ala Gln Ala Asp Asp Glu Ser Asp Tyr Tyr Cys
        210                 215                 220

Ala Ile His Val Asp Arg Asp Ile Trp Val Phe Gly Gly Gly Thr Lys
```

```
                225                 230                 235                 240
Leu Thr Val Leu Gly Gly Asp Lys Thr His Thr Cys Pro Pro Cys
                    245                 250                 255

Pro Ala Pro Glu Ala Ala Gly Gly Pro Ser Val Phe Leu Phe Pro Pro
                260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
        290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
                355                 360                 365

Gln Pro Arg Glu Pro Gln Val Cys Thr Leu Pro Pro Ser Arg Glu Glu
            370                 375                 380

Met Thr Lys Asn Gln Val Ser Leu Ser Cys Ala Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
                420                 425                 430

Leu Val Ser Lys Leu Thr Val Asp Lys Ser Arg Trp Gln Gln Gly Asn
                435                 440                 445

Val Phe Ser Cys Ser Val Met His Glu Ala Leu His Asn His Tyr Thr
                450                 455                 460

Gln Lys Ser Leu Ser Leu Ser Pro Gly Lys
465                 470

<210> SEQ ID NO 89
<211> LENGTH: 730
<212> TYPE: PRT
<213> ORGANISM: Artificial Sequence
<220> FEATURE:
<221> NAME/KEY: PEPTIDE
<223> OTHER INFORMATION: NC1 chain 1

<400> SEQUENCE: 89

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Glu Tyr Ile Ser Tyr Trp
            100                 105                 110
```

-continued

```
Ala Tyr Trp Gly Gln Gly Thr Leu Val Thr Val Ser Ser Gly Gly Gly
            115                 120                 125
Gly Ser Gly Gly Gly Gly Ser Gly Gly Gly Ser Gln Thr Val Val
    130                 135                 140
Thr Gln Glu Pro Ser Leu Thr Val Ser Pro Gly Gly Thr Val Thr Leu
145                 150                 155                 160
Thr Cys Gly Ser Ser Thr Gly Ala Val Thr Ser Gly Asn Tyr Pro Asn
                165                 170                 175
Trp Val Gln Gln Lys Pro Gly Gln Ala Pro Arg Gly Leu Ile Gly Gly
                180                 185                 190
Thr Lys Phe Leu Ala Pro Gly Thr Pro Ala Arg Phe Ser Gly Ser Leu
                195                 200                 205
Leu Gly Gly Lys Ala Ala Leu Thr Leu Ser Gly Val Gln Pro Glu Asp
    210                 215                 220
Glu Ala Glu Tyr Tyr Cys Val Leu Trp Tyr Ser Asn Arg Trp Val Phe
225                 230                 235                 240
Gly Gly Gly Thr Lys Leu Thr Val Leu Gly Gly Gly Ser Asp Ile
                245                 250                 255
Gln Met Thr Gln Ser Pro Ser Ser Val Ser Ala Ser Val Gly Asp Arg
                260                 265                 270
Val Thr Ile Thr Cys Arg Ala Ser Gln Asp Ile Ala Asn Tyr Leu Ser
            275                 280                 285
Trp Tyr Gln Gln Lys Pro Gly Lys Ser Pro Lys Leu Leu Ile Tyr Gly
        290                 295                 300
Thr Ser Asn Leu Glu Val Gly Val Pro Ser Arg Phe Ser Gly Ser Arg
305                 310                 315                 320
Ser Gly Thr Asp Phe Thr Leu Thr Ile Ser Ser Leu Gln Pro Glu Asp
                325                 330                 335
Phe Ala Thr Tyr Tyr Cys Leu Gln Asp Lys Glu Phe Pro Arg Thr Phe
                340                 345                 350
Gly Gly Gly Thr Lys Val Glu Ile Lys Gly Gly Gly Ser Gly Gly
                355                 360                 365
Gly Gly Ser Gly Gly Gly Gly Ser Glu Val Gln Leu Val Glu Ser Gly
    370                 375                 380
Gly Gly Leu Val Gln Pro Gly Gly Ser Leu Arg Leu Ser Cys Ala Ala
385                 390                 395                 400
Ser Gly Phe Thr Phe Ser His Tyr Tyr Met Ala Trp Val Arg Gln Ala
                405                 410                 415
Pro Gly Lys Gly Leu Glu Trp Val Thr Ser Ile Ser Tyr Glu Gly Asp
                420                 425                 430
Ile Thr Tyr Tyr Gly Asp Ser Val Lys Gly Arg Phe Thr Ile Ser Arg
            435                 440                 445
Asp Asn Ser Lys Asn Thr Leu Tyr Leu Gln Met Asn Ser Leu Arg Ala
        450                 455                 460
Glu Asp Thr Ala Thr Tyr Tyr Cys Ala Ser Gln Thr Leu Arg Glu Ser
465                 470                 475                 480
Phe Asp Tyr Trp Gly Gln Gly Thr Leu Val Thr Val Ser Ser Gly Gly
                485                 490                 495
Gly Asp Lys Thr His Thr Cys Pro Pro Cys Pro Ala Pro Glu Ala Ala
                500                 505                 510
Gly Gly Pro Ser Val Phe Leu Phe Pro Pro Lys Pro Lys Asp Thr Leu
    515                 520                 525
Met Ile Ser Arg Thr Pro Glu Val Thr Cys Val Val Val Asp Val Ser
```

```
                530                 535                 540
His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Asn Ser Thr
                565                 570                 575

Tyr Arg Val Val Ser Val Leu Thr Val Leu His Gln Asp Trp Leu Asn
                580                 585                 590

Gly Lys Glu Tyr Lys Cys Lys Val Ser Asn Lys Ala Leu Pro Ala Pro
                595                 600                 605

Ile Glu Lys Thr Ile Ser Lys Ala Lys Gly Gln Pro Arg Glu Pro Gln
610                 615                 620

Val Tyr Thr Leu Pro Pro Cys Arg Glu Glu Met Thr Lys Asn Gln Val
625                 630                 635                 640

Ser Leu Trp Cys Leu Val Lys Gly Phe Tyr Pro Ser Asp Ile Ala Val
                645                 650                 655

Glu Trp Glu Ser Asn Gly Gln Pro Glu Asn Asn Tyr Lys Thr Thr Pro
                660                 665                 670

Pro Val Leu Asp Ser Asp Gly Ser Phe Phe Leu Tyr Ser Lys Leu Thr
                675                 680                 685

Val Asp Lys Ser Arg Trp Gln Gln Gly Asn Val Phe Ser Cys Ser Val
690                 695                 700

Met His Glu Ala Leu His Asn His Tyr Thr Gln Lys Ser Leu Ser Leu
705                 710                 715                 720

Ser Pro Gly Lys His His His His His His
                725                 730

<210> SEQ ID NO 90
<211> LENGTH: 470
<212> TYPE: PRT
<213> ORGANISM: Artificial Sequence
<220> FEATURE:
<221> NAME/KEY: PEPTIDE
<223> OTHER INFORMATION: NC1 chain 2

<400> SEQUENCE: 90

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ala Asn Tyr
                20                  25                  30

Leu Ser Trp Tyr Gln Gln Lys Pro Gly Lys Ser Pro Lys Leu Leu Ile
            35                  40                  45

Tyr Gly Thr Ser Asn Leu Glu Val Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Lys Glu Phe Pro Arg
                85                  90                  95

Thr Phe Gly Gly Gly Thr Lys Val Glu Ile Lys Gly Gly Gly Gly Ser
                100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
            130                 135                 140

Ala Ala Ser Gly Phe Thr Phe Ser His Tyr Tyr Met Ala Trp Val Arg
145                 150                 155                 160
```

```
Gln Ala Pro Gly Lys Gly Leu Glu Trp Val Thr Ser Ile Ser Tyr Glu
                165                 170                 175

Gly Asp Ile Thr Tyr Tyr Gly Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Thr Tyr Tyr Cys Ala Ser Gln Thr Leu Arg
    210                 215                 220

Glu Ser Phe Asp Tyr Trp Gly Gln Gly Thr Leu Val Thr Val Ser Ser
225                 230                 235                 240

Gly Gly Gly Asp Lys Thr His Thr Cys Pro Pro Cys Pro Ala Pro Glu
                245                 250                 255

Ala Ala Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Cys Thr Leu Pro Pro Ser Arg Glu Glu Met Thr Lys Asn
    370                 375                 380

Gln Val Ser Leu Ser Cys Ala Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Val Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 91
<211> LENGTH: 725
<212> TYPE: PRT
<213> ORGANISM: Artificial Sequence
<220> FEATURE:
<221> NAME/KEY: PEPTIDE
<223> OTHER INFORMATION: NC2  chain 1

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Tyr Met Ala Trp Val Arg Gln Ala Pro Gly Lys Gly Leu Glu Trp Val
        35                  40                  45
```

```
Thr Ser Ile Ser Tyr Glu Gly Asp Ile Thr Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Ser Gln Thr Leu Arg Glu Ser Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Asp Ile Gln Met Thr Gln Ser Pro Ser Ser Val
    130                 135                 140

Ser Ala Ser Val Gly Asp Arg Val Thr Ile Thr Cys Arg Ala Ser Gln
145                 150                 155                 160

Asp Ile Ala Asn Tyr Leu Ser Trp Tyr Gln Gln Lys Pro Gly Lys Ser
                165                 170                 175

Pro Lys Leu Leu Ile Tyr Gly Thr Ser Asn Leu Glu Val Gly Val Pro
            180                 185                 190

Ser Arg Phe Ser Gly Ser Arg Ser Gly Thr Asp Phe Thr Leu Thr Ile
        195                 200                 205

Ser Ser Leu Gln Pro Glu Asp Phe Ala Thr Tyr Tyr Cys Leu Gln Asp
    210                 215                 220

Lys Glu Phe Pro Arg Thr Phe Gly Gly Gly Thr Lys Val Glu Ile Lys
225                 230                 235                 240

Gly Gly Gly Gly Ser Gln Thr Val Val Thr Gln Glu Pro Ser Phe Ser
                245                 250                 255

Val Ser Pro Gly Gly Thr Val Thr Leu Thr Cys Gly Leu Ser Ser Gly
            260                 265                 270

Ser Val Ser Thr Ser His Tyr Pro Ser Trp Tyr Gln Gln Thr Pro Gly
        275                 280                 285

Gln Ala Pro Arg Met Leu Ile Tyr Asn Thr Asn Thr Arg Ser Ser Gly
    290                 295                 300

Val Pro Asp Arg Phe Ser Gly Ser Ile Leu Gly Asn Lys Ala Ala Leu
305                 310                 315                 320

Thr Ile Thr Gly Ala Gln Ala Asp Asp Glu Ser Asp Tyr Tyr Cys Ala
                325                 330                 335

Ile His Val Asp Arg Asp Ile Trp Val Phe Gly Gly Gly Thr Lys Leu
            340                 345                 350

Thr Val Leu Gly Gly Gly Gly Ser Gly Gly Gly Gly Ser Gly Gly Gly
        355                 360                 365

Gly Ser Gln Val Gln Leu Val Gln Ser Gly Gly Gly Val Val Gln Pro
    370                 375                 380

Gly Thr Ser Leu Arg Leu Ser Cys Ala Ala Ser Gly Phe Ile Phe Ser
385                 390                 395                 400

Ser Ser Ala Met His Trp Val Arg Gln Ala Pro Gly Lys Gly Leu Glu
                405                 410                 415

Trp Val Ala Val Ile Ser Tyr Asp Gly Ser Asn Lys Tyr Tyr Val Asp
            420                 425                 430

Ser Val Lys Gly Arg Phe Thr Ile Ser Arg Asp Asn Ser Lys Asn Thr
        435                 440                 445

Leu Tyr Leu Gln Met Asn Ser Leu Arg Ala Glu Asp Thr Ala Val Tyr
    450                 455                 460
```

```
Tyr Cys Ala Arg Ser Ala Arg Leu Tyr Ala Ser Phe Asp Tyr Trp Gly
465                 470                 475                 480

Gln Gly Ala Leu Val Thr Val Ser Ser Gly Gly Gly Asp Lys Thr His
                485                 490                 495

Thr Cys Pro Pro Cys Pro Ala Pro Glu Ala Ala Gly Gly Pro Ser Val
                500                 505                 510

Phe Leu Phe Pro Pro Lys Pro Lys Asp Thr Leu Met Ile Ser Arg Thr
            515                 520                 525

Pro Glu Val Thr Cys Val Val Val Asp Val Ser His Glu Asp Pro Glu
            530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
                580                 585                 590

Cys Lys Val Ser Asn Lys Ala Leu Pro Ala Pro Ile Glu Lys Thr Ile
            595                 600                 605

Ser Lys Ala Lys Gly Gln Pro Arg Glu Pro Gln Val Tyr Thr Leu Pro
            610                 615                 620

Pro Cys Arg Glu Glu Met Thr Lys Asn Gln Val Ser Leu Trp Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
                660                 665                 670

Asp Gly Ser Phe Phe Leu Tyr Ser Lys Leu Thr Val Asp Lys Ser Arg
            675                 680                 685

Trp Gln Gln Gly Asn Val Phe Ser Cys Ser Val Met His Glu Ala Leu
            690                 695                 700

His Asn His Tyr Thr Gln Lys Ser Leu Ser Leu Ser Pro Gly Lys His
705                 710                 715                 720

His His His His
                725

<210> SEQ ID NO 92
<211> LENGTH: 474
<212> TYPE: PRT
<213> ORGANISM: Artificial Sequence
<220> FEATURE:
<221> NAME/KEY: PEPTIDE
<223> OTHER INFORMATION: NC2  chain 2

<400> SEQUENCE: 92

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
                20                  25                  30

His Tyr Pro Ser Trp Tyr Gln Gln Thr Pro Gly Gln Ala Pro Arg Met
            35                  40                  45

Leu Ile Tyr Asn Thr Asn Thr Arg Ser Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95
```

-continued

```
Asp Ile Trp Val Phe Gly Gly Thr Lys Leu Thr Val Leu Gly
                100                 105                 110

Gly Gly Ser Gly Gly Gly Ser Gly Gly Gly Ser Gln Val Gln
            115                 120                 125

Leu Val Gln Ser Gly Gly Val Val Gln Pro Gly Thr Ser Leu Arg
130                 135                 140

Leu Ser Cys Ala Ala Ser Gly Phe Ile Phe Ser Ser Ala Met His
145                 150                 155                 160

Trp Val Arg Gln Ala Pro Gly Lys Gly Leu Glu Trp Val Ala Val Ile
                165                 170                 175

Ser Tyr Asp Gly Ser Asn Lys Tyr Tyr Val Asp Ser Val Lys Gly Arg
            180                 185                 190

Phe Thr Ile Ser Arg Asp Asn Ser Lys Asn Thr Leu Tyr Leu Gln Met
                195                 200                 205

Asn Ser Leu Arg Ala Glu Asp Thr Ala Val Tyr Tyr Cys Ala Arg Ser
210                 215                 220

Ala Arg Leu Tyr Ala Ser Phe Asp Tyr Trp Gly Gln Gly Ala Leu Val
225                 230                 235                 240

Thr Val Ser Ser Gly Gly Gly Asp Lys Thr His Thr Cys Pro Pro Cys
                245                 250                 255

Pro Ala Pro Glu Ala Ala Gly Gly Pro Ser Val Phe Leu Phe Pro Pro
            260                 265                 270

Lys Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
                355                 360                 365

Gln Pro Arg Glu Pro Gln Val Cys Thr Leu Pro Pro Ser Arg Glu Glu
            370                 375                 380

Met Thr Lys Asn Gln Val Ser Leu Ser Cys Ala Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Val Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
            450                 455                 460

Gln Lys Ser Leu Ser Leu Ser Pro Gly Lys
465                 470
```

<210> SEQ ID NO 93
<211> LENGTH: 730
<212> TYPE: PRT
<213> ORGANISM: Artificial Sequence
<220> FEATURE:

<221> NAME/KEY: PEPTIDE
<223> OTHER INFORMATION: NC3  chain 1

<400> SEQUENCE: 93

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ala Asn Tyr
            20                  25                  30

Leu Ser Trp Tyr Gln Gln Lys Pro Gly Lys Ser Pro Lys Leu Leu Ile
        35                  40                  45

Tyr Gly Thr Ser Asn Leu Glu Val Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Lys Glu Phe Pro Arg
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Phe Thr Phe Ser His Tyr Tyr Met Ala Trp Val Arg
145                 150                 155                 160

Gln Ala Pro Gly Lys Gly Leu Glu Trp Val Thr Ser Ile Ser Tyr Glu
                165                 170                 175

Gly Asp Ile Thr Tyr Tyr Gly Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Thr Tyr Tyr Cys Ala Ser Gln Thr Leu Arg
    210                 215                 220

Glu Ser Phe Asp Tyr Trp Gly Gln Gly Thr Leu Val Thr Val Ser Ser
225                 230                 235                 240

Gly Gly Gly Gly Ser Glu Val Gln Leu Val Glu Ser Gly Gly Gly Leu
                245                 250                 255

Val Gln Pro Gly Gly Ser Leu Lys Leu Ser Cys Ala Ala Ser Gly Phe
            260                 265                 270

Thr Phe Asn Lys Tyr Ala Met Asn Trp Val Arg Gln Ala Pro Gly Lys
        275                 280                 285

Gly Leu Glu Trp Val Ala Arg Ile Arg Ser Lys Tyr Asn Asn Tyr Ala
    290                 295                 300

Thr Tyr Tyr Ala Asp Ser Val Lys Asp Arg Phe Thr Ile Ser Arg Asp
305                 310                 315                 320

Asp Ser Lys Asn Thr Ala Tyr Leu Gln Met Asn Asn Leu Lys Thr Glu
                325                 330                 335

Asp Thr Ala Val Tyr Tyr Cys Val Arg His Gly Asn Phe Gly Asn Glu
            340                 345                 350

Tyr Ile Ser Tyr Trp Ala Tyr Trp Gly Gln Gly Thr Leu Val Thr Val
        355                 360                 365

Ser Ser Gly Gly Gly Gly Ser Gly Gly Gly Gly Ser Gly Gly Gly Gly
    370                 375                 380

Ser Gln Thr Val Val Thr Gln Glu Pro Ser Leu Thr Val Ser Pro Gly
385                 390                 395                 400

Gly Thr Val Thr Leu Thr Cys Gly Ser Ser Thr Gly Ala Val Thr Ser
            405                 410                 415

Gly Asn Tyr Pro Asn Trp Val Gln Gln Lys Pro Gly Gln Ala Pro Arg
        420                 425                 430

Gly Leu Ile Gly Gly Thr Lys Phe Leu Ala Pro Gly Thr Pro Ala Arg
            435                 440                 445

Phe Ser Gly Ser Leu Leu Gly Gly Lys Ala Ala Leu Thr Leu Ser Gly
        450                 455                 460

Val Gln Pro Glu Asp Glu Ala Glu Tyr Tyr Cys Val Leu Trp Tyr Ser
465                 470                 475                 480

Asn Arg Trp Val Phe Gly Gly Gly Thr Lys Leu Thr Val Leu Gly Gly
                485                 490                 495

Gly Asp Lys Thr His Thr Cys Pro Pro Cys Pro Ala Pro Glu Ala Ala
            500                 505                 510

Gly Gly Pro Ser Val Phe Leu Phe Pro Pro Lys Pro Lys Asp Thr Leu
        515                 520                 525

Met Ile Ser Arg Thr Pro Glu Val Thr Cys Val Val Val Asp Val Ser
        530                 535                 540

His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Asn Ser Thr
                565                 570                 575

Tyr Arg Val Val Ser Val Leu Thr Val Leu His Gln Asp Trp Leu Asn
            580                 585                 590

Gly Lys Glu Tyr Lys Cys Lys Val Ser Asn Lys Ala Leu Pro Ala Pro
        595                 600                 605

Ile Glu Lys Thr Ile Ser Lys Ala Lys Gly Gln Pro Arg Glu Pro Gln
        610                 615                 620

Val Tyr Thr Leu Pro Pro Cys Arg Glu Glu Met Thr Lys Asn Gln Val
625                 630                 635                 640

Ser Leu Trp Cys Leu Val Lys Gly Phe Tyr Pro Ser Asp Ile Ala Val
                645                 650                 655

Glu Trp Glu Ser Asn Gly Gln Pro Glu Asn Asn Tyr Lys Thr Thr Pro
            660                 665                 670

Pro Val Leu Asp Ser Asp Gly Ser Phe Phe Leu Tyr Ser Lys Leu Thr
        675                 680                 685

Val Asp Lys Ser Arg Trp Gln Gln Gly Asn Val Phe Ser Cys Ser Val
        690                 695                 700

Met His Glu Ala Leu His Asn His Tyr Thr Gln Lys Ser Leu Ser Leu
705                 710                 715                 720

Ser Pro Gly Lys His His His His His His
                725                 730

<210> SEQ ID NO 94
<211> LENGTH: 470
<212> TYPE: PRT
<213> ORGANISM: Artificial Sequence
<220> FEATURE:
<221> NAME/KEY: PEPTIDE
<223> OTHER INFORMATION: NC3 chain 2

<400> SEQUENCE: 94

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ala Asn Tyr

```
                  20                  25                  30
Leu Ser Trp Tyr Gln Gln Lys Pro Gly Lys Ser Pro Lys Leu Leu Ile
            35                  40                  45
Tyr Gly Thr Ser Asn Leu Glu Val Gly Val Pro Ser Arg Phe Ser Gly
        50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Leu Gln Asp Lys Glu Phe Pro Arg
                85                  90                  95
Thr Phe Gly Gly Gly Thr Lys Val Glu Ile Lys Gly Gly Gly Gly Ser
            100                 105                 110
Gly Gly Gly Gly Ser Gly Gly Gly Ser Glu Val Gln Leu Val Glu
        115                 120                 125
Ser Gly Gly Gly Leu Val Gln Pro Gly Gly Ser Leu Arg Leu Ser Cys
        130                 135                 140
Ala Ala Ser Gly Phe Thr Phe Ser His Tyr Tyr Met Ala Trp Val Arg
145                 150                 155                 160
Gln Ala Pro Gly Lys Gly Leu Glu Trp Val Thr Ser Ile Ser Tyr Glu
            165                 170                 175
Gly Asp Ile Thr Tyr Tyr Gly Asp Ser Val Lys Gly Arg Phe Thr Ile
        180                 185                 190
Ser Arg Asp Asn Ser Lys Asn Thr Leu Tyr Leu Gln Met Asn Ser Leu
            195                 200                 205
Arg Ala Glu Asp Thr Ala Thr Tyr Tyr Cys Ala Ser Gln Thr Leu Arg
        210                 215                 220
Glu Ser Phe Asp Tyr Trp Gly Gln Gly Thr Leu Val Thr Val Ser Ser
225                 230                 235                 240
Gly Gly Gly Asp Lys Thr His Thr Cys Pro Pro Cys Pro Ala Pro Glu
            245                 250                 255
Ala Ala Gly Gly Pro Ser Val Phe Leu Phe Pro Pro Lys Pro Lys Asp
        260                 265                 270
Thr Leu Met Ile Ser Arg Thr Pro Glu Val Thr Cys Val Val Val Asp
        275                 280                 285
Val Ser His Glu Asp Pro Glu Val Lys Phe Asn Trp Tyr Val Asp Gly
        290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
            325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
            355                 360                 365
Pro Gln Val Cys Thr Leu Pro Pro Ser Arg Glu Glu Met Thr Lys Asn
            370                 375                 380
Gln Val Ser Leu Ser Cys Ala Val Lys Gly Phe Tyr Pro Ser Asp Ile
385                 390                 395                 400
Ala Val Glu Trp Glu Ser Asn Gly Gln Pro Glu Asn Asn Tyr Lys Thr
            405                 410                 415
Thr Pro Pro Val Leu Asp Ser Asp Gly Ser Phe Phe Leu Val Ser Lys
        420                 425                 430
Leu Thr Val Asp Lys Ser Arg Trp Gln Gln Gly Asn Val Phe Ser Cys
        435                 440                 445
```

```
Ser Val Met His Glu Ala Leu His Asn His Tyr Thr Gln Lys Ser Leu
    450                 455                 460

Ser Leu Ser Pro Gly Lys
465                 470

<210> SEQ ID NO 95
<211> LENGTH: 504
<212> TYPE: PRT
<213> ORGANISM: Artificial Sequence
<220> FEATURE:
<221> NAME/KEY: PEPTIDE
<223> OTHER INFORMATION: MGD009  chain 1

<400> SEQUENCE: 95

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
    130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Asp Arg Phe Thr Ile Ser Arg Asp Asp Ser
            180                 185                 190

Lys Asn Ser Leu Tyr Leu Gln Met Asn Ser Leu Lys Thr Glu Asp Thr
        195                 200                 205

Ala Val Tyr Tyr Cys Val Arg His Gly Asn Phe Gly Asn Ser Tyr Val
    210                 215                 220

Ser Trp Phe Ala Tyr Trp Gly Gln Gly Thr Leu Val Thr Val Ser Ser
225                 230                 235                 240

Gly Gly Cys Gly Gly Gly Glu Val Ala Ala Leu Glu Lys Glu Val Ala
                245                 250                 255

Ala Leu Glu Lys Glu Val Ala Ala Leu Glu Lys Glu Val Ala Ala Leu
            260                 265                 270

Glu Lys Gly Gly Gly Asp Lys Thr His Thr Cys Pro Pro Cys Pro Ala
        275                 280                 285

Pro Glu Ala Ala Gly Gly Pro Ser Val Phe Leu Phe Pro Pro Lys Pro
    290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
```

```
              325                 330                 335
Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
            355                 360                 365

Asp Trp Leu Asn Gly Lys Glu Tyr Lys Cys Lys Val Ser Asn Lys Ala
            370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415

Lys Asn Gln Val Ser Leu Trp Cys Leu Val Lys Gly Phe Tyr Pro Ser
            420                 425                 430

Asp Ile Ala Val Glu Trp Glu Ser Asn Gly Gln Pro Glu Asn Asn Tyr
            435                 440                 445

Lys Thr Thr Pro Pro Val Leu Asp Ser Asp Gly Ser Phe Phe Leu Tyr
            450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500

<210> SEQ ID NO 96
<211> LENGTH: 274
<212> TYPE: PRT
<213> ORGANISM: Artificial Sequence
<220> FEATURE:
<221> NAME/KEY: PEPTIDE
<223> OTHER INFORMATION: MGD009  chain 2

<400> SEQUENCE: 96

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Thr Phe Ser Ser Phe Gly Met His Trp Val Arg Gln Ala Pro Gly
145                 150                 155                 160

Lys Gly Leu Glu Trp Val Ala Tyr Ile Ser Ser Asp Ser Ser Ala Ile
                165                 170                 175
```

```
Tyr Tyr Ala Asp Thr Val Lys Gly Arg Phe Thr Ile Ser Arg Asp Asn
                180                 185                 190

Ala Lys Asn Ser Leu Tyr Leu Gln Met Asn Ser Leu Arg Asp Glu Asp
            195                 200                 205

Thr Ala Val Tyr Tyr Cys Gly Arg Gly Arg Glu Asn Ile Tyr Tyr Gly
        210                 215                 220

Ser Arg Leu Asp Tyr Trp Gly Gln Gly Thr Thr Val Thr Val Ser Ser
225                 230                 235                 240

Gly Gly Cys Gly Gly Gly Lys Val Ala Ala Leu Lys Glu Lys Val Ala
                245                 250                 255

Ala Leu Lys Glu Lys Val Ala Ala Leu Lys Glu Lys Val Ala Ala Leu
                260                 265                 270

Lys Glu

<210> SEQ ID NO 97
<211> LENGTH: 227
<212> TYPE: PRT
<213> ORGANISM: Artificial Sequence
<220> FEATURE:
<221> NAME/KEY: PEPTIDE
<223> OTHER INFORMATION: MGD009  chain 3

<400> SEQUENCE: 97

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Lys
225

<210> SEQ ID NO 98
<211> LENGTH: 13
```

```
<212> TYPE: PRT
<213> ORGANISM: Artificial Sequence
<220> FEATURE:
<221> NAME/KEY: PEPTIDE
<223> OTHER INFORMATION: linker

<400> SEQUENCE: 98

Gly Gly Gly Asp Lys Thr His Thr Cys Pro Pro Cys Pro
1               5                   10

<210> SEQ ID NO 99
<211> LENGTH: 513
<212> TYPE: PRT
<213> ORGANISM: Artificial Sequence
<220> FEATURE:
<221> NAME/KEY: CHAIN
<223> OTHER INFORMATION: 201 chain 1

<400> SEQUENCE: 99

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
                20                  25                  30

His Tyr Pro Ser Trp Tyr Gln Gln Thr Pro Gly Gln Ala Pro Arg Met
            35                  40                  45

Leu Ile Tyr Asn Thr Asn Thr Arg Ser Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gly
            100                 105                 110

Gly Ser Gly Gly Gly Gly Glu Val Gln Leu Val Glu Ser Gly Gly Gly
        115                 120                 125

Leu Val Gln Pro Gly Gly Ser Leu Lys Leu Ser Cys Ala Ala Ser Gly
    130                 135                 140

Phe Thr Phe Asn Lys Tyr Ala Met Asn Trp Val Arg Gln Ala Pro Gly
145                 150                 155                 160

Lys Gly Leu Glu Trp Val Ala Arg Ile Arg Ser Lys Tyr Asn Asn Tyr
                165                 170                 175

Ala Thr Tyr Tyr Ala Asp Ser Val Lys Asp Arg Phe Thr Ile Ser Arg
            180                 185                 190

Asp Asp Ser Lys Asn Thr Ala Tyr Leu Gln Met Asn Asn Leu Lys Thr
        195                 200                 205

Glu Asp Thr Ala Val Tyr Tyr Cys Val Arg His Gly Asn Phe Gly Asn
    210                 215                 220

Glu Tyr Ile Ser Tyr Trp Ala Tyr Trp Gly Gln Gly Thr Leu Val Thr
225                 230                 235                 240

Val Ser Ser Gly Gly Cys Gly Gly Gly Glu Val Ala Ala Leu Glu Lys
                245                 250                 255

Glu Val Ala Ala Leu Glu Lys Glu Val Ala Ala Leu Glu Lys Glu Val
            260                 265                 270

Ala Ala Leu Glu Lys Gly Gly Gly Asp Lys Thr His Thr Cys Pro Pro
        275                 280                 285

Cys Pro Ala Pro Glu Ala Ala Gly Gly Pro Ser Val Phe Leu Phe Pro
    290                 295                 300
```

```
Pro Lys Pro Lys Asp Thr Leu Met Ile Ser Arg Thr Pro Glu Val Thr
305                 310                 315                 320

Cys Val Val Asp Val Ser His Glu Asp Pro Glu Val Lys Phe Asn
            325                 330                 335

Trp Tyr Val Asp Gly Val Glu Val His Asn Ala Lys Thr Lys Pro Arg
                340                 345                 350

Glu Glu Gln Tyr Asn Ser Thr Tyr Arg Val Val Ser Val Leu Thr Val
            355                 360                 365

Leu His Gln Asp Trp Leu Asn Gly Lys Glu Tyr Lys Cys Lys Val Ser
        370                 375                 380

Asn Lys Ala Leu Pro Ala Pro Ile Glu Lys Thr Ile Ser Lys Ala Lys
385                 390                 395                 400

Gly Gln Pro Arg Glu Pro Gln Val Tyr Thr Leu Pro Pro Ser Arg Glu
                405                 410                 415

Glu Met Thr Lys Asn Gln Val Ser Leu Trp Cys Leu Val Lys Gly Phe
            420                 425                 430

Tyr Pro Ser Asp Ile Ala Val Glu Trp Glu Ser Asn Gly Gln Pro Glu
                435                 440                 445

Asn Asn Tyr Lys Thr Thr Pro Pro Val Leu Asp Ser Asp Gly Ser Phe
450                 455                 460

Phe Leu Tyr Ser Lys Leu Thr Val Asp Lys Ser Arg Trp Gln Gln Gly
465                 470                 475                 480

Asn Val Phe Ser Cys Ser Val Met His Glu Ala Leu His Asn His Tyr
                485                 490                 495

Thr Gln Lys Ser Leu Ser Leu Ser Pro Gly Lys His His His His His
            500                 505                 510

His

<210> SEQ ID NO 100
<211> LENGTH: 271
<212> TYPE: PRT
<213> ORGANISM: Artificial Sequence
<220> FEATURE:
<221> NAME/KEY: CHAIN
<223> OTHER INFORMATION: 201 chain 2

<400> SEQUENCE: 100

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Gly Gly
        115                 120                 125

Val Val Gln Pro Gly Thr Ser Leu Arg Leu Ser Cys Ala Ala Ser Gly
    130                 135                 140
```

```
Phe Ile Phe Ser Ser Ser Ala Met His Trp Val Arg Gln Ala Pro Gly
145                 150                 155                 160
Lys Gly Leu Glu Trp Val Ala Val Ile Ser Tyr Asp Gly Ser Asn Lys
                165                 170                 175
Tyr Tyr Val Asp Ser Val Lys Gly Arg Phe Thr Ile Ser Arg Asp Asn
            180                 185                 190
Ser Lys Asn Thr Leu Tyr Leu Gln Met Asn Ser Leu Arg Ala Glu Asp
        195                 200                 205
Thr Ala Val Tyr Tyr Cys Ala Arg Ser Ala Arg Leu Tyr Ala Ser Phe
    210                 215                 220
Asp Tyr Trp Gly Gln Gly Ala Leu Val Thr Val Ser Ser Gly Gly Cys
225                 230                 235                 240
Gly Gly Gly Lys Val Ala Ala Leu Lys Glu Lys Val Ala Ala Leu Lys
                245                 250                 255
Glu Lys Val Ala Ala Leu Lys Glu Lys Val Ala Ala Leu Lys Glu
                260                 265                 270

<210> SEQ ID NO 101
<211> LENGTH: 455
<212> TYPE: PRT
<213> ORGANISM: Artificial Sequence
<220> FEATURE:
<221> NAME/KEY: CHAIN
<223> OTHER INFORMATION: 202 chain 1

<400> SEQUENCE: 101

Gln Val Gln Leu Val Gln Ser Gly Gly Gly Val Val Gln Pro Gly Thr
1               5                   10                  15
Ser Leu Arg Leu Ser Cys Ala Ala Ser Gly Phe Ile Phe Ser Ser Ser
                20                  25                  30
Ala Met His Trp Val Arg Gln Ala Pro Gly Lys Gly Leu Glu Trp Val
            35                  40                  45
Ala Val Ile Ser Tyr Asp Gly Ser Asn Lys Tyr Tyr Val Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Ala Arg Leu Tyr Ala Ser Phe Asp Tyr Trp Gly Gln Gly
            100                 105                 110
Ala Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Ala Ala Gly Gly Pro
225                 230                 235                 240
```

-continued

```
Ser Val Phe Leu Phe Pro Pro Lys Pro Lys Asp Thr Leu Met Ile Ser
                245             250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys His His His His His His
    450                 455

<210> SEQ ID NO 102
<211> LENGTH: 217
<212> TYPE: PRT
<213> ORGANISM: Artificial Sequence
<220> FEATURE:
<221> NAME/KEY: CHAIN
<223> OTHER INFORMATION: 202 chain 2

<400> SEQUENCE: 102

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
```

```
                130             135             140
Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
                195                 200                 205

Thr Lys Ser Phe Asn Arg Gly Glu Cys
            210                 215

<210> SEQ ID NO 103
<211> LENGTH: 692
<212> TYPE: PRT
<213> ORGANISM: Artificial Sequence
<220> FEATURE:
<221> NAME/KEY: CHAIN
<223> OTHER INFORMATION: 202 chain 3

<400> SEQUENCE: 103

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Arg Leu Tyr Ala Ser Phe Asp Tyr Trp Gly Gln Gly
                100                 105                 110

Ala Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Gly
        210                 215                 220

Gly Gly Gly Ser Gly Gly Gly Ser Glu Val Gln Leu Val Glu Ser
225                 230                 235                 240

Gly Gly Gly Leu Val Gln Pro Gly Gly Ser Leu Lys Leu Ser Cys Ala
                245                 250                 255

Ala Ser Gly Phe Thr Phe Asn Lys Tyr Ala Met Asn Trp Val Arg Gln
            260                 265                 270
```

```
Ala Pro Gly Lys Gly Leu Glu Trp Val Ala Arg Ile Arg Ser Lys Tyr
            275                 280                 285

Asn Asn Tyr Ala Thr Tyr Tyr Ala Asp Ser Val Lys Asp Arg Phe Thr
            290                 295                 300

Ile Ser Arg Asp Asp Ser Lys Asn Thr Ala Tyr Leu Gln Met Asn Asn
305                 310                 315                 320

Leu Lys Thr Glu Asp Thr Ala Val Tyr Tyr Cys Val Arg His Gly Asn
            325                 330                 335

Phe Gly Asn Glu Tyr Ile Ser Tyr Trp Ala Tyr Trp Gly Gln Gly Thr
            340                 345                 350

Leu Val Thr Val Ser Ser Ala Ser Val Ala Ala Pro Ser Val Phe Ile
            355                 360                 365

Phe Pro Pro Ser Asp Glu Gln Leu Lys Ser Gly Thr Ala Ser Val Val
            370                 375                 380

Cys Leu Leu Asn Asn Phe Tyr Pro Arg Glu Ala Lys Val Gln Trp Lys
385                 390                 395                 400

Val Asp Asn Ala Leu Gln Ser Gly Asn Ser Gln Glu Ser Val Thr Glu
            405                 410                 415

Gln Asp Ser Lys Asp Ser Thr Tyr Ser Leu Ser Ser Thr Leu Thr Leu
            420                 425                 430

Ser Lys Ala Asp Tyr Glu Lys His Lys Val Tyr Ala Cys Glu Val Thr
            435                 440                 445

His Gln Gly Leu Ser Ser Pro Val Thr Lys Ser Phe Asn Arg Gly Glu
            450                 455                 460

Cys Asp Lys Thr His Thr Cys Pro Pro Cys Pro Ala Pro Glu Ala Ala
465                 470                 475                 480

Gly Gly Pro Ser Val Phe Leu Phe Pro Pro Lys Pro Lys Asp Thr Leu
            485                 490                 495

Met Ile Ser Arg Thr Pro Glu Val Thr Cys Val Val Val Asp Val Ser
            500                 505                 510

His Glu Asp Pro Glu Val Lys Phe Asn Trp Tyr Val Asp Gly Val Glu
            515                 520                 525

Val His Asn Ala Lys Thr Lys Pro Arg Glu Glu Gln Tyr Asn Ser Thr
            530                 535                 540

Tyr Arg Val Val Ser Val Leu Thr Val Leu His Gln Asp Trp Leu Asn
545                 550                 555                 560

Gly Lys Glu Tyr Lys Cys Lys Val Ser Asn Lys Ala Leu Pro Ala Pro
            565                 570                 575

Ile Glu Lys Thr Ile Ser Lys Ala Lys Gly Gln Pro Arg Glu Pro Gln
            580                 585                 590

Val Cys Thr Leu Pro Pro Ser Arg Glu Glu Met Thr Lys Asn Gln Val
            595                 600                 605

Ser Leu Ser Cys Ala Val Lys Gly Phe Tyr Pro Ser Asp Ile Ala Val
            610                 615                 620

Glu Trp Glu Ser Asn Gly Gln Pro Glu Asn Asn Tyr Lys Thr Thr Pro
625                 630                 635                 640

Pro Val Leu Asp Ser Asp Gly Ser Phe Phe Leu Val Ser Lys Leu Thr
            645                 650                 655

Val Asp Lys Ser Arg Trp Gln Gln Gly Asn Val Phe Ser Cys Ser Val
            660                 665                 670

Met His Glu Ala Leu His Asn His Tyr Thr Gln Lys Ser Leu Ser Leu
            675                 680                 685

Ser Pro Gly Lys
```

<210> SEQ ID NO 104
<211> LENGTH: 214
<212> TYPE: PRT
<213> ORGANISM: Artificial Sequence
<220> FEATURE:
<221> NAME/KEY: CHAIN
<223> OTHER INFORMATION: 202 chain 4

<400> SEQUENCE: 104

```
Gln Thr Val Val Thr Gln Glu Pro Ser Leu Thr Val Ser Pro Gly Gly
1               5                   10                  15
Thr Val Thr Leu Thr Cys Gly Ser Ser Thr Gly Ala Val Thr Ser Gly
            20                  25                  30
Asn Tyr Pro Asn Trp Val Gln Gln Lys Pro Gly Gln Ala Pro Arg Gly
        35                  40                  45
Leu Ile Gly Gly Thr Lys Phe Leu Ala Pro Gly Thr Pro Ala Arg Phe
    50                  55                  60
Ser Gly Ser Leu Leu Gly Gly Lys Ala Ala Leu Thr Leu Ser Gly Val
65                  70                  75                  80
Gln Pro Glu Asp Glu Ala Glu Tyr Tyr Cys Val Leu Trp Tyr Ser Asn
                85                  90                  95
Arg Trp Val Phe Gly Gly Gly Thr Lys Leu Thr Val Leu Ser Ser Ala
            100                 105                 110
Ser Thr Lys Gly Pro Ser Val Phe Pro Leu Ala Pro Ser Ser Lys Ser
        115                 120                 125
Thr Ser Gly Gly Thr Ala Ala Leu Gly Cys Leu Val Lys Asp Tyr Phe
    130                 135                 140
Pro Glu Pro Val Thr Val Ser Trp Asn Ser Gly Ala Leu Thr Ser Gly
145                 150                 155                 160
Val His Thr Phe Pro Ala Val Leu Gln Ser Ser Gly Leu Tyr Ser Leu
                165                 170                 175
Ser Ser Val Val Thr Val Pro Ser Ser Ser Leu Gly Thr Gln Thr Tyr
            180                 185                 190
Ile Cys Asn Val Asn His Lys Pro Ser Asn Thr Lys Val Asp Lys Lys
        195                 200                 205
Val Glu Pro Lys Ser Cys
    210
```

<210> SEQ ID NO 105
<211> LENGTH: 5
<212> TYPE: PRT
<213> ORGANISM: Artificial Sequence
<220> FEATURE:
<223> OTHER INFORMATION: linker

<400> SEQUENCE: 105

```
Gly Gly Gly Gly Ser
1               5
```

<210> SEQ ID NO 106
<211> LENGTH: 10
<212> TYPE: PRT
<213> ORGANISM: Artificial Sequence
<220> FEATURE:
<223> OTHER INFORMATION: linker

<400> SEQUENCE: 106

```
Gly Gly Gly Gly Ser Gly Gly Gly Gly Ser
```

```
<210> SEQ ID NO 107
<211> LENGTH: 15
<212> TYPE: PRT
<213> ORGANISM: Artificial Sequence
<220> FEATURE:
<223> OTHER INFORMATION: linker

<400> SEQUENCE: 107

Gly Gly Gly Gly Ser Gly Gly Gly Gly Ser Gly Gly Gly Gly Ser
1               5                   10                  15

<210> SEQ ID NO 108
<211> LENGTH: 20
<212> TYPE: PRT
<213> ORGANISM: Artificial Sequence
<220> FEATURE:
<223> OTHER INFORMATION: linker

<400> SEQUENCE: 108

Gly Gly Gly Gly Ser Gly Gly Gly Gly Ser Gly Gly Gly Gly Ser Gly
1               5                   10                  15

Gly Gly Gly Ser
            20

<210> SEQ ID NO 109
<211> LENGTH: 8
<212> TYPE: PRT
<213> ORGANISM: Artificial Sequence
<220> FEATURE:
<223> OTHER INFORMATION: linker

<400> SEQUENCE: 109

Gly Gly Gly Gly Ser Gly Gly Gly
1               5

<210> SEQ ID NO 110
<211> LENGTH: 13
<212> TYPE: PRT
<213> ORGANISM: Artificial Sequence
<220> FEATURE:
<223> OTHER INFORMATION: linker

<400> SEQUENCE: 110

Gly Gly Gly Gly Ser Gly Gly Gly Gly Ser Gly Gly Gly
1               5                   10

<210> SEQ ID NO 111
<211> LENGTH: 18
<212> TYPE: PRT
<213> ORGANISM: Artificial Sequence
<220> FEATURE:
<223> OTHER INFORMATION: linker

<400> SEQUENCE: 111

Gly Gly Gly Gly Ser Gly Gly Gly Gly Ser Gly Gly Gly Gly Ser Gly
1               5                   10                  15

Gly Gly

<210> SEQ ID NO 112
<211> LENGTH: 23
<212> TYPE: PRT
<213> ORGANISM: Artificial Sequence
<220> FEATURE:
<223> OTHER INFORMATION: linker
```

```
<400> SEQUENCE: 112

Gly Gly Gly Gly Ser Gly Gly Gly Gly Ser Gly Gly Gly Gly Ser Gly
1               5                   10                  15

Gly Gly Gly Ser Gly Gly Gly
            20
```